US006929870B2

(12) United States Patent
Ishida et al.

(10) Patent No.: US 6,929,870 B2
(45) Date of Patent: Aug. 16, 2005

(54) HYDROCARBON COMPOUNDS, MATERIALS FOR ORGANIC ELECTROLUMINESCENT ELEMENTS AND ORGANIC ELECTROLUMINESCENT ELEMENTS

(75) Inventors: Tsutomu Ishida, Chiba (JP); Takehiko Shimamura, Chiba (JP); Yoshiyuki Totani, Chiba (JP); Masakatsu Nakatsuka, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 221 days.

(21) Appl. No.: 10/110,241

(22) PCT Filed: Aug. 10, 2001

(86) PCT No.: PCT/JP01/06920

§ 371 (c)(1),
(2), (4) Date: Apr. 10, 2002

(87) PCT Pub. No.: WO02/14244

PCT Pub. Date: Feb. 21, 2002

(65) Prior Publication Data

US 2003/0087126 A1 May 8, 2003

(30) Foreign Application Priority Data

Aug. 10, 2000 (JP) ........................................ 2000-242476
Sep. 5, 2000 (JP) ........................................ 2000-268568

(51) Int. Cl.⁷ ............................................. H05B 33/14
(52) U.S. Cl. ....................... 428/690; 428/704; 428/917; 313/504; 313/506; 252/301.16; 252/301.35; 257/40; 257/103; 564/426; 564/427; 564/431; 564/433; 564/434; 585/19; 585/25; 585/26
(58) Field of Search ................................ 428/690, 704, 428/917; 313/504, 506; 252/301.16, 301.35; 257/40, 103; 564/426, 427, 431, 433, 434; 585/19, 25, 26

(56) References Cited

U.S. PATENT DOCUMENTS 6,479,172 B2 * 11/2002 Hu et al. .................... 428/690

FOREIGN PATENT DOCUMENTS

JP         11-111460 A        4/1999

OTHER PUBLICATIONS

C.W. Tang et al., "Organic electroluminescent diodes," Appl. Phys. Lett., vol. 51, No. 12, Sep. 21, 1987, pp. 913–915, 1987 American Institute of Physics (U.S.).
C.W. Tang et al., "Electroluminescence of doped organic thin films," J. Appl. Phys., vol. 65, No. 9, May 1, 1989, pp. 3610–3616, 1989 American Institute of Physics (U.S.).
N. Miyaura et al., "Palladium–Catalyzed Cross–Coupling Reactions of Organoboron Compounds," Chemical Reviews, 1995, vol. 95, No. 7, pp. 2457–2483, 1985 American Chemical Society (U.S.).
Edwin Weber et al., "Versatile and Convenient Lattice Hosts Derived from Singly Bridged Triarylmethane Frameworks, X–Ray Crystal Structures of Three Inclusion Compounds", J. Chem Soc., Perkin Trans. 2, (1990), No. 12, pp. 2167 to 2177, Stockholm, Sweden.

* cited by examiner

Primary Examiner—Deborah Jones
Assistant Examiner—Ling Xu
(74) Attorney, Agent, or Firm—Burns, Doane, Swecker & Mathis, L.L.P.

(57) ABSTRACT

An electroluminescent element in which at least one layer containing at least one of novel hydrocarbon compounds with an anthracene ring and a fluorene ring directly bound is held between a pair of electrodes. The compounds can advantageously be used in a luminescent element and provide an organic electroluminescent element having an excellent luminescent efficiency and a long luminescent life.

16 Claims, 4 Drawing Sheets

HYDROCARBON COMPOUNDS, MATERIALS FOR ORGANIC ELECTROLUMINESCENT ELEMENTS AND ORGANIC ELECTROLUMINESCENT ELEMENTS

TECHNICAL FIELD

The present invention relates to organic electroluminescent elements, materials for organic electroluminescent elements which can advantageously be used in the luminescent elements and novel hydrocarbon compounds.

BACKGROUND OF THE INVENTION

Inorganic electroluminescent elements have been so far used as, for example, panel-type light sources of back light and the like. However, a high AC voltage is required to drive the luminescent elements. Recently, organic electroluminescent elements (organic EL elements) using organic materials as luminescent materials have been developed [Appl. Phys. Lett., 51, 913 (1987)]. The organic electroluminescent element is an element having a structure that a thin film containing a compound having a luminescent performance is held between an anode and a cathode, in which electrons and holes are injected in the thin film for recombination to generate excitons and luminescence occurs using light released in deactivating the excitons. The organic electroluminescent element enables luminescence at a low DC voltage of several volts to several tens of volts. Further, luminescence of various colors (for example, red, blue and green) is possible by selecting types of fluorescent organic compounds. The organic electroluminescent element having such characteristics is expected to be applied to various luminescent elements, display devices and the like. However, a luminescent brightness is generally low, which is unsatisfactory in practice.

As a method for improving a luminescent brightness, an organic electroluminescent element using, for example, tris(8-quinolinolato)aluminum as a host compound and coumalin derivatives or pyran derivatives as a guest compound (dopant) in a luminescent layer is proposed [J. Appl. Phys., 65, 3610 (1989)]. Further, an organic electroluminescent element using anthracene derivatives as a material of a luminescent layer is proposed (Japanese Patent Laid-Open Nos. 12,600/1996 and 111,458/1999). Still further, an organic electroluminescent element using anthracene derivatives as a guest compound of a luminescent layer is proposed (Japanese Patent Laid-Open Nos. 36,832/1998 and 294,179/1998).

However, these luminescent elements are not said either to have a satisfactory luminescent brightness and a satisfactory luminescent life.

Organic electroluminescent elements that allow luminescence with a higher luminescent brightness and a longer life have been currently in demand.

DISCLOSURE OF THE INVENTION

The invention aims to provide an organic electroluminescent element which is excellent in luminescent efficiency and allows luminescence with a high brightness and a long life. Further, it aims to provide materials for an organic electroluminescent element which can advantageously be used in the luminescent element. Still further, it aims to provide novel hydrocarbon compounds.

The present inventors have assiduously conducted investigations on organic electroluminescent elements, and have consequently come to complete the invention.

That is, the invention relates to (1) hydrocarbon compounds in which an anthracene ring and a fluorene ring are directly bound, (2) the hydrocarbon compounds as recited in 1, wherein the fluorene ring is bound in the position except the 9-position, (3) hydrocarbon compounds represented by the formula (1)

$$X_1\text{-}(F_1)_j\text{-}(A_1)_k\text{-}(F_2)_l\text{-}(A_2)_m\text{-}(F_3)_n\text{-}X_2 \quad (1)$$

wherein $A_1$ and $A_2$, independently from each other, represent a substituted or unsubstituted anthracen-diyl group, $F_1$, $F_2$ and $F_3$, independently from each other, represent a substituted or unsubstituted fluoren-diyl group, $X_1$ and $X_2$, independently from each other, represent a hydrogen atom, a halogen atom, a linear, branched or cyclic alkyl group, a linear, branched or cyclic alkoxy group, a substituted or unsubstituted amino group, a substituted or unsubstituted aryl group, or a substituted or unsubstituted aralkyl group, j, m and n represent 0 or 1, k and l represent 1 or 2, when k is 2 $A_1$'s may be the same or different, and when l is 2 $F_2$'s may be the same or different, (4) the hydrocarbon compounds as recited in 3, wherein k is 1, (5) the hydrocarbon compounds as recited in 4, wherein $A_1$ and $A_2$ are an anthracen-9,10-diyl group, and $F_1$, $F_2$ and $F_3$ are a fluoren-2,7-diyl group, (6) the hydrocarbon compounds as recited in 3, wherein j and n are 0, l is 1, and k+m is 2, (7) the hydrocarbon compounds as recited in (6) wherein $A_1$ and $A_2$ are an anthracen-9,10-diyl group, and $F_2$ is a fluoren-2,7-diyl group, (8) the hydrocarbon compounds as recited in (3) wherein j+l+n is 2, k is 1, and m is 0, (9) the hydrocarbon compounds as recited in 8, wherein $A_1$ is an anthracen-9,10-diyl group, and $F_1$, $F_2$ and $F_3$ are a fluoren-2,7-diyl group,

(10) the hydrocarbon compounds as recited in 3, wherein j, m and n are 0, and k and l are 1,

(11) the hydrocarbon compounds as recited in 10, wherein $A_1$ is an anthracen-9,10-diyl group, and $F_2$ is a fluoren-2,7-diyl group,

(12) hydrocarbon compounds represented by the formula (2)

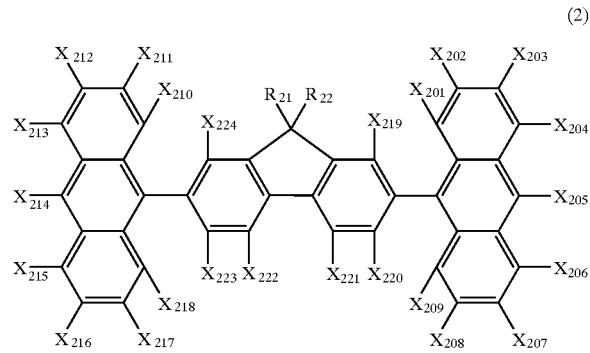

wherein $R_{21}$ and $R_{22}$, independently from each other, represent a hydrogen atom, a linear, branched or cyclic alkyl group, a substituted or unsubstituted aryl group, or a substituted or unsubstituted aralkyl group, and $X_{201}$ to $X_{214}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $R_{21}$, $R_{22}$ and $X_{201}$ to $X_{224}$ are not an anthryl group or a fluorenyl group,

(13) the hydrocarbon compounds as recited in 12, wherein $X_{205}$ and $X_{214}$ are a halogen atom, a linear, branched or cyclic alkyl group, a linear, branched or cyclic alkoxy group, or a substituted or unsubstituted aryl group,

(14) the hydrocarbon compounds as recited in 12, wherein $X_{205}$ and $X_{214}$ are a halogen atom, a linear, branched or cyclic alkyl group, a linear, branched or cyclic alkoxy group, or a substituted or unsubstituted heterocyclic aromatic group,

(15) the hydrocarbon compounds as recited in 12, wherein $X_{201}$, $X_{204}$, $X_{206}$, $X_{209}$, $X_{210}$, $X_{213}$, $X_{215}$ and $X_{218}$ are a hydrogen atom, a halogen atom, a linear, branched or cyclic alkyl group, or a linear, branched or cyclic alkoxy group,

(16) hydrocarbon compounds represented by the formula (3)

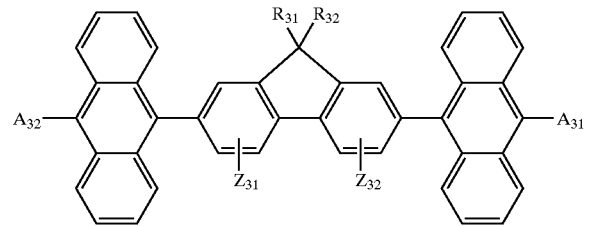

wherein $R_{31}$ and $R_{32}$, independently from each other, represent a hydrogen atom, a linear, branched or cyclic alkyl group, a substituted or unsubstituted aryl group, or a substituted or unsubstituted aralkyl group, $A_{31}$ and $A_{32}$, independently from each other, represent a substituted or unsubstituted aryl group, and $Z_{31}$ and $Z_{32}$, independently from each other, represent a hydrogen atom, a halogen atom, a linear, branched or cyclic alkyl group, a linear, branched or cyclic alkoxy group, or a substituted or unsubstituted aryl group,

(17) hydrocarbon compounds represented by the formula (4)

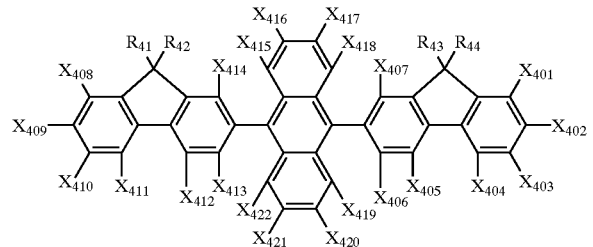

wherein $R_{41}$ to $R_{44}$, independently from each other, represent a hydrogen atom, a linear, branched or cyclic alkyl group, a substituted or unsubstituted aryl group, or a substituted or unsubstituted aralkyl group, and $X_{401}$ to $X_{422}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $R_{41}$ to $R_{44}$ and $X_{401}$ to $X_{422}$ are not an anthryl group or a fluorenyl group,

(18) the hydrocarbon compounds as recited in 17, wherein $X_{415}$, $X_{418}$, $X_{419}$ and $X_{422}$ are a hydrogen atom, a halogen atom, a linear, branched or cyclic alkyl group, or a linear, branched or cyclic alkoxy group,

(19) hydrocarbon compounds represented by the formula (5)

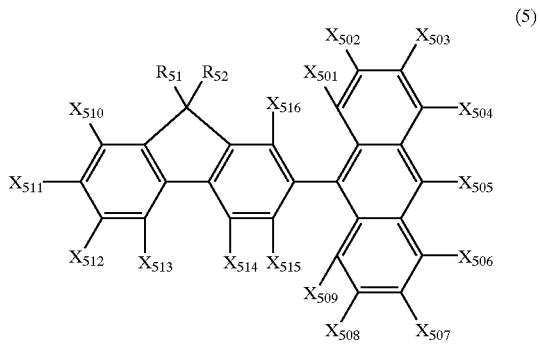

wherein $R_{51}$ and $R_{52}$, independently from each other, represent a hydrogen atom, a linear, branched or cyclic alkyl group, a substituted or unsubstituted aryl group, or a substituted or unsubstituted aralkyl group, and $X_{501}$ to $X_{516}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $R_{51}$, $R_{52}$ and $X_{501}$ to $X_{516}$ are not an anthryl group or a fluorenyl group,

(20) the hydrocarbon compounds as recited in 19, wherein $X_{505}$ is a halogen atom, a linear, branched or cyclic alkyl group, a linear, branched or cyclic alkoxy group, or a substituted or unsubstituted aryl group,

(21) the hydrocarbon compounds as recited in 19, wherein $X_{501}$, $X_{504}$, $X_{506}$ and $X_{509}$ are a hydrogen atom, a halogen atom, a linear, branched or cyclic alkyl group, or a linear, branched or cyclic alkoxy group,

(22) hydrocarbon compounds represented by the formula (6)

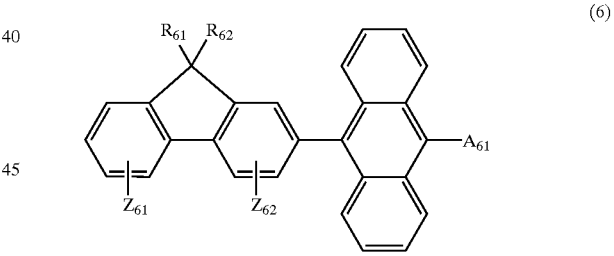

wherein $R_{61}$ and $R_{62}$, independently from each other, represent a hydrogen atom, a linear, branched or cyclic alkyl group, a substituted or unsubstituted aryl group, or a substituted or unsubstituted aralkyl group, $A_{61}$ represents a substituted or unsubstituted aryl group, and $Z_{61}$ and $Z_{62}$, independently from each other, represent a hydrogen atom, a halogen atom, a linear, branched or cyclic alkyl group, a linear, branched or cyclic alkoxy group, or a substituted or unsubstituted aryl group,

(23) materials for an organic electroluminescent element as recited in any one of 1 to 22,

(24) an organic electroluminescent element in which at least one layer containing at least one of the materials for the organic electroluminescent element as recited in 23 is held between a pair of electrodes,

(25) the organic electroluminescent element as recited in 24, wherein the layer containing the material for the organic electroluminescent element as recited in 23 is a luminescent layer,

(26) the organic electroluminescent element as recited in 24 or 25, wherein the layer containing the material for the organic electroluminescent element as recited in 23 further contains a luminescent organic metal complex,

(27) the organic electroluminescent element as recited in 24 or 25, wherein the layer containing the material for the organic electroluminescent element as recited in 23 further contains triarylamine derivatives,

(28) the organic electroluminescent element as recited in any one of 24 to 27, wherein a hole injection transport layer is further provided between a pair of electrodes, and

(29) the organic electroluminescent element as recited in any one of 24 to 28, wherein an electron injection transport layer is further provided between a pair of electrodes.

BRIEF DESCRIPTION OF THE DRAWINGS

FIG. 1 is (A) an anode/hole injection transport layer/luminescent layer/electron injection transport layer/cathode-type element;

FIG. 2 is (B) an anode/hole injection transport layer/luminescent layer/cathode-type element;

FIG. 3 is (C) an anode/luminescent layer/electron injection transport layer/cathode-type element;

FIG. 4 is (D) an anode/luminescent layer/cathode-type element; further,

FIG. 5 is (E) an anode/hole injection transport layer/electron injection transport layer/luminescent layer/electron injection transport layer/cathode-type element which is an element of a type with a luminescent layer held between electron injection transport layers;

FIG. 6 is, while the structure of the (D)-type element includes an element of a type in which the luminescent component in the form of one layer is held between the pair of electrodes, for example, (F) an element of a type in which a combination of a hole injection transport component, a luminescent component and an electron injection transport component in the form of one layer is held between a pair of electrodes;

FIG. 7 is (G) an element of a type in which a combination of a hole injection transport component and a luminescent component in the form of one layer is held between a pair of electrodes; and FIG. 8 is (H) an element of a type in which a combination of a luminescent component and an electron injection transport component in the form of one layer is held between a pair of electrodes.

Figure 1:
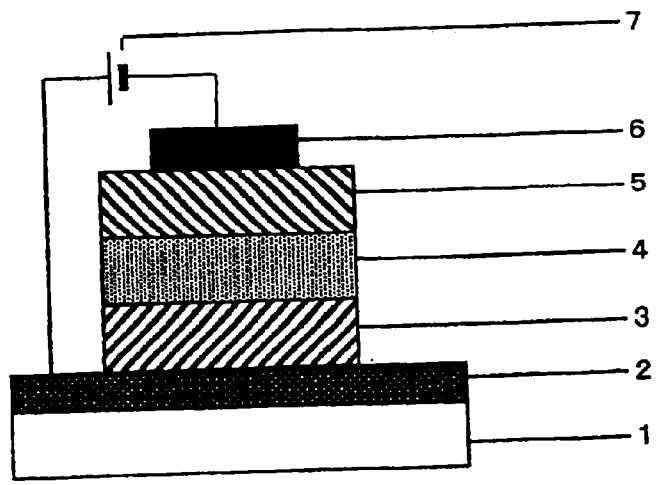
FIGS. 1 to 8 are each a schematic view showing a structure of an organic electroluminescent element.

In these drawings, the numerals are as follows.

| | |
|---|---|
| 1 | substrate |
| 2 | anode |
| 3 | hole injection transport layer |
| 3a | hole injection transport component |
| 4 | luminescent layer |
| 4' | luminescent layer (combined layer of a hole injection transport component and a luminescent component) |
| 4" | luminescent layer (combined layer of a luminescent component and a electron injection transport component) |
| 4"' | luminescent layer (combined layer of a hole injection transport component, a luminescent component and a electron injection transport component) |
| 5 | electron injection transport layer |
| 6 | cathode |
| 7 | power supply |

BEST MODE FOR CARRYING OUT THE INVENTION

The invention is described in detail below.

The invention relates to hydrocarbon compounds in which an antracene ring and a fluorene ring are directly bound.

The hydrocarbon compounds in which the anthracene ring and the fluorene ring are directly bound according to the invention (hereinafter abbreviated as compounds A according to the invention) do not include polymers, and are preferably compounds having a molecular weight of 2,000 or less, more preferably compounds having a molecular weight of 1,000 or less.

Compounds A according to the invention are preferably compounds in which the fluorene ring is bound to the anthracene ring in the position except the 9-position, more preferably compounds represented by the formula (1)

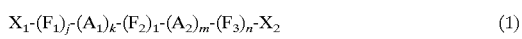

$$X_1\text{-}(F_1)_j\text{-}(A_1)_k\text{-}(F_2)_l\text{-}(A_2)_m\text{-}(F_3)_n\text{-}X_2 \qquad (1)$$

wherein $A_1$ and $A_2$, independently from each other, represent a substituted or unsubstituted anthracen-diyl group, $F_1$, $F_2$ and $F_3$, independently from each other, represent a substituted or unsubstituted fluoren-diyl group, $X_1$ and $X_2$, independently from each other, represent a hydrogen atom, a halogen atom, a linear, branched or cyclic alkyl group, a linear, branched or cyclic alkoxy group, a substituted or unsubstituted amino group, a substituted or unsubstituted aryl group, or a substituted or unsubstituted aralkyl group, j, m and n represent 0 or 1, k and l represent 1 or 2, when k is 2 $A_1$'s may be the same or different, and when l is 2 $F_2$'s may be the same or different.

In the compounds represented by the formula (1), $X_1$ and $X_2$, independently from each other, represent a hydrogen atom, a halogen atom, a linear, branched or cyclic alkyl group, a linear, branched or cyclic alkoxy group, a substituted or unsubstituted amino group, a substituted or unsubstituted aryl group, or a substituted or unsubstituted aralkyl group.

Incidentally, the aryl group refers to carbocyclic aromatic groups such as a phenyl group, a naphthyl group and the like, and heterocyclic aromatic groups such as a furfuryl group, a thienyl group, a pyridyl group and the like.

Further, in the compounds represented by the formula (1), the amino group of $X_1$ and $X_2$ may have a substituent, and may be mono-substituted or di-substituted with a substituent such as an alkyl group having 1 to 20 carbon atoms, an aryl group having 3 to 20 carbon atoms, an aralkyl group having 4 to 20 carbon atoms or the like.

Moreover, in the compounds represented by the formula (1), the aryl group and the aralkyl group of $X_1$ and $X_2$ may have a substituent, and may be mono-substituted or poly-substituted with a substituent such as a halogen atom, a linear, branched or cyclic alkyl group having 1 to 16 carbon atoms, a linear, branched or cyclic alkoxy group having 1 to 16 carbon atoms, an N-mono-substituted amino group having 1 to 20 carbon atoms, an N,N-di-substituted amino group having 2 to 40 carbon atoms, an aryl group having 3 to 25 carbon atoms, an aralkyl group having 5 to 16 carbon atoms or the like.

$X_1$ and $X_2$ are preferably a hydrogen atom, a halogen atom, a linear, branched or cyclic alkyl group having 1 to 16 carbon atoms, a linear, branched or cyclic alkoxy group having 1 to 16 carbon atoms, an unsubstituted amino group, a substituted amino group having 1 to 24 carbon atoms, a substituted or unsubstituted carbocyclic aromatic group having 6 to 25 carbon atoms, a substituted or unsubstituted heterocyclic aromatic group having 3 to 25 carbon atoms, or a substituted or unsubstituted aralkyl group having 5 to 16 carbon atoms, more preferably a hydrogen atom, a halogen atom, a linear, branched or cyclic alkyl group having 1 to 10 carbon atoms, a linear, branched or cyclic alkoxy group having 1 to 10 carbon atoms, a substituted amino group having 1 to 20 carbon atoms, a substituted or unsubstituted carbocyclic aromatic group having 6 to 12 carbon atoms, a substituted or unsubstituted heterocyclic aromatic group having 4 to 12 carbon atoms, or a substituted or unsubstituted aralkyl group having 7 to 12 carbon atoms, further preferably a hydrogen atom, a halogen atom, a linear, branched or cyclic alkyl group having 1 to 8 carbon atoms, a linear, branched or cyclic alkoxy group having 1 to 8 carbon atoms, a substituted amino group having 2 to 20 carbon atoms, a substituted or unsubstituted carbocyclic aromatic group having 6 to 10 carbon atoms, a substituted or unsubstituted heterocyclic aromatic group having 4 to 10 carbon atoms, or a substituted or unsubstituted aralkyl group having 7 to 10 carbon atoms.

Specific examples of $X_1$ and $X_2$ include a hydrogen atom; halogen atoms such as a fluorine atom, a chlorine atom, a bromine atom and the like;

linear, branched or cyclic alkyl groups such as a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a cyclopentyl group, an n-hexyl group, a 1-methylpentyl group, a 4-methyl-2-pentyl group, a 3,3-dimethylbutyl group, a 2-ethylbutyl group, a cyclohexyl group, an n-heptyl group, a 1-methylhexyl group, a cyclohexylmethyl group, a 4-tert-butylcyclohexyl group, an n-heptyl group, a cycloheptyl group, an n-octyl group, a cyclooctyl group, a tert-octyl group, a 1-methylheptyl group, a 2-ethylhexyl group, a 2-propylpentyl group, an n-nonyl group, a 2,2-dimethylheptyl group, a 2,6-dimethyl-4-heptyl group, a 3,5,5-trimethylhexyl group, an n-decyl group, an n-undecyl group, a 1-methyldecyl group, an n-dodecyl group, an n-tridecyl group, a 1-hexylheptyl group, an n-tetradecyl group, an n-pentadecyl group, an n-hexadecyl group, an n-heptadecyl group, an n-octadecyl group, an n-eicosyl group and the like; a linear, branched or cyclic alkoxy group such as a methoxy group, an ethoxy group, an n-propoxy group, an isopropoxy group, an n-butoxy group, an isobutoxy group, a sec-butoxy group, an n-pentyloxy group, a neopentyloxy group, a cyclopentyloxy group, an n-hexyloxy group, a 3,3-dimethylbutyloxy group, a 2-ethylbutyloxy group, a cyclohexyloxy group, an n-heptyloxy group, an n-octyloxy group, a 2-ethylhexyloxy group, an n-nonyloxy group, an n-decyloxy group, an n-undecyloxy group, an n-dodecyloxy group, an n-tridecyloxy group, an n-tetradecyloxy group, an n-pentadecyloxy group, an n-hexadecyloxy group, an n-heptadecyloxy group, an n-octadecyloxy group, an n-eicosyloxy group and the like; substituted or unsubstituted amino groups such as an amino group, an N-methylamino group, an N-ethylamino group, an N-n-butylamino group, an N-cyclohexylamino group, an N-n-octylamino group, an N-n-decylamino group, an N-benzylamino group, an N-phenylamino group, an N-(3-methylphenyl)amino group, an N-(4-methylphenyl)amino group, an N-(4-n-butylphenyl)amino group, an N-(4-methoxyphenyl)amino group, an N-(3-fluorophenyl)amino group, an N-(4-chlorophenyl)amino group, an N-(1-naphthyl)amino group, an N-(2-naphthyl)amino group, an N,N-dimethylamino group, an N,N-diethylamino group, an N,N-di-n-butylamino group, an N,N-di-n-hexylamino group, an N,N-di-n-octylamino group, an N,N-di-n-decylamino group, an N,N-di-n-dodecylamino group, an N-methyl-N-ethylamino group, an N-ethyl-N-n-butylamino group, an N-methyl-N-phenylamino group, an N-n-butyl-N-phenylamino group, an N,N-diphenylamino group, an N,N-di(3-methylphenyl)amino group, an N,N-di(4-methylphenyl)amino group, an N,N-di(4-ethylphenyl)amino group, an N,N-di(4-tert-butylphenyl)amino group, an N,N-di(4-n-hexylphenyl)amino group, an N,N-di(4-methoxyphenyl)amino group, an N,N-di(4-ethoxyphenyl)amino group, an N,N-di(4-n-butyloxyphenyl)amino group, an N,N-di(4-n-hexyloxyphenyl)amino group, an N,N-di(1-naphthyl)amino group, an N,N-di(2-naphthyl)amino group, an N-phenyl-N-(3-methylphenyl)amino group, an N-phenyl-N-(4-methylphenyl)amino group, an N-phenyl-N-(4-octylphenyl)amino group, an N-phenyl-N-(4-methoxyphenyl)amino group, an N-phenyl-N-(4-ethoxyphenyl)amino group, an N-phenyl-N-(4-n-hexyloxyphenyl)amino group, an N-phenyl-N-(4-fluorophenyl)amino group, an N-phenyl-N-(1-naphthyl)amino group, an N-phenyl-N-(2-naphthyl)amino group, an N-phenyl-N-(4-phenylphenyl)amino group and the like; substituted or unsubstituted carbocyclic aromatic groups such as a phenyl group, a 4-methylphenyl group, a 3-methylphenyl group, a 2-methylphenyl group, a 4-ethylphenyl group, a 3-ethylphenyl group, a 2-ethylphenyl group, a 4-n-propylphenyl group, a 4-isopropylphenyl group, a 2-isopropylphenyl group, a 4-n-butylphenyl group, a 4-isobutylphenyl group, a 4-sec-butylphenyl group, a 2-sec-butylphenyl group, a 4-tert-butylphenyl group, a 3-tert-butylphenyl group, a 2-tert-butylphenyl group, a 4-n-pentylphenyl group, a 4-isopentylphenyl group, a 4-neopentylphenyl group, a 4-tert-pentylphenyl group, a 4-n-hexylphenyl group, a 4-(2'-ethylbutyl)phenyl group, a 4-n-heptylphenyl group, a 4-n-octylphenyl group, a 4-(2'-ethylhexyl)phenyl group, a 4-n-nonylphenyl group, a 4-n-decylphenyl group, a 4-n-undecylphenyl group, a 4-n-dodecylphenyl group, a 4-n-tetradecylphenyl group, a 4-cyclohexylphenyl group, a 4-(4'-methylcyclohexyl)phenyl group, a 4-(4'-tert-butylcyclohexyl)phenyl group, a 3-cyclohexylphenyl group, a 2-cyclohexylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 3,4,5-trimethylphenyl group, a 2,3,5,6-tetramethylphenyl group, a 2,4-diethylphenyl group, a 2,6-diethylphenyl group, a 2,5-diisopropylphenyl group, a 2,6-diisopropylphenyl group, a 2,6-diisobutylphenyl group, a 2,4-di-tert-butylphenyl group, a 2,5-di-tert-butylphenyl group, a 4,6-di-tert-butyl-2-methylphenyl group, a 5-tert-butyl-2-methylphenyl group, a 4-tert-butyl-2,6-dimethylphenyl group, a 1-naphthyl group, a 2-naphthyl group, a 1,2,3,4-tetrahydro-5-naphthyl group, a 1,2,3,4-tetrahydro-6-naphthyl group, a 4-ethyl-1-naphthyl group, a 6-n-butyl-2-naphthyl group, a 5-indanyl group, a 4-methoxyphenyl group, a 3-methoxyphenyl group, a 2-methoxyphenyl group, a 4-ethoxyphenyl group, a 3-ethoxyphenyl group, a 2-ethoxyphenyl group, a 4-n-propyloxyphenyl group, a 3-n-propyloxyphenyl group, a 4-isopropyloxyphenyl group, a 2-isopropyloxyphenyl group, a 4-n-butyloxyphenyl group, a 4-isobutyloxyphenyl group, a 2-sec-butyloxyphenyl group, a 4-n-pentyloxyphenyl group, a 4-isopentyloxyphenyl group, a 2-isopentyloxyphenyl group, a 4-neopentyloxyphenyl group, a 2-neopentyloxypenyl group, a 4-n-hexyloxyphenyl group, a 4-(2'-ethylbutyl)oxyphenyl group, a 4-n-heptyloxyphenyl group, a 4-n-octyloxyphenyl group, a 4-n-nonyloxyphenyl group, a 4-n-decyloxyphenyl group, a 4-n-undecyloxyphenyl group, a 4-n- dodecyloxyphenyl group, a 4-n-tetradecyloxyphenyl group, a 4-cyclohexyloxyphenyl group, a 2-cyclohexyloxyphenyl group, a 2,3-dimethoxyphenyl group, a 2,4-dimethoxyphenyl group, a 2,5-dimethoxyphenyl group, a 3,4-dimethoxyphenyl group, a 3,5-dimethoxyphenyl group, a 3,5-diethoxyphenyl group, a 2-methoxy-4-methylphenyl group, a 2-methoxy-5-methylphenyl group, a 2-methyl-4-methoxyphenyl group, a 3-methyl-4-methoxyphenyl group, a 3-methyl-5-methoxyphenyl group, a 2-methoxy-1-naphthyl group, a 4-methoxy-1-naphthyl group, a 4-n-butyloxy-1-naphthyl group, a 5-ethoxy-1-naphthyl group, a 6-methoxy-2-naphthyl group, a 6-ethoxy-2-naphthyl group, a 6-n-butyloxy-2-naphthyl group, a 6-n-hexyloxy-2-naphthyl group, a 7-methoxy-2-naphthyl group, a 7-n-butyloxy-2-naphthyl group, a 4-phenylphenyl group, a 3-phenylphenyl group, a 2-phenylphenyl group, a 4-(4'-methylphenyl)phenyl group, a 4-(3'-methylphenyl)phenyl group, a 4-(4'-ethylphenyl)phenyl group, a 4-(4'-isopropylphenyl)phenyl group, a 4-(4'-tert-butylphenyl) phenyl group, a 4-(4'-n-hexylphenyl)phenyl group, a 4-(4'-n-octylphenyl)phenyl group, a 4-(4'-methoxypenyl)phenyl group, a 4-(4'-n-butyloxyphenyl)phenyl group, a 2-(2'-methoxyphenyl)phenyl group, a 4-(4'-chlorophenyl)phenyl group, a 3-methyl-4-phenylphenyl group, a 3-methoxy-4-phenylphenyl group, a 9-phenyl-2-fluorenyl group, a 9,9-diphenyl-2-fluorenyl group, a 9-methyl-9-phenyl-2-fluorenyl group, a 9-ethyl-9-phenyl-2-fluorenyl group, a 4-fluorophenyl group, a 3-fluorophenyl group, a 2-fluorophenyl group, a 4-chlorophenyl group, a 3-chlorophenyl group, a 2-chlorophenyl group, a 4-bromophenyl group, a 2-bromophenyl group, a 4-trifluoromethylphenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3-dichlorophenyl group, a 2,4-dichlorophenyl group, a 2,5-dichlorophenyl group, a 3,4-dichlorophenyl group, a 3,5-dichlorophenyl group, a 2,5-dibromophenyl group, a 2,4,6-trichlorophenyl group, a 2-fluoro-4-methylphenyl group, a 2-fluoro-5-methylphenyl group, a 3-fluoro-2-methylphenyl group, a 3-fluoro-4-methylphenyl group, a 2-methyl-4-fluorophenyl group, a 2-methyl-5-fluorophenyl group, a 3-methyl-4-fluorophenyl group, a 2-chloro-4-methylphenyl group, a 2-chloro-5-methylphenyl group, a 2-chloro-6-methylphenyl group, a 3-chloro-4-methylphenyl group, a 2-methyl-3-chlorophenyl group, a 2-methyl-4-chlorophenyl group, a 3-methyl-4-chlorophenyl group, a 2-chloro-4,6-dimethylphenyl group, a 2,4-dichloro-1-naphthyl group, a 1,6-dichloro-2-naphthyl group, a 2-methoxy-4-fluorophenyl group, a 3-methoxy-4-fluorophenyl group, a 2-fluoro-4-methoxyphenyl group, a 2-fluoro-4-ethoxyphenyl group, a 2-fluoro-6-methoxyphenyl group, a 3-fluoro-4-methoxyphenyl group, a 3-fluoro-4-ethoxyphenyl group, a 2-chloro-4-methoxyphenyl group, a 3-chloro-4-methoxyphenyl group, a 2-methoxy-5-chlorophenyl group, a 3-methoxy-4-chlorophenyl group, a 3-methoxy-6-chlorophenyl group, a 5-chloro-2,4-dimethoxyphenyl group and the like;
and substituted or unsubstituted heterocyclic aromatic groups such as a 4-quinolyl group, a 3-quinolyl group, a 4-methyl-2-quinolyl group, a 4-pyridyl group, a 3-pyridyl group, a 2-pyridyl group, a 4-methyl-2-pyridyl group, a 5-methyl-2-pyridyl group, a 6-methyl-2-pyridyl group, a 6-fluoro-3-pyridyl group, a 6-methoxy-3-pyridyl group, a 6-methoxy-2-pyridyl group, a 3-furyl group, a 2-furyl group, a 3-thienyl group, a 2-thienyl group, a 4-methyl-3-thienyl group, a 5-methyl-2-thienyl group, a 3-methyl-2-thienyl group, a 2-oxazolyl group, a 2-thiazolyl group, a 2-benzoxazolyl group, a 2-benzothiazolyl group, a 2-benzoimidazolyl group and the like; and substituted or unsubstituted aralkyl groups such as a benzyl group, a phenetyl group, an α-methylbenzyl group, an α,α-dimethylbenzyl group, a 1-naphthylmethyl group, a 2-naphthylmethyl group, a furfuryl group, a 2-methylbenzyl group, a 3-methylbenzyl group, a 4-methylbenzyl group, a 4-ethylbenzyl group, a 4-isopropylbenzyl group, a 4-tert-butylbenzyl group, a 4-n-hexylbenzyl group, a 4-n-nonylbenzyl group, a 3,4-dimethylbenzyl group, a 3-methoxybenzyl group, a 4-methoxybenzyl group, a 4-ethoxybenzyl group, a 4-n-butyloxybenzyl group, a 4-n-hexyloxybenzyl group, a 4-n-nonyloxybenzyl group, a 3-fluorobenzyl group, a 4-fluorobenzyl group, a 2-chlorobenzyl group, a 4-chlorobenzyl group and the like.

In the compounds represented by the formula (1), $A_1$ and $A_2$, independently from each other, represent a substituted or unsubstituted anthracen-diyl group, and $F_1$, $F_2$ and $F_3$, independently from each other, represent a substituted or unsubstituted fluoren-diyl group.

Examples of the substituent when $A_1$, $A_2$, $F_1$, $F_2$ and $F_3$ have a substituent include a halogen atom, a linear, branched or cyclic alkyl group, a linear, branched or cyclic alkoxy group, a substituted or unsubstituted amino group, a substituted or unsubstituted aryl group, and a substituted or unsubstituted aralkyl group.

Incidentally, the aryl group refers to carbocyclic aromatic groups such as a phenyl group, a naphthyl group and the like, and heterocyclic aromatic groups such as a furfuryl group, a thienyl group, a pyridyl group and the like.

Specific examples of the substituent when $A_1$, $A_2$, $F_1$, $F_2$ and $F_3$ have a substituent can include a halogen atom, a linear, branched or cyclic alkyl group, a linear, branched or cyclic alkoxy group, a substituted or unsubstituted amino group, a substituted or unsubstituted carbocyclic aromatic group, a substituted or unsubstituted heterocyclic aromatic group, and a substituted or unsubstituted aralkyl group listed as specific examples of $X_1$ and $X_2$.

Examples of $A_1$ and $A_2$ include
a substituted or unsubstituted anthracen-1,4-diyl group,
a substituted or unsubstituted anthracen-1,5-diyl group,
a substituted or unsubstituted anthracen-1,8-diyl group,
a substituted or unsubstituted anthracen-1,9-diyl group,
a substituted or unsubstituted anthracen-1,10-dinyl group,
a substituted or unsubstituted anthracen-2,3-diyl group,
a substituted or unsubstituted anthracen-2,6-diyl group,
a substituted or unsubstituted anthracen-2,7-diyl group,
a substituted or unsubstituted anthracen-2,9-diyl group,
a substituted or unsubstituted anthracen-2,10-dinyl group,
and a substituted or unsubstituted anthracen-9,10-diyl group.

Preferable are
a substituted or unsubstituted anthracen-1,4-diyl group,
a substituted or unsubstituted anthracen-1,5-diyl group,
a substituted or unsubstituted anthracen-2,6-diyl group,
a substituted or unsubstituted anthracen-2,7-diyl group, and
a substituted or unsubstituted anthracen-9,10-diyl group.

More preferable is a substituted or unsubstituted anthracen-9,10-diyl group.

Examples of $F_1$, $F_2$ and $F_3$ include
a substituted or unsubstituted fluoren-1,3-diyl group,
a substituted or unsubstituted fluoren-1,6-diyl group,
a substituted or unsubstituted fluoren-1,7-diyl group,
a substituted or unsubstituted fluoren-1,8-diyl group,
a substituted or unsubstituted fluoren-2,6-diyl group,
a substituted or unsubstituted fluoren-2,7-diyl group, and
a substituted or unsubstituted fluoren-3,6-diyl group.

Preferable are
a substituted or unsubstituted fluoren-1,6-diyl group,
a substituted or unsubstituted fluoren-1,7-diyl group,
a substituted or unsubstituted fluoren-1,8-diyl group,
a substituted or unsubstituted fluoren-2,6-diyl group,
a substituted or unsubstituted fluoren-2,7-diyl group, and
a substituted or unsubstituted fluoren-3,6-diyl group.

More preferable are
a substituted or unsubstituted fluoren-1,8-diyl group,
a substituted or unsubstituted fluoren-2,7-diyl group, and
a substituted or unsubstituted fluoren-3,6-diyl group.

Further preferable is a substituted or unsubstituted fluoren-2,7-diyl group.

In the compounds represented by the formula (1), j, m and n represent 0 or 1, and k and l represent 1 or 2. Preferable examples can include cases where (1) k is 1, (2) j and n are 0, 1 is l and k+m is 2, (3) j+l+n is 2, k is 1 and m is 0 and (4) j, m and n are 0 and k and l are 1.

The compounds represented by the formula (1) are roughly classified into the following structures depending on values of j, k, l, m and n.

$X_1$-$A_1$-$F_2$-$X_2$ (1a)

$X_1$-$F_1$-$A_1$-$F_2$-$X_2$ (1b)

$X_1$-$A_1$-$F_2$-$A_2$-$X_2$ (1c)

$X_1$-$A_1$-$F_2$-$F_2$-$X_2$ (1d)

$X_1$-$A_1$-$A_1$-$F_2$-$X_2$ (1e)

$X_1$-$F_1$-$A_1$-$F_2$-$A_2$-$X_2$ (1f)

$X_1$-$F_1$-$A_1$-$F_2$-$F_2$-$X_2$ (1g)

$X_1$-$F_1$-$A_1$-$A_1$-$F_2$-$X_2$ (1h)

$X_1$-$A_1$-$F_2$-$F_2$-$A_2$-$X_2$ (1i)

$X_1$-$A_1$-$A_1$-$F_2$-$A_2$-$X_2$ (1j)

$X_1$-$A_1$-$A_1$-$F_2$-$F_2$-$X_2$ (1k)

$X_1$-$A_1F_2$-$F_2$-$F_3$-$X_2$ (1l)

$X_1$-$F_1$-$A_1$-$F_2$-$A_2$-$F_3$-$X_2$ (1m)

$X_1$-$F_1$-$A_1$-$F_2$-$F_2$-$A_2$-$X_2$ (1n)

$X_1$-$F_1$-$A_1$-$A_1$-$F_2$-$A_2$-$X_2$ (1o)

$X_1$-$F_1$-$A_1$-$F_2$-$F_2$-$X_2$ (1p)

$X_1$-$A_1$-$A_1$-$F_2$-$F_2$-$A_2$-$X_2$ (1q)

$X_1$-$F_1$-$A_1$-$F_2$-$F_2$-$F_3$-$X_2$ (1r)

$X_1$-$A_1$-$A_1$-$F_2$-$A_2$-$F_3$-$X_2$ (1s)

$X_1$-$A_1$-$A_1$-$F_2$-$F_2$-$F_3$-$X_2$ (1t)

$X_1$-$F_1$-$A_1$-$A_1$-$F_2$-$F_2$-$A_2$-$X_2$ (1u)

$X_1$-$F_1$-$A_1$-$F_2$-$F_2$-$A_2$-$F_3$-$X_2$ (1v)

$X_1$-$F_1$-$A_1$-$A_1$-$F_2$-$A_2$-$F_3$-$X_2$ (1w)

$X_1$-$F_1$-$A_1$-$A_1$-$F_2$-$F_2$-$F_3$-$X_2$ (1x)

$X_1$-$A_1$-$A_1$-$F_2$-$A_2$-$F_3$-$X_2$ (1y)

$X_1$-$F_1$-$A_1$-$A_1$-$F_2$-$F_2$-$A_2$-$F_3$-$X_2$ (1z)

wherein $A_1$, $A_2$, $F_1$, $F_2$, $F_3$, $X_1$ and $X_2$ have the same meanings as in the formula (1).

Of these structures, the structures represented by (1a), (1b), (1c), (1d), (1f), (1g), (1i), (1l), (1m), (1n), (1r), (1v) and (1y) are preferable. The structures represented by (1a), (1b), (1c), (1f), (1g), (1i), (1m) and (1v) are more preferable. The structures represented by (1a), (1b), (1c) and (1m) are further preferable.

Moreover, preferable examples of the compounds represented by the formula (1) can include compounds represented by the following the formula (2), the formula (4) and the formula (5).

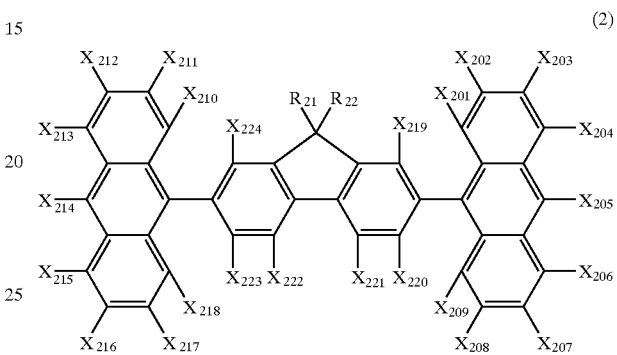

(2)

wherein $R_{21}$ and $R_{22}$, independently from each other, represent a hydrogen atom, a linear, branched or cyclic alkyl group, a substituted or unsubstituted aryl group, or a substituted or unsubstituted aralkyl group, and $X_{201}$ to $X_{214}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $R_{21}$, $R_{22}$ and $X_{201}$ to $X_{224}$ are not an anthryl group or a fluorenyl group,

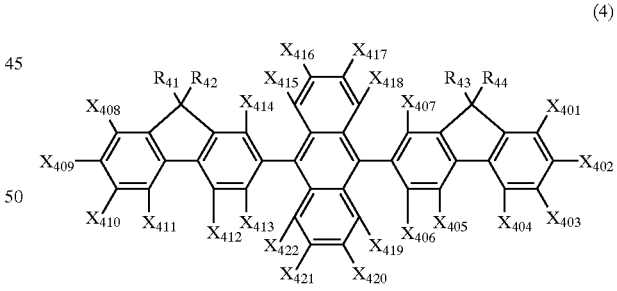

(4)

wherein $R_{41}$ to $R_{44}$, independently from each other, represent a hydrogen atom, a linear, branched or cyclic alkyl group, a substituted or unsubstituted aryl group, or a substituted or unsubstituted aralkyl group, and $X_{401}$ to $X_{422}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $R_{41}$ to $R_{44}$ and $X_{401}$ to $X_{422}$ are not an anthryl group or a fluorenyl group,

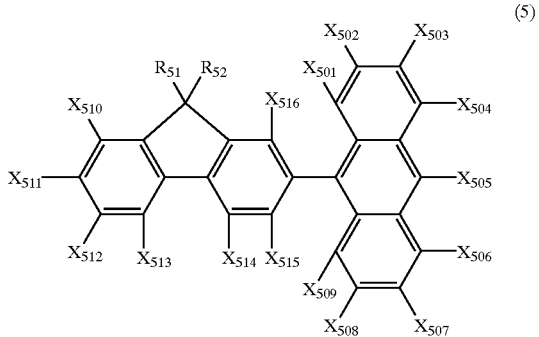

(5)

wherein $R_{51}$ and $R_{52}$, independently from each other, represent a hydrogen atom, a linear, branched or cyclic alkyl group, a substituted or unsubstituted aryl group, or a substituted or unsubstituted aralkyl group, and $X_{501}$ to $X_{516}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $R_{51}$, $R_{52}$ and $X_{501}$ to $X_{516}$ are not an anthryl group or a fluorenyl group.

In the compounds represented by the formula (2), the formula (4) and the formula (5), $R_{21}$, $R_{22}$, $R_{41}$ to $R_{44}$, $R_{51}$ and $R_{52}$, independently from each other, represent a hydrogen atom, a linear, branched or cyclic alkyl group, a substituted or unsubstituted aryl group, or a substituted or unsubstituted aralkyl group, provided $R_{21}$, $R_{22}$, $R_{41}$ to $R_{44}$, $R_{51}$ and $R_{52}$ are not an anthryl group or a fluorenyl group.

Incidentally, the aryl group refers to carbocyclic aromatic groups such as a phenyl group, a naphthyl group and the like, and heterocyclic aromatic groups such as a furfuryl group, a thienyl group, a pyridyl group and the like.

$R_{21}$, $R_{22}$, $R_{41}$ to $R_{44}$, $R_{51}$ and $R_{52}$ are preferably a hydrogen atom, a linear, branched or cyclic alkyl group having 1 to 16 carbon atoms, a substituted or unsubstituted carbocyclic aromatic group having 6 to 25 carbon atoms, a substituted or unsubstituted heterocyclic aromatic group having 3 to 25 carbon atoms, or a substituted or unsubstituted aralkyl group having 5 to 16 carbon atoms, more preferably a hydrogen atom, a linear, branched or cyclic alkyl group having 1 to 10 carbon atoms, a substituted or unsubstituted carbocyclic aromatic group having 6 to 12 carbon atoms, a substituted or unsubstituted heterocyclic aromatic group having 4 to 12 carbon atoms, or a substituted or unsubstituted aralkyl group having 7 to 12 carbon atoms, further preferably a hydrogen atom, a linear, branched or cyclic alkyl group having 1 to 8 carbon atoms, a substituted or unsubstituted carbocyclic aromatic group having 6 to 10 carbon atoms, a substituted or unsubstituted heterocyclic aromatic group having 4 to 10 carbon atoms, or a substituted or unsubstituted aralkyl group having 7 to 10 carbon atoms.

Specific examples of $R_{21}$, $R_{22}$, $R_{41}$ to $R_{44}$, $R_{51}$ and $R_{52}$ can include a hydrogen atom, and a linear, branched or cyclic alkyl group, a substituted or unsubstituted carbocyclic aromatic group, a substituted or unsubstituted heterocyclic aromatic group and a substituted or unsubstituted aralkyl group listed as specific examples of $X_1$ and $X_2$.

In the compounds represented by the formula (2), the formula (4) and the formula (5), $X_{201}$ to $X_{224}$, $X_{401}$ to $X_{422}$ and $X_{501}$ to $X_{516}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $X_{201}$ to $X_{224}$, $X_{401}$ to $X_{422}$ and $X_{501}$ to $X_{516}$ are not an anthryl group or a fluorenyl group.

Incidentally, the aryl group refers to carbocyclic aromatic groups such as a phenyl group, a naphthyl group and the like, and heterocyclic aromatic groups such as a furfuryl group, a thienyl group, a pyridyl group and the like.

$X_{201}$ to $X_{224}$, $X_{401}$ to $X_{422}$ and $X_{501}$ to $X_{516}$ are preferably a hydrogen atom, a halogen atom, a linear, branched or cyclic alkyl group having 1 to 16 carbon atoms, a linear, branched or cyclic alkoxy group having 1 to 16 carbon atoms, a substituted amino group having 1 to 24 carbon atoms, a substituted or unsubstituted carbocyclic aromatic group having 6 to 25 carbon atoms, or a substituted or unsubstituted heterocyclic aromatic group having 3 to 25 carbon atoms, more preferably a hydrogen atom, a halogen atom, a linear, branched or cyclic alkyl group having 1 to 10 carbon atoms, a linear, branched or cyclic alkoxy group having 1 to 10 carbon atoms, a substituted amino group having 1 to 20 carbon atoms, a substituted or unsubstituted carbocyclic aromatic group having 6 to 12 carbon atoms, or a substituted or unsubstituted heterocyclic aromatic group having 4 to 12 carbon atoms, further preferably a hydrogen atom, a halogen atom, a linear, branched or cyclic alkyl group having 1 to 8 carbon atoms, a linear, branched or cyclic alkoxy group having 1 to 8 carbon atoms, a substituted amino group having 2 to 20 carbon atoms, a substituted or unsubstituted carbocyclic aromatic group having 6 to 10 carbon atoms, or a substituted or unsubstituted heterocyclic aromatic group having 4 to 10 carbon atoms.

Specific examples of $X_{201}$ to $X_{224}$, $X_{401}$ to $X_{422}$ and $X_{501}$ to $X_{516}$ can include a hydrogen atom, and a halogen atom, a linear, branched or cyclic alkyl group, a linear, branched or cyclic alkoxy group, a substituted or unsubstituted amino group, a substituted or unsubstituted carbocyclic aromatic group and a substituted or unsubstituted heterocyclic aromatic group listed as specific examples of $X_1$ and $X_2$.

The compounds represented by the formula (2) are preferably compounds in which $X_{205}$ and $X_{214}$ are a halogen atom, a linear, branched or cyclic alkyl group, a linear, branched or cyclic alkoxy group, or a substituted or unsubstituted aryl group, and compounds in which $X_{201}$, $X_{204}$, $X_{206}$, $X_{209}$, $X_{210}$, $X_{213}$, $X_{215}$ and $X_{218}$ are a hydrogen atom, a halogen atom, a linear, branched or cyclic alkyl group, or a linear, branched or cyclic alkoxy group, more preferably compounds in which $X_{205}$ and $X_{214}$ are a halogen atom, a linear, branched or cyclic alkyl group, a linear, branched or cyclic alkoxy group, or a substituted or unsubstituted heterocyclic aromatic group.

The compounds represented by the formula (4) are preferably compounds in which $X_{415}$, $X_{418}$, $X_{419}$ and $X_{422}$ are a hydrogen atom, a halogen atom, a linear, branched or cyclic alkyl group, or a linear, branched or cyclic alkoxy group.

The compounds represented by the formula (5) are preferably compounds in which $X_{505}$ is a halogen atom, a linear, branched or cyclic alkyl group, a linear, branched or cyclic alkoxy group, or a substituted or unsubstituted aryl group, and compounds in which $X_{501}$, $X_{504}$, $X_{506}$ and $X_{509}$ are a hydrogen atom, a halogen atom, a linear, branched or cyclic alkyl group, or a linear, branched or cyclic alkoxy group.

Specific examples of compounds A according to the invention can include the following compounds. However, the invention is not limited thereto.

Illustrative Compound No.
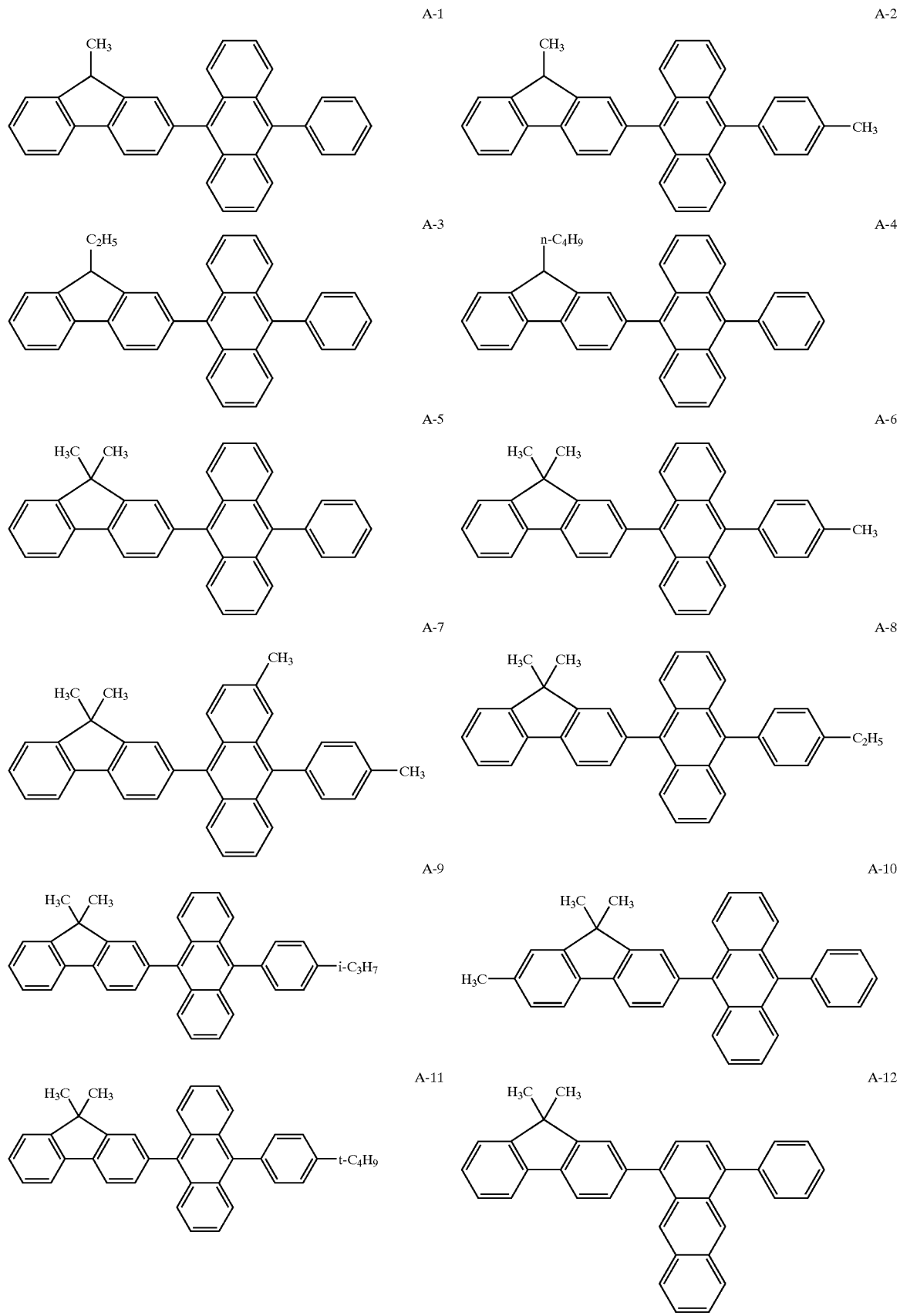

-continued
A-13
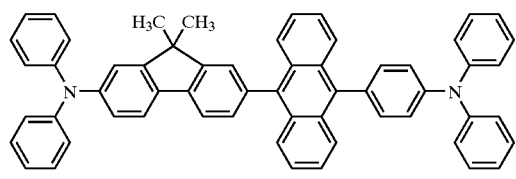
A-14
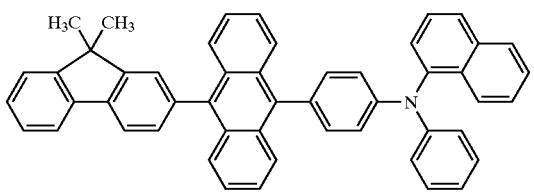
A-15
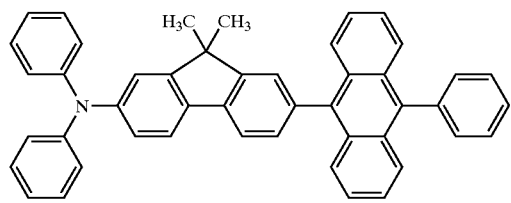
A-16
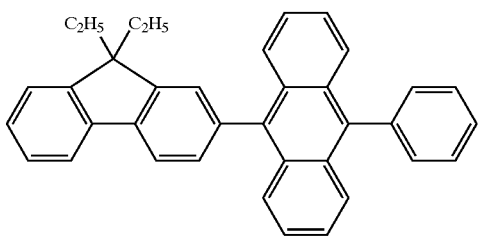
A-17
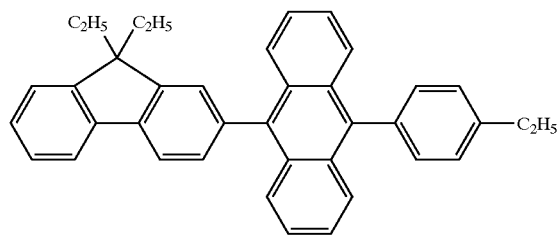
A-18
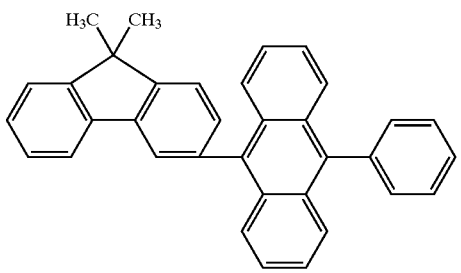
A-19
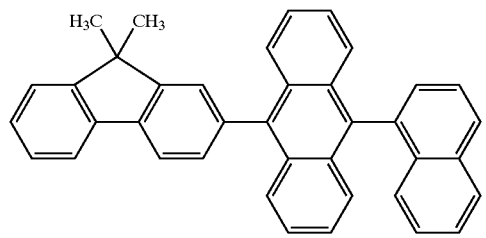
A-20
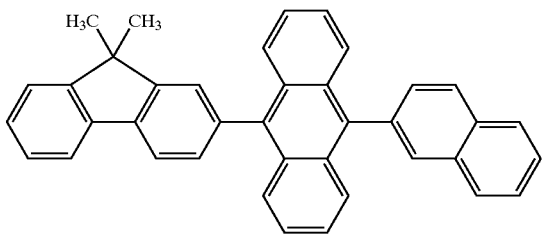
A-21
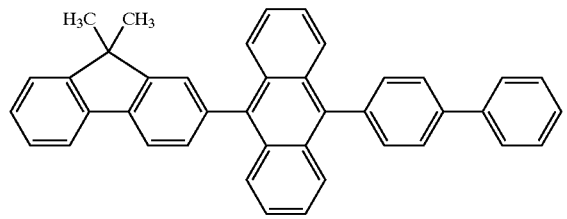
A-22
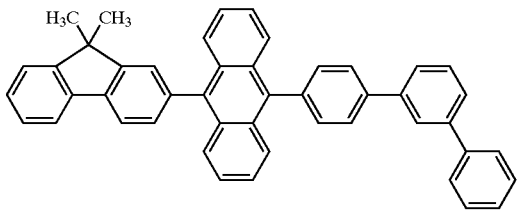
A-23
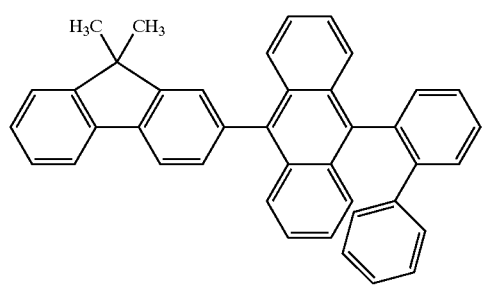
A-24
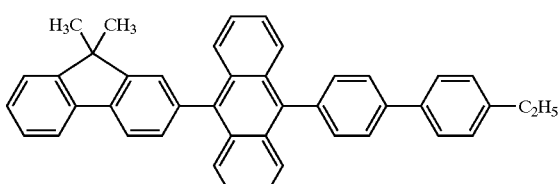

-continued
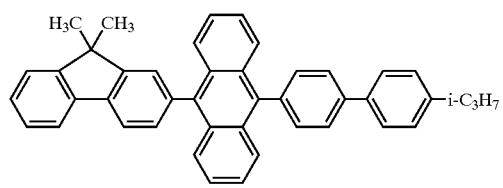
A-25
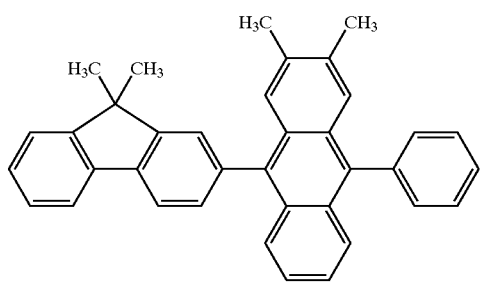
A-26
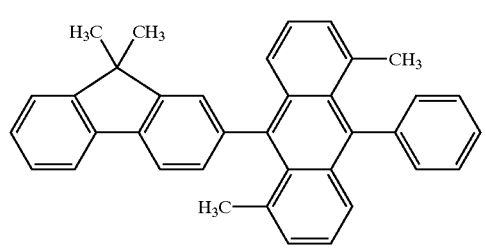
A-27
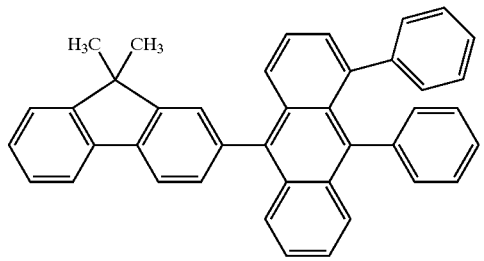
A-28
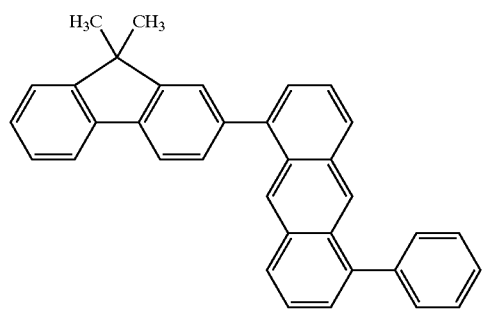
A-29
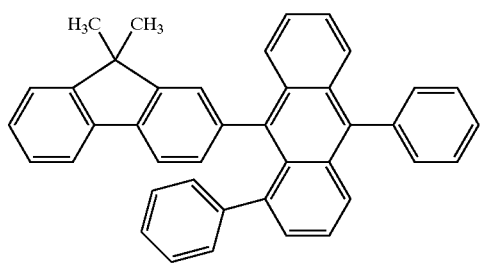
A-30
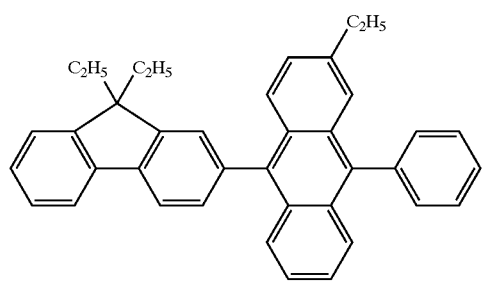
A-31
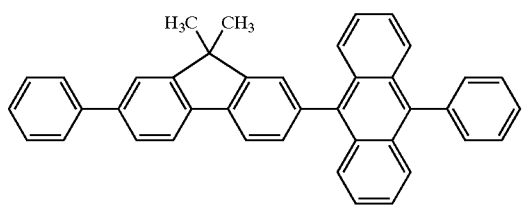
A-32
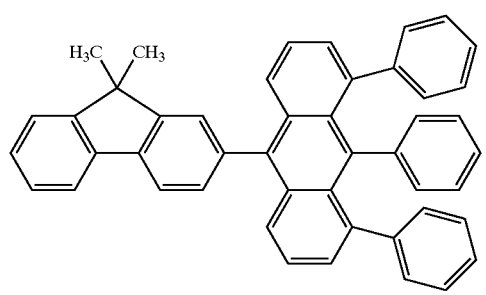
A-33
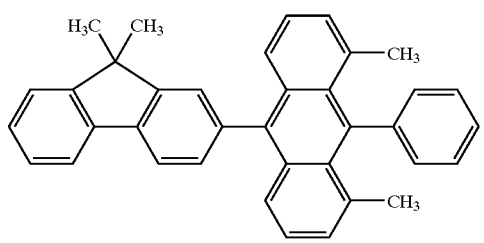
A-34

-continued
A-35
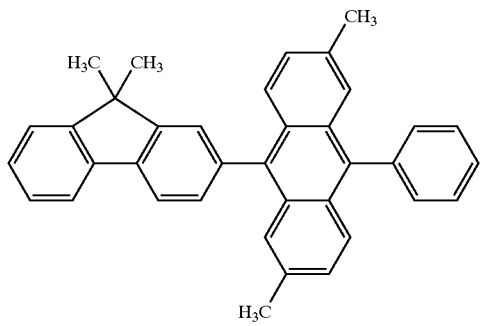
A-36
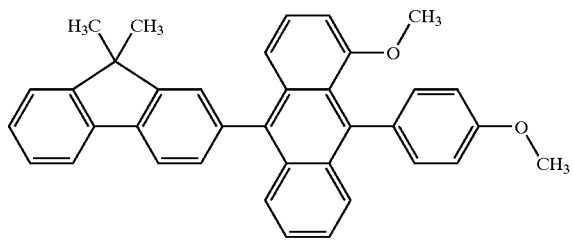
A-37
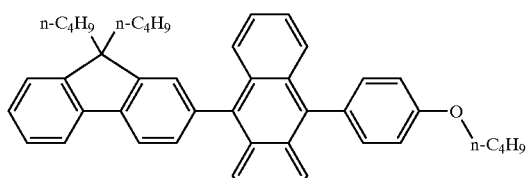
A-38
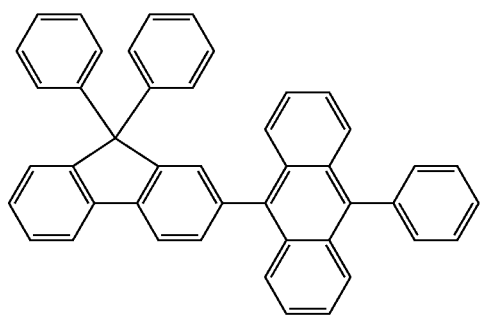
A-39
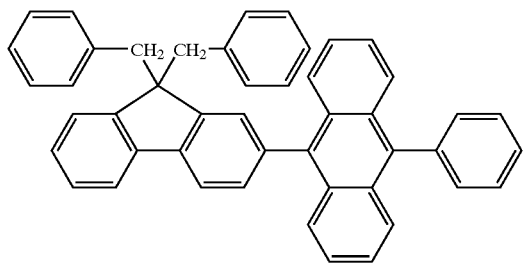
A-40
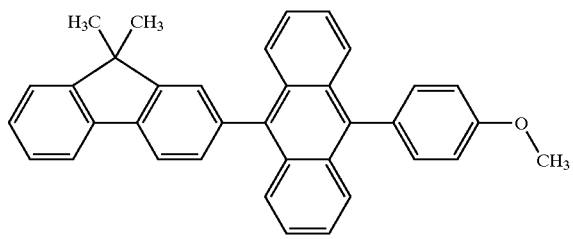
A-41
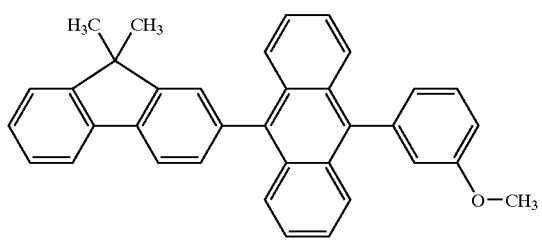
A-42
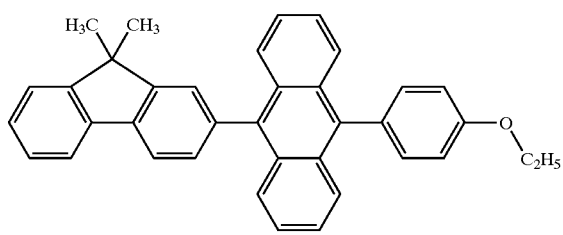
A-43
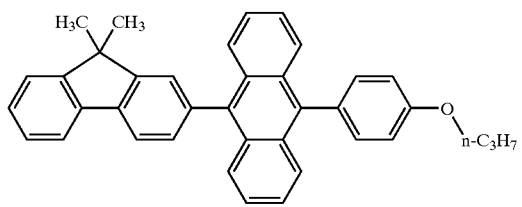
A-44
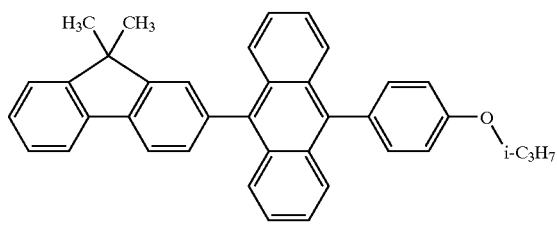

-continued
A-45
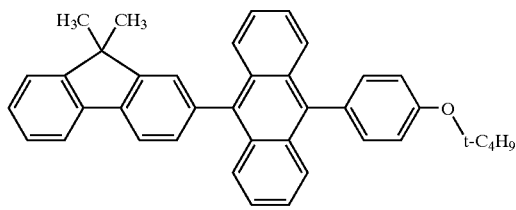
A-46
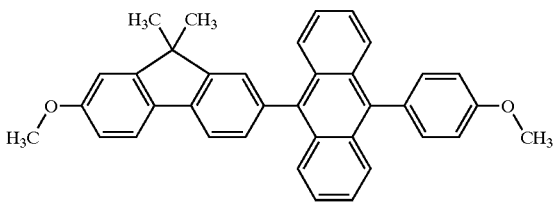
A-47
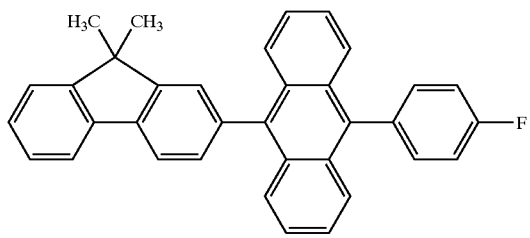
A-48
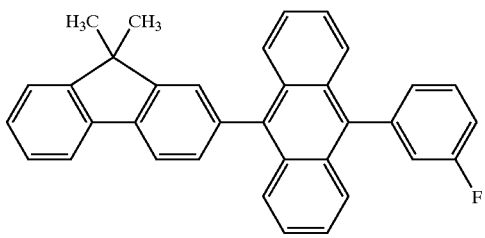
A-49
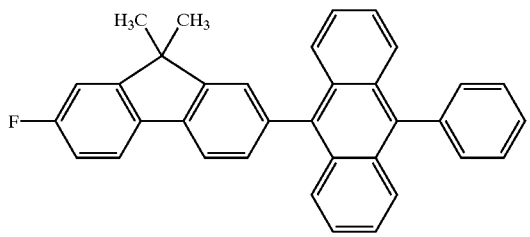
A-50
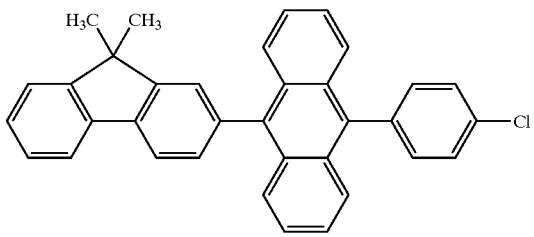
A-51
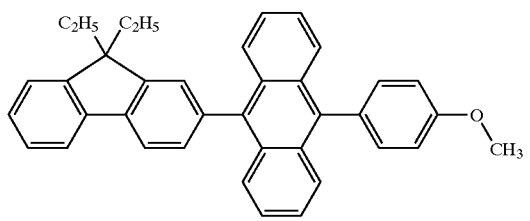
A-52
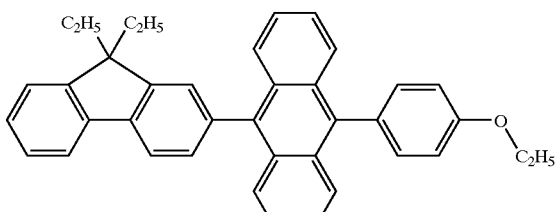
A-53
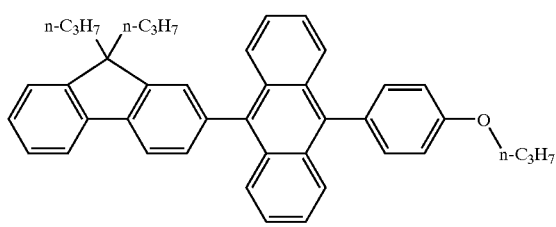
A-54
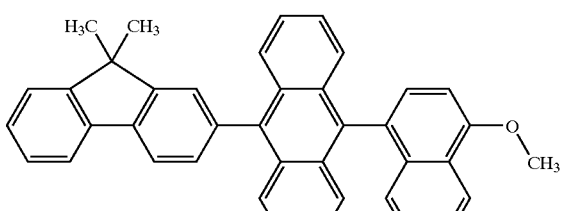
A-55
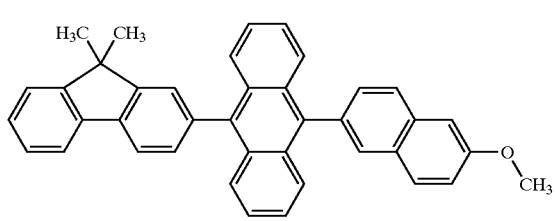
A-56
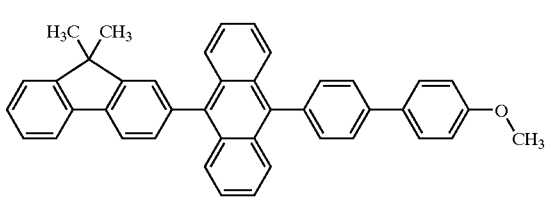

-continued
A-57
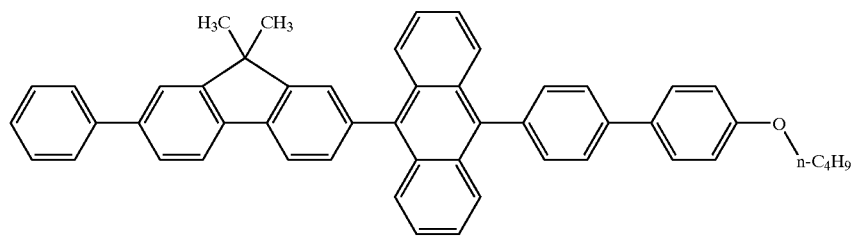
A-58
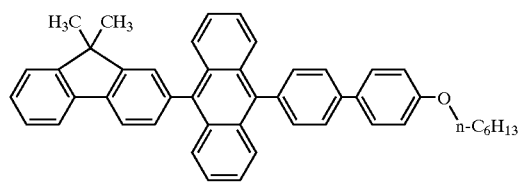
A-59
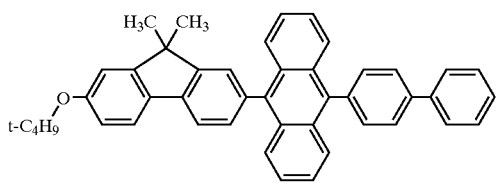
A-60
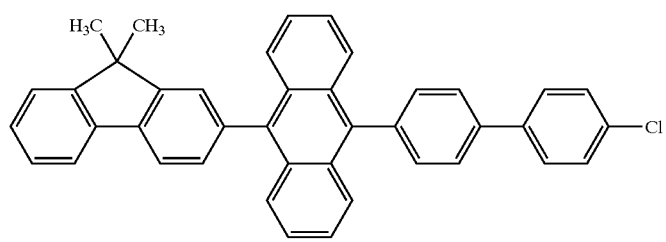
B-1
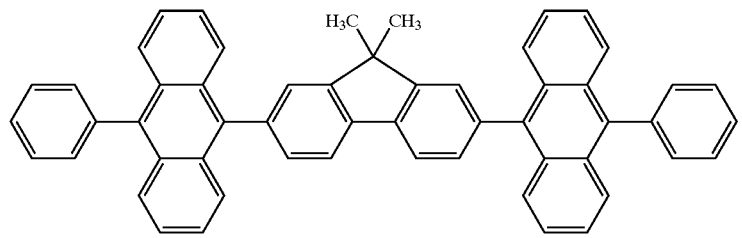
B-2
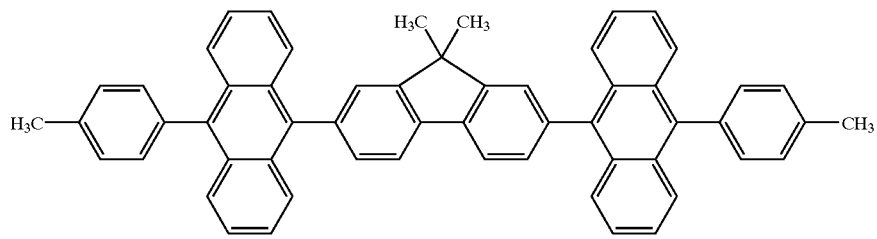
B-3
B-4
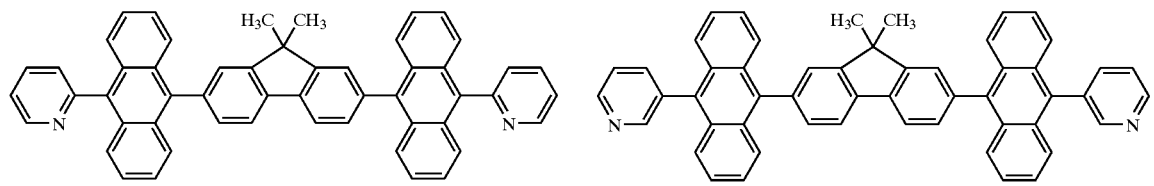
B-5
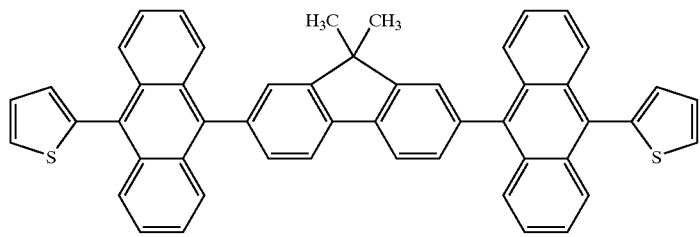

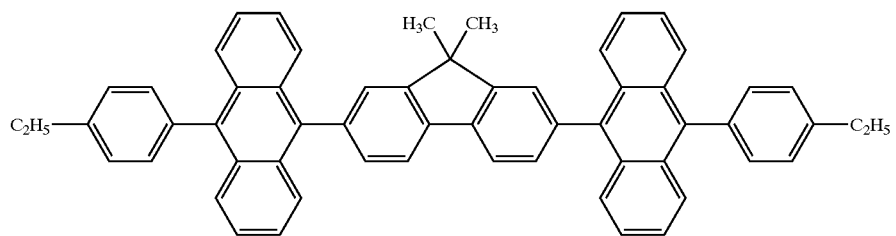
B-6
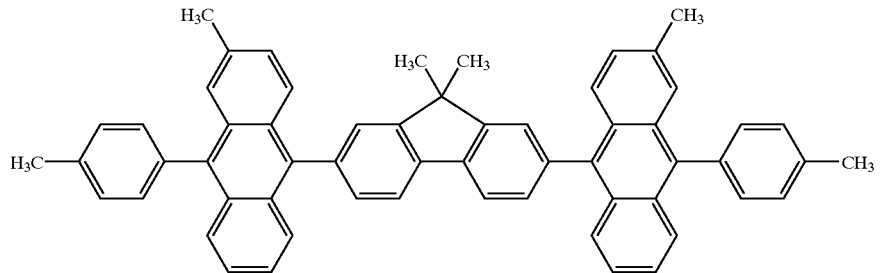
B-7
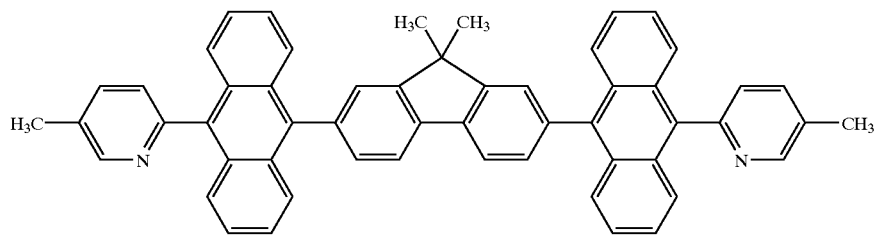
B-8
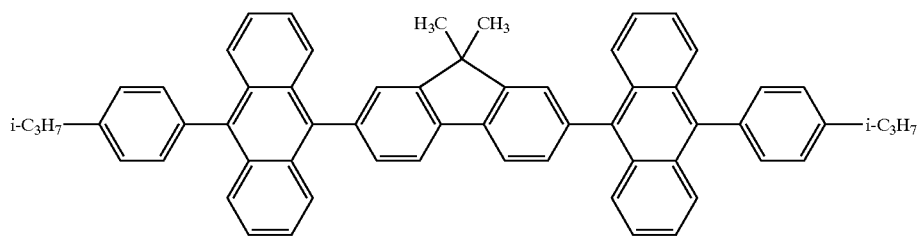
B-9
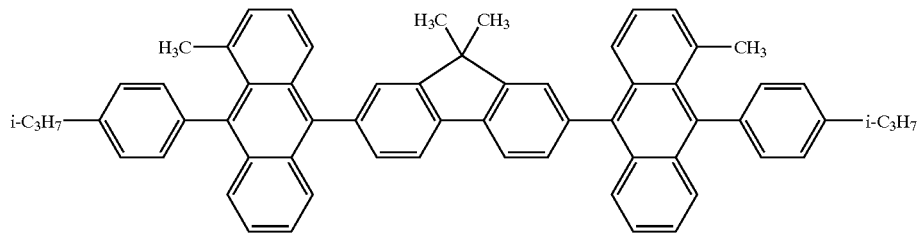
B-10
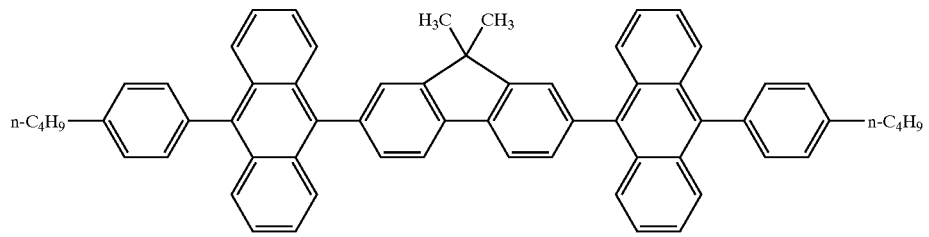
B-11

-continued
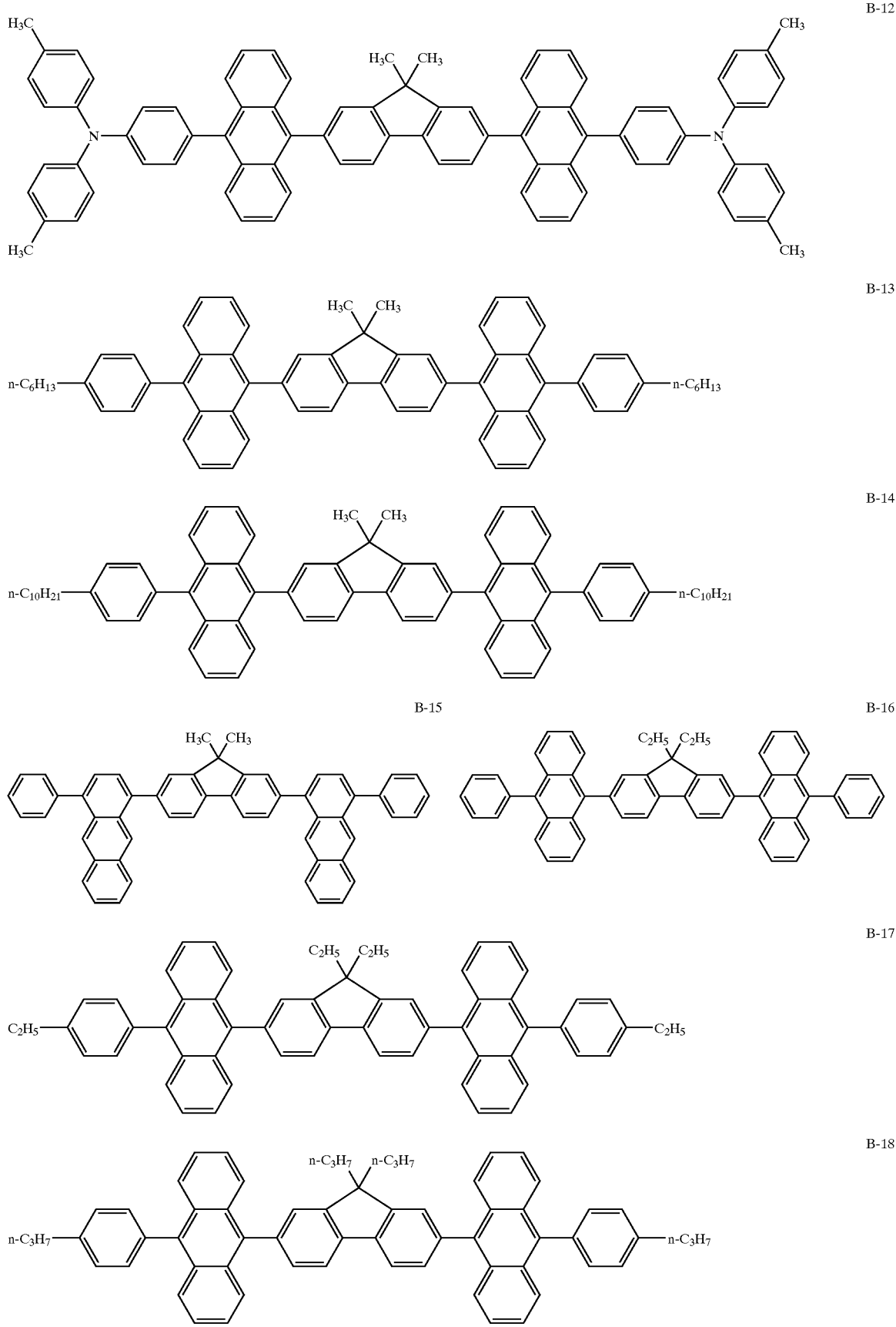

-continued
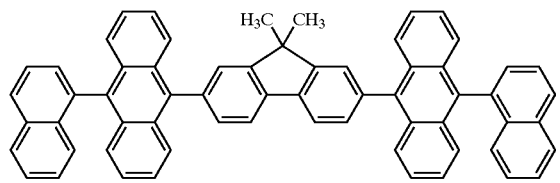
B-19
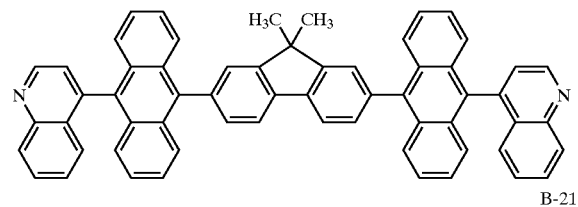
B-20
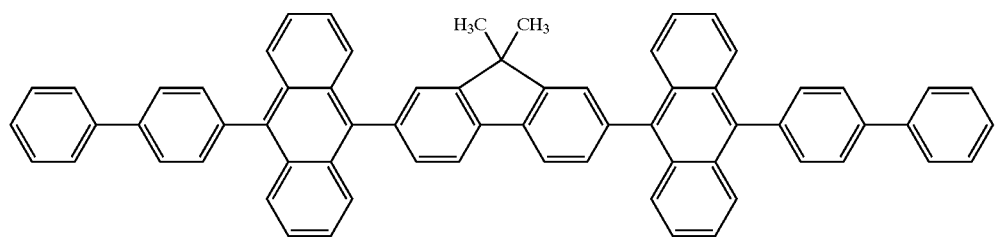
B-21
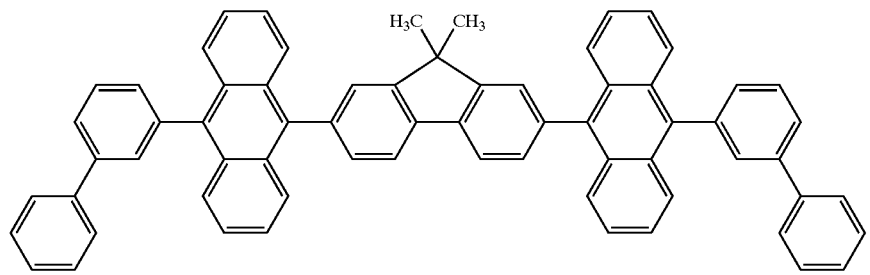
B-22
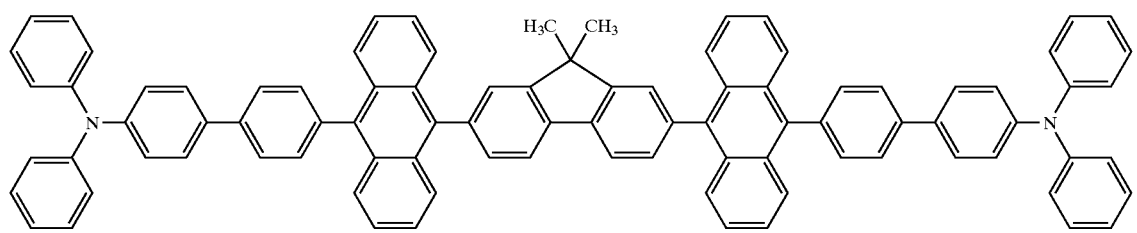
B-23
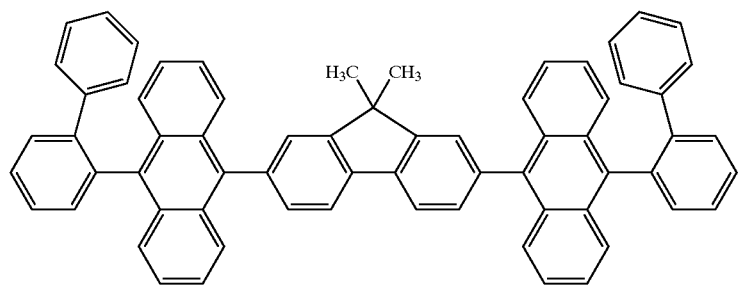
B-24
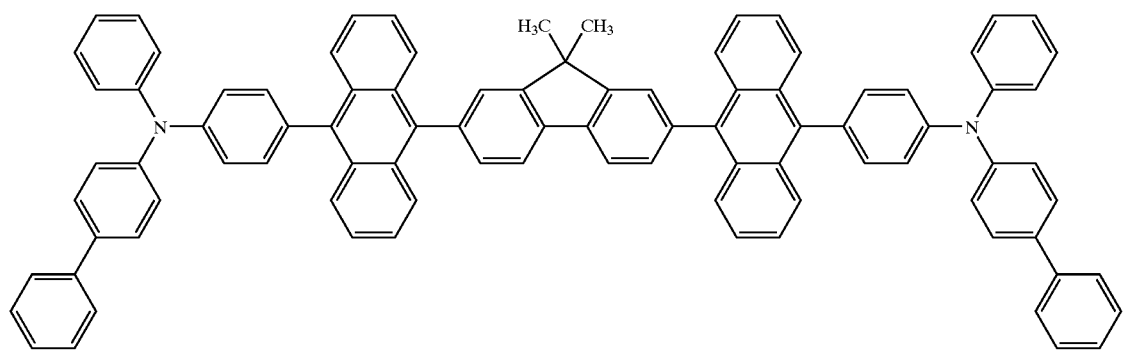
B-25

-continued
B-26
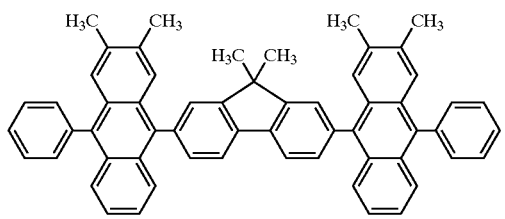
B-27
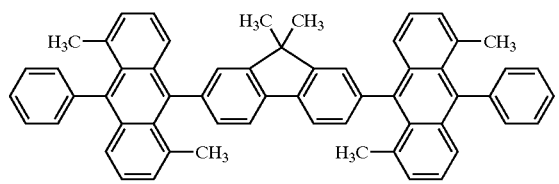
B-28
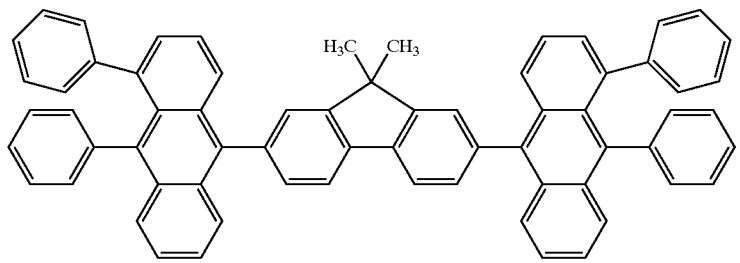
B-29
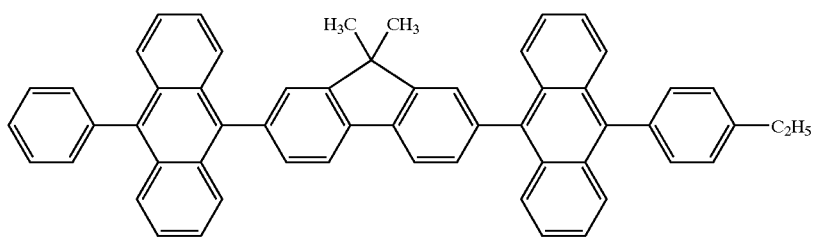
B-30
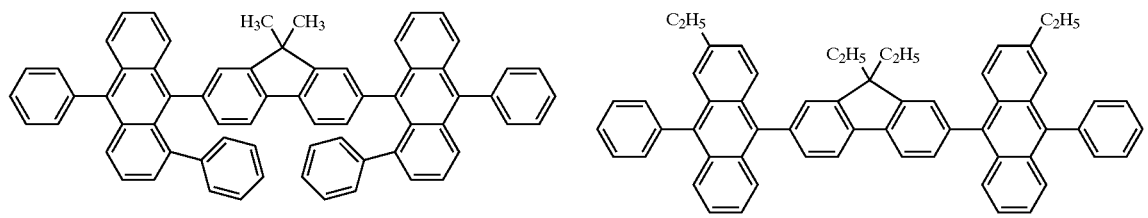
B-31
B-32
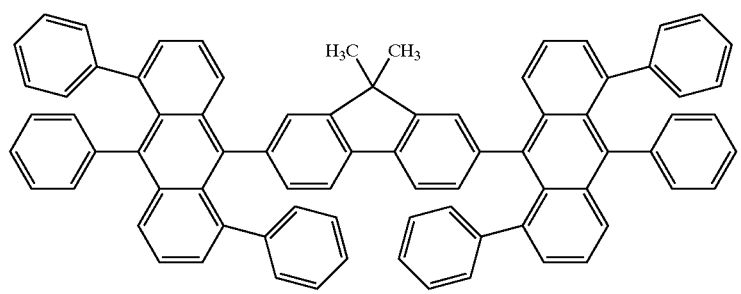
B-33
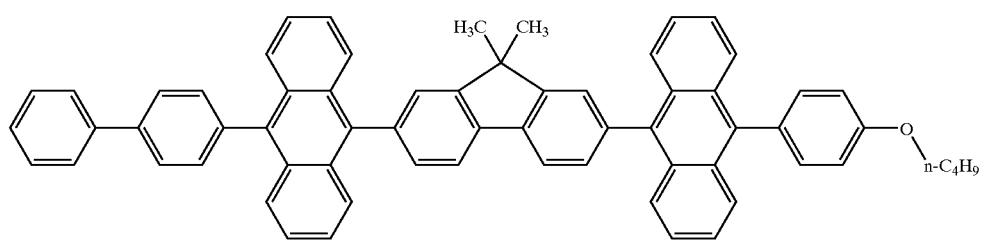

-continued
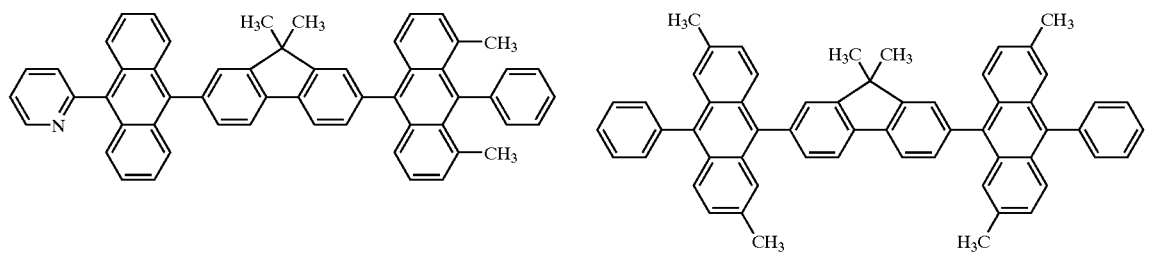
B-34
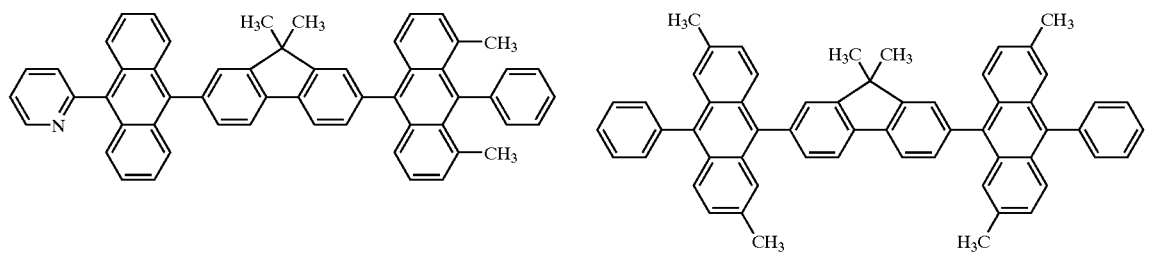
B-35
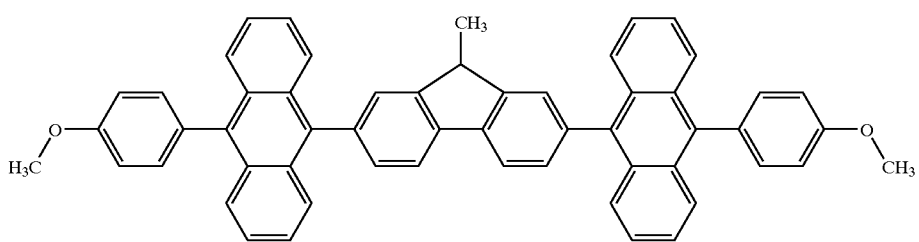
B-36
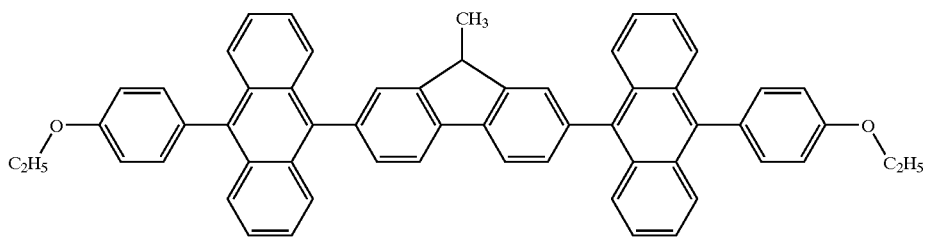
B-37
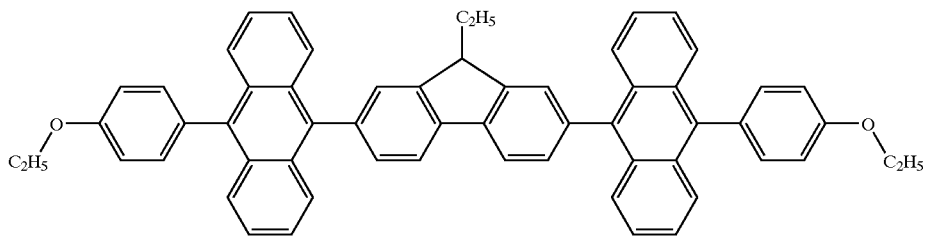
B-38
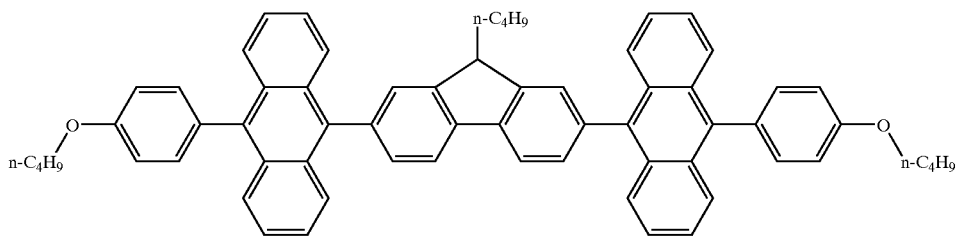
B-39
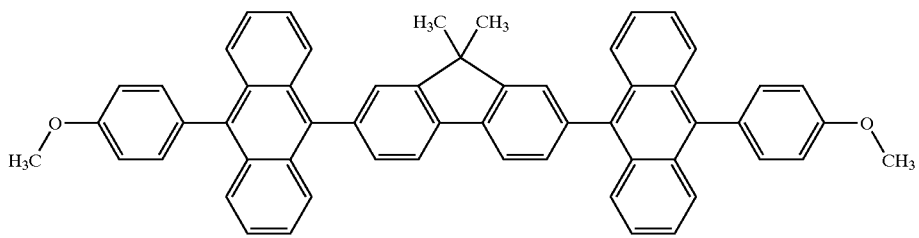
B-40

-continued
B-41
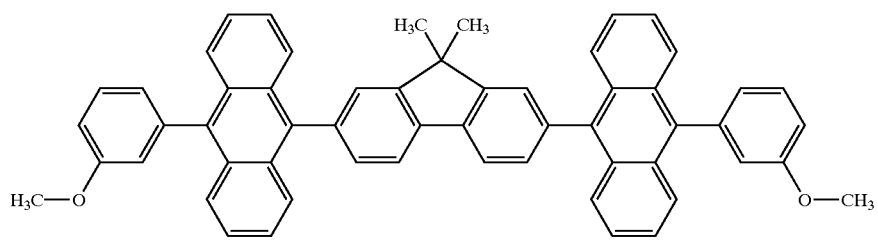
B-42
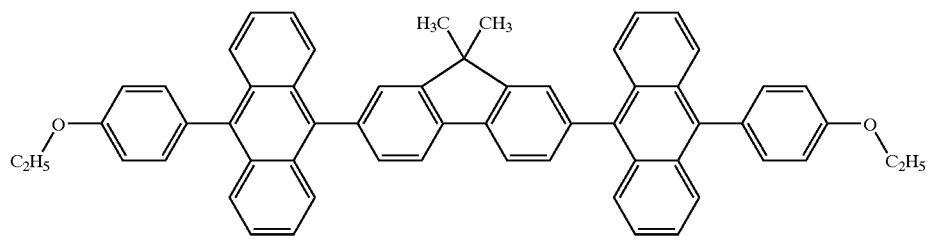
B-43
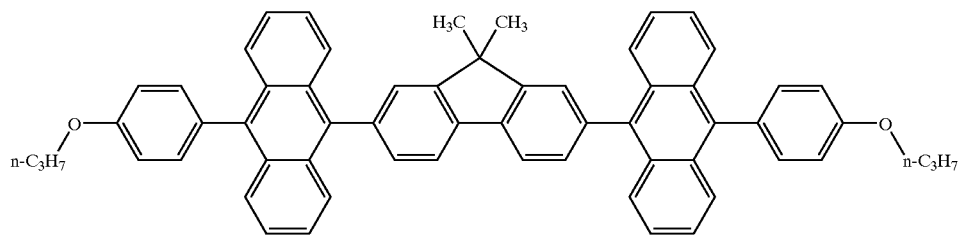
B-44
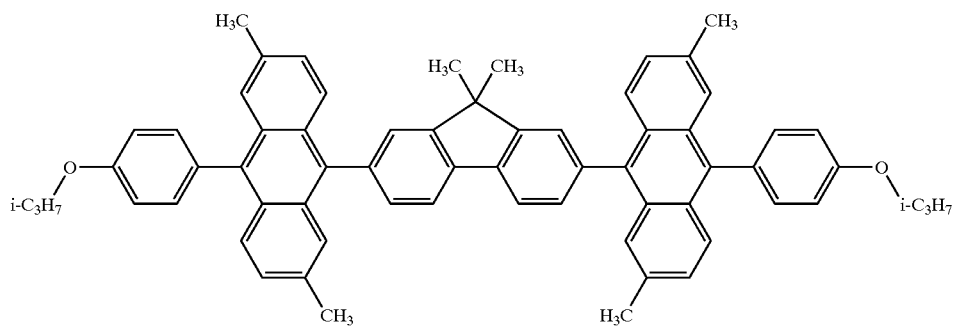
B-45
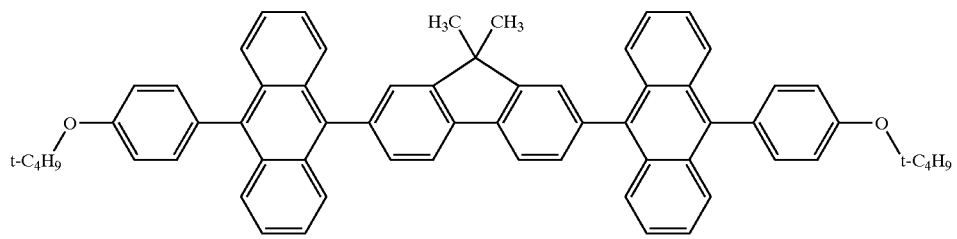
B-46
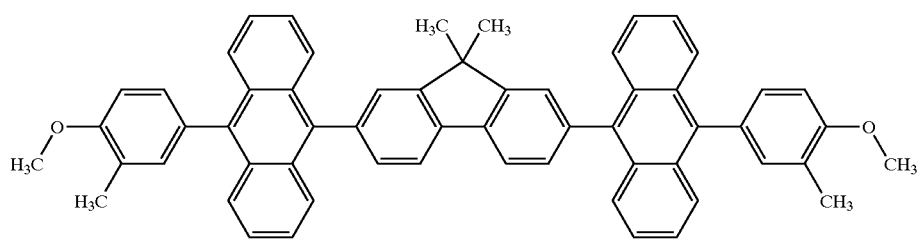

-continued
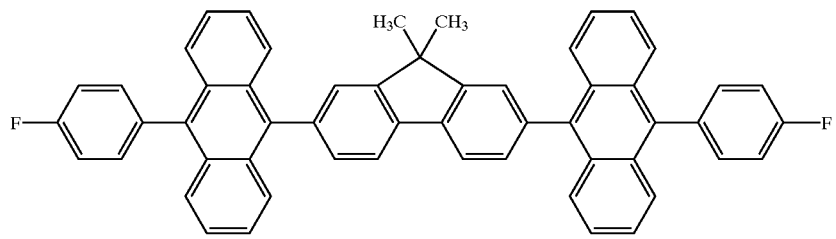
B-47
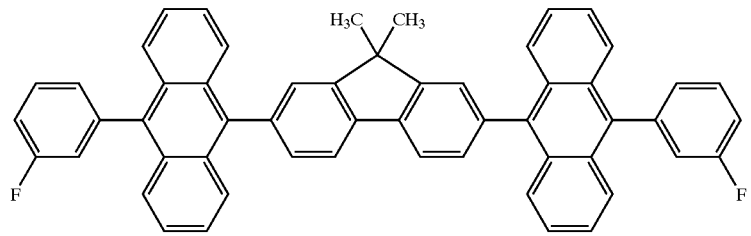
B-48
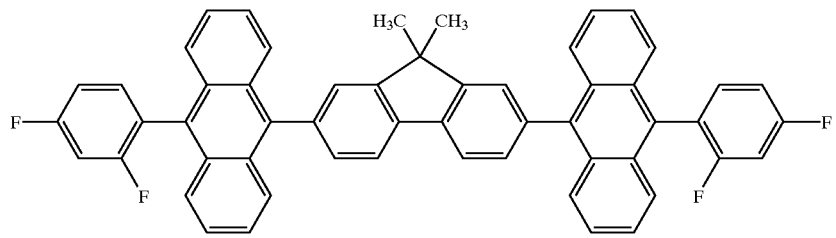
B-49
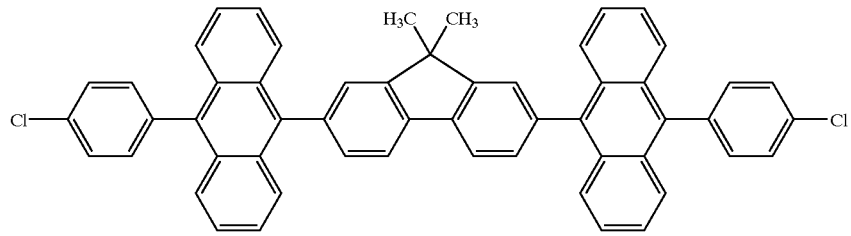
B-50
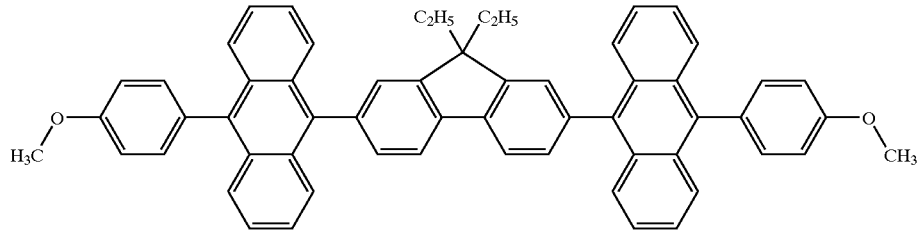
B-51
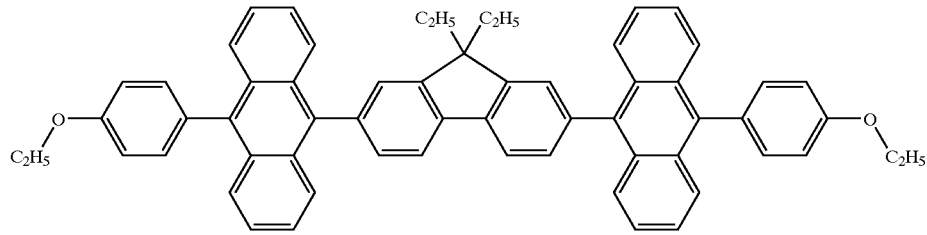
B-52

-continued
B-53
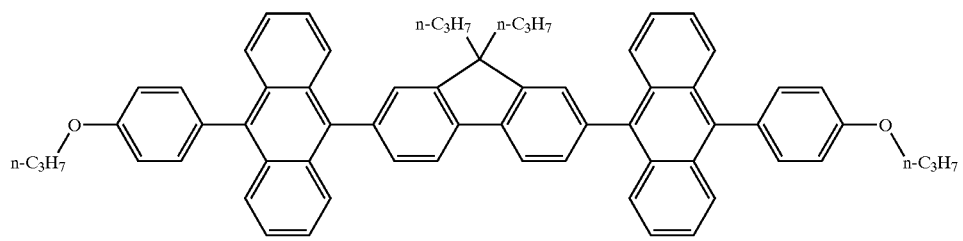
B-54
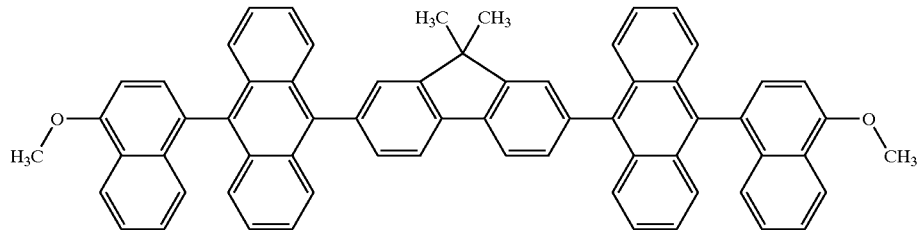
B-55
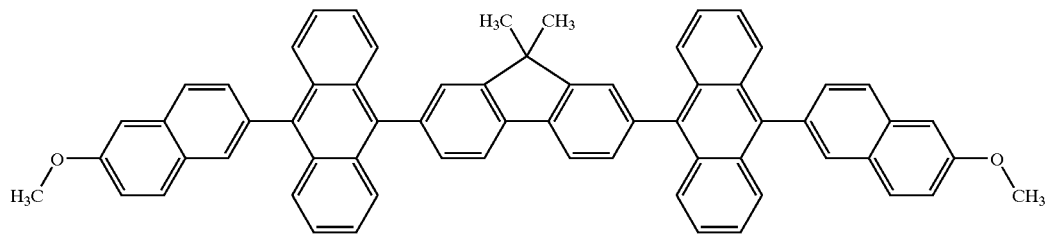
B-56
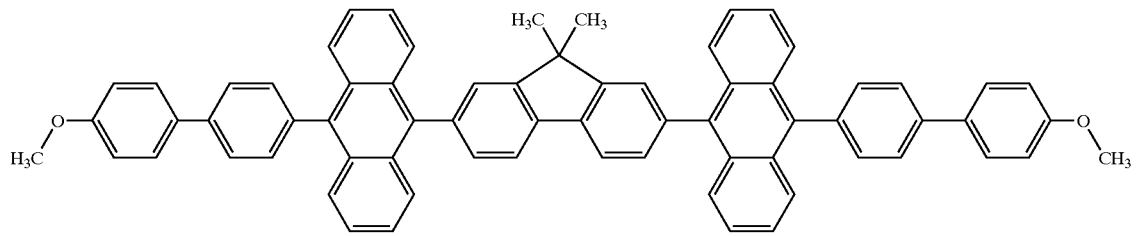
B-57
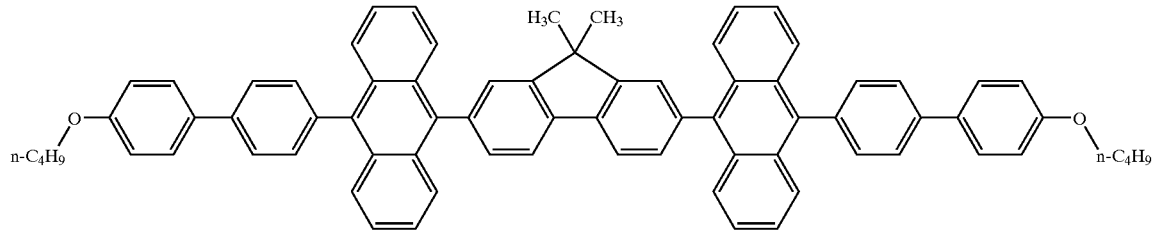
B-58
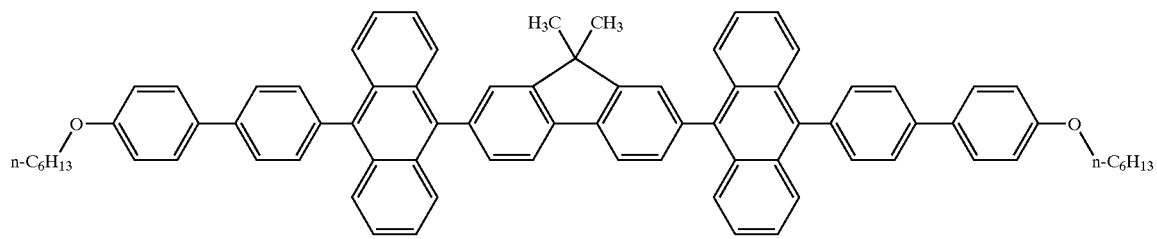

-continued
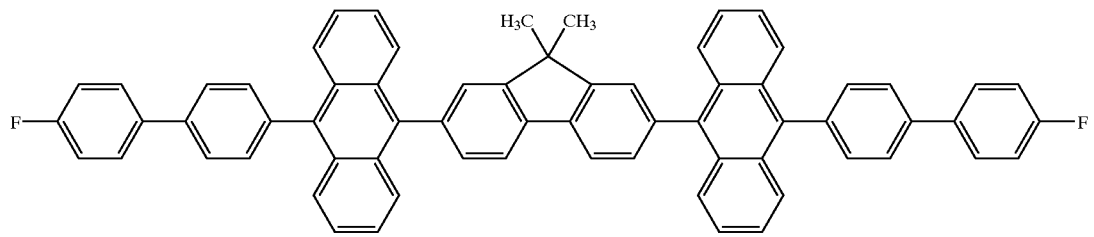
B-59
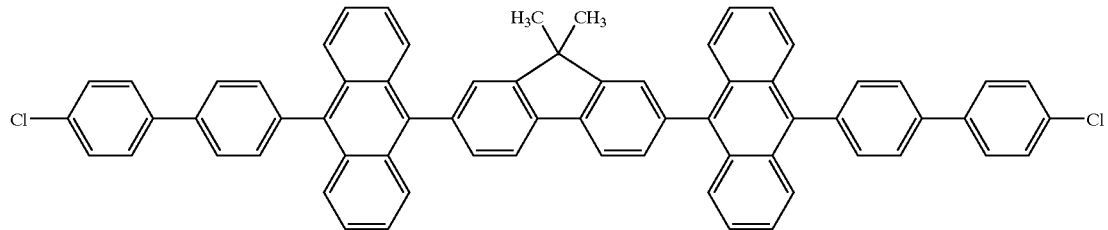
B-60
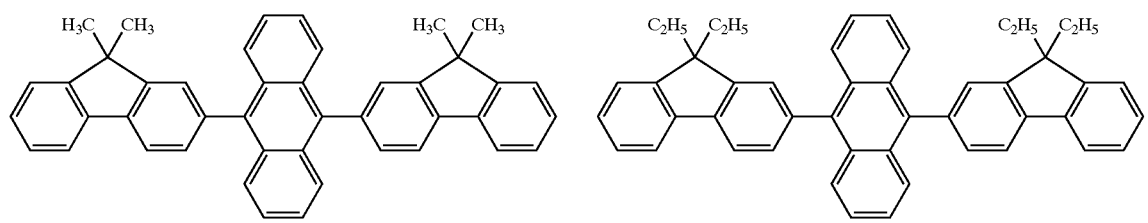
C-1   C-2
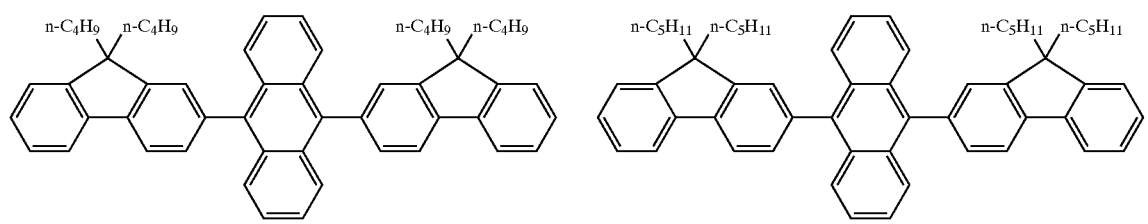
C-3   C-4
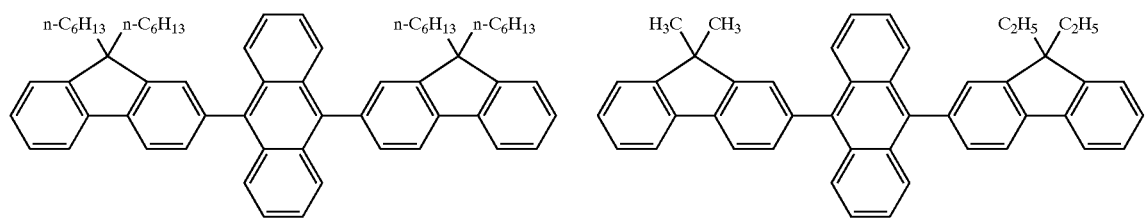
C-5   C-6
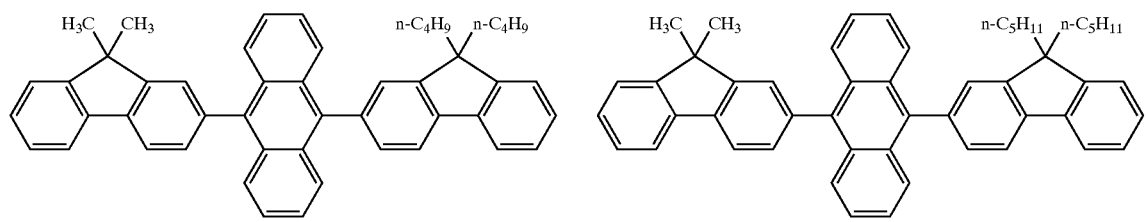
C-7   C-8

-continued
C-9
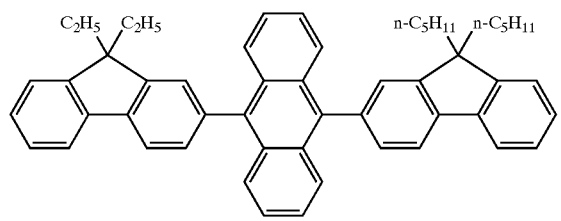
C-10
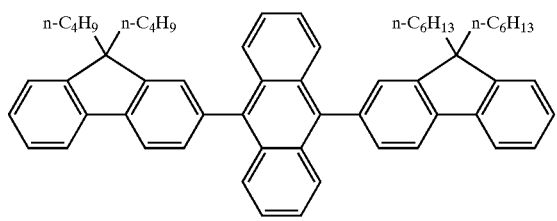
C-11
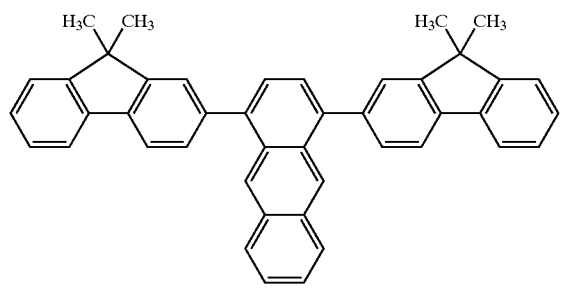
C-12
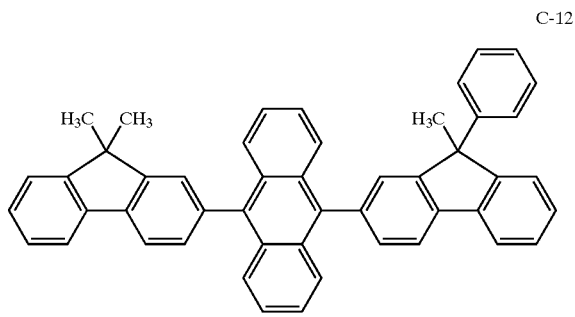
C-13
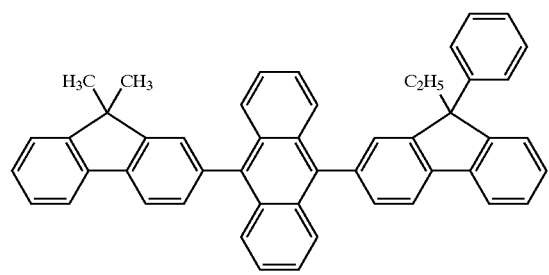
C-14
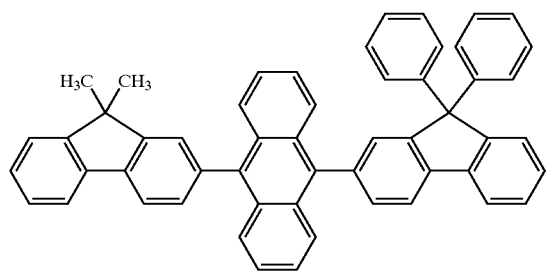
C-15
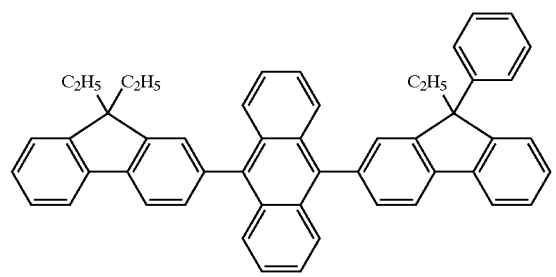
C-16
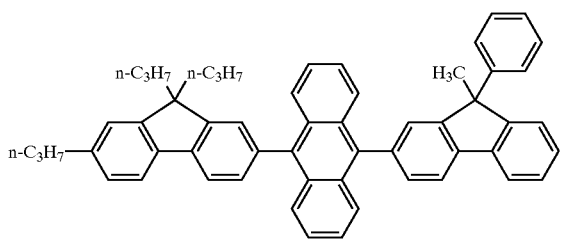
C-17
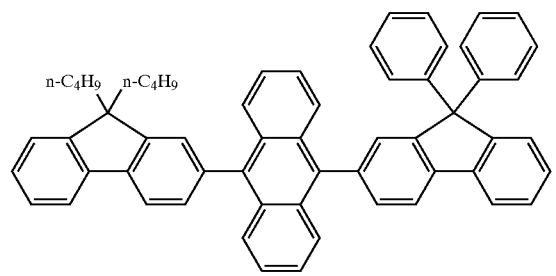
C-18
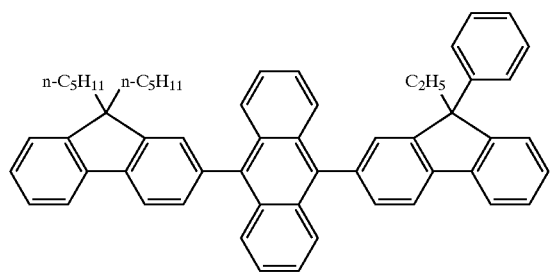

-continued
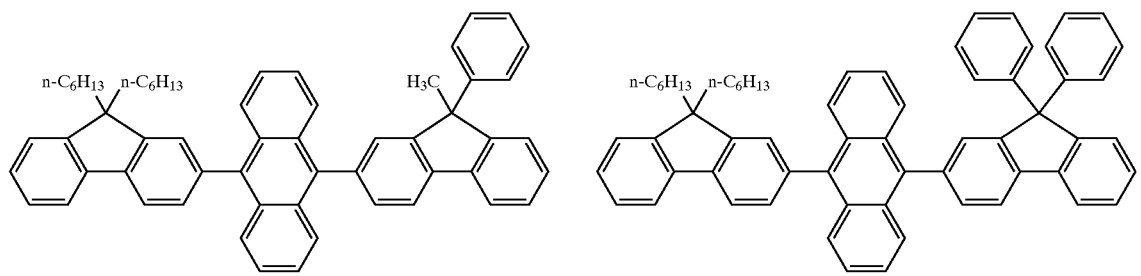
C-19
C-20
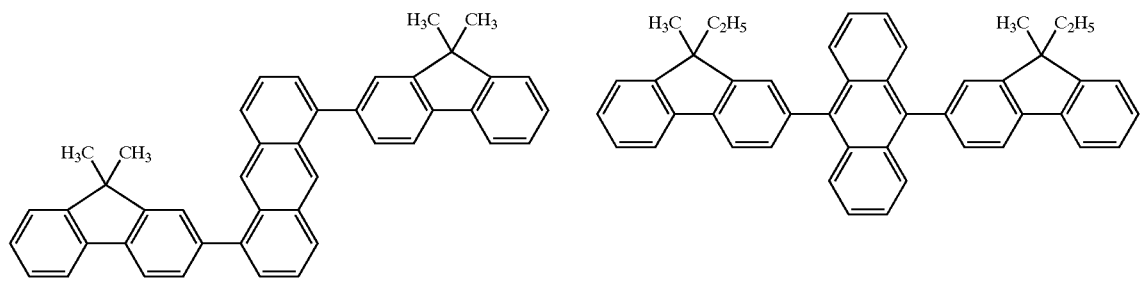
C-21
C-22
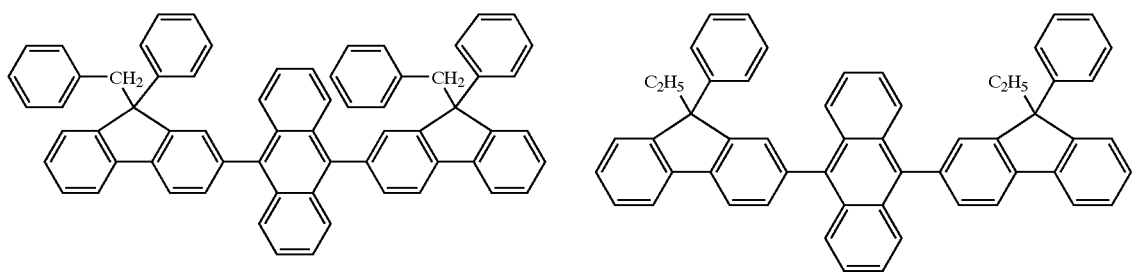
C-23
C-24
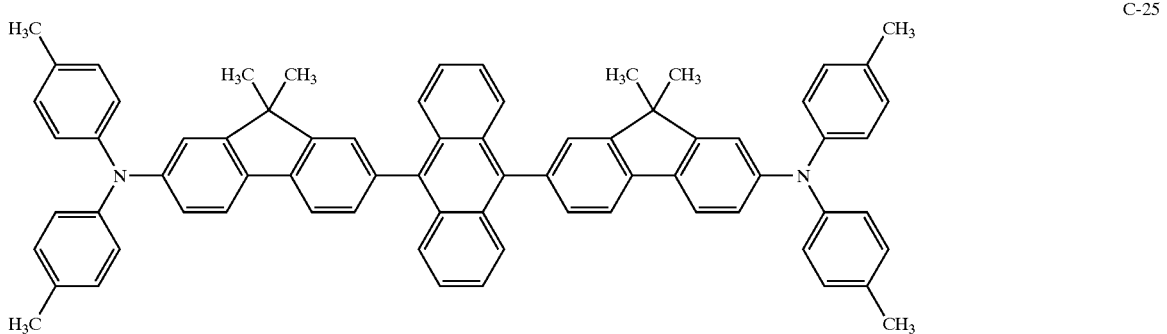
C-25
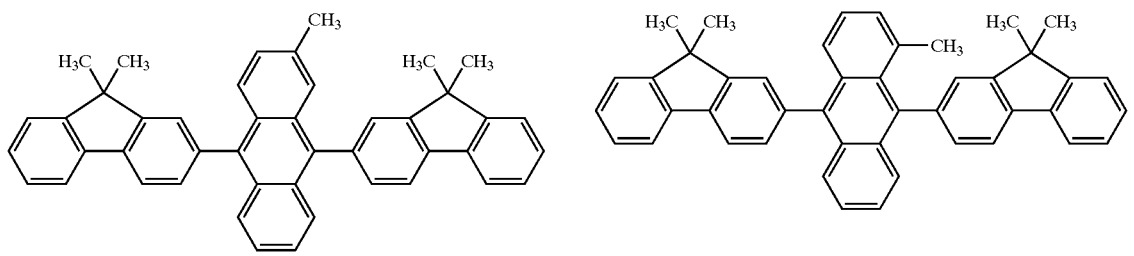
C-26
C-27

-continued
C-28
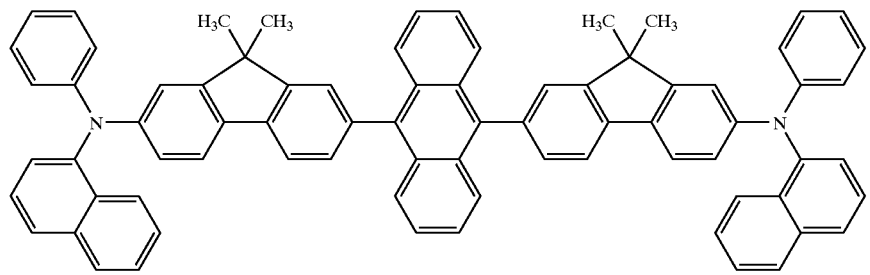
C-29
C-30
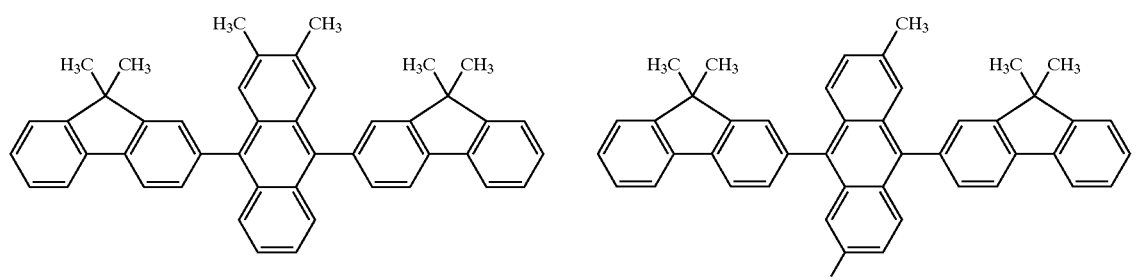
C-31
C-32
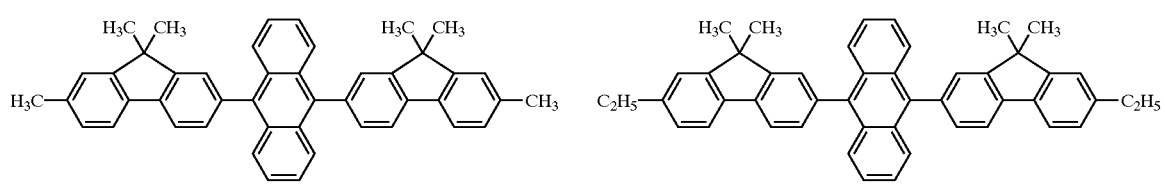
C-33
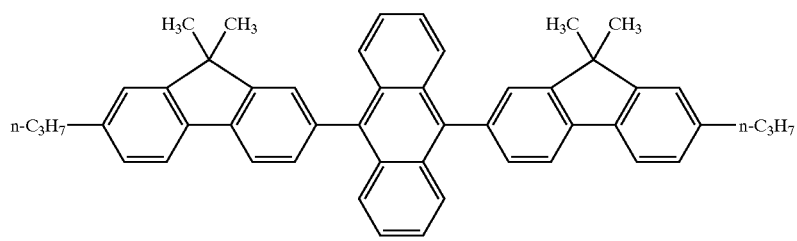
C-34
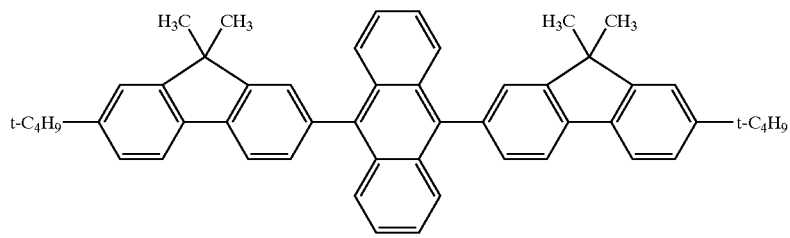
C-35
C-36
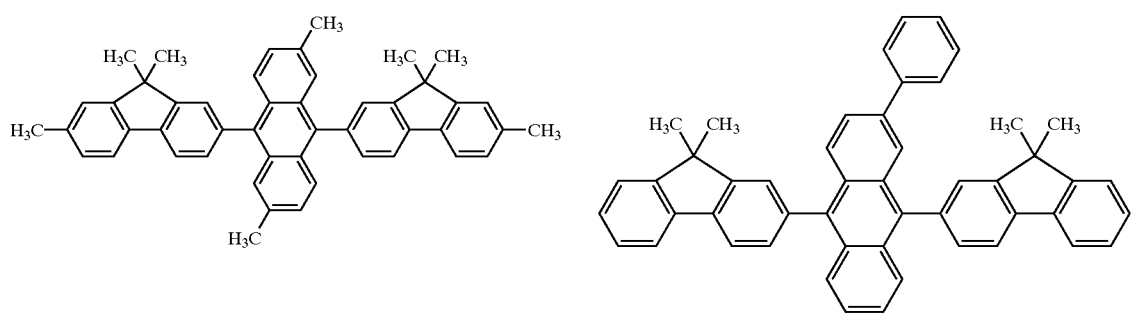

-continued
C-37
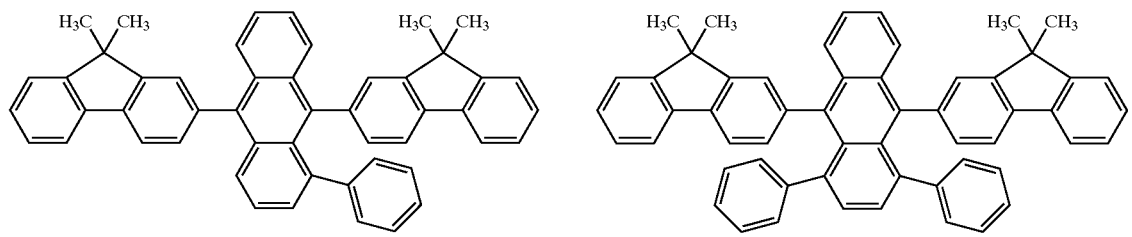
C-38
C-39
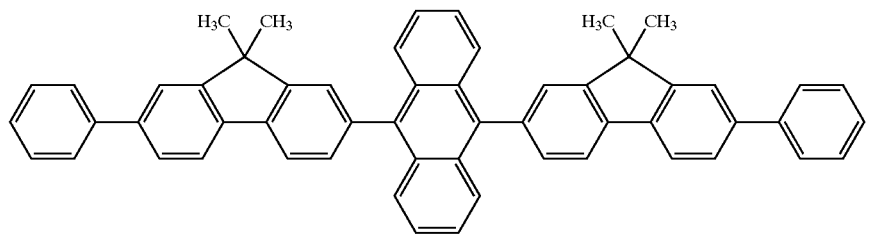
C-40
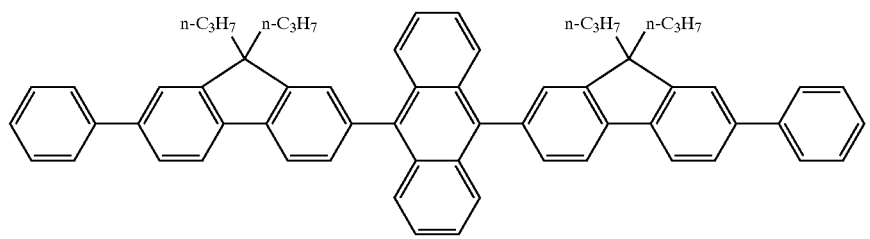
C-41
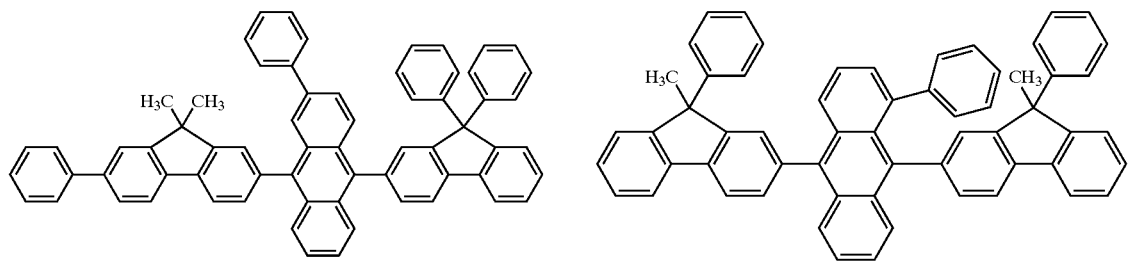
C-42
C-43
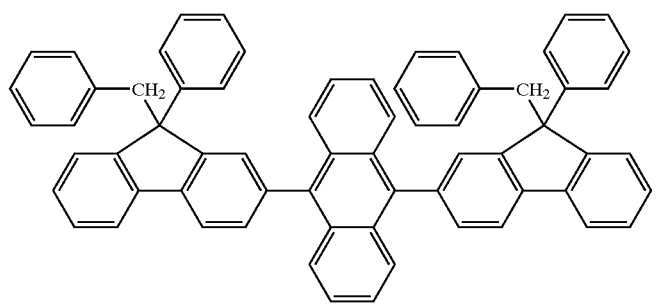
C-44
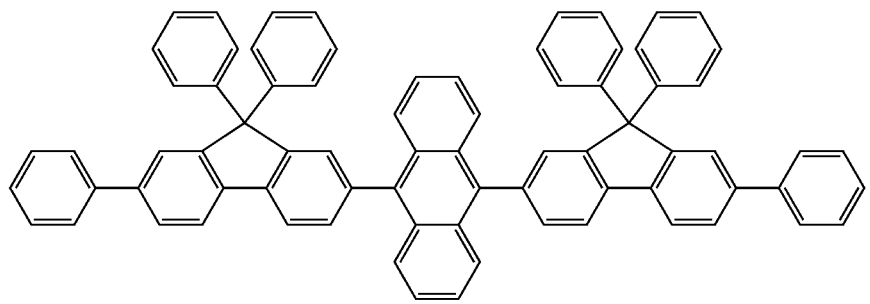

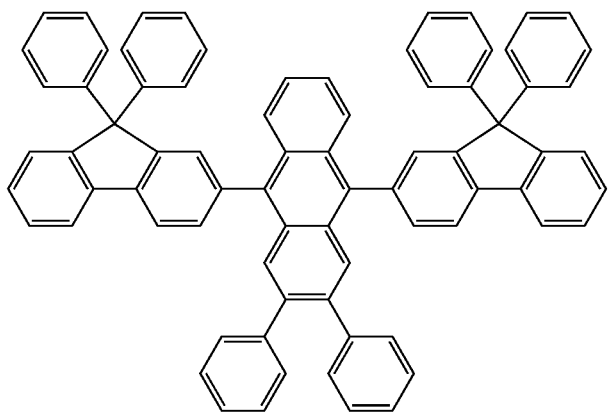
C-45
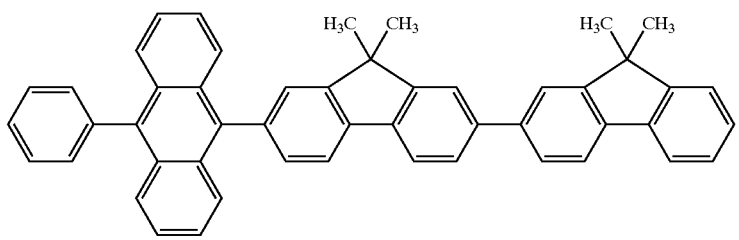
D-1
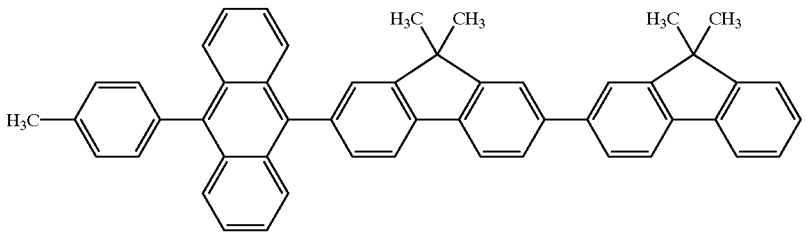
D-2
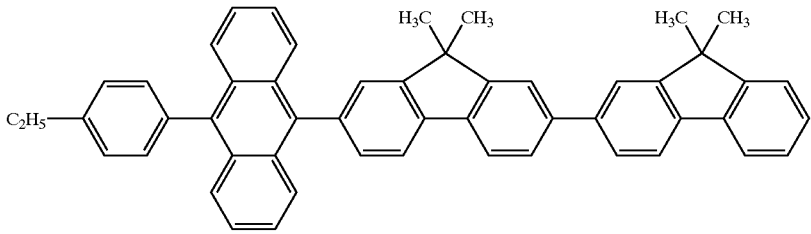
D-3
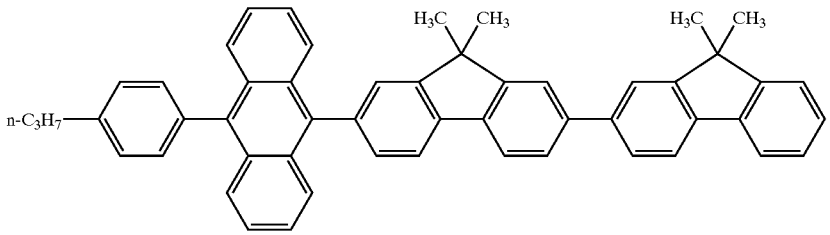
D-4
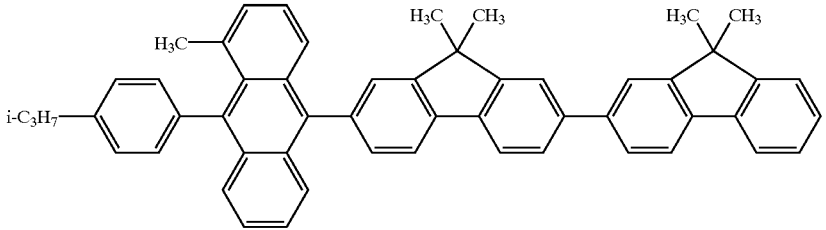
D-5

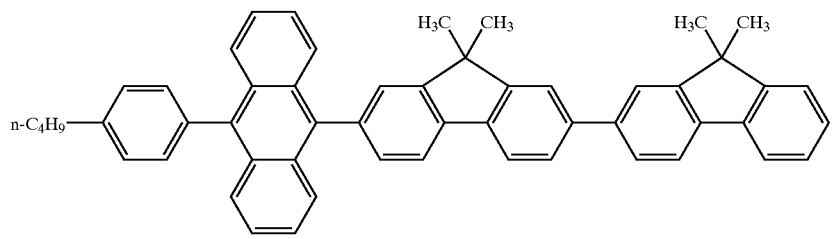
D-6
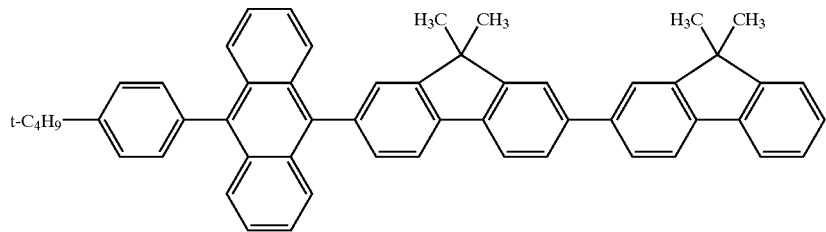
D-7
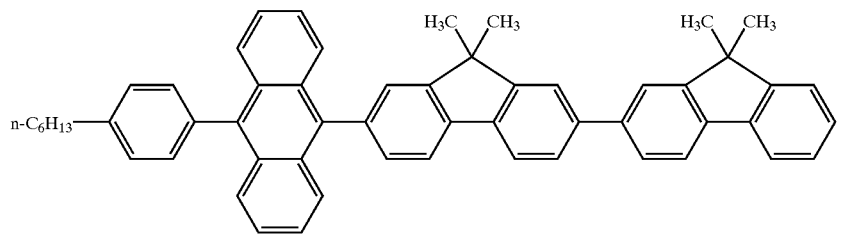
D-8
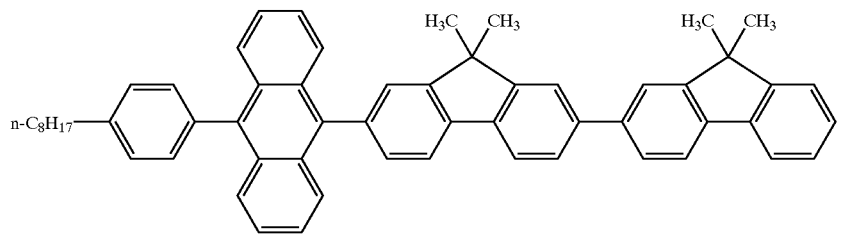
D-9
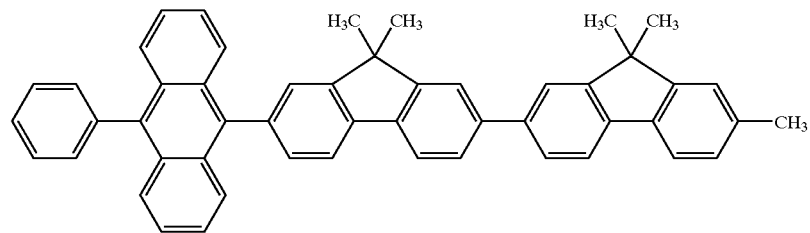
D-10
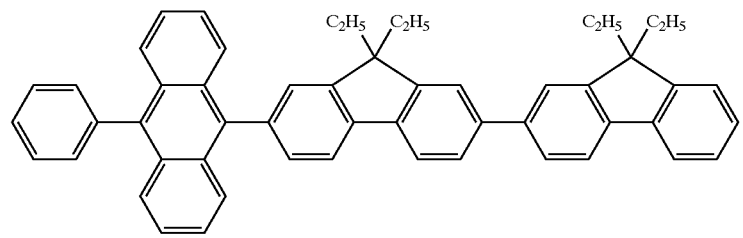
D-11

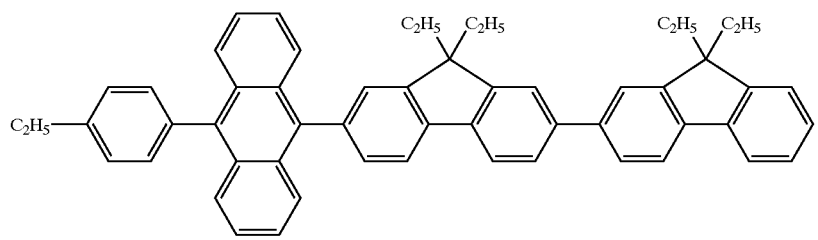
D-12
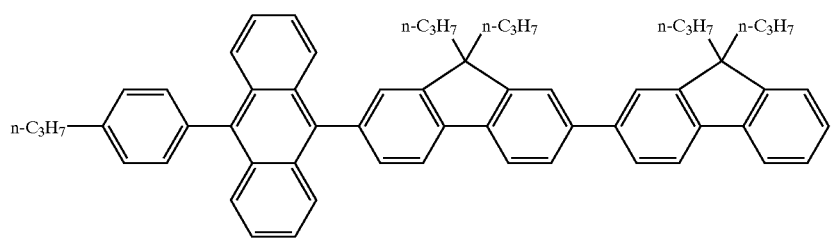
D-13
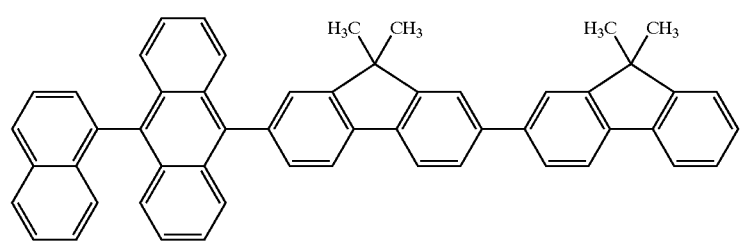
D-14
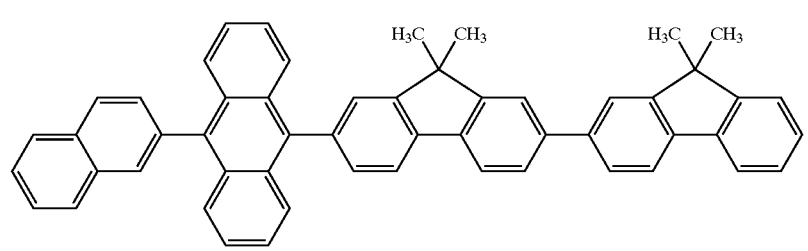
D-15
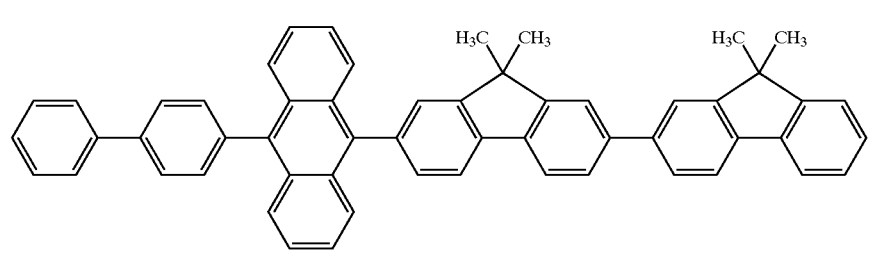
D-16
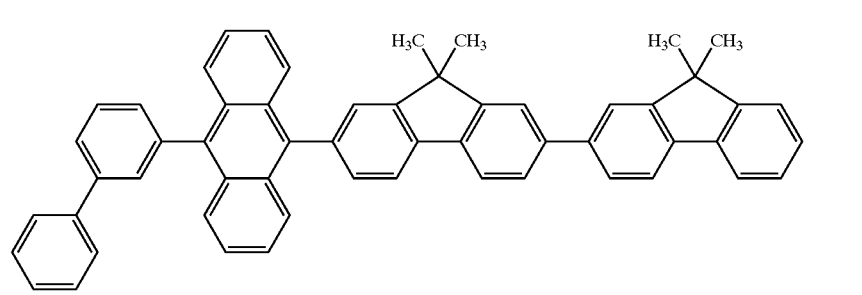
D-17

-continued
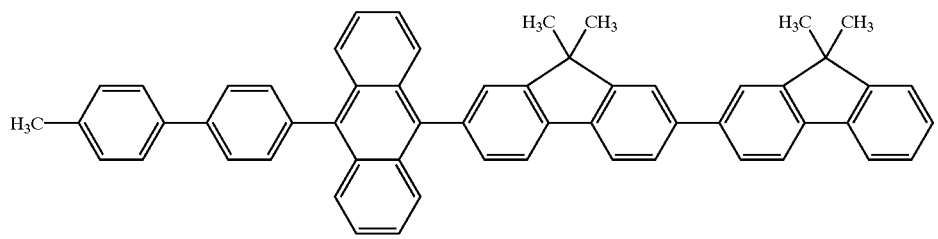
D-18
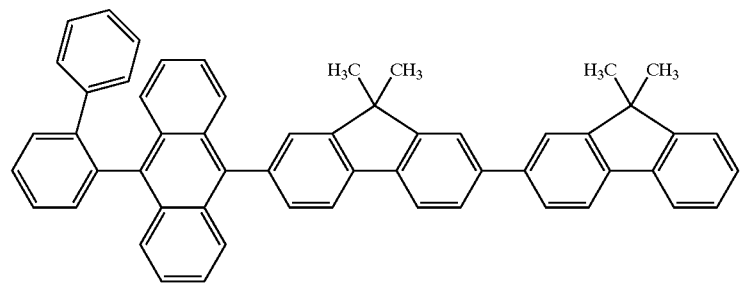
D-19
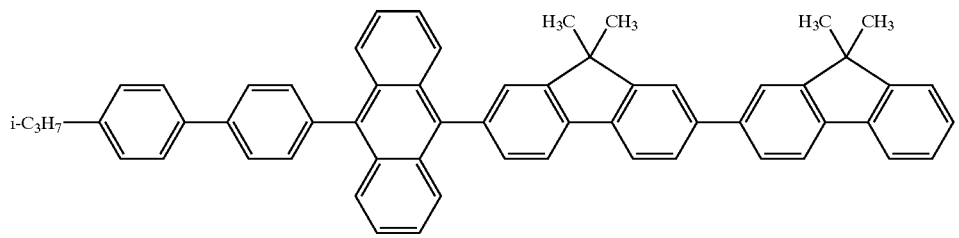
D-20
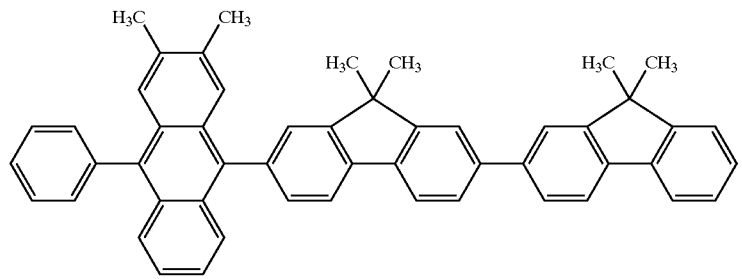
D-21
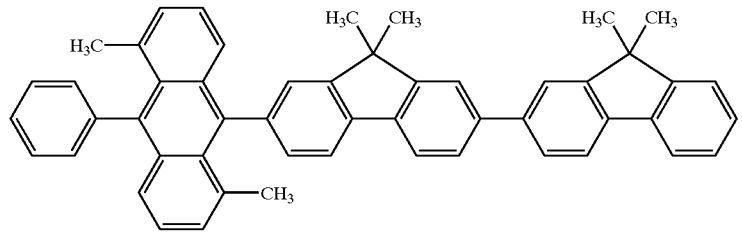
D-22
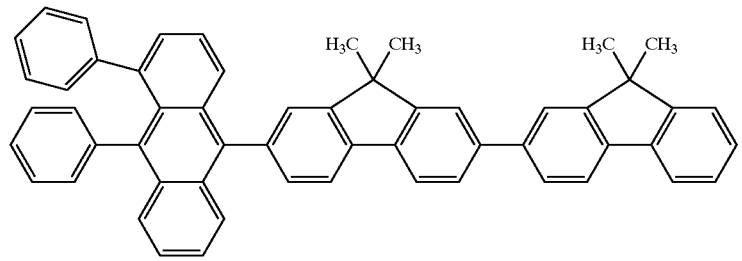
D-23

-continued
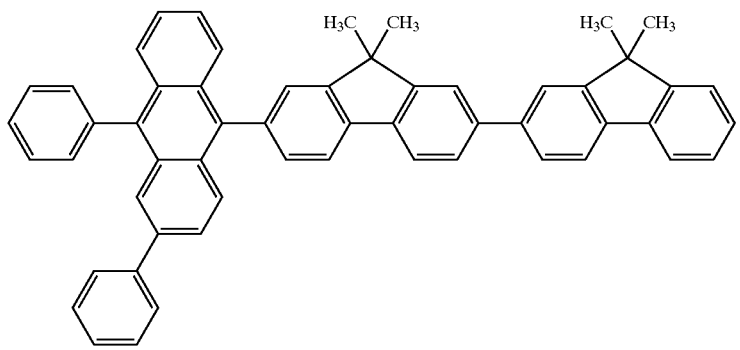
D-24
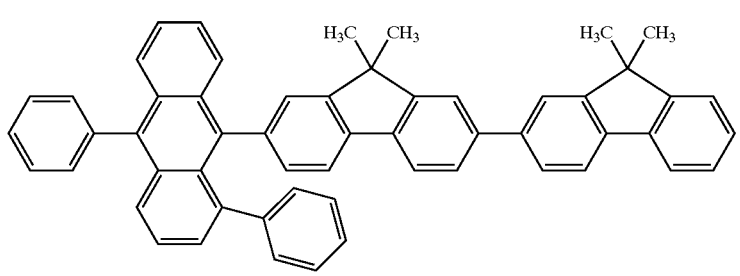
D-25
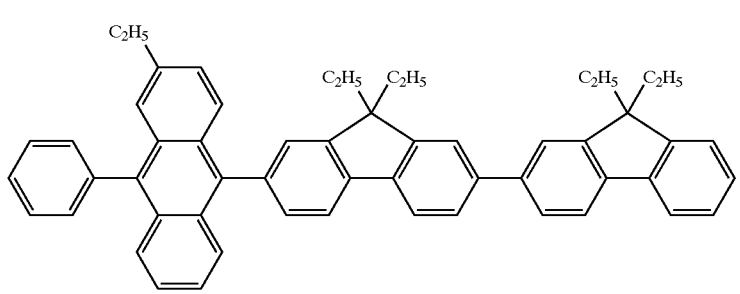
D-26
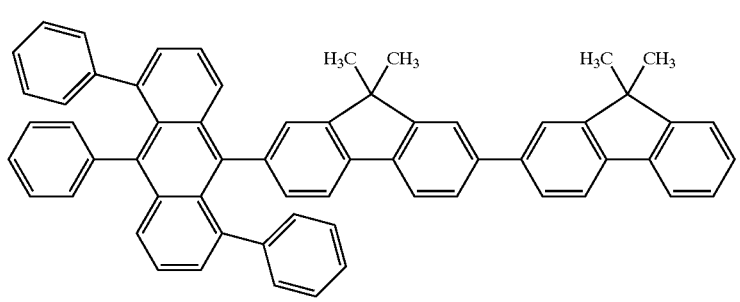
D-27
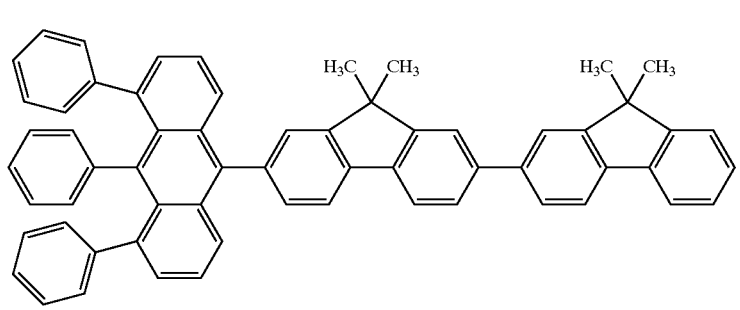
D-28

-continued
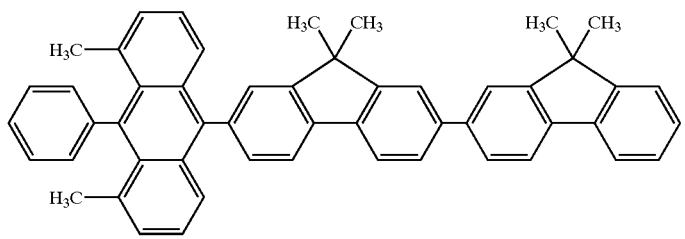
D-29
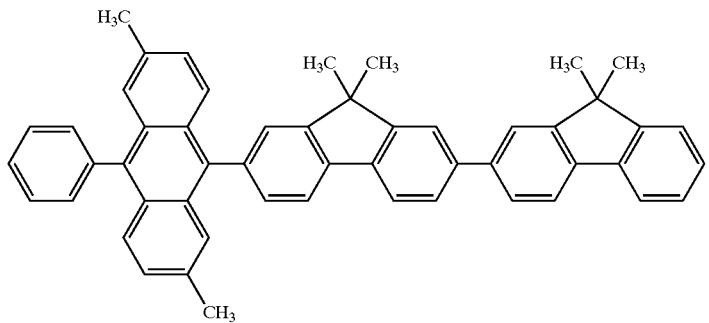
D-30
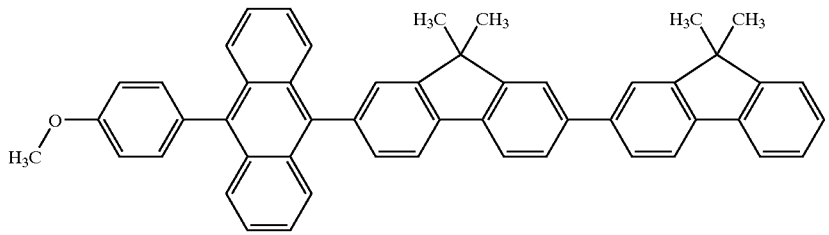
D-31
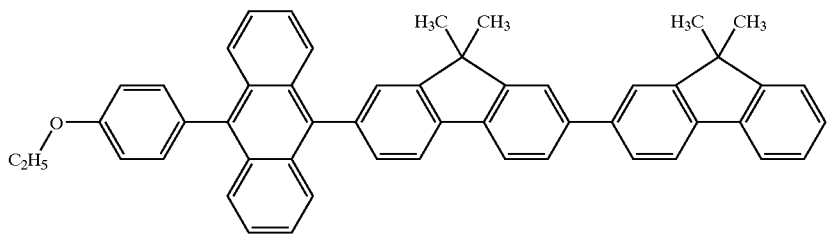
D-32
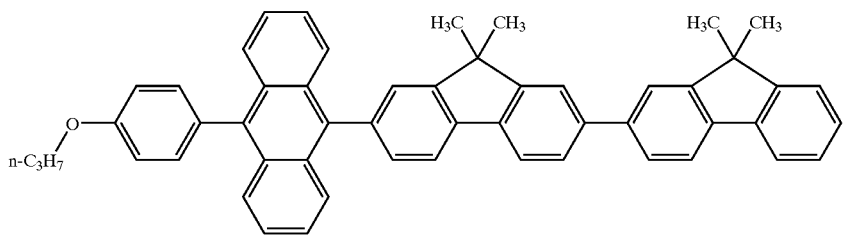
D-33
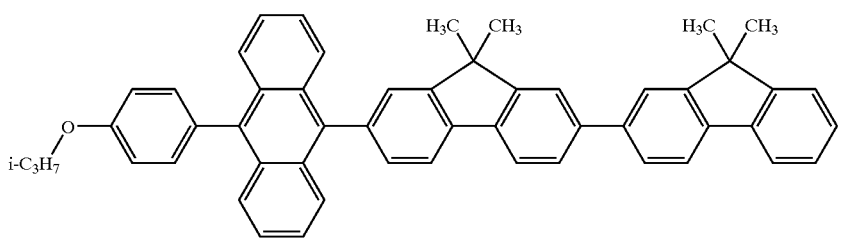
D-34

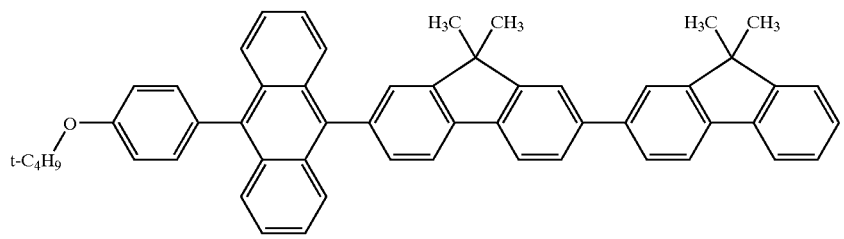
D-35
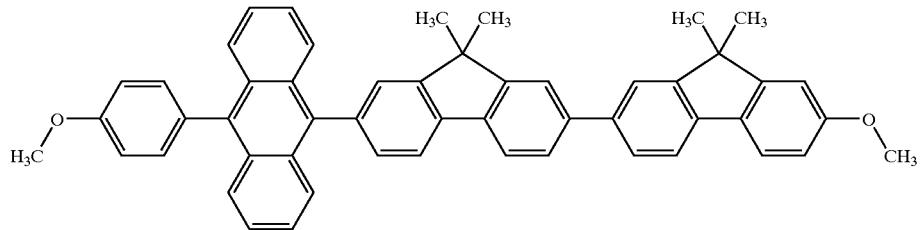
D-36
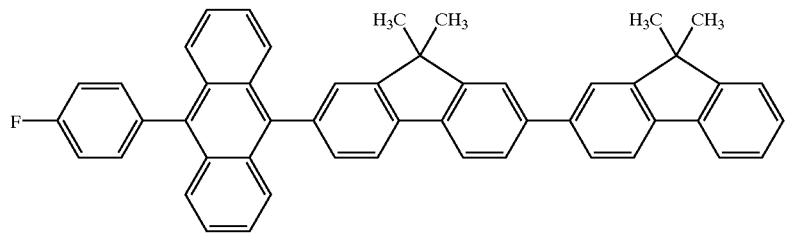
D-37
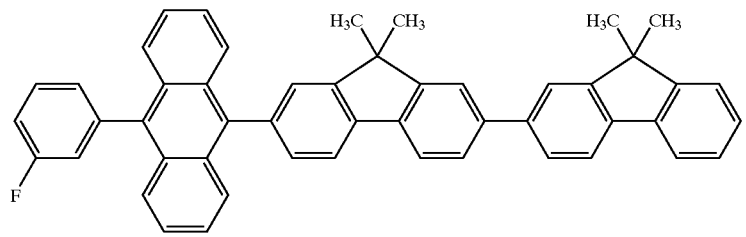
D-38
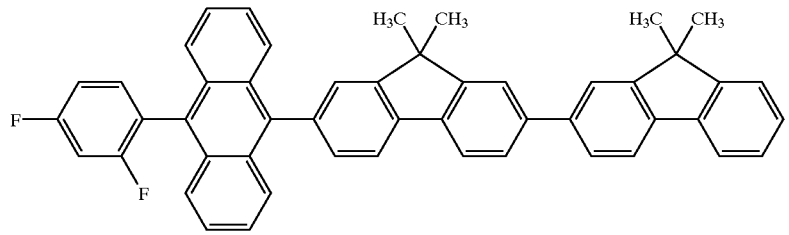
D-39
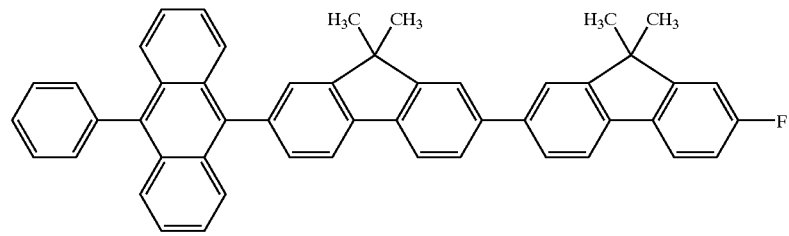
D-40

-continued
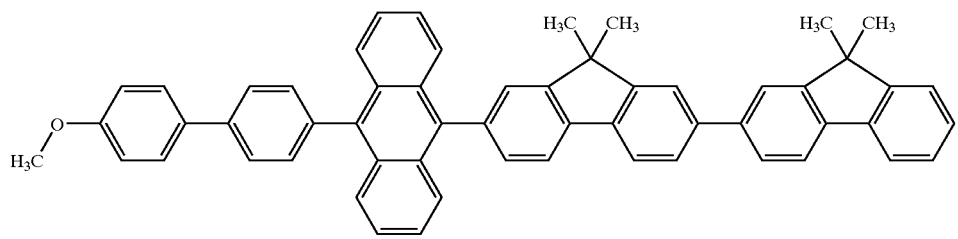
D-41
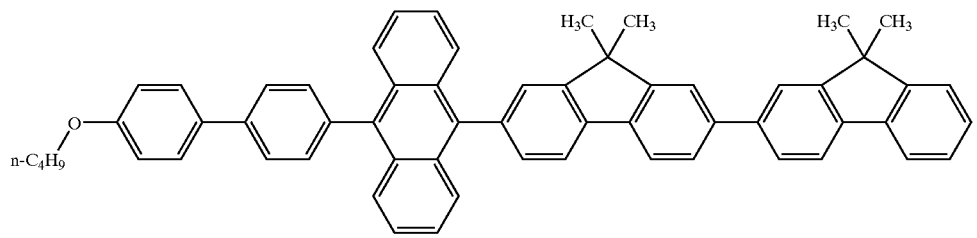
D-42
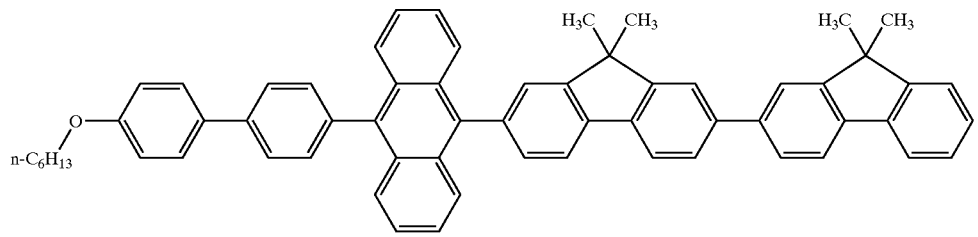
D-43
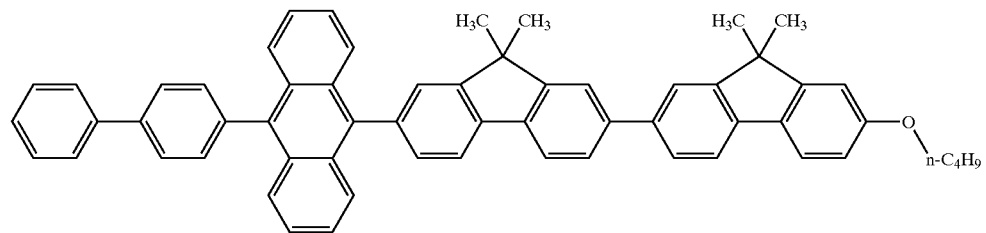
D-44
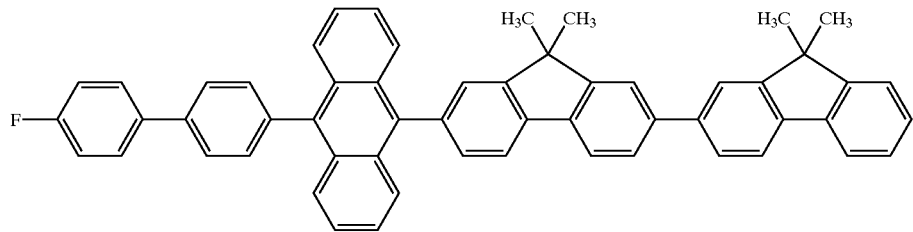
D-45
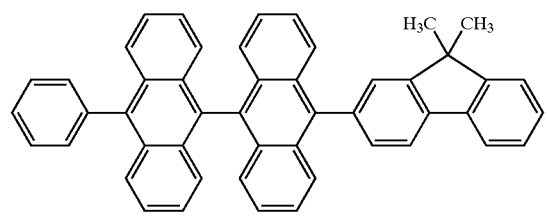
E-1
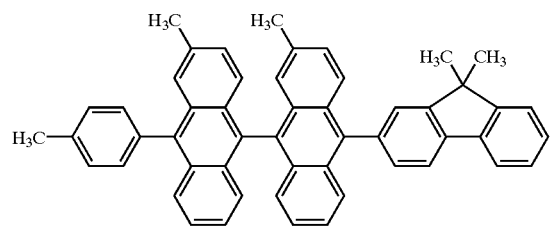
E-2

-continued
E-3
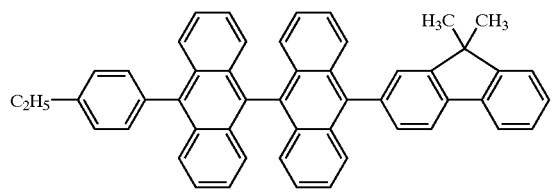
E-4
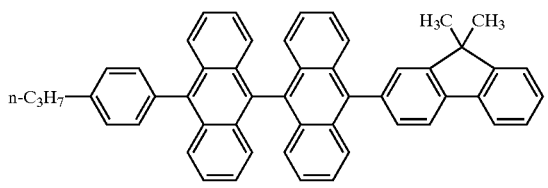
E-5
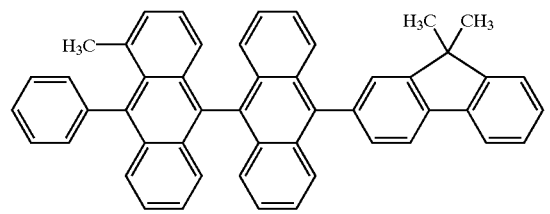
E-6
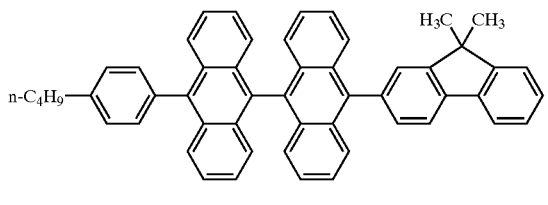
E-7
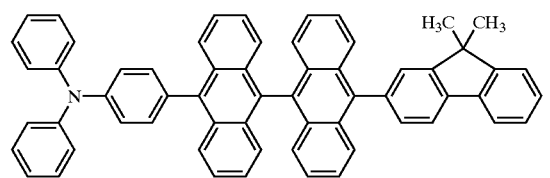
E-8
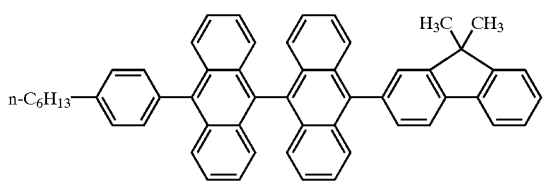
E-9
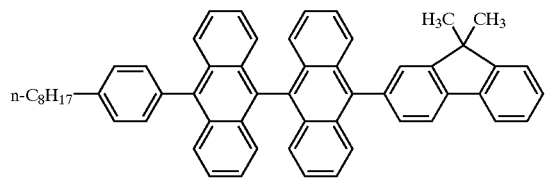
E-10
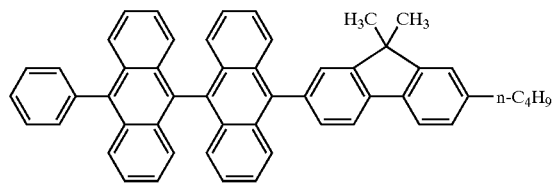
E-11
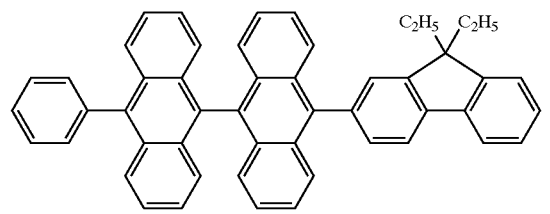
E-12
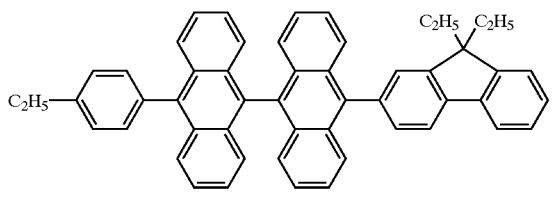
E-13
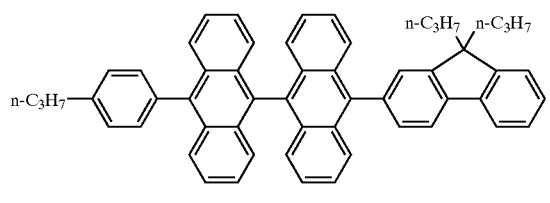
E-14
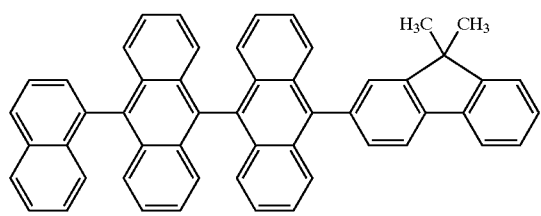
E-15
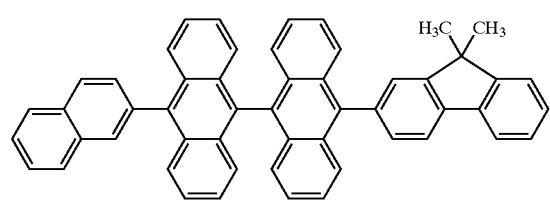
E-16
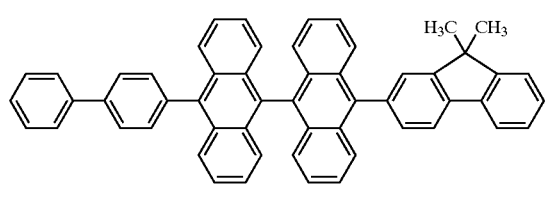

-continued
E-17
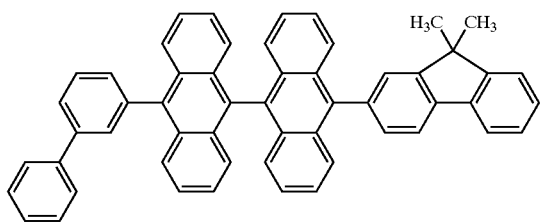
E-18
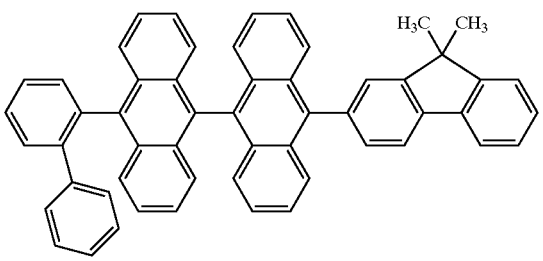
E-19
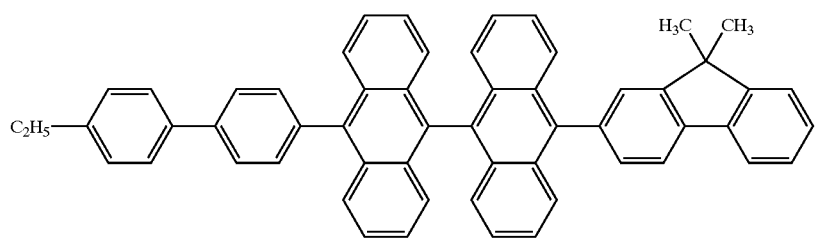
E-20
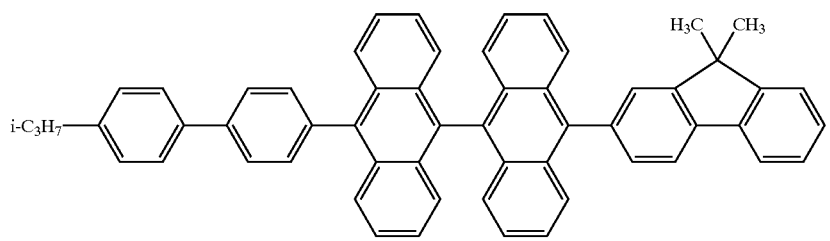
E-21
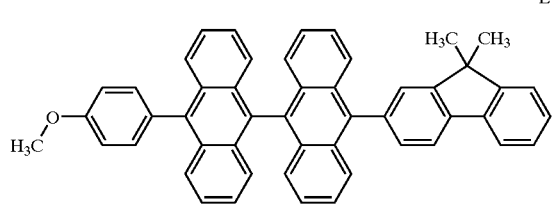
E-22
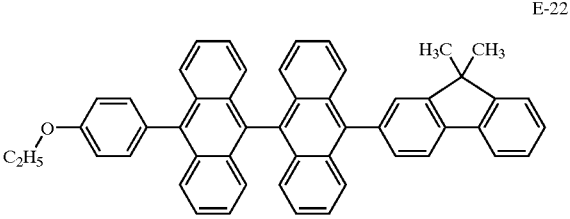
E-23
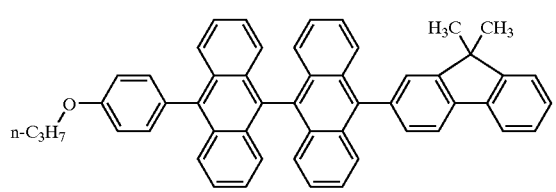
E-24
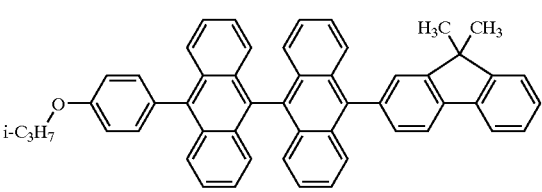
E-25
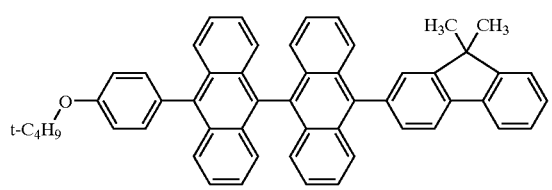
E-26
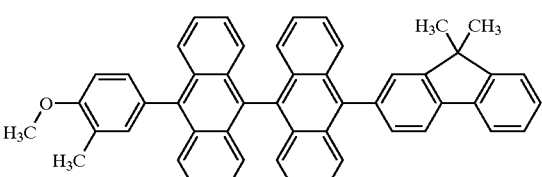
E-27
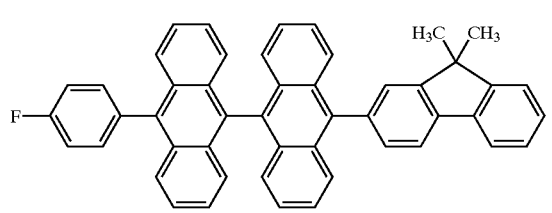
E-28
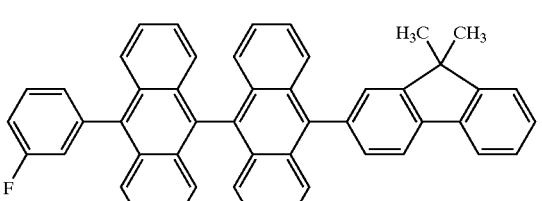

-continued
E-29
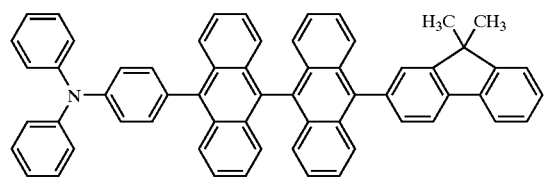
E-30
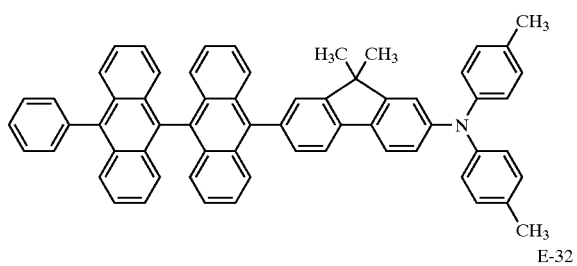
E-31
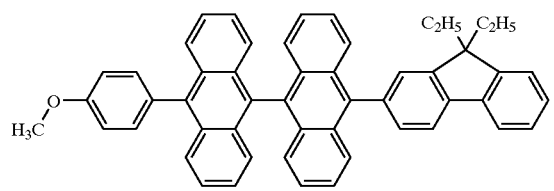
E-32
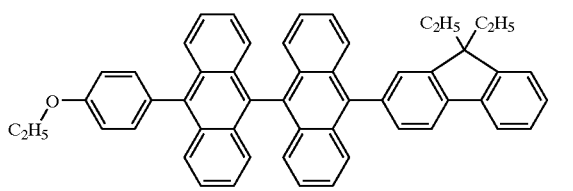
E-33
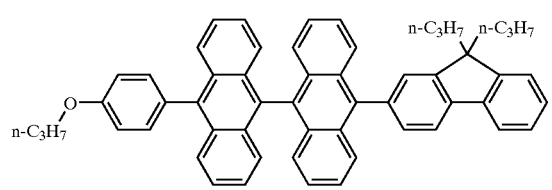
E-34
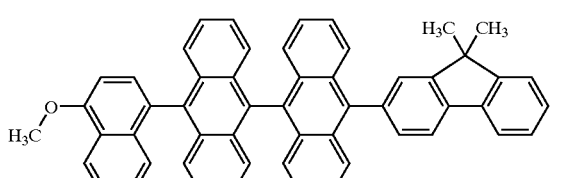
E-35
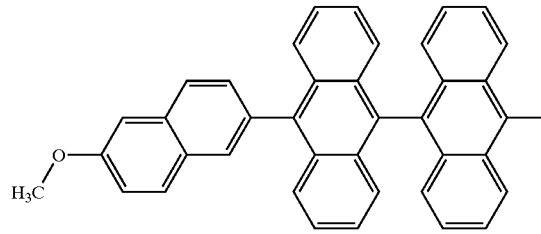
E-36
E-36
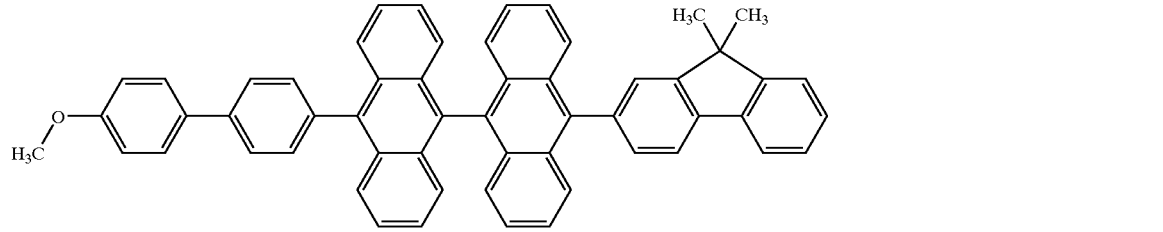
E-37
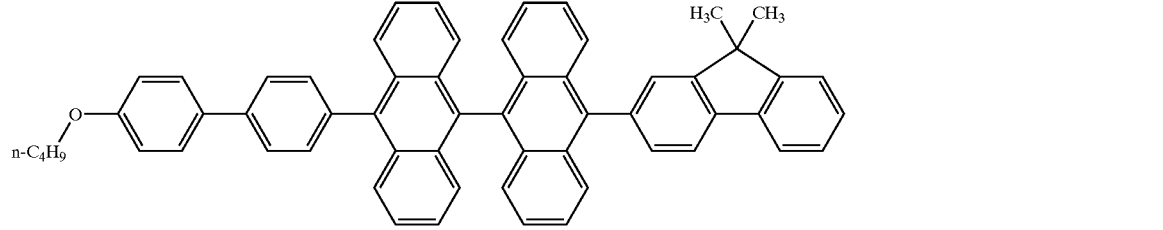
E-38
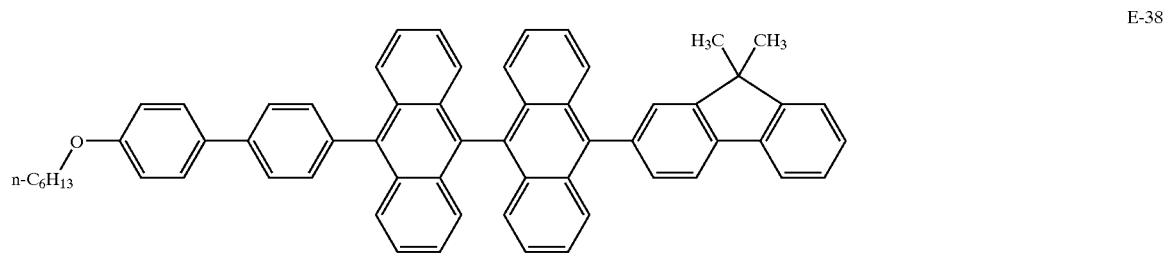

-continued
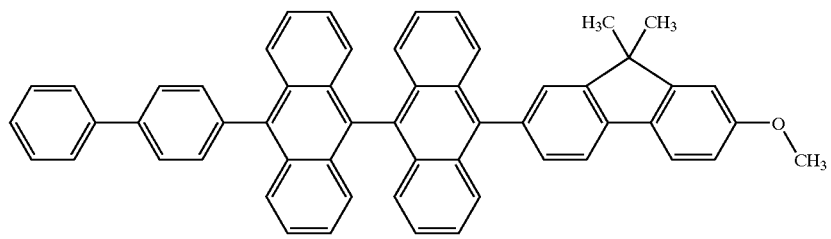
E-39
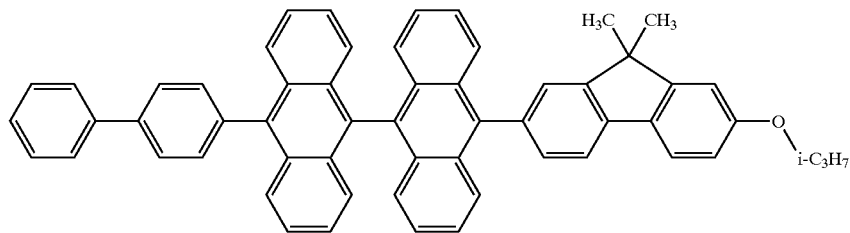
E-40
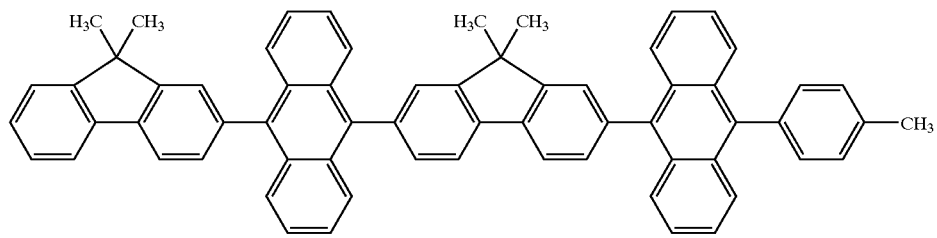
F-1
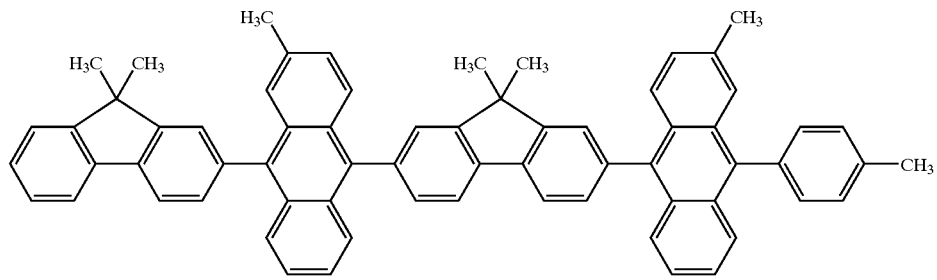
F-2
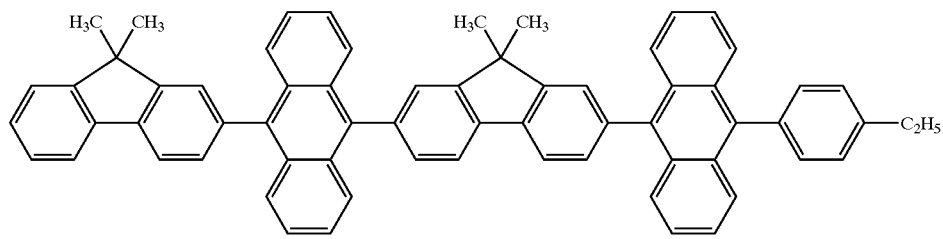
F-3
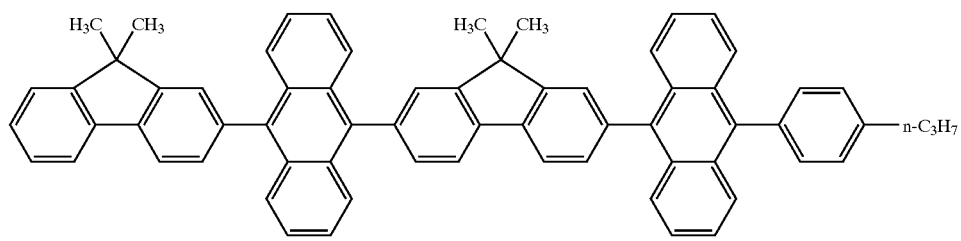
F-4

-continued
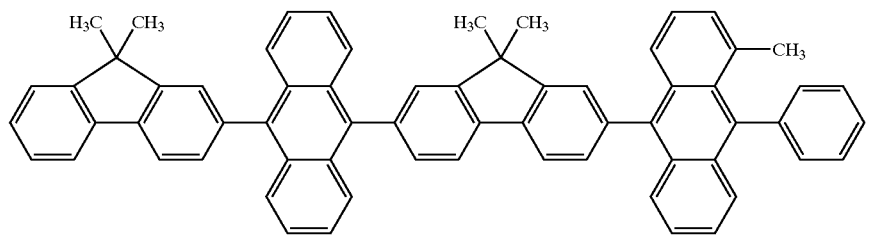
F-5
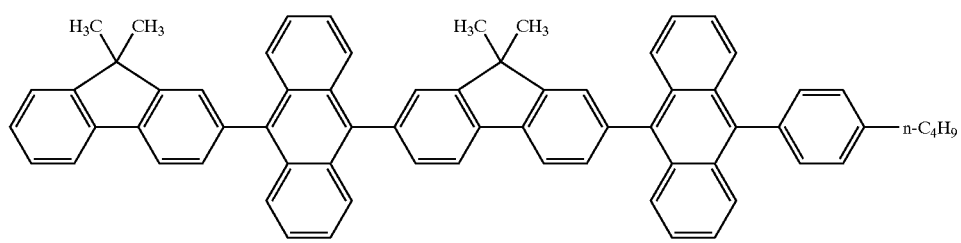
F-6
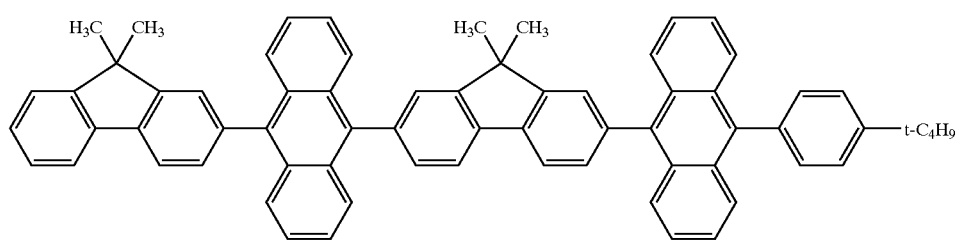
F-7
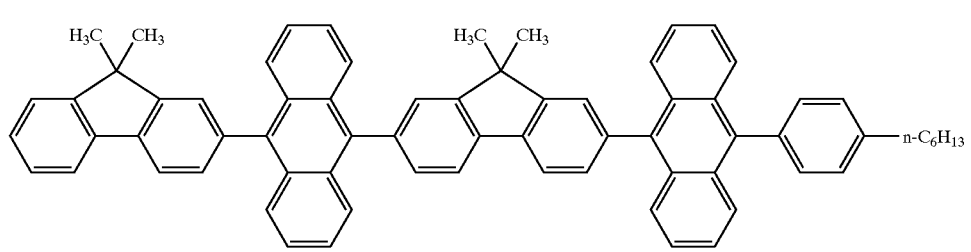
F-8
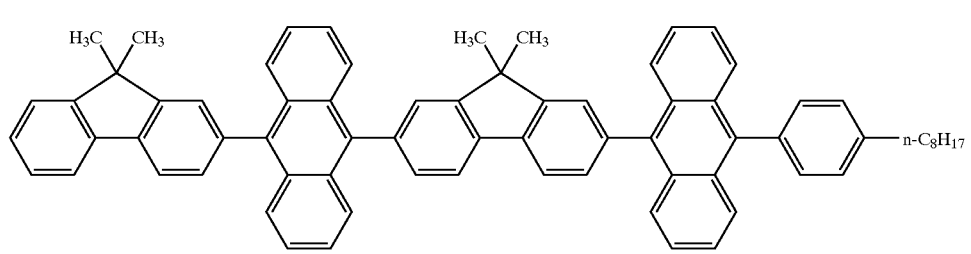
F-9
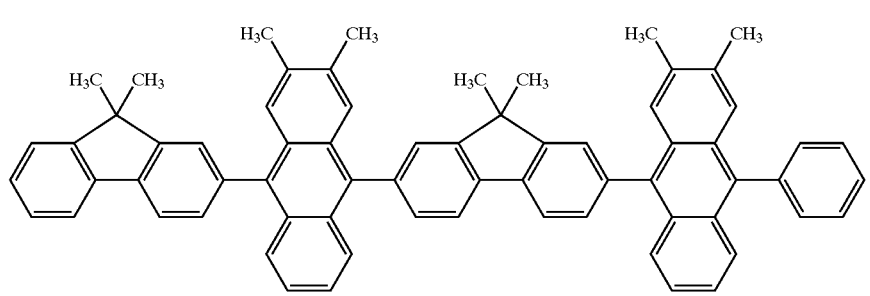
F-10

-continued
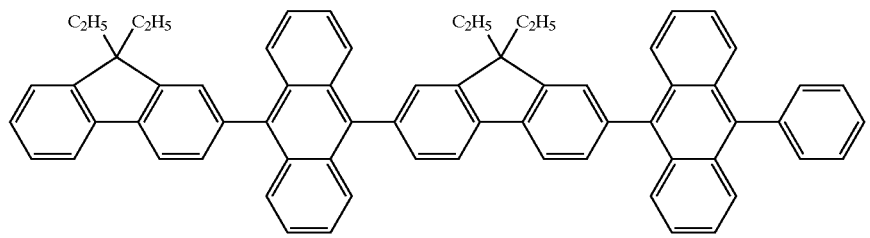
F-11
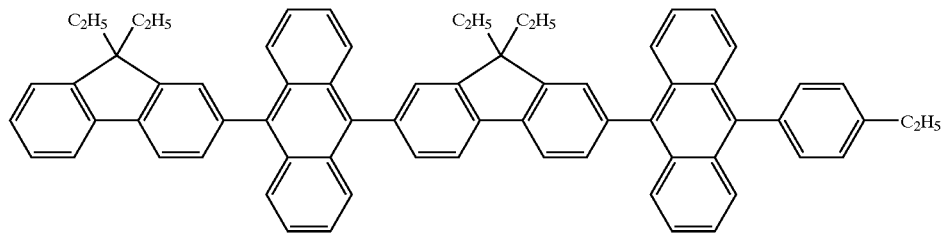
F-12
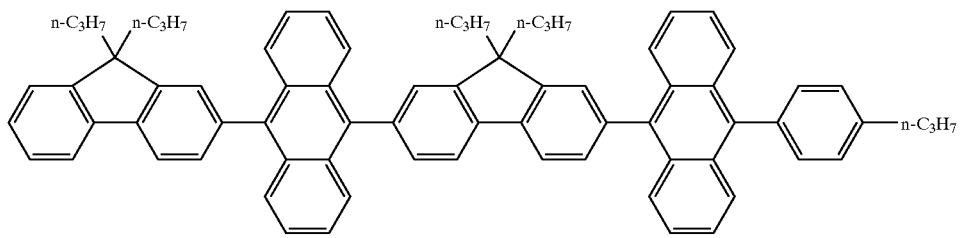
F-13
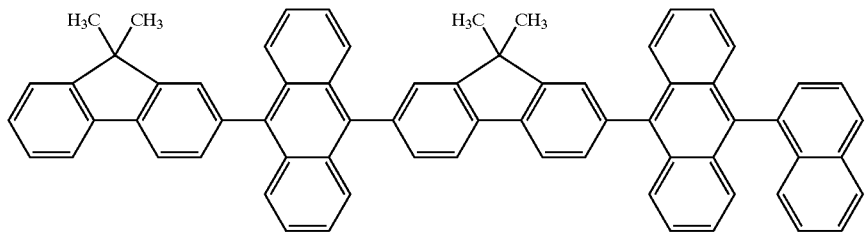
F-14
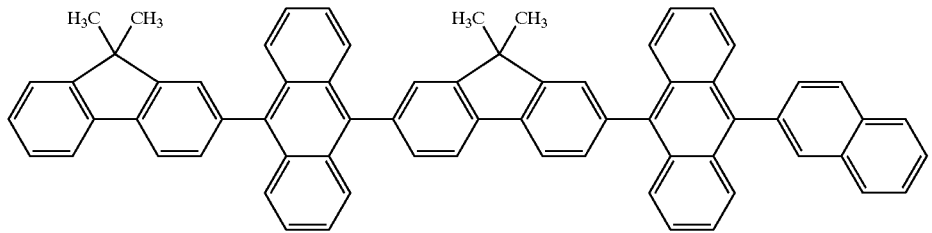
F-15
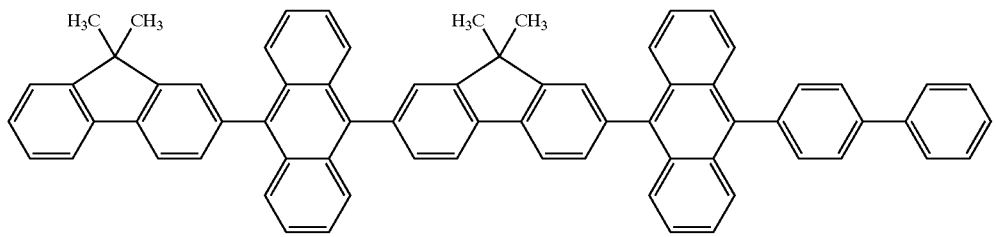
F-16

-continued
F-17
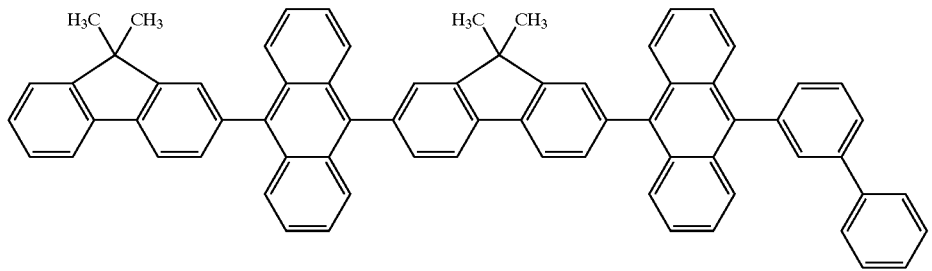
F-18
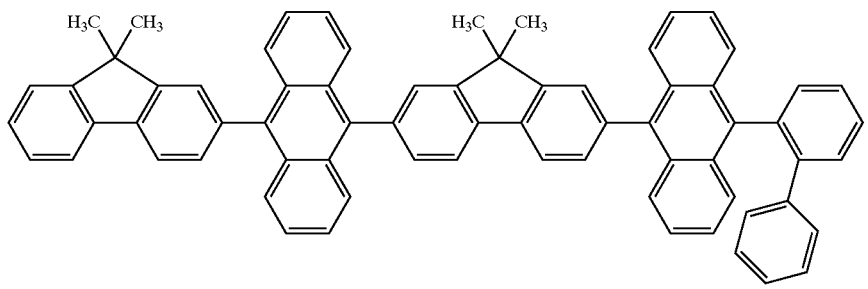
F-19
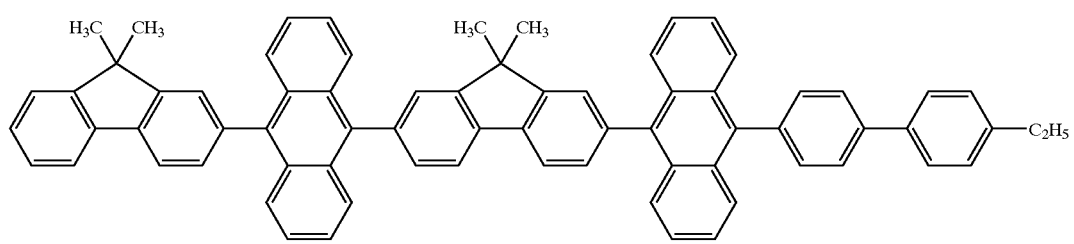
F-20
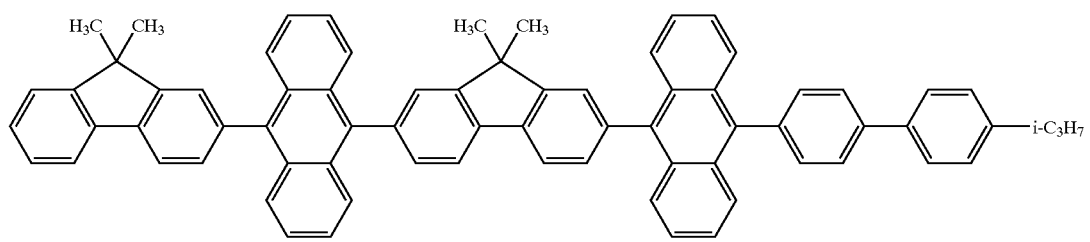
F-21
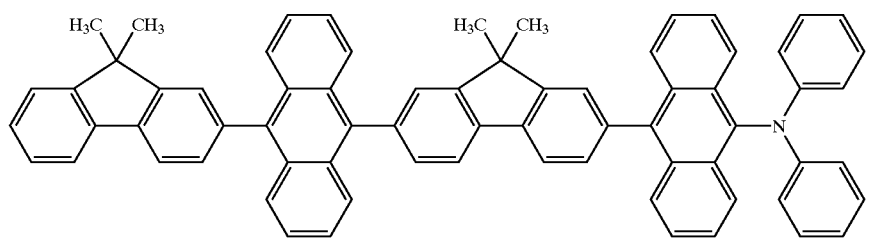
F-22
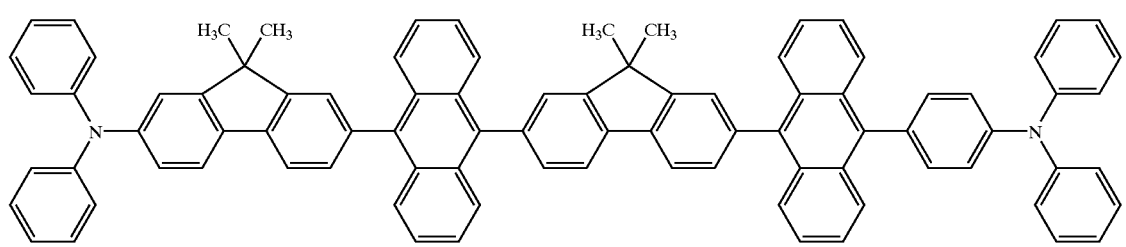

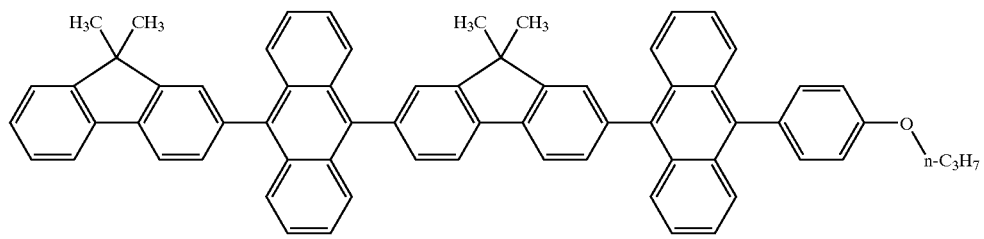
F-23
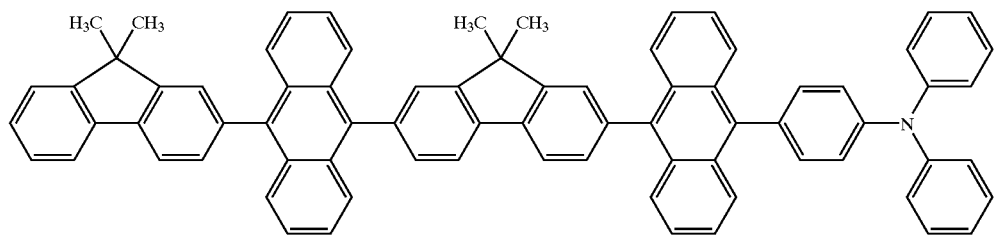
F-24
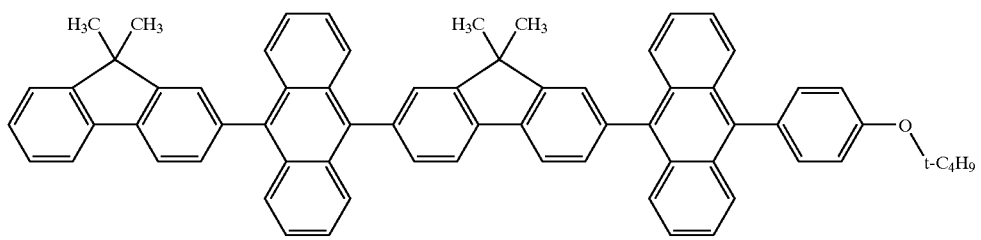
F-25
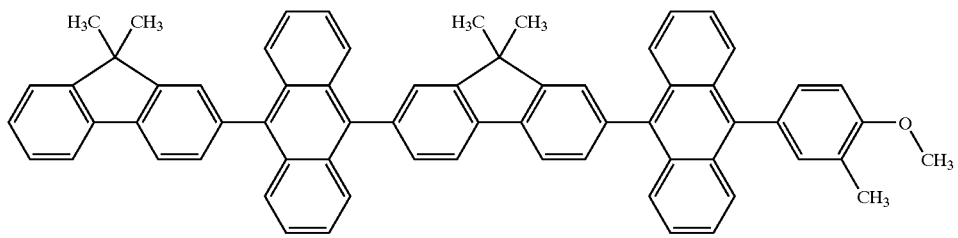
F-26
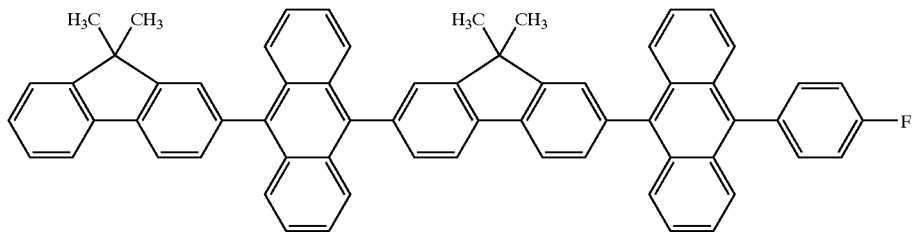
F-27
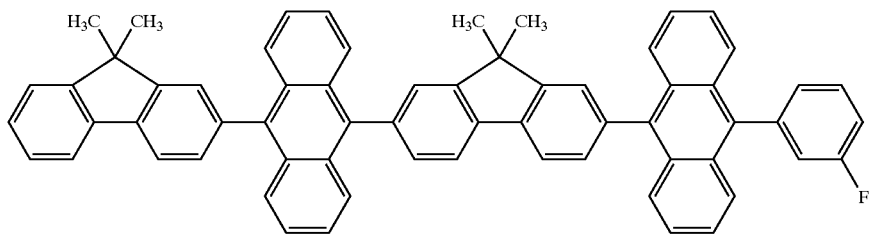
F-28

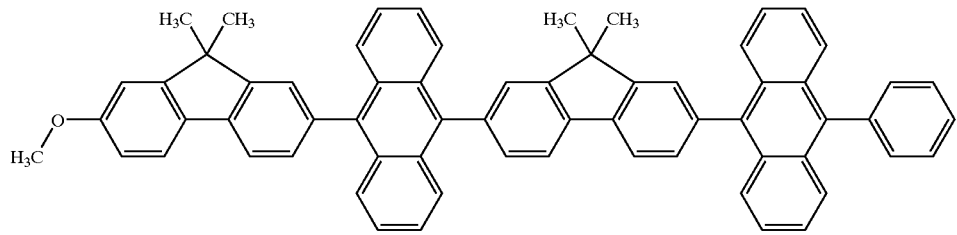
F-29
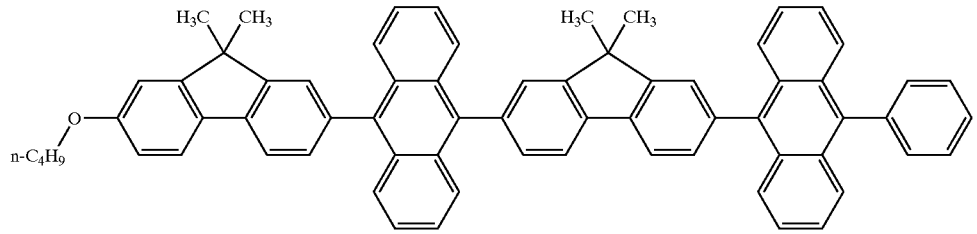
F-30
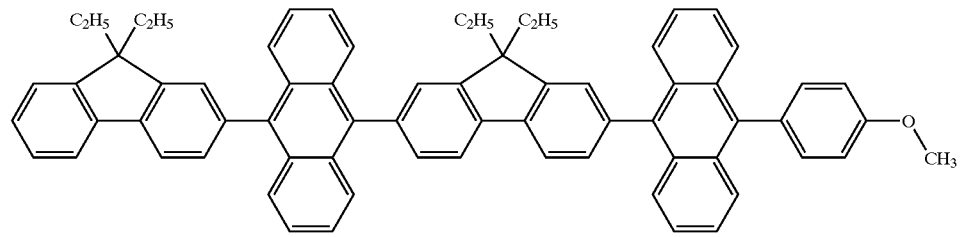
F-31
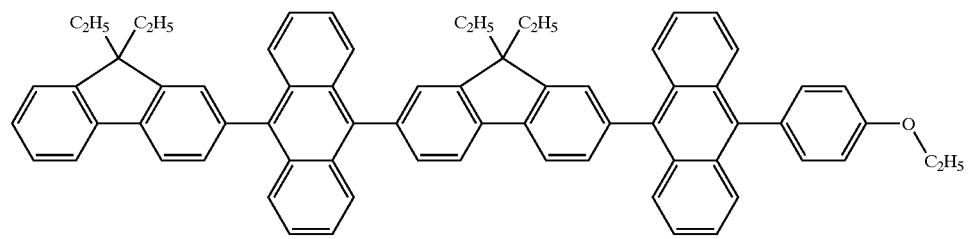
F-32
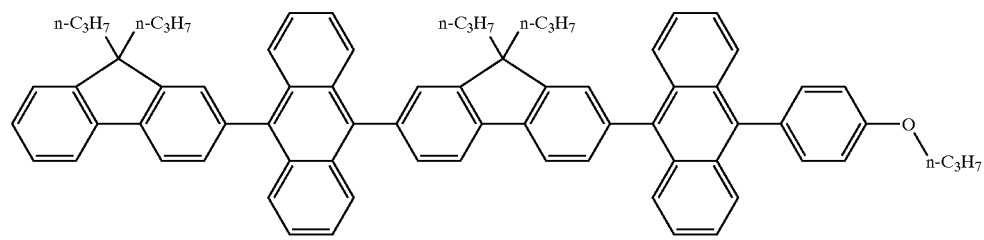
F-33
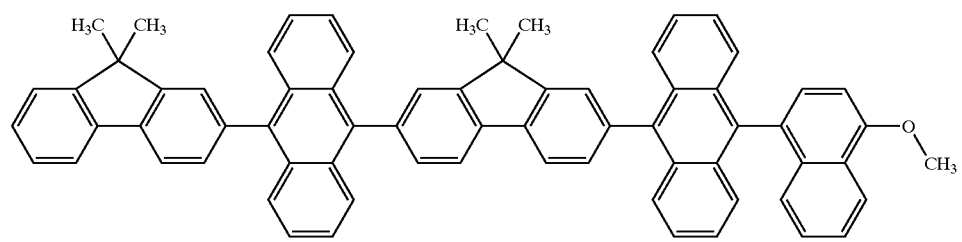
F-34

-continued
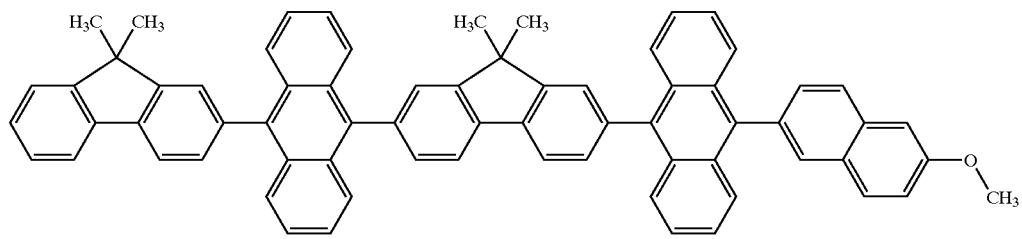
F-35
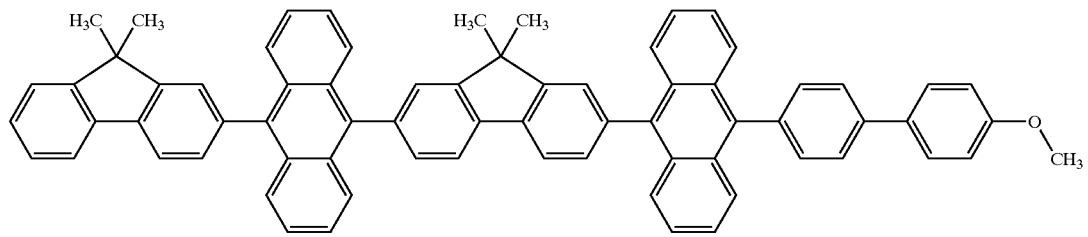
F-36
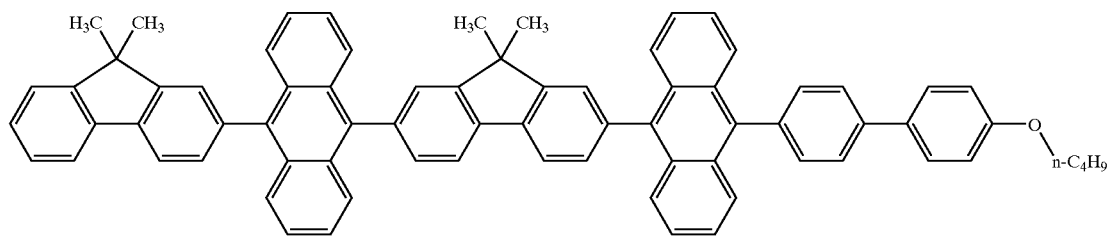
F-37
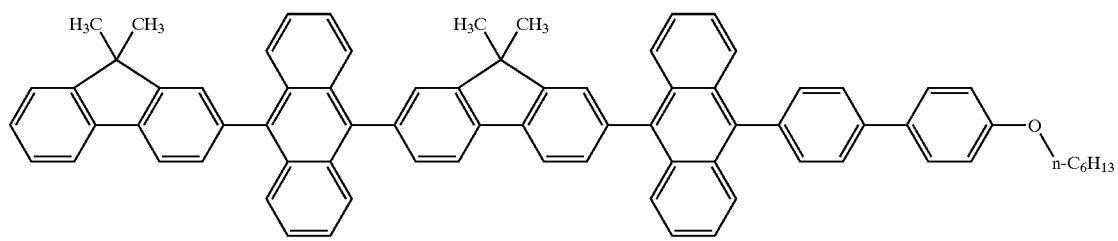
F-38
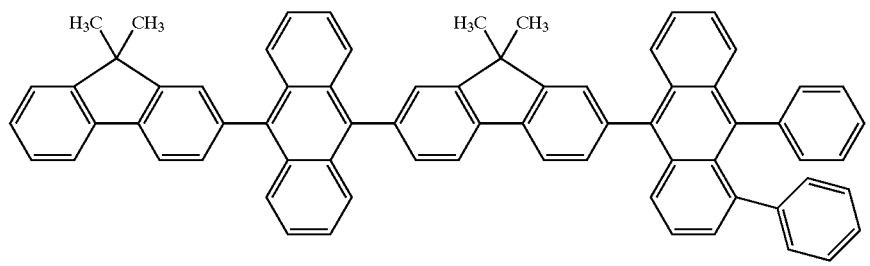
F-39
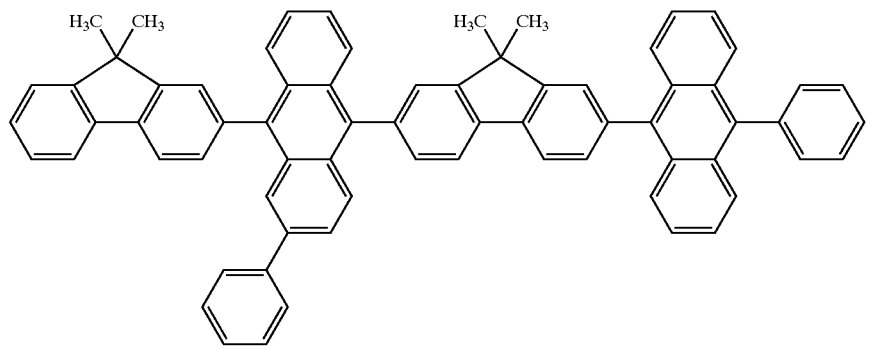
F-40

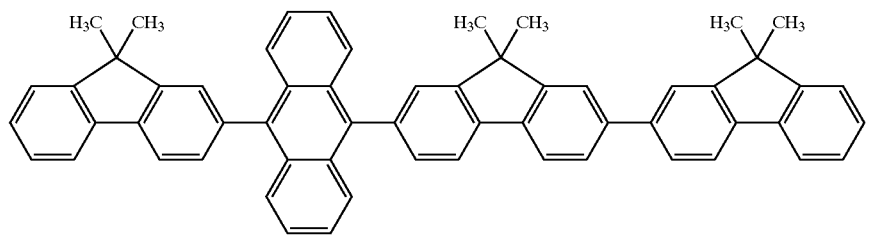
G-1
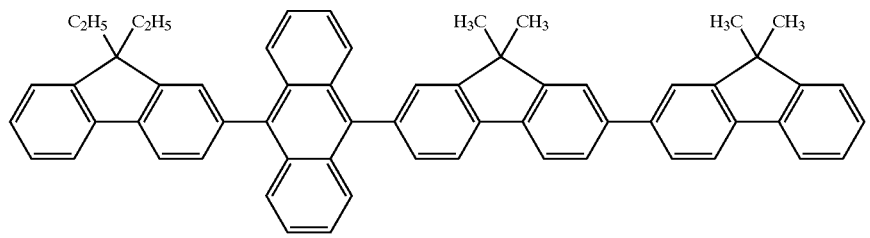
G-2
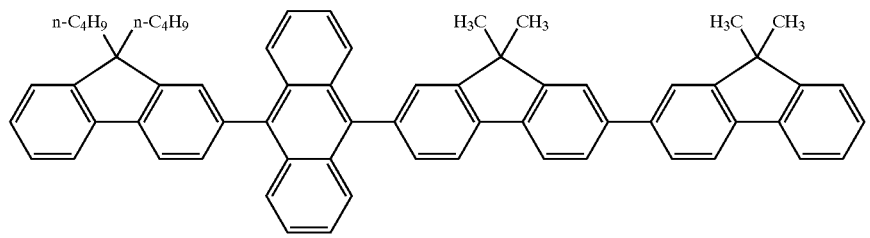
G-3
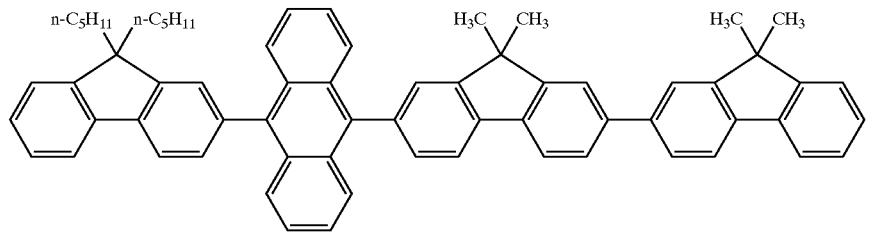
G-4
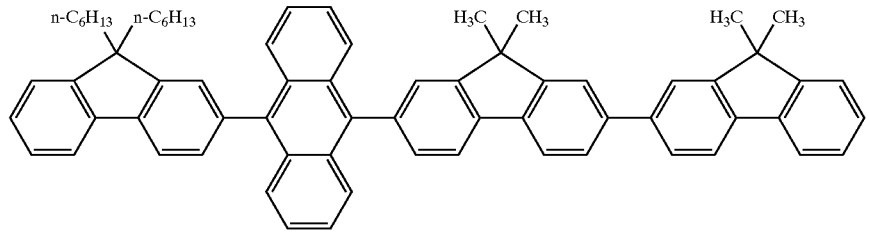
G-5
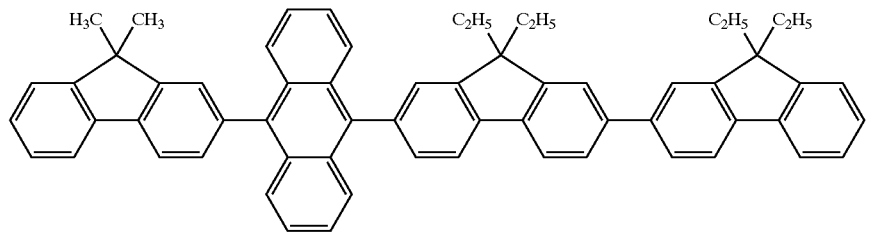
G-6

-continued
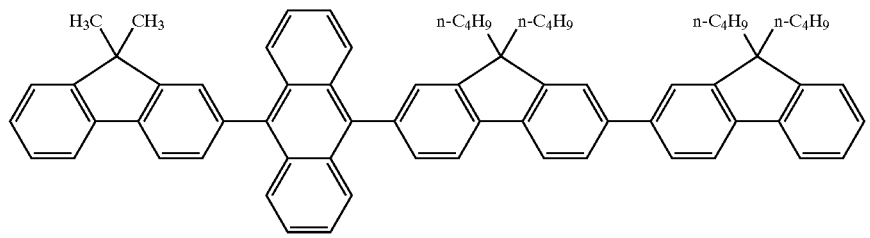
G-7
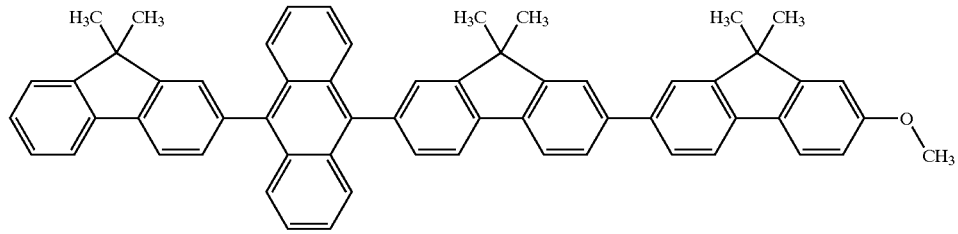
G-8
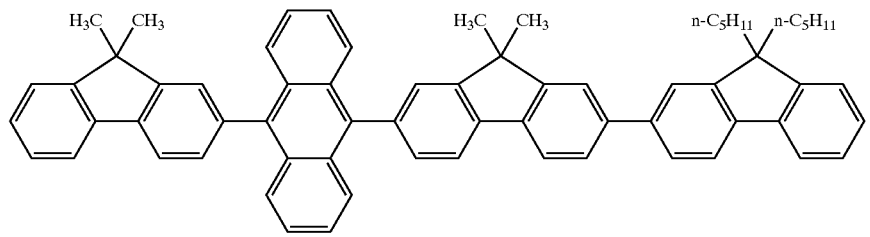
G-9
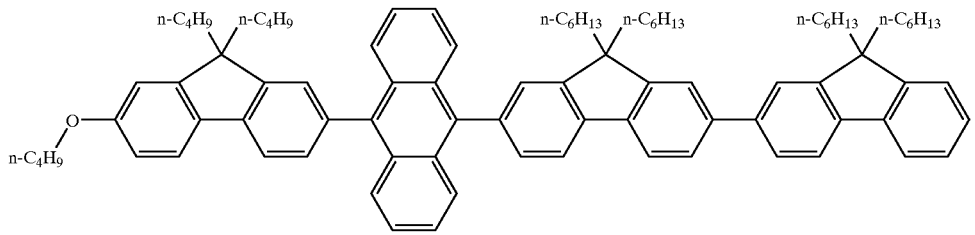
G-10
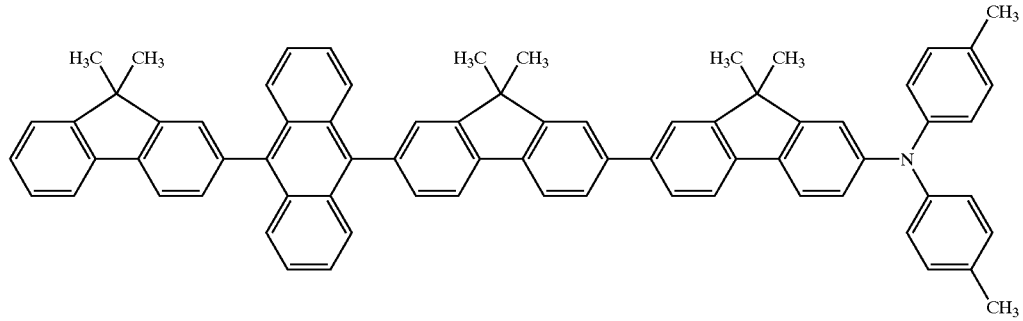
G-11
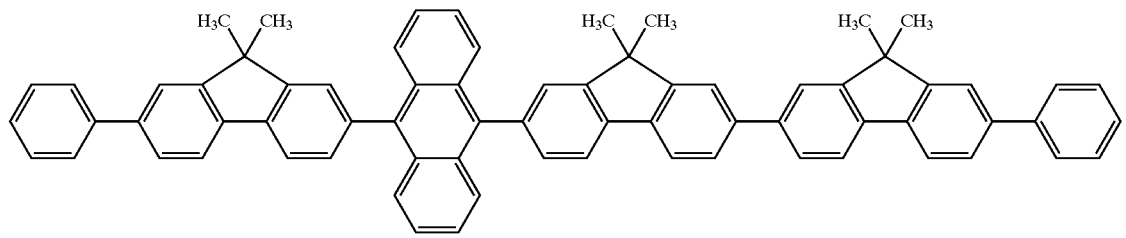
G-12

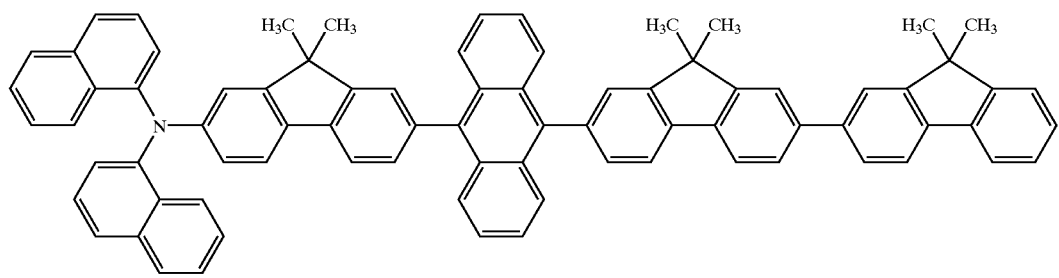
G-13
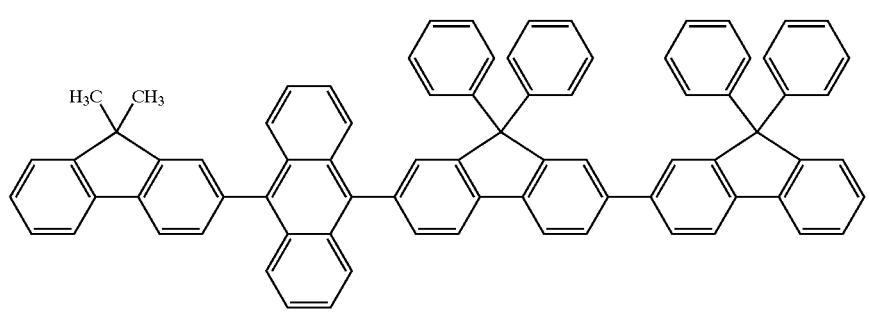
G-14
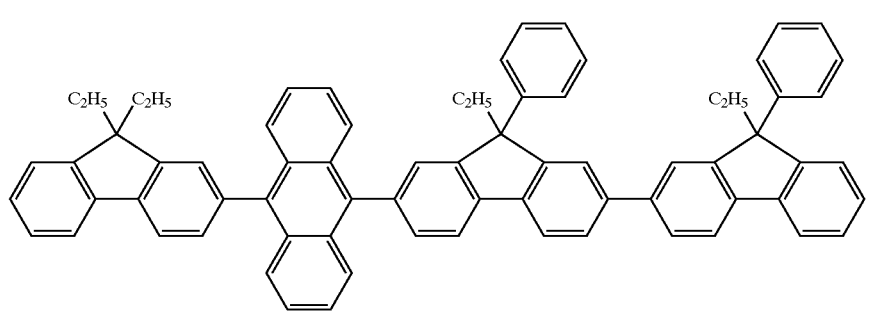
G-15
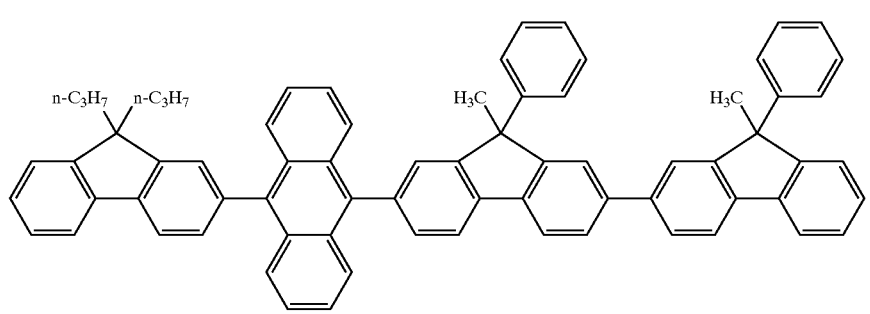
G-16
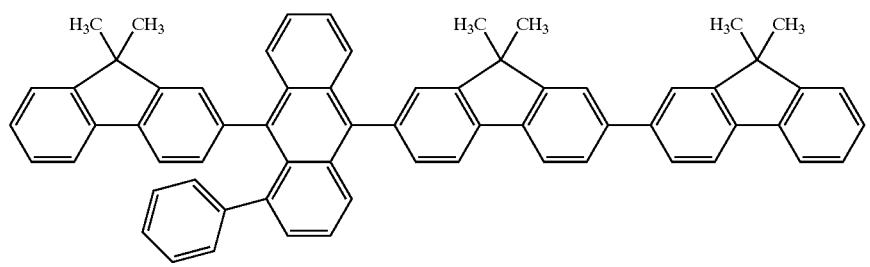
G-17

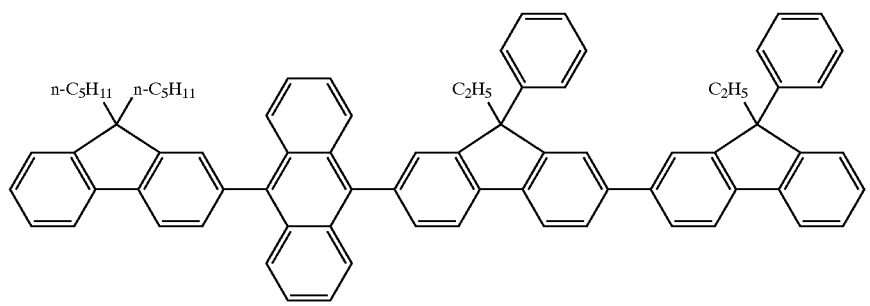
G-18
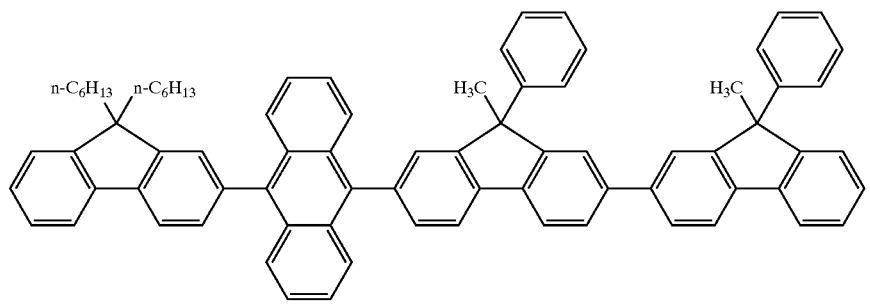
G-19
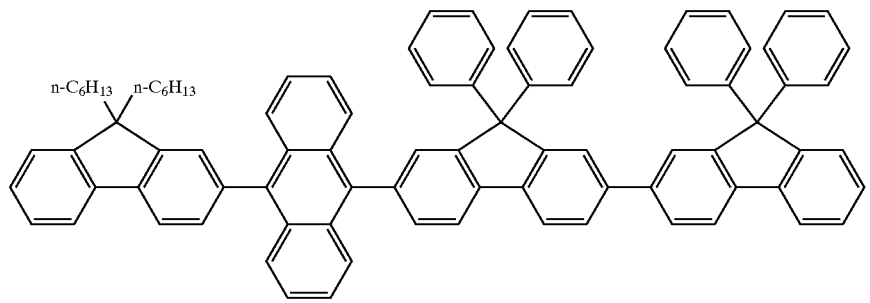
G-20
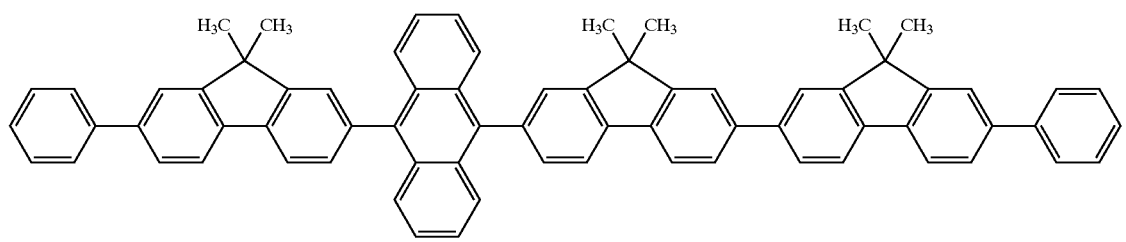
G-21
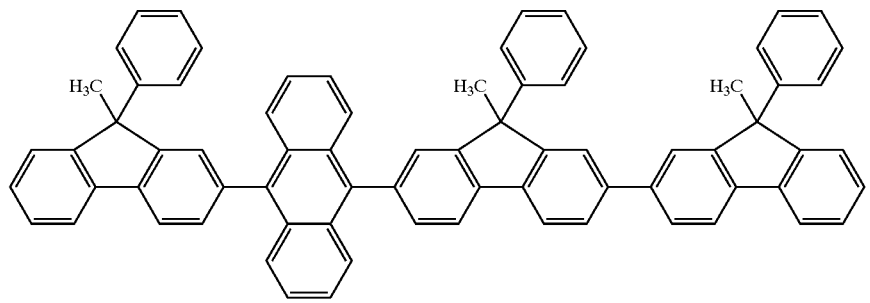
G-22

-continued
G-23
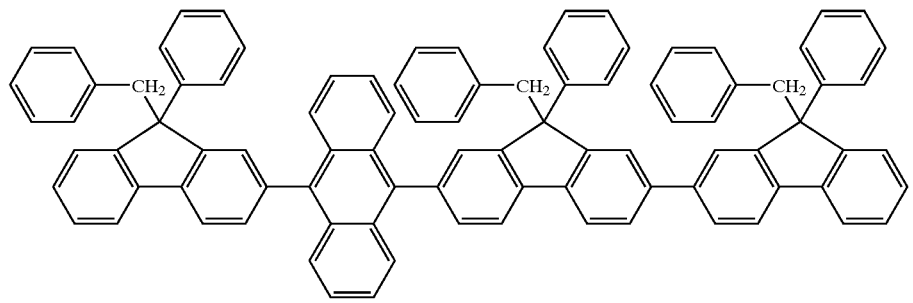
G-24
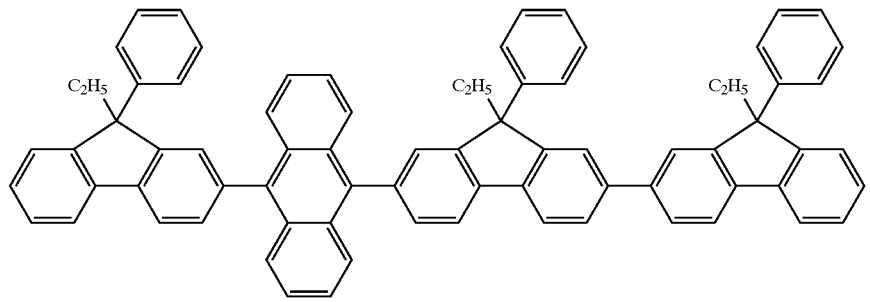
G-25
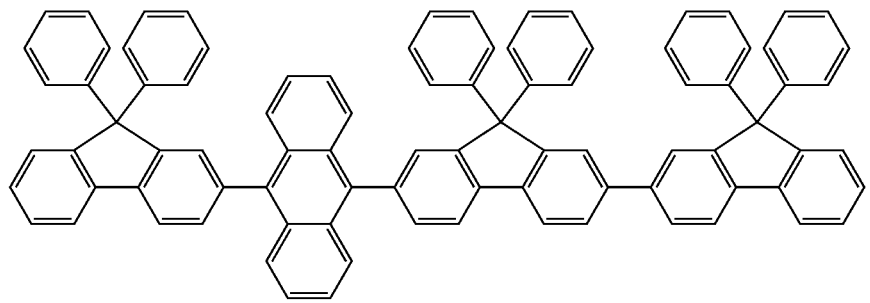
H-1　　　　　　　　　　　　　　　H-2
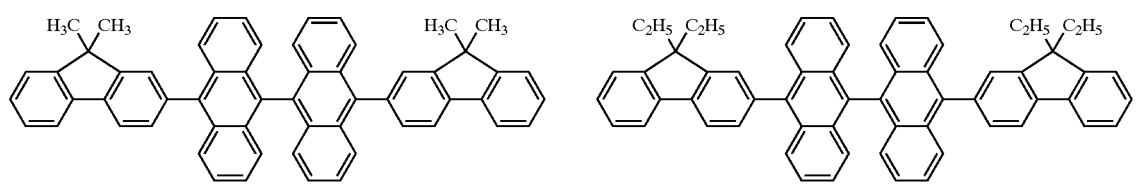
H-3　　　　　　　　　　　　　　　H-4
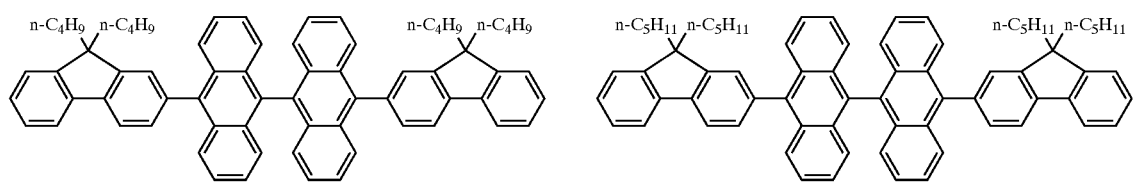
H-5　　　　　　　　　　　　　　　H-6
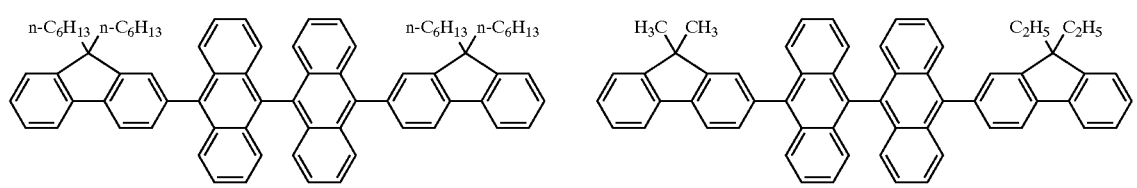

-continued
H-7
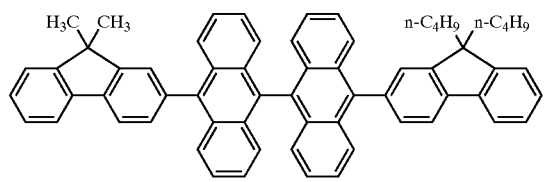
H-8
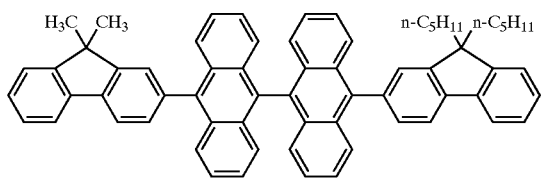
H-9
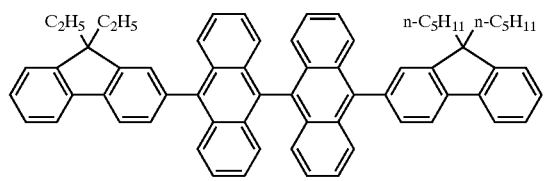
H-10
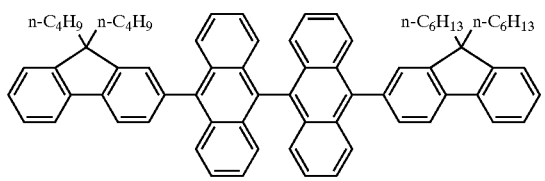
H-11
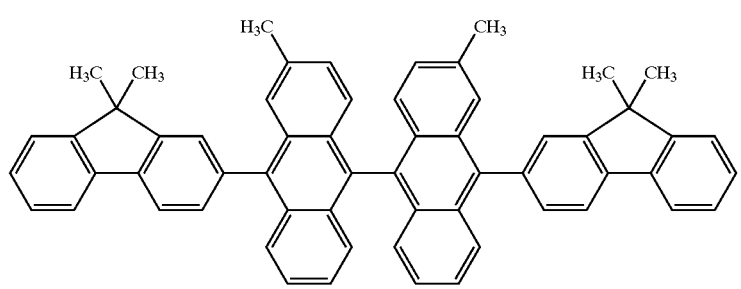
H-12
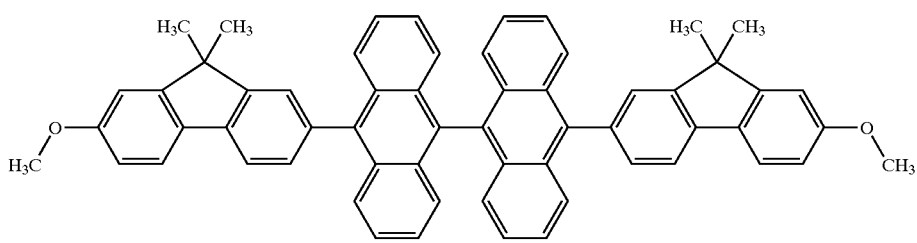
H-13
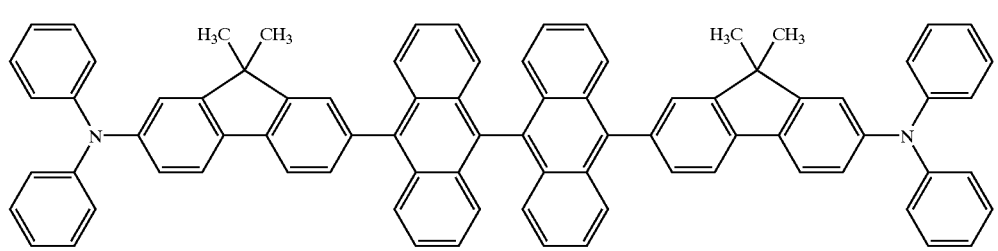
H-14
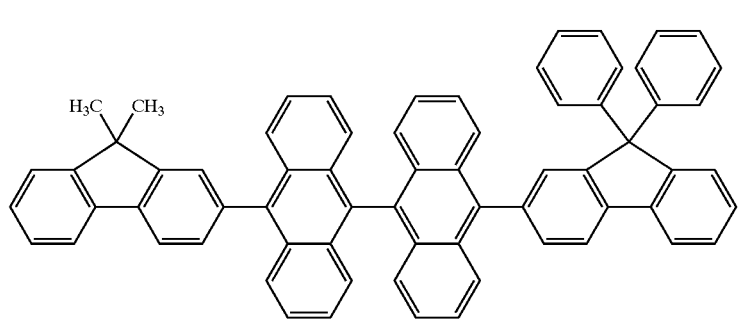

-continued
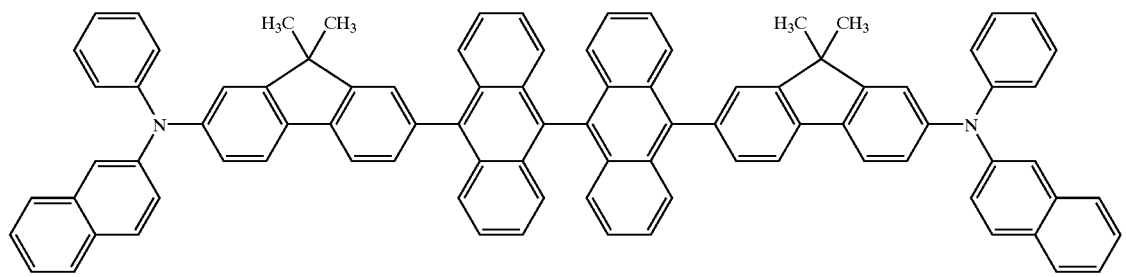
H-15
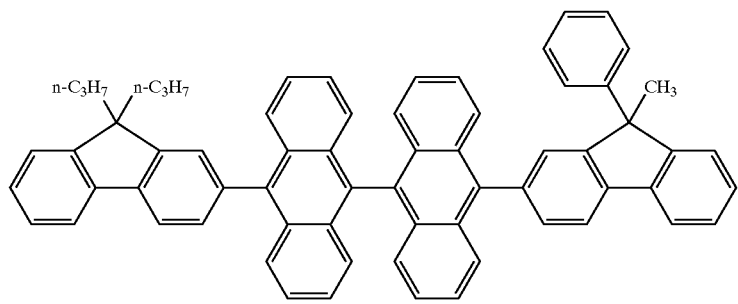
H-16
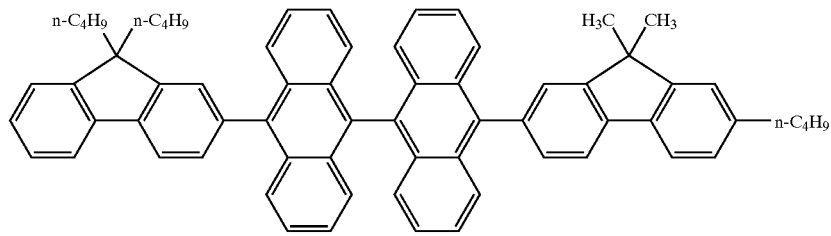
H-17
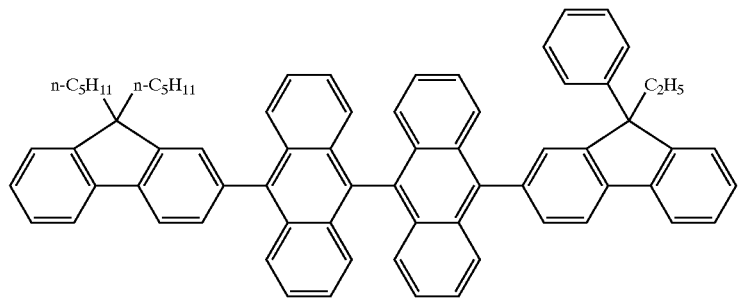
H-18
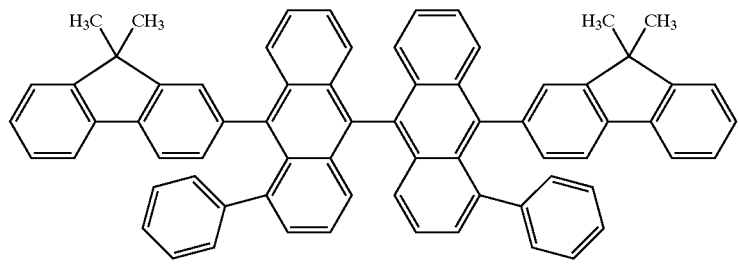
H-19

-continued
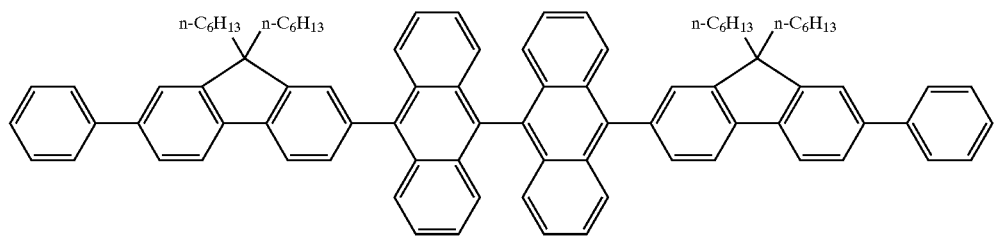
H-20
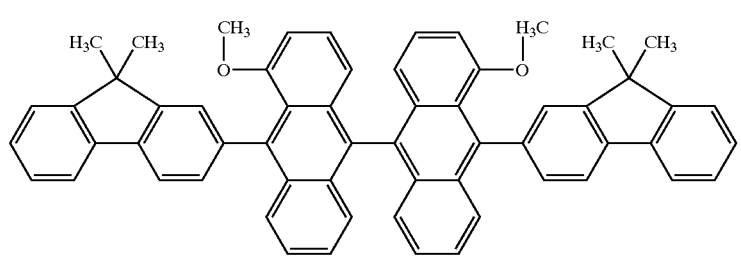
H-21
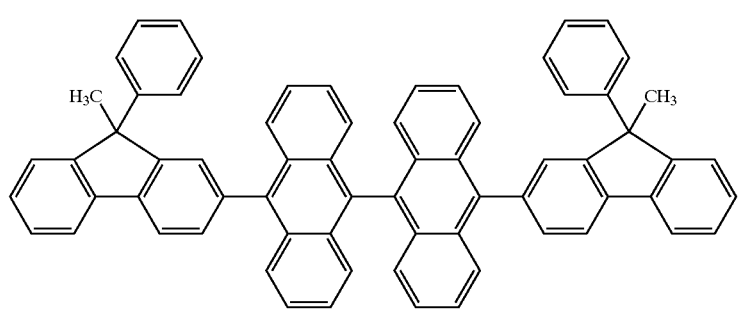
H-22
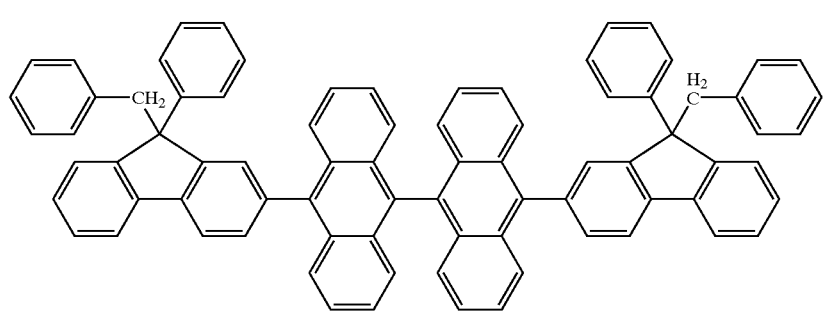
H-23
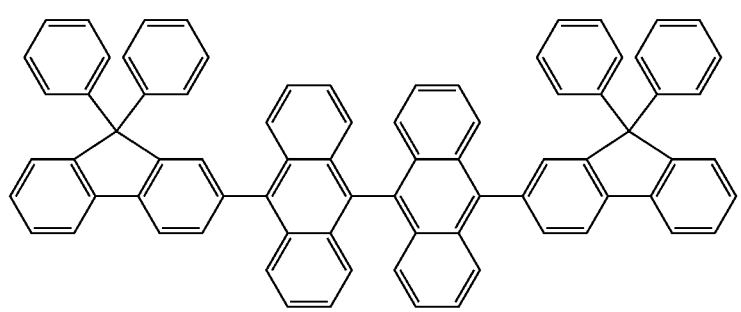
H-24

H-25
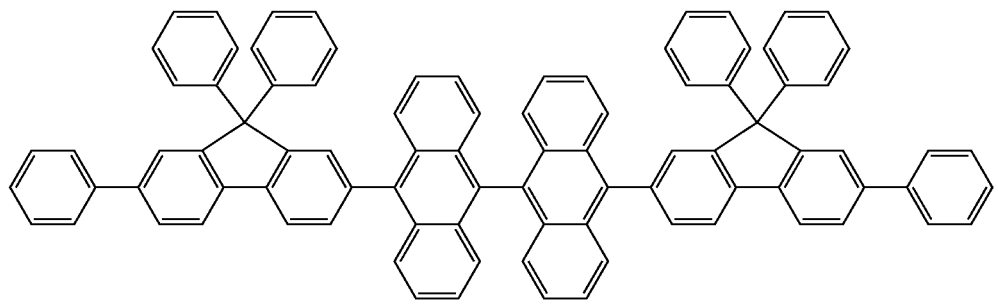
I-1
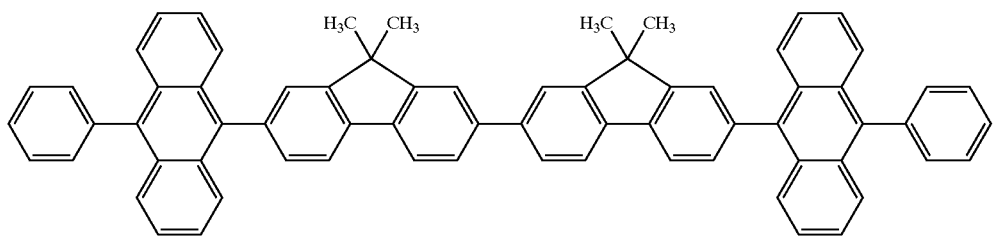
I-2
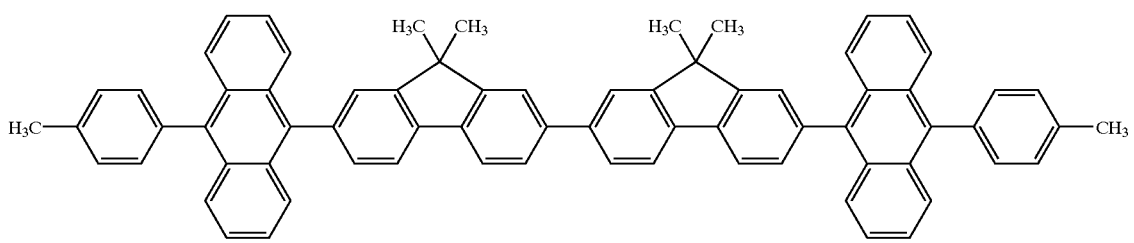
I-3
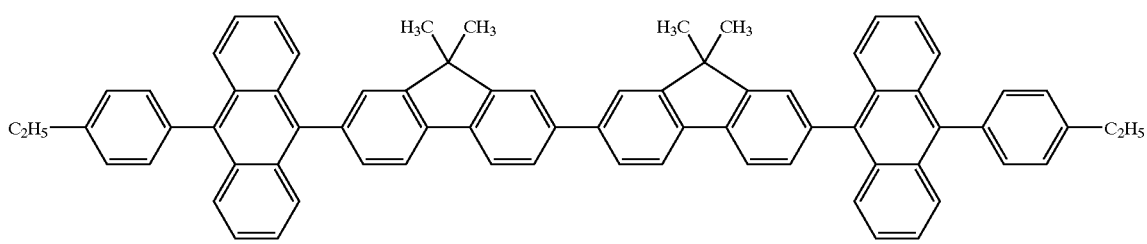
I-4
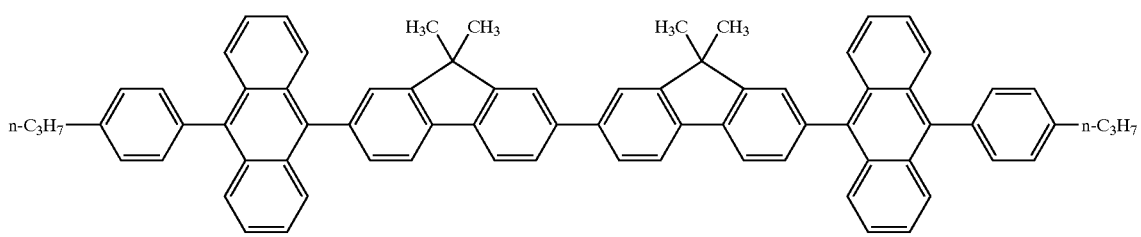
I-5
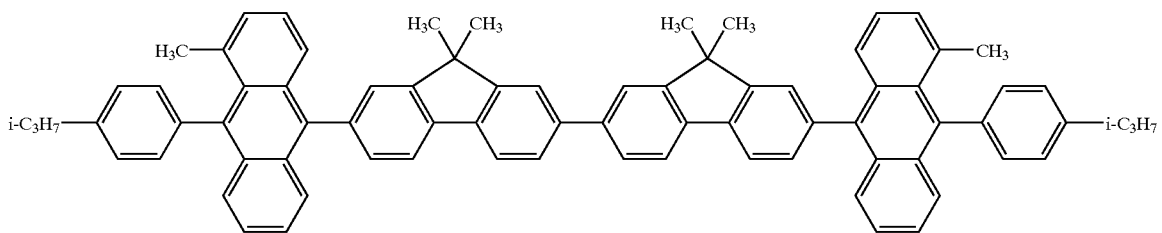

-continued
I-6
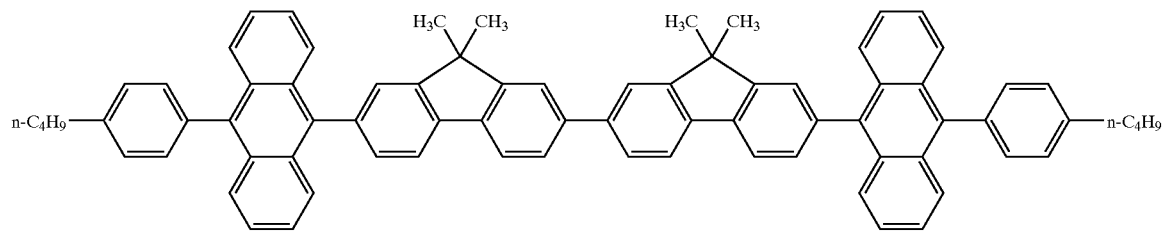
I-7
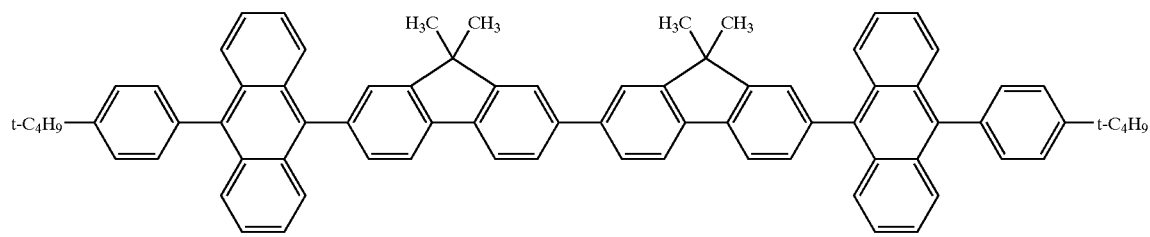
I-8
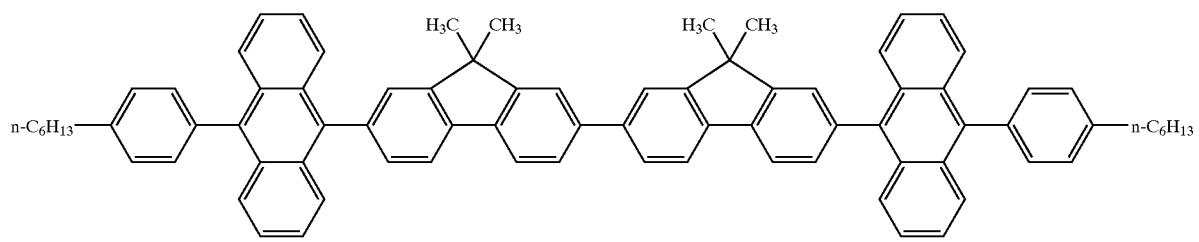
I-9
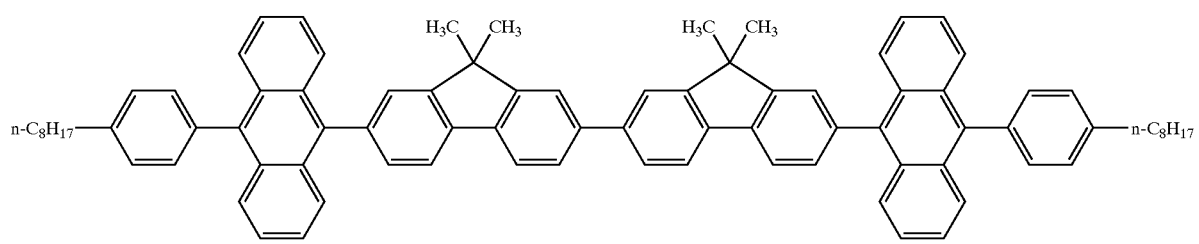
I-10
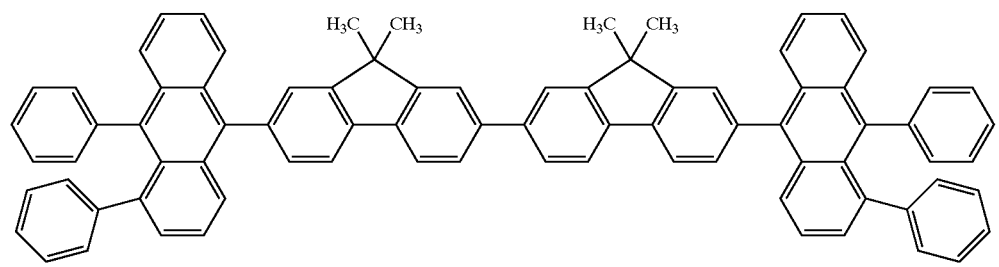
I-11
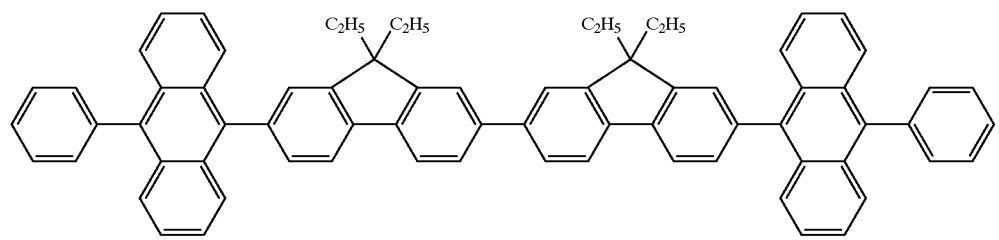

-continued
I-12
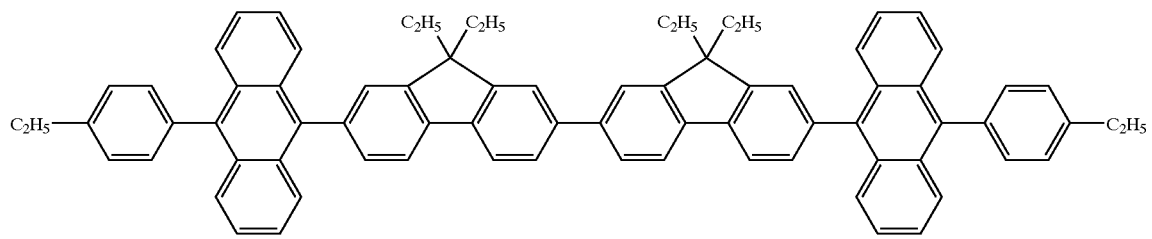
I-13
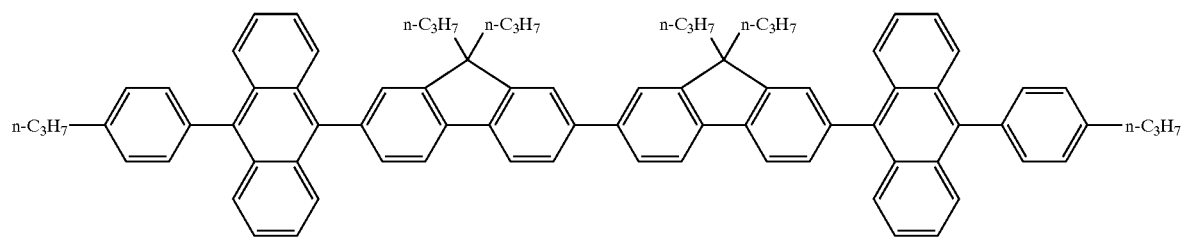
I-14
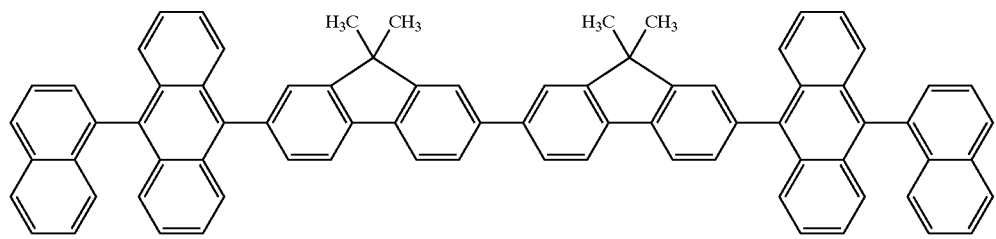
I-15
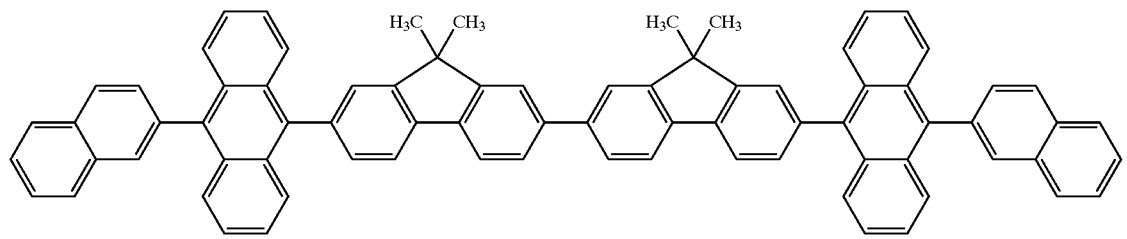
I-16
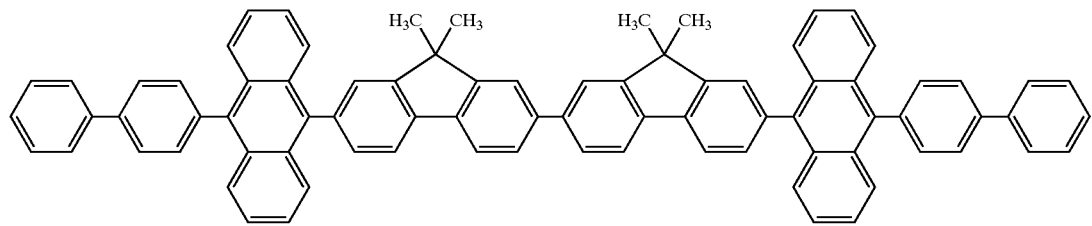
I-17
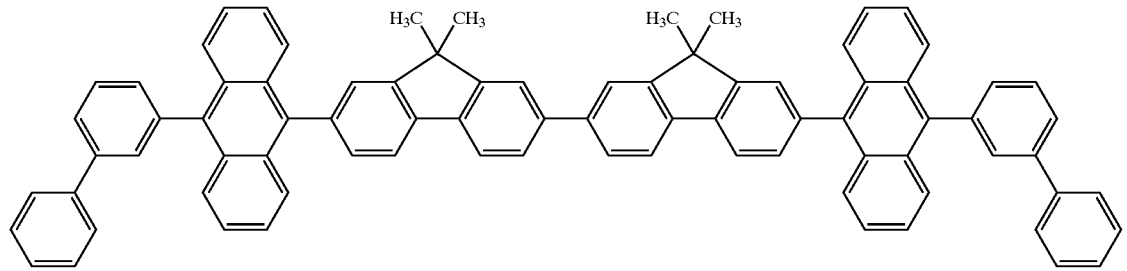

-continued
I-18
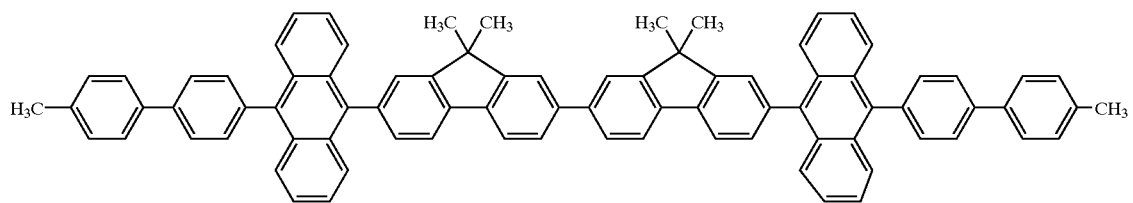
I-19
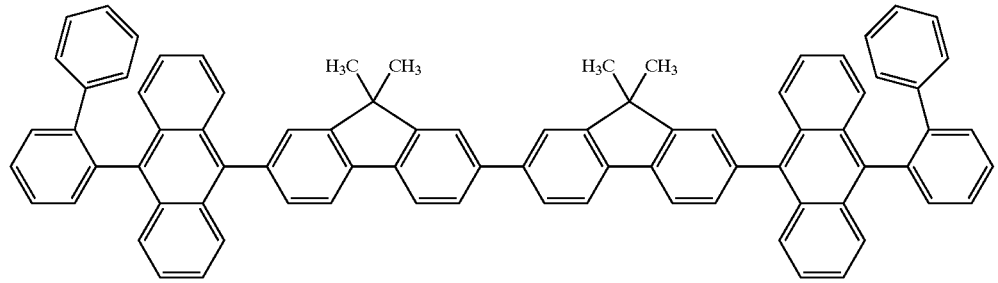
I-20
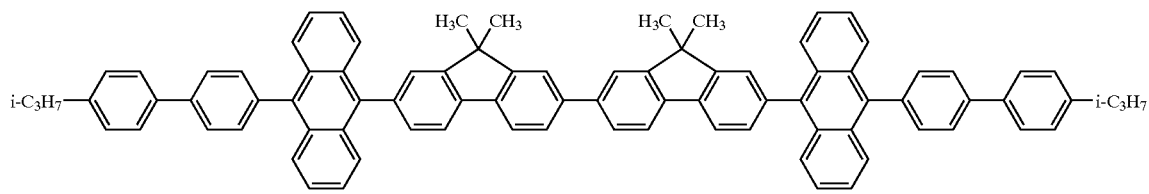
I-21
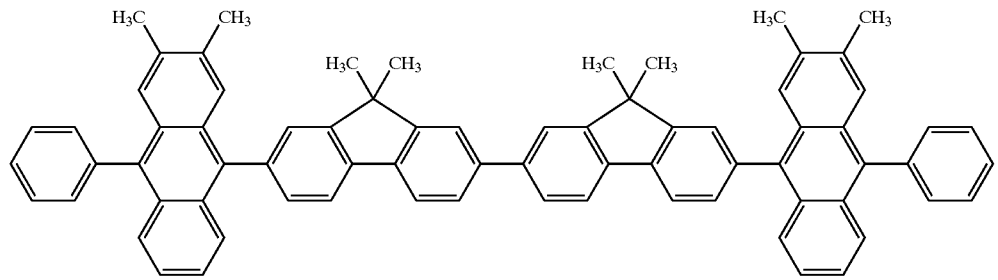
I-22
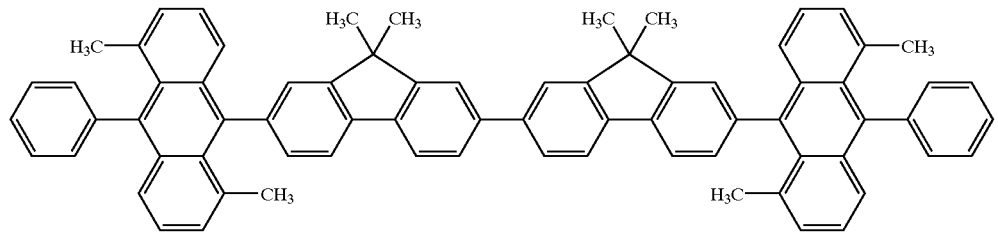
I-23
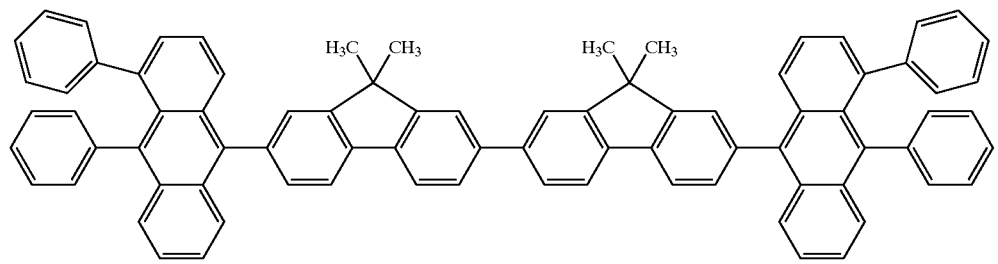

-continued
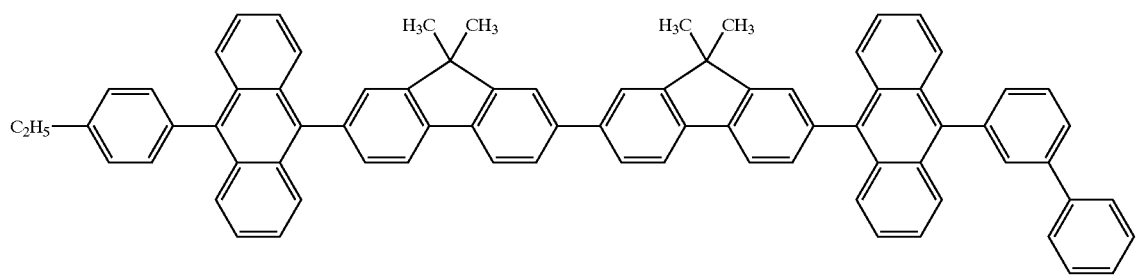
I-24
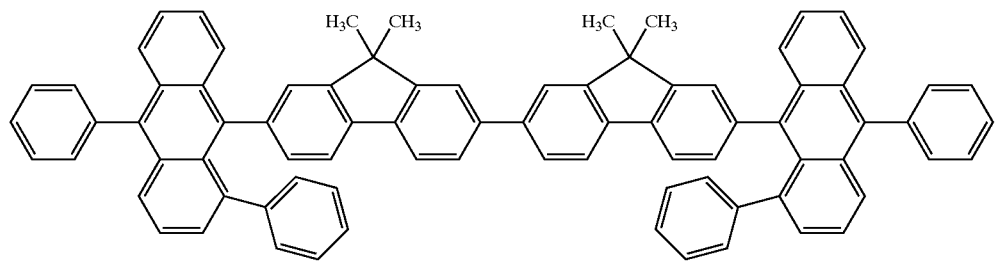
I-25
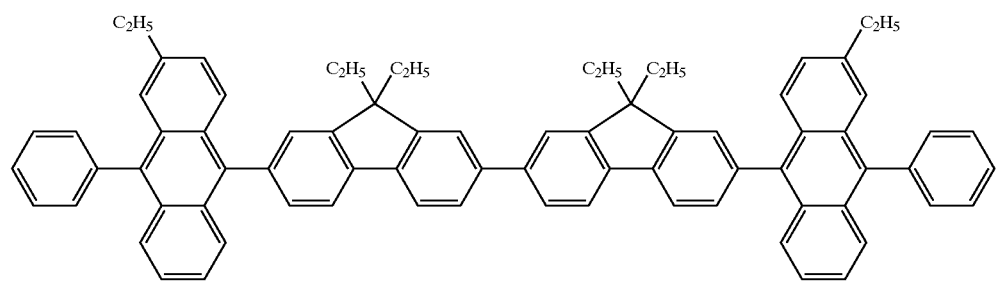
I-26
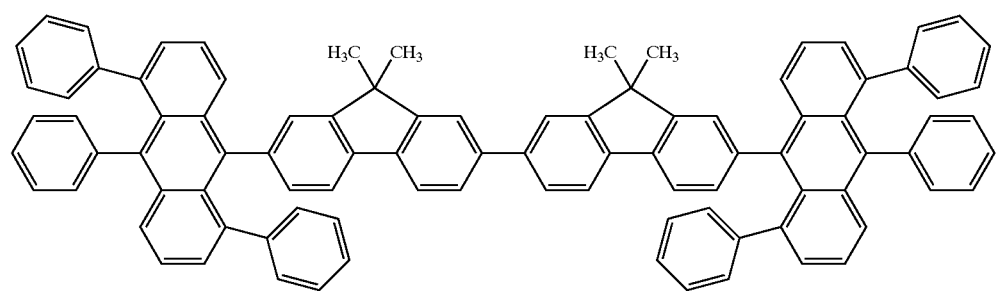
I-27
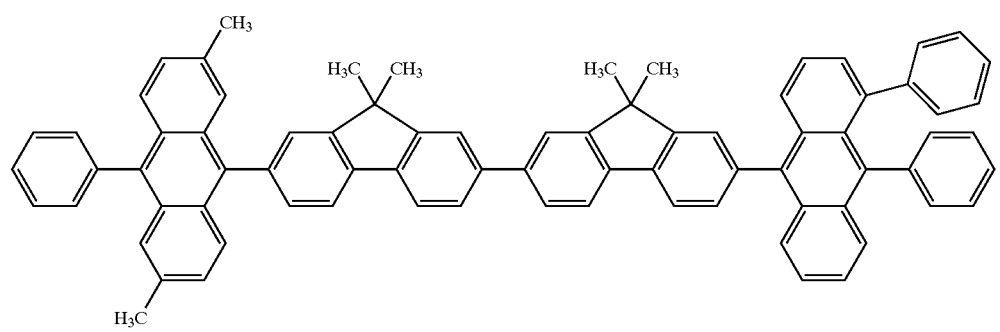
I-28

I-29
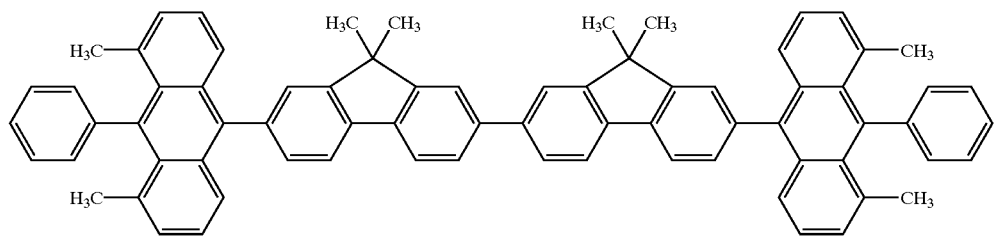
I-30
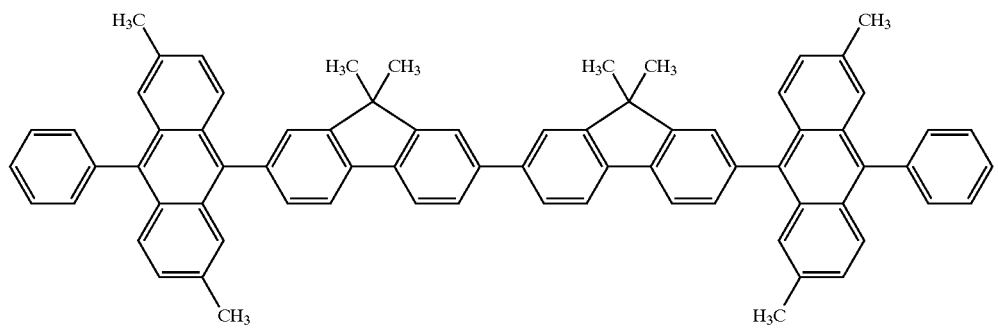
I-31
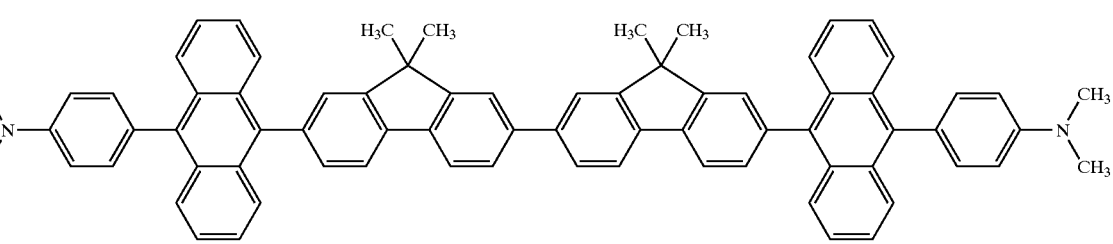
I-32
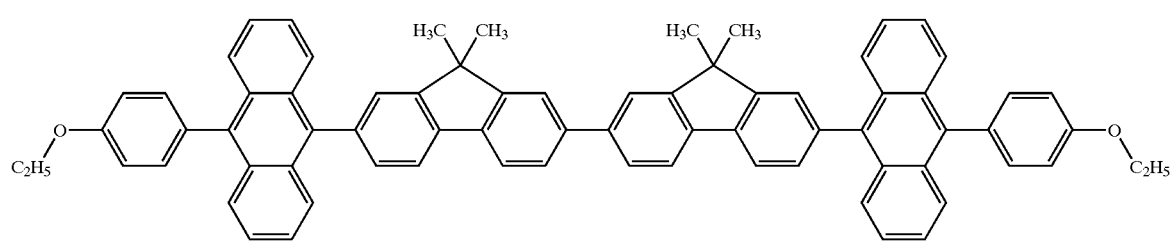
I-33
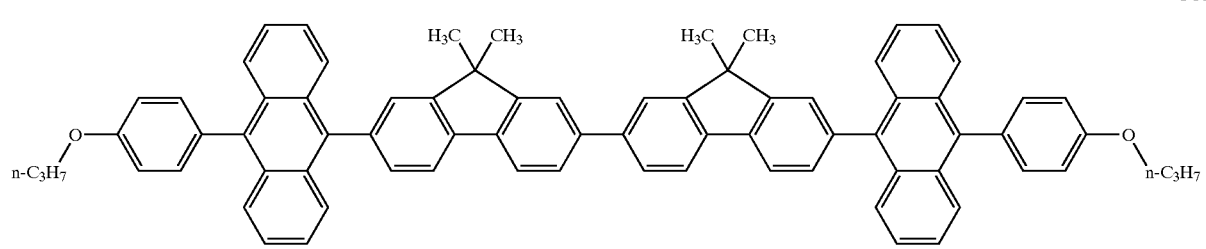
I-34
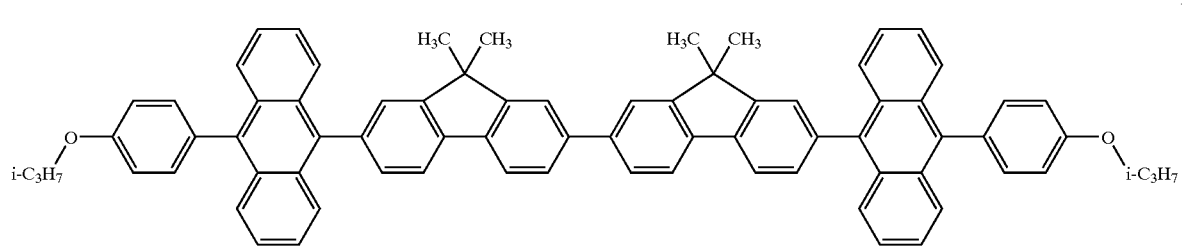

-continued
I-35
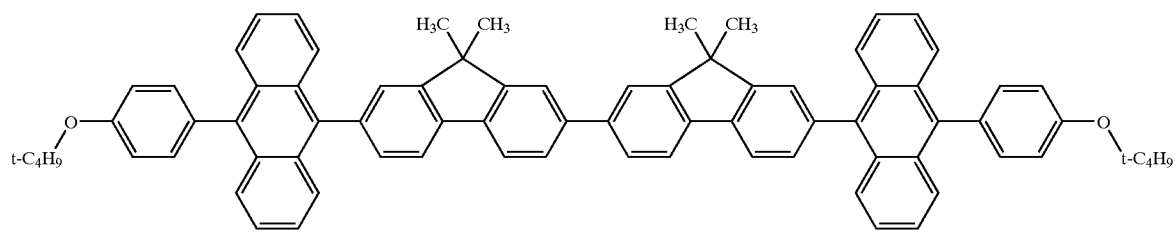
I-36
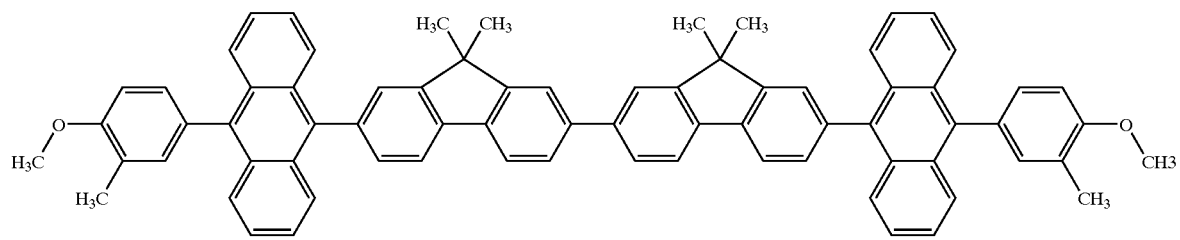
I-37
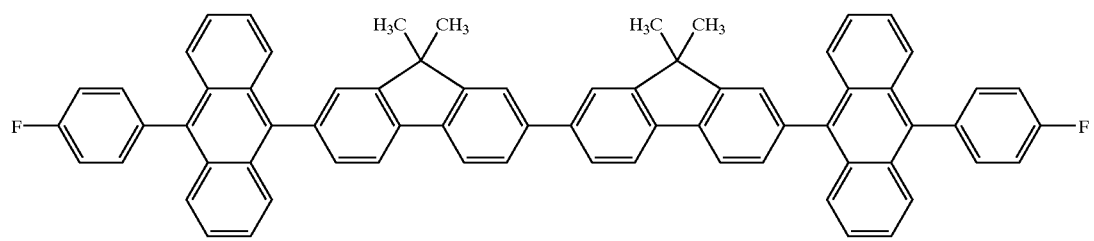
I-38
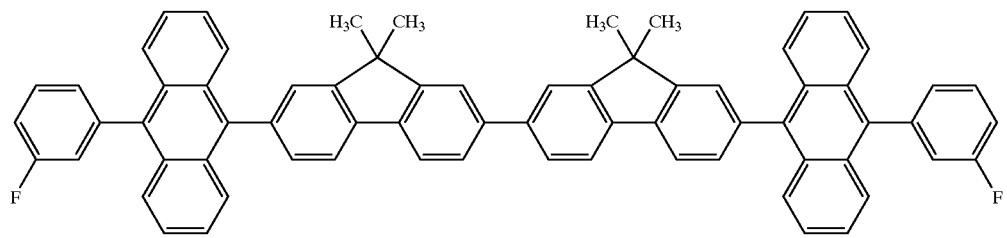
I-39
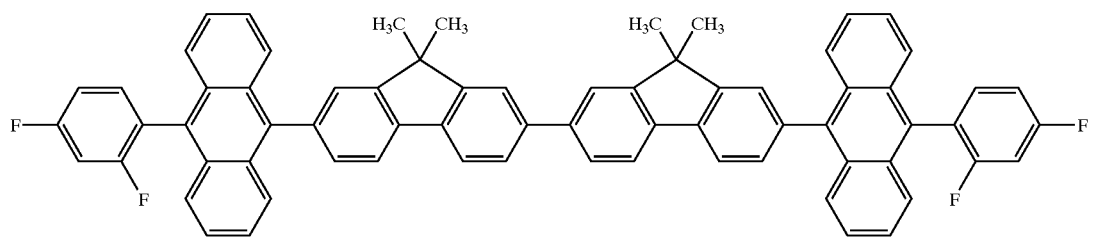
I-40
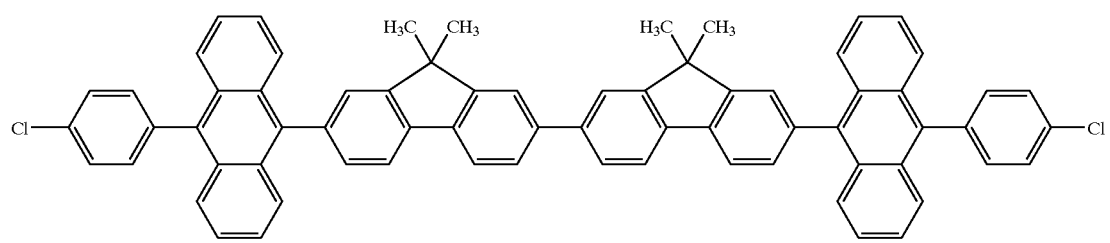

I-41
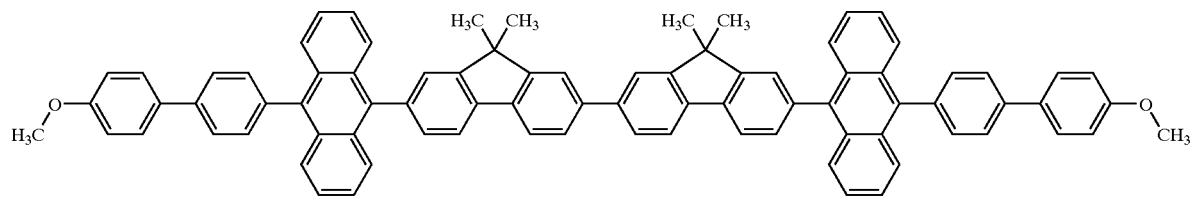
I-42
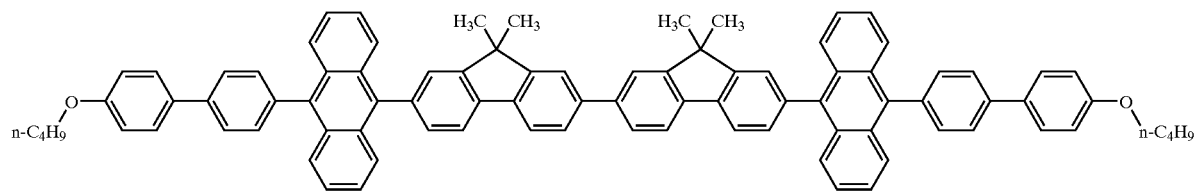
I-43
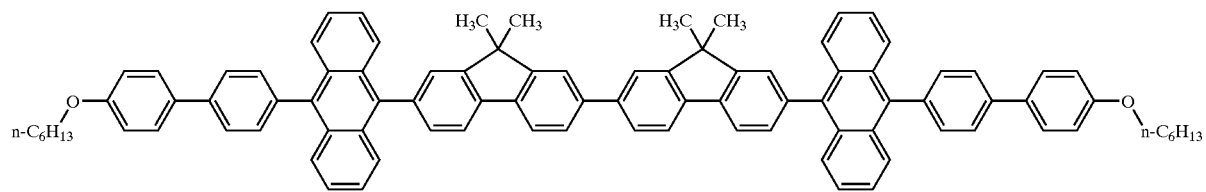
I-44
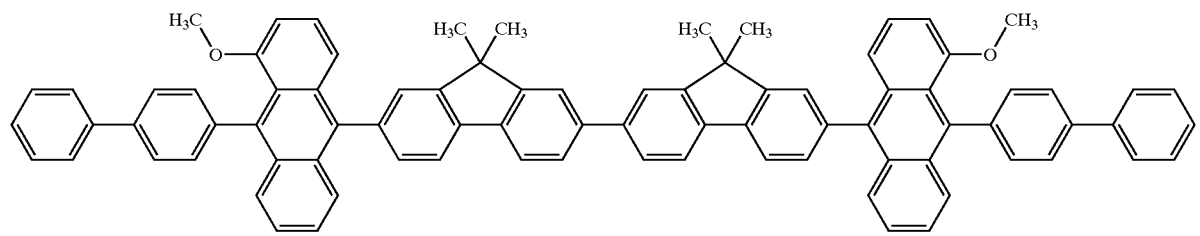
I-45
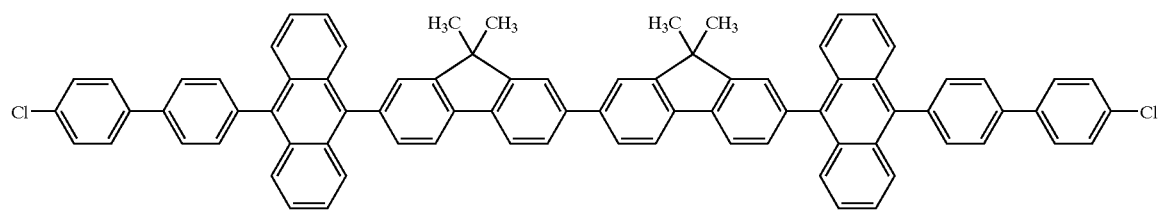
J-1
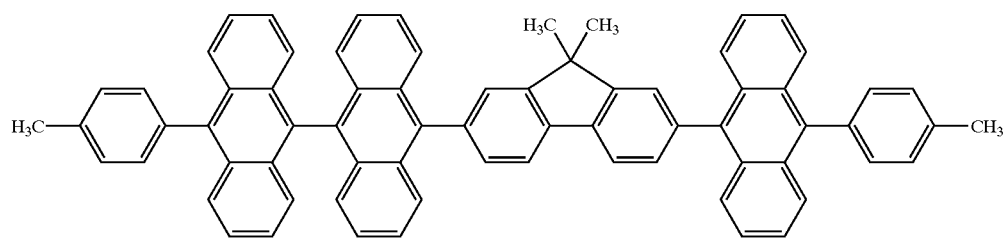

-continued
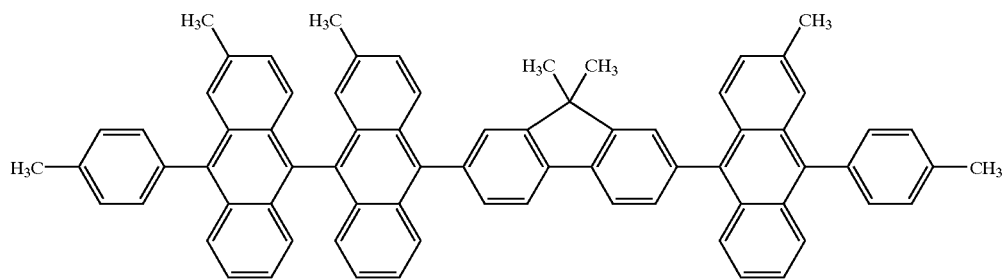
J-2
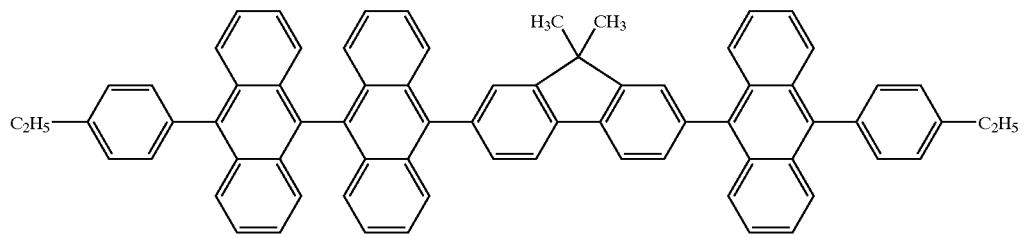
J-3
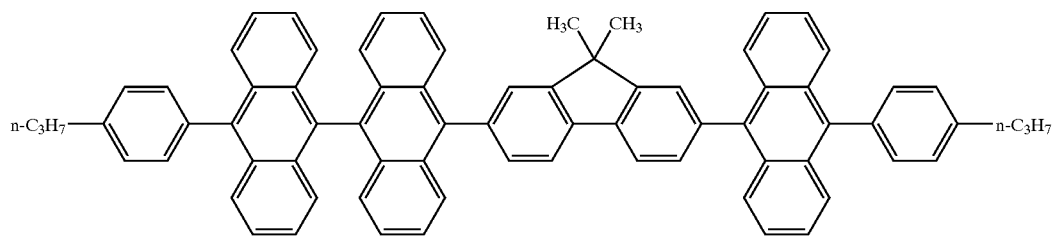
J-4
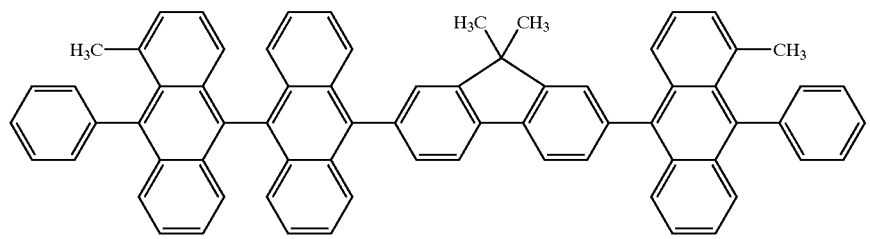
J-5
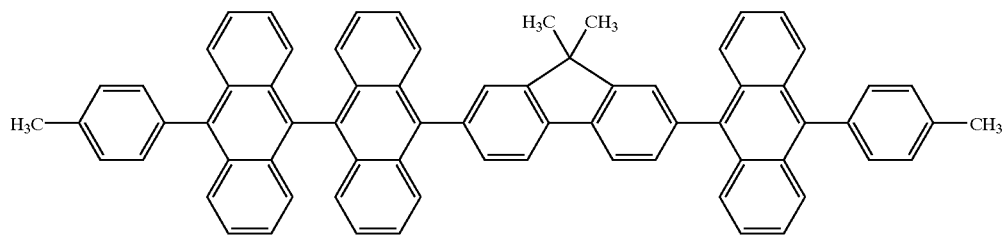
J-1
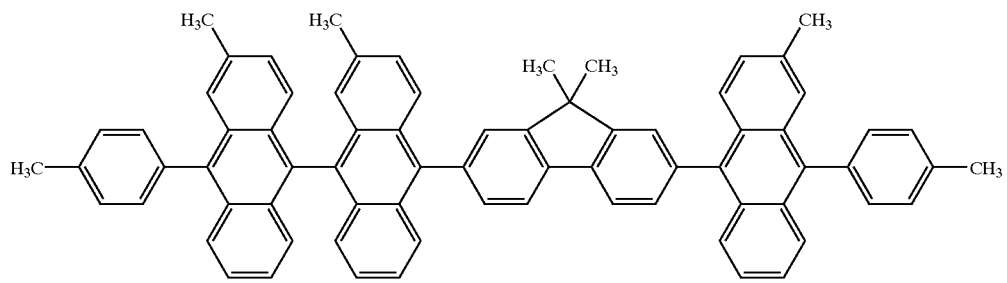
J-2

-continued
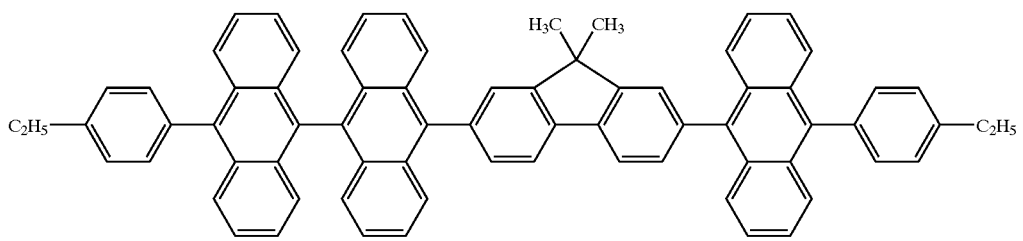
J-3
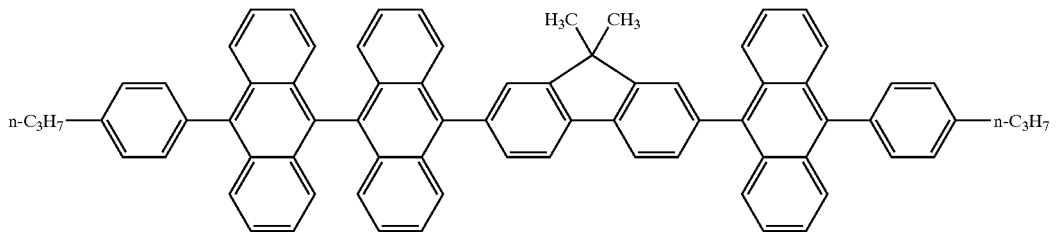
J-4
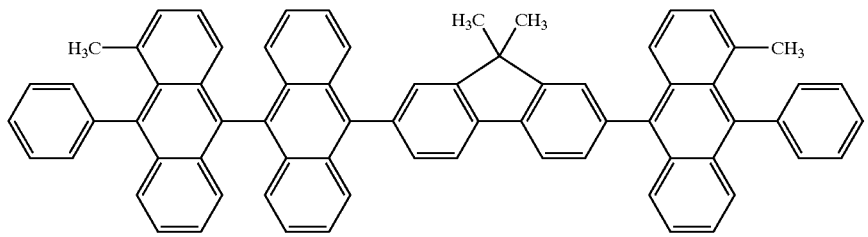
J-5
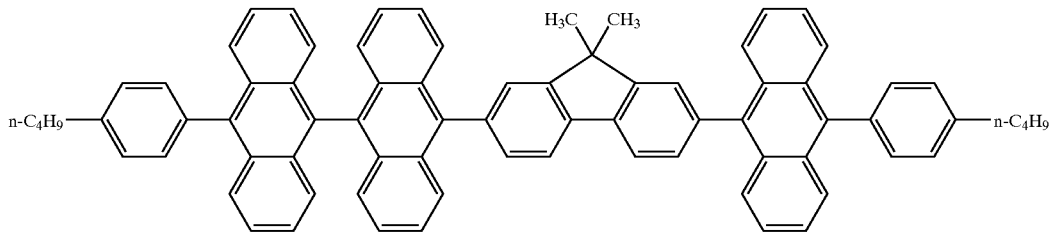
J-6
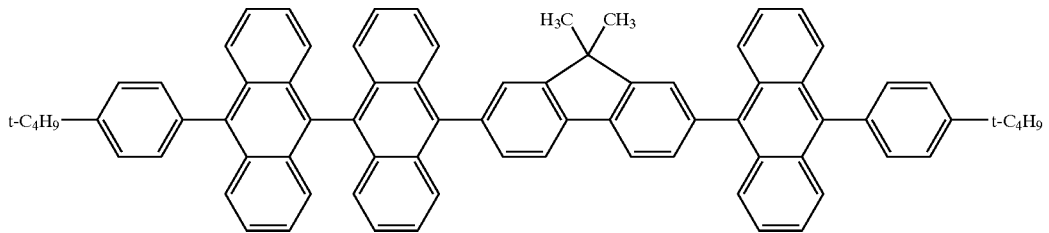
J-7
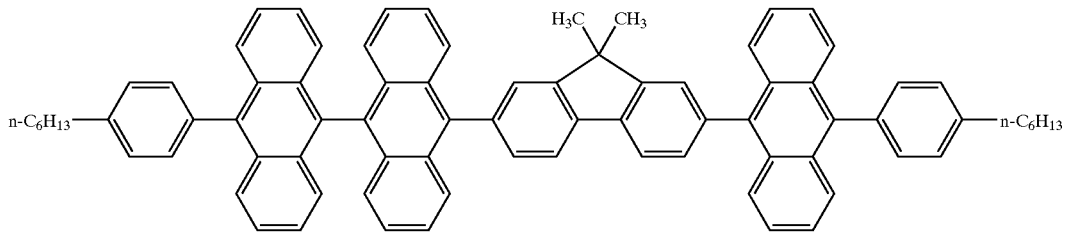
J-8

-continued
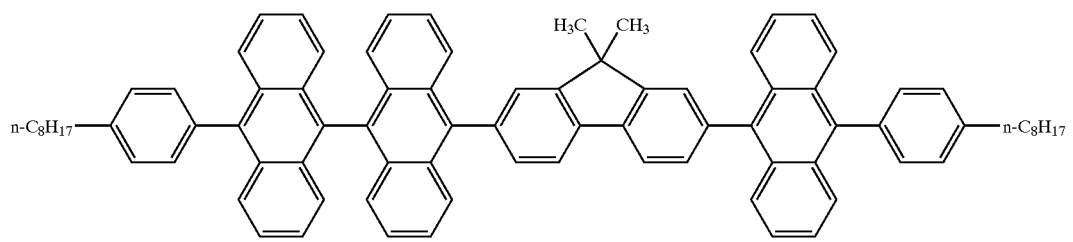
J-9
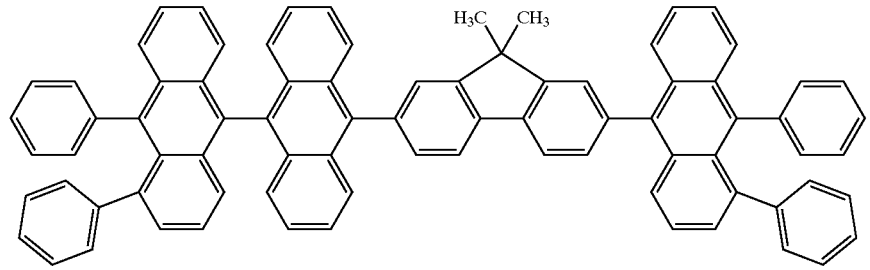
J-10
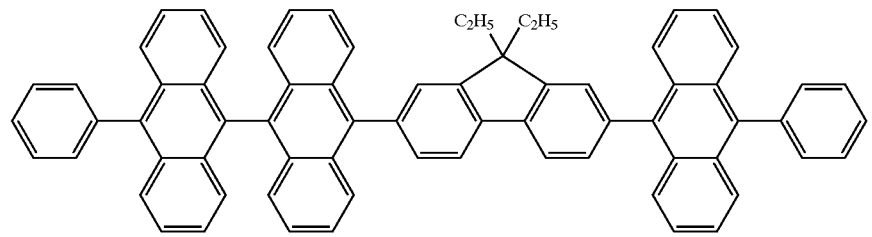
J-11
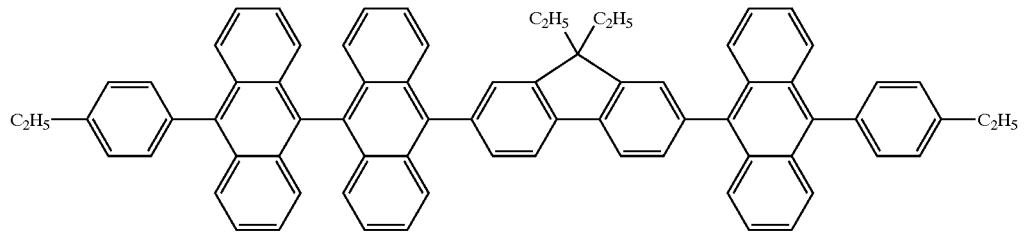
J-12
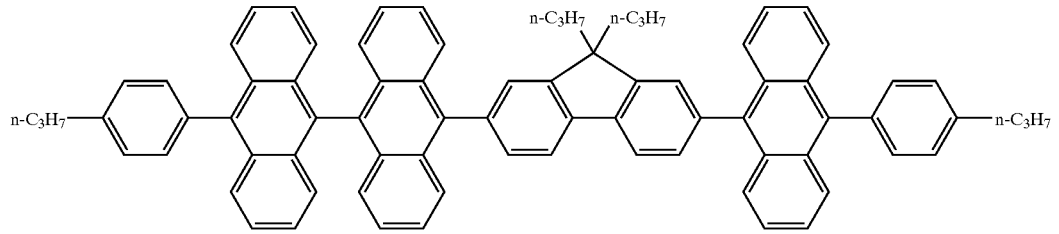
J-13
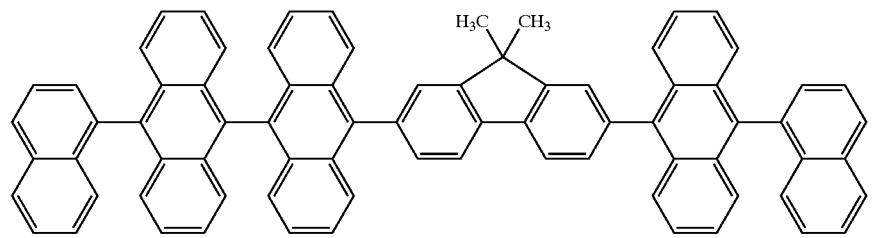
J-14

-continued
J-15
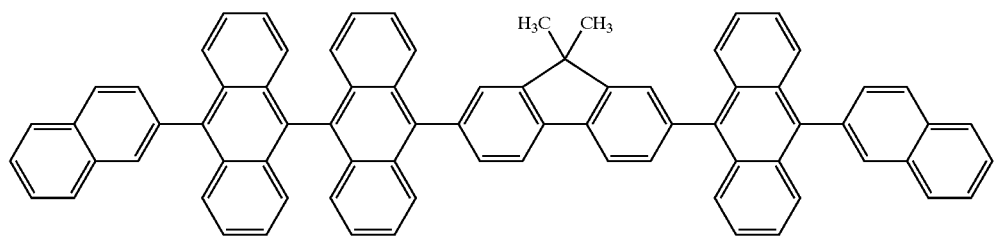
J-16
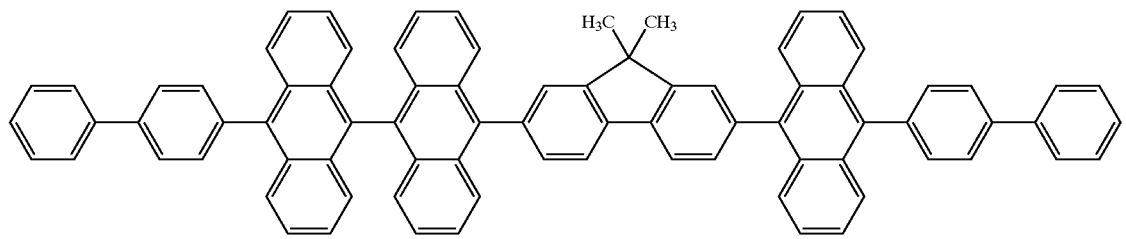
J-17
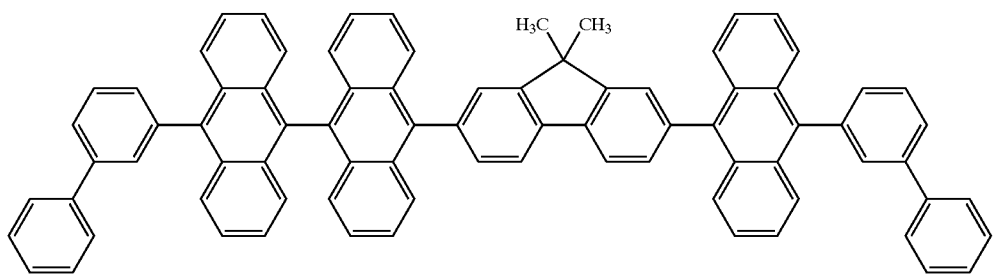
J-18
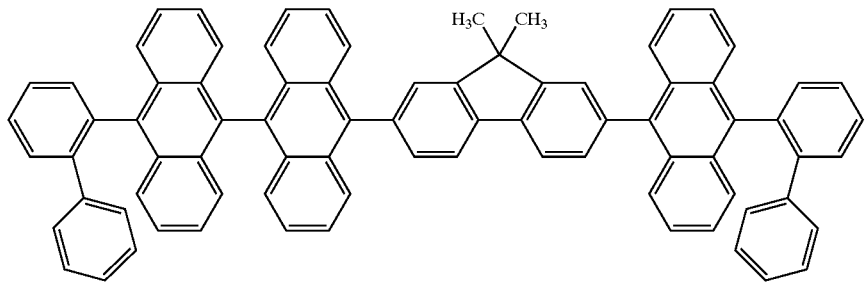
J-19
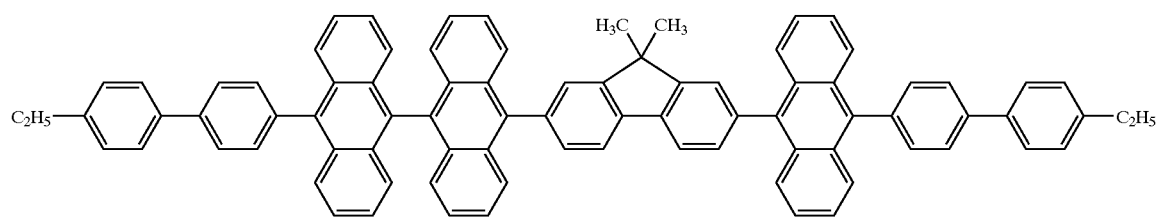
J-20
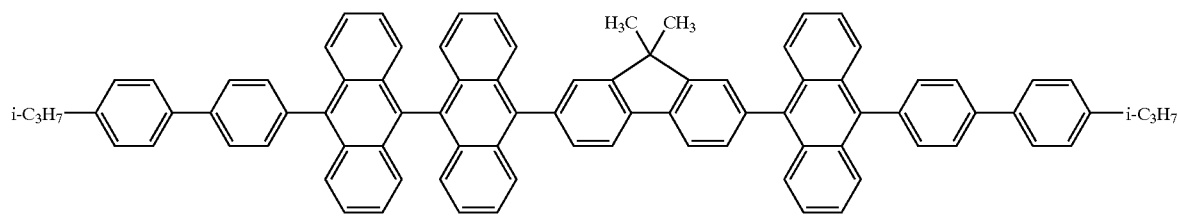

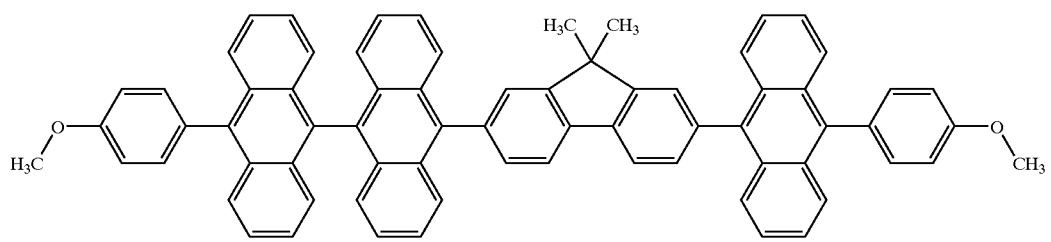
J-21
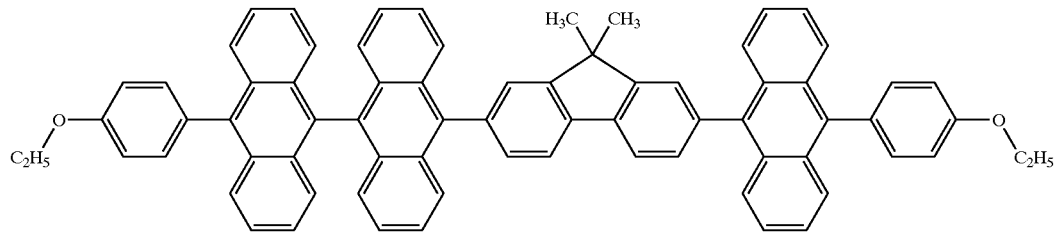
J-22
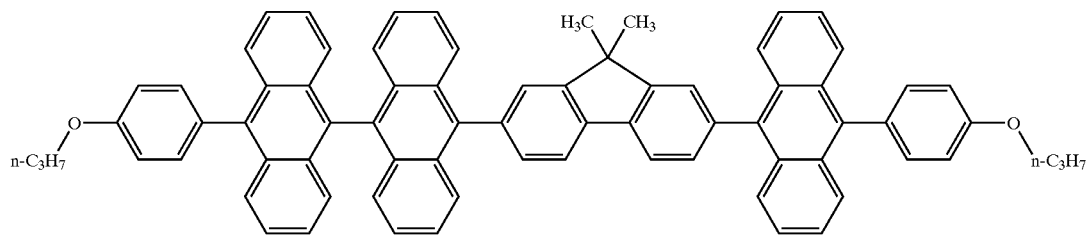
J-23
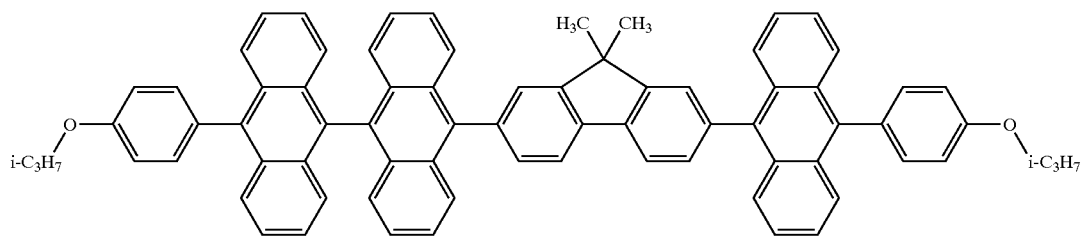
J-24
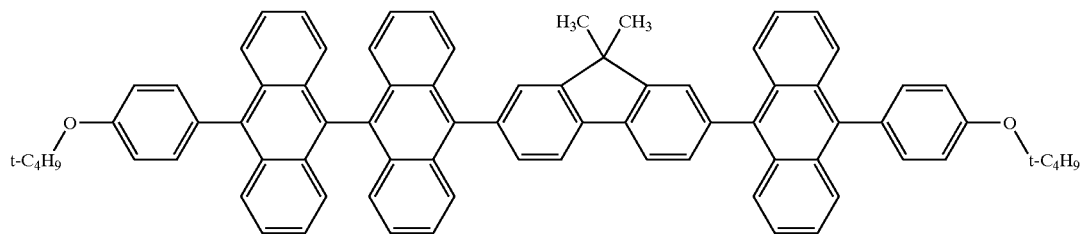
J-25
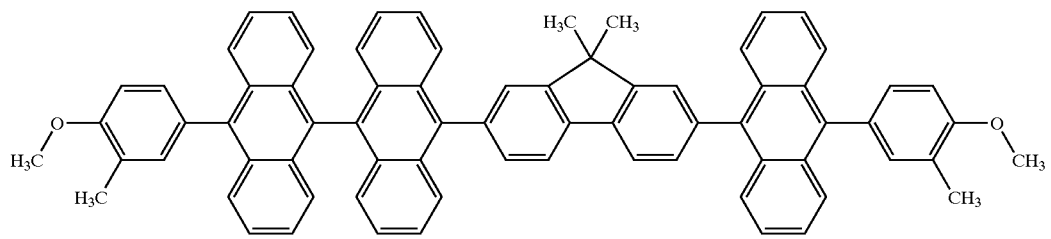
J-26

-continued
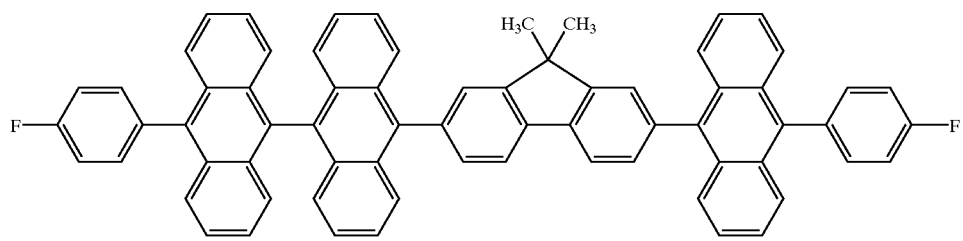
J-27
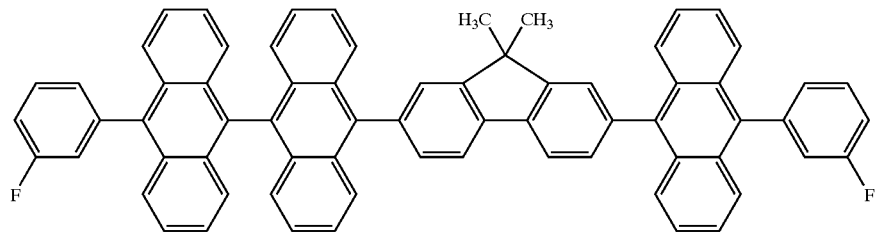
J-28
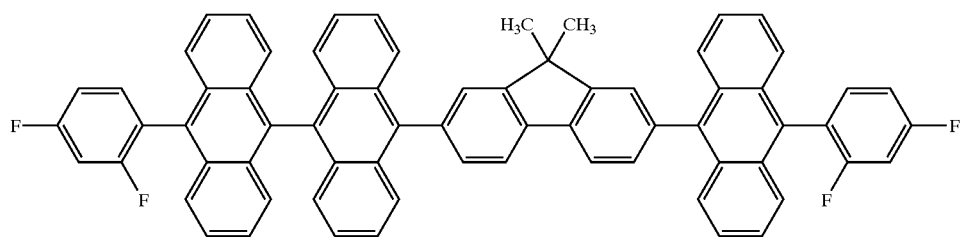
J-29
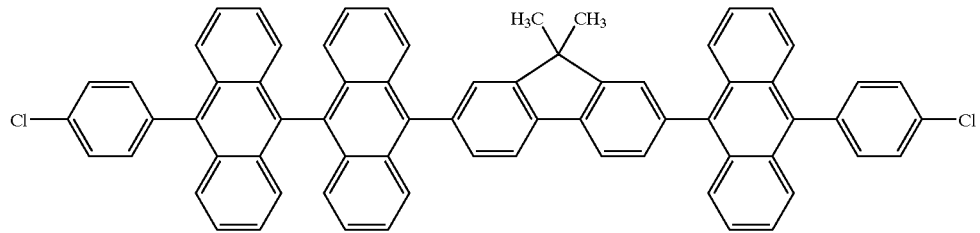
J-30
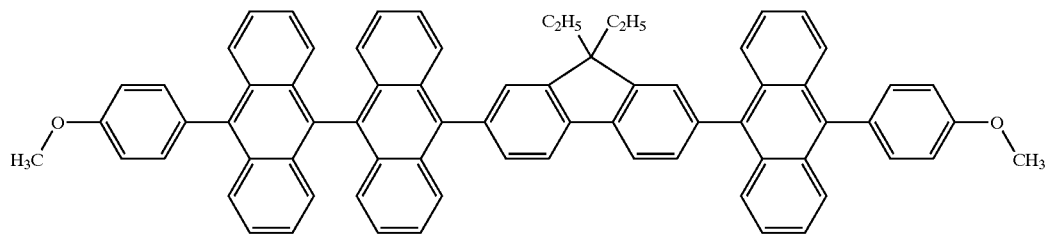
J-31
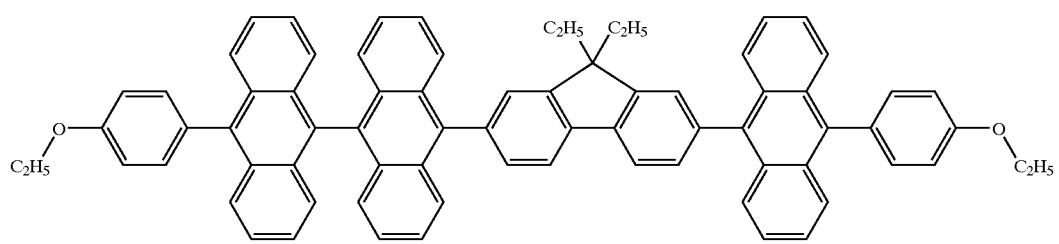
J-32

-continued
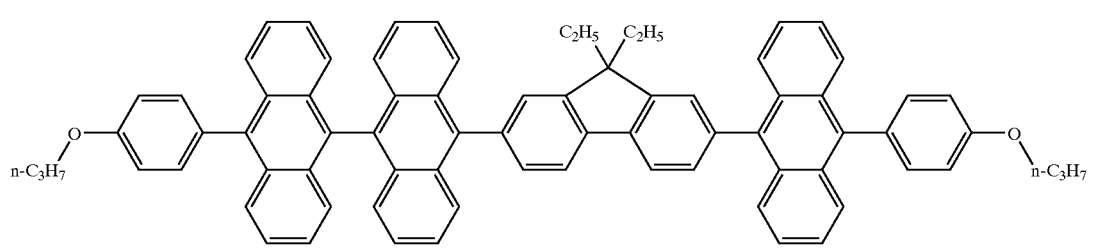
J-33
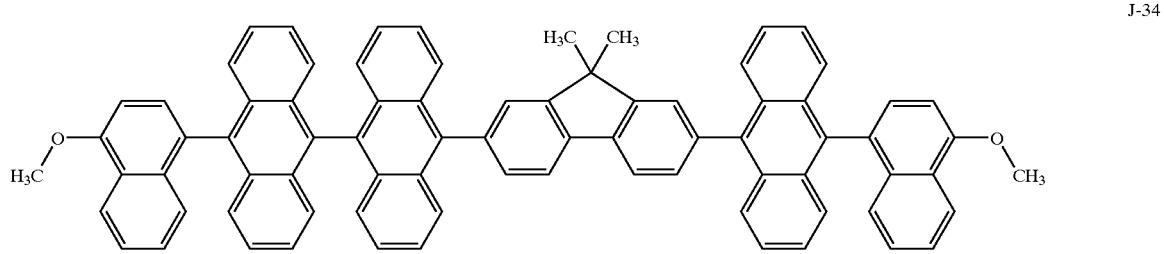
J-34
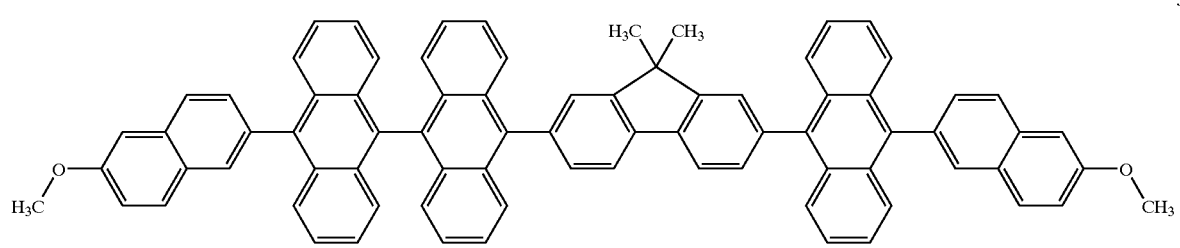
J-35
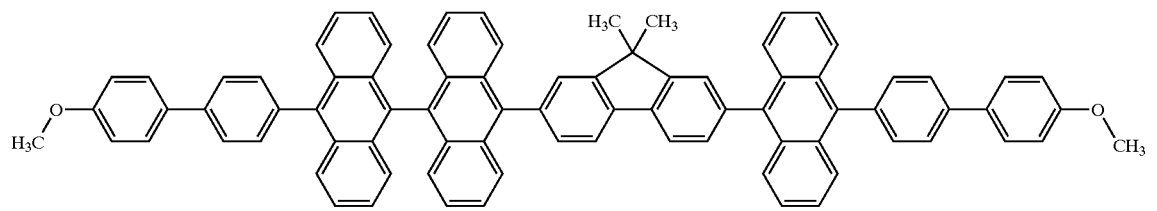
J-36
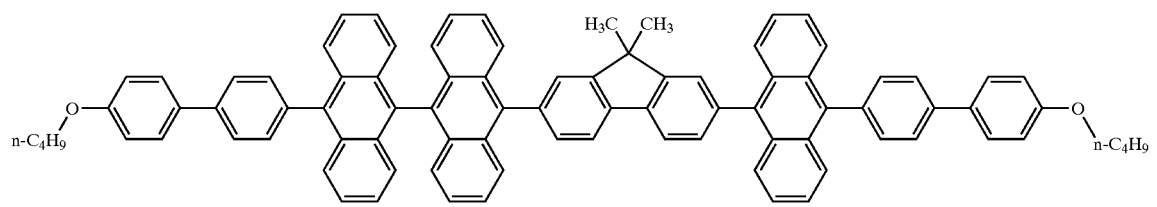
J-37
J-38
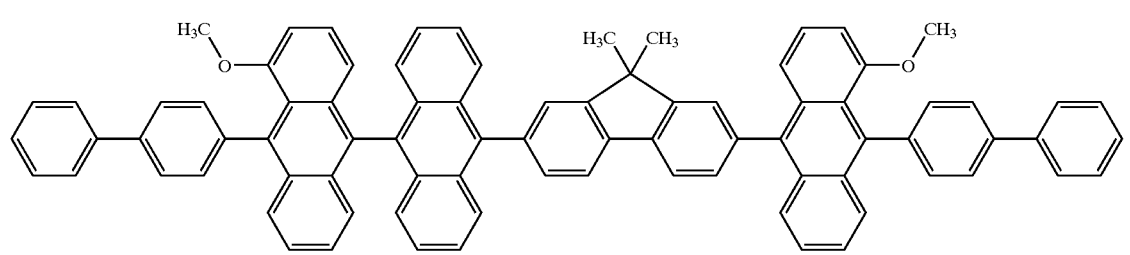
J-39

-continued
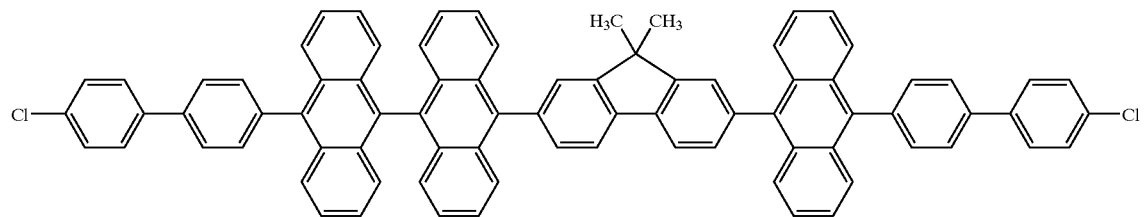
J-40
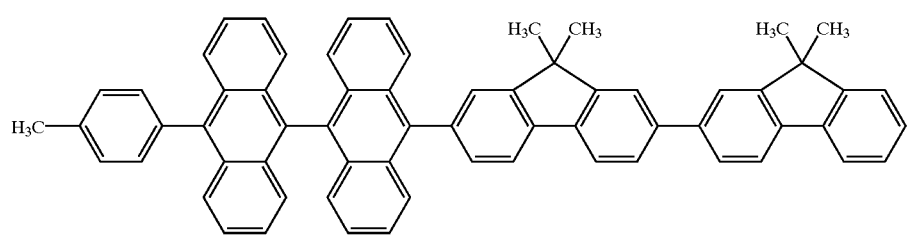
K-1
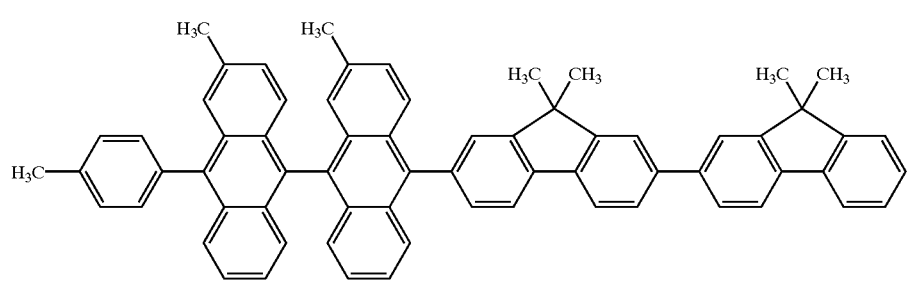
K-2
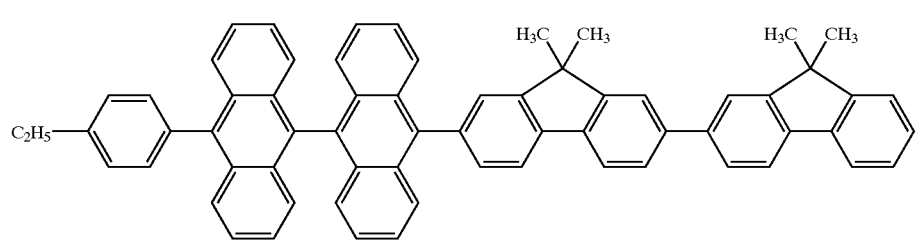
K-3
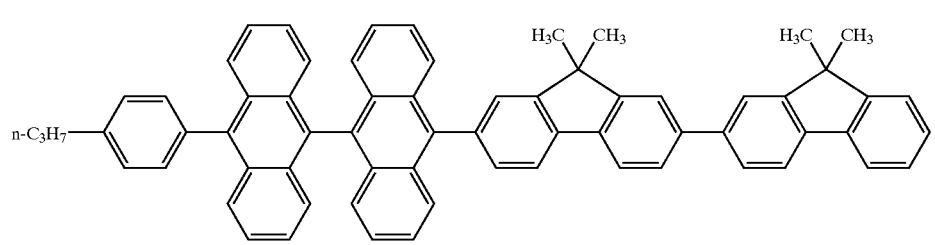
K-4
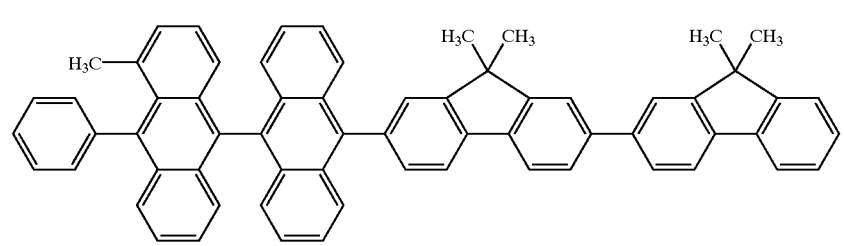
K-5

-continued
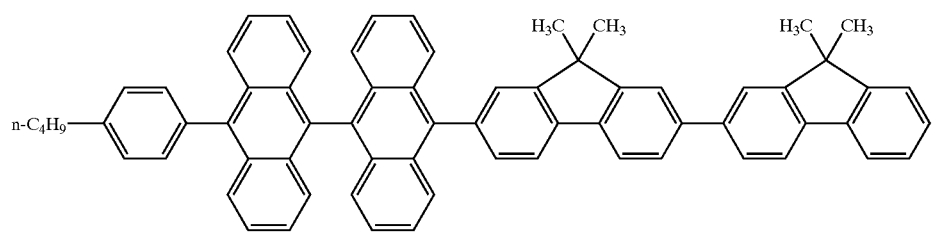 K-6
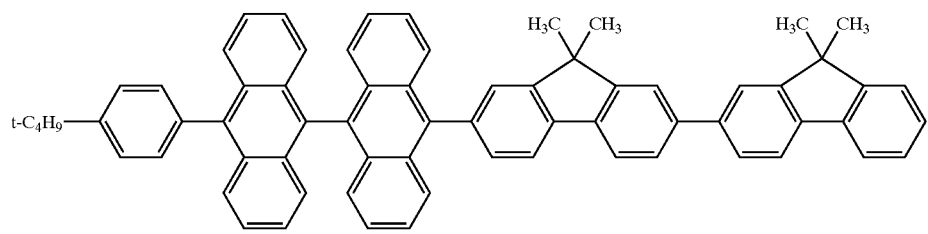 K-7
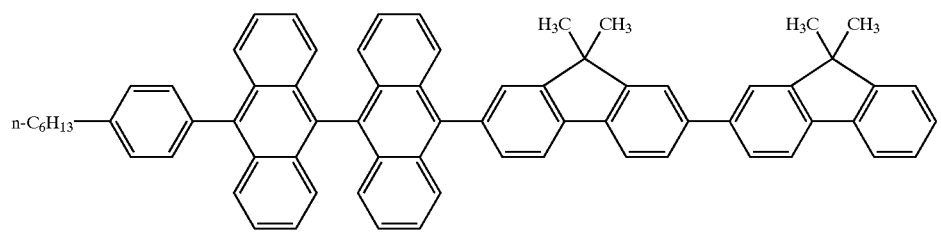 K-8
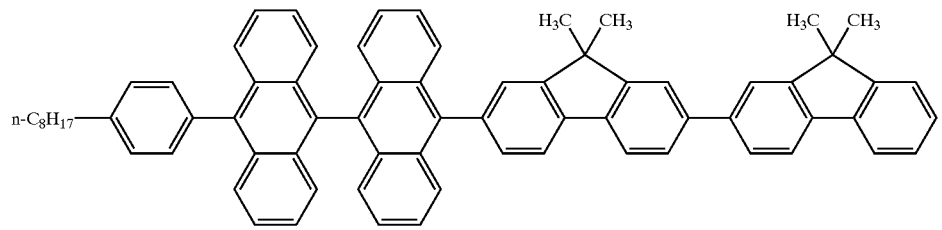 K-9
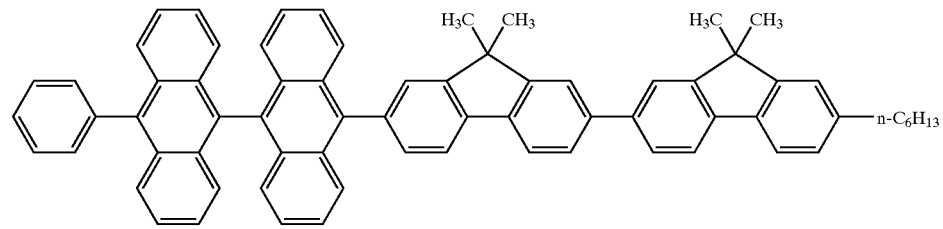 K-10
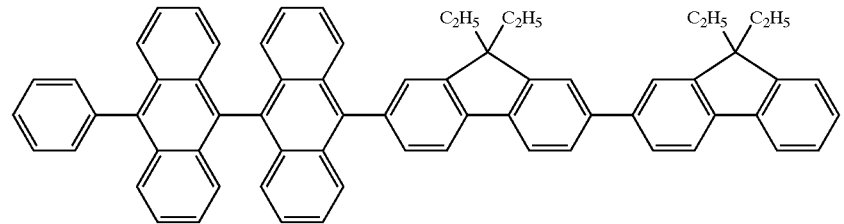 K-11
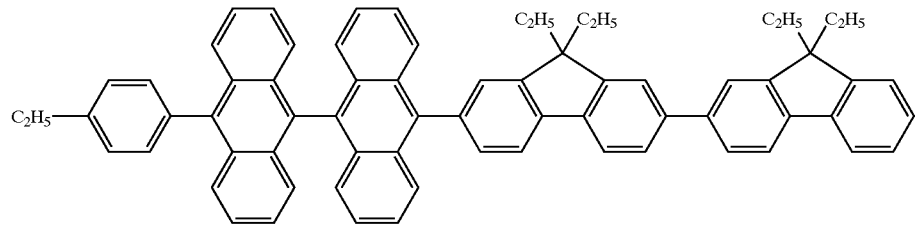 K-12

-continued
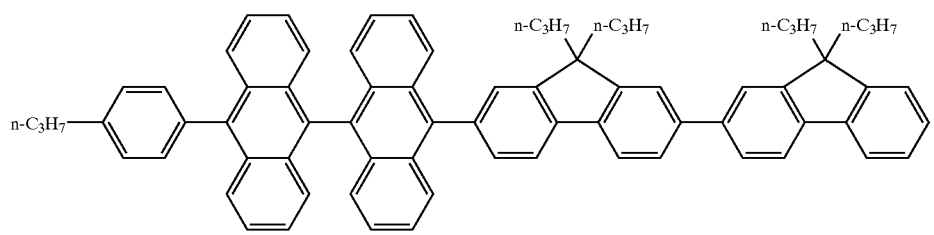
K-13
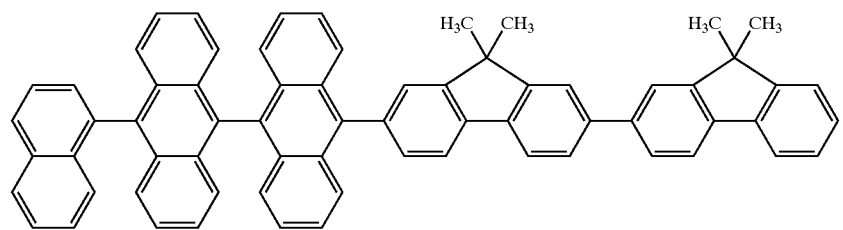
K-14
K-15
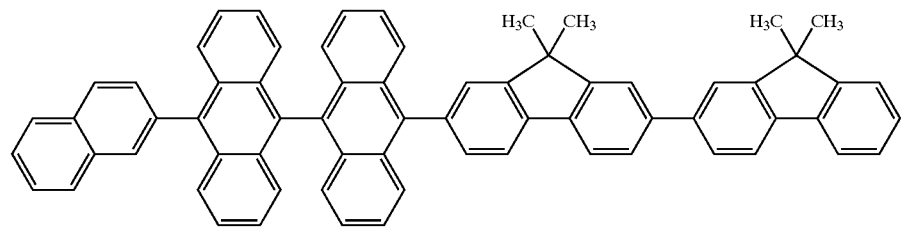
K-16
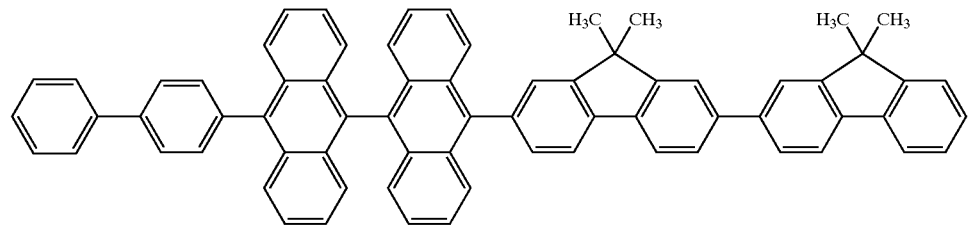
K-17
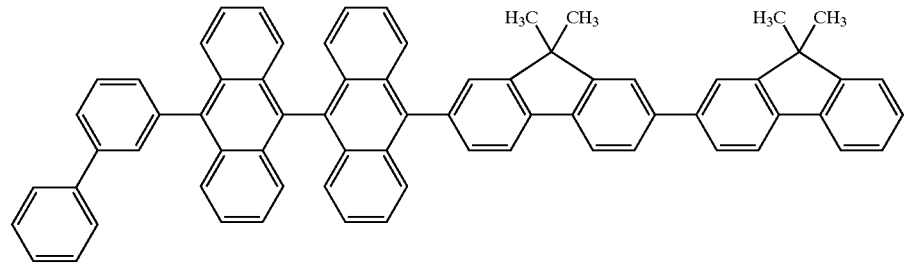
K-18
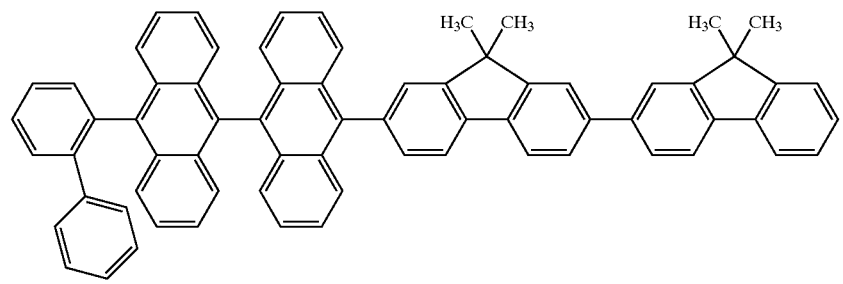

-continued
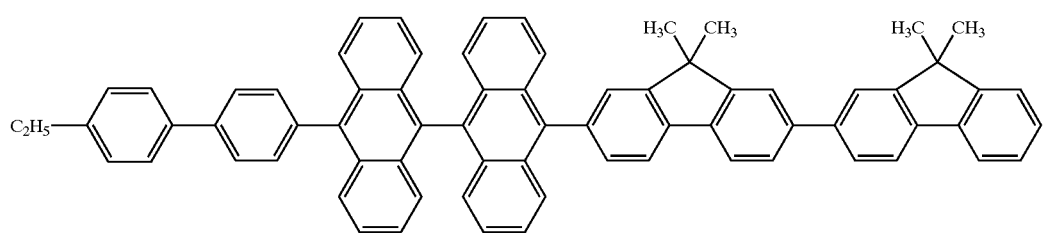
K-19
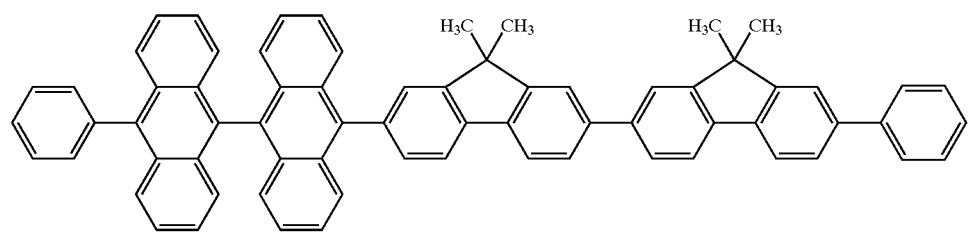
K-20
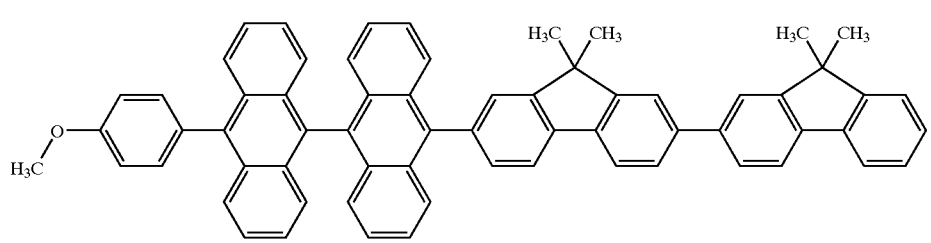
K-21
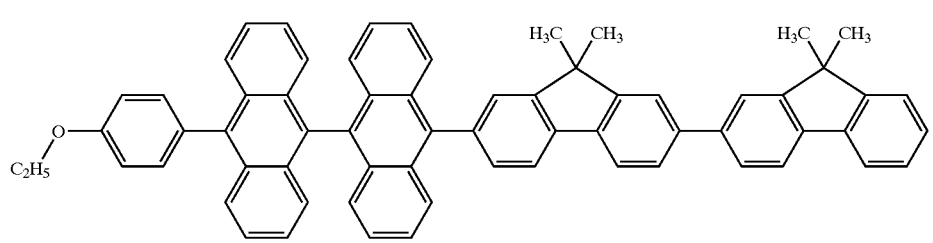
K-22
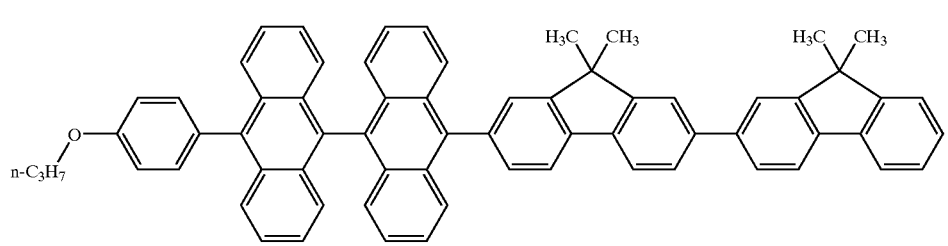
K-23
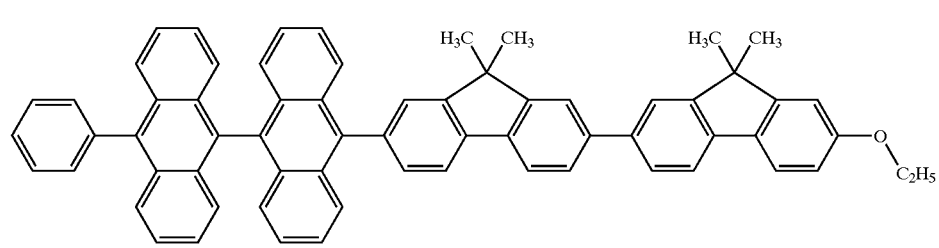
K-24
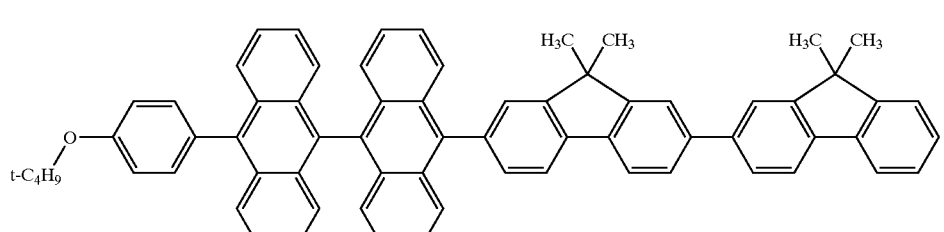
K-25

-continued
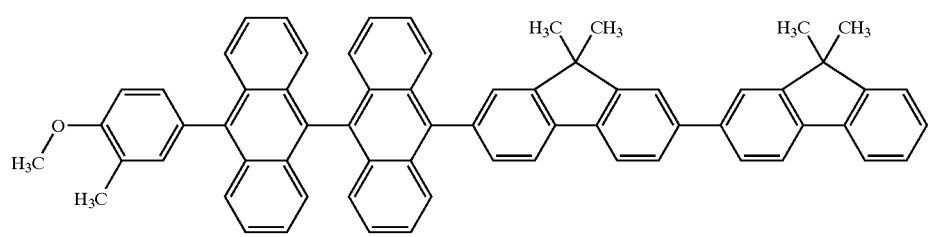
K-26
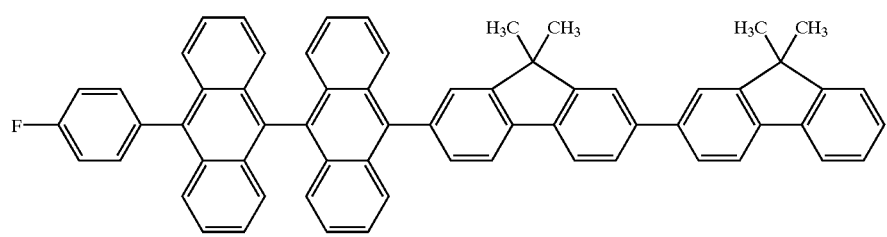
K-27
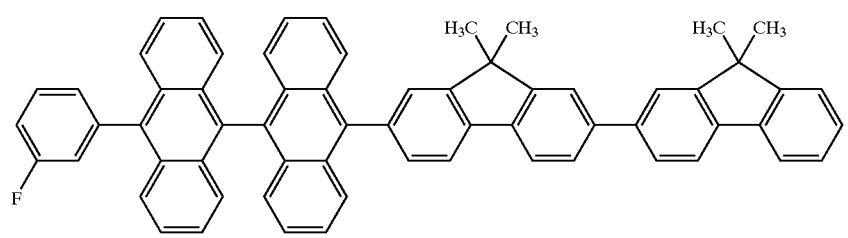
K-28
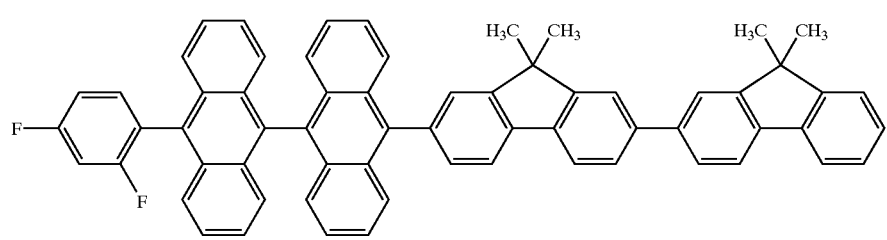
K-29
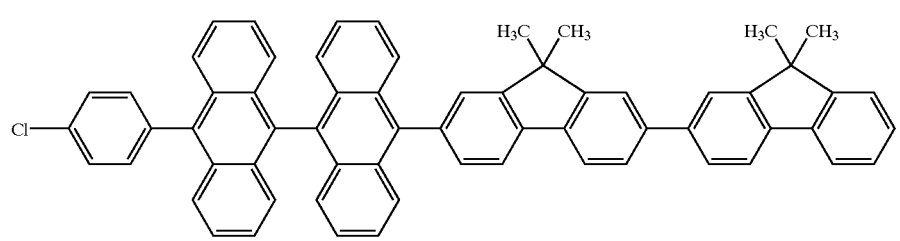
K-30
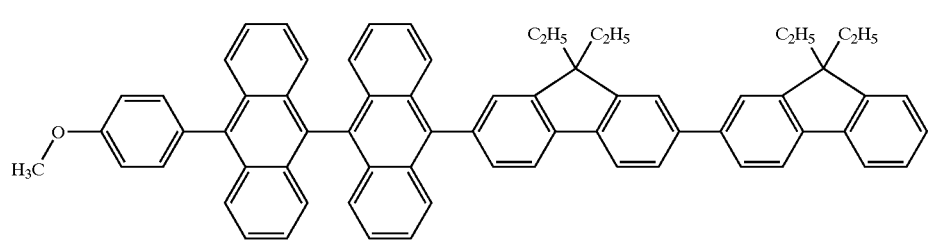
K-31
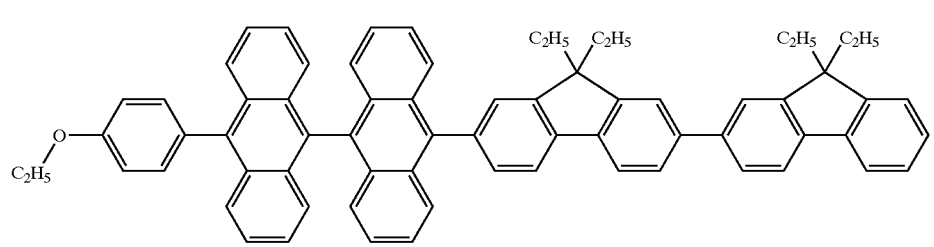
K-32

-continued
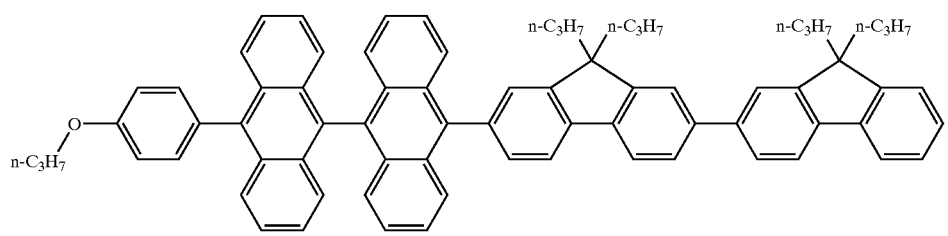
K-33
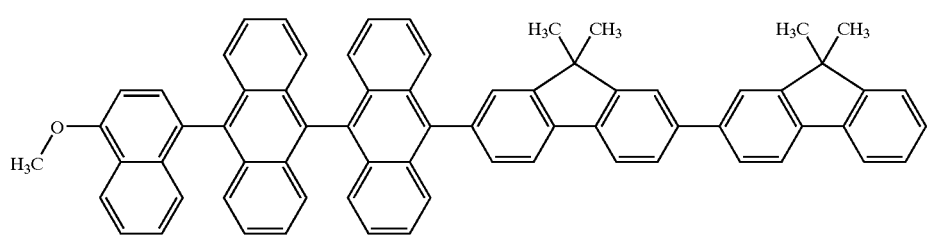
K-34
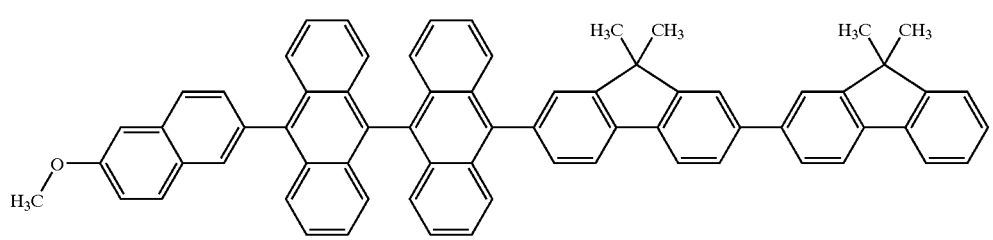
K-35
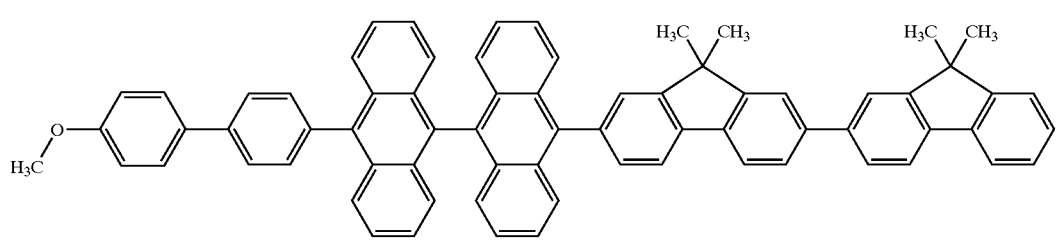
K-36
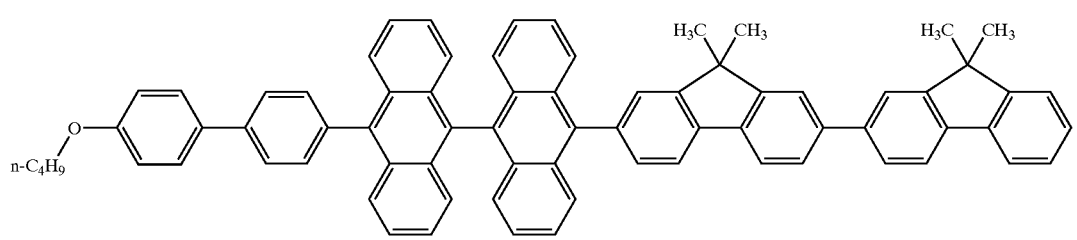
K-37
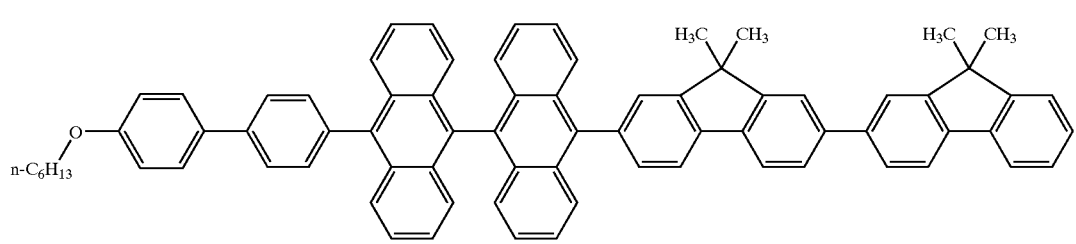
K-38

K-39
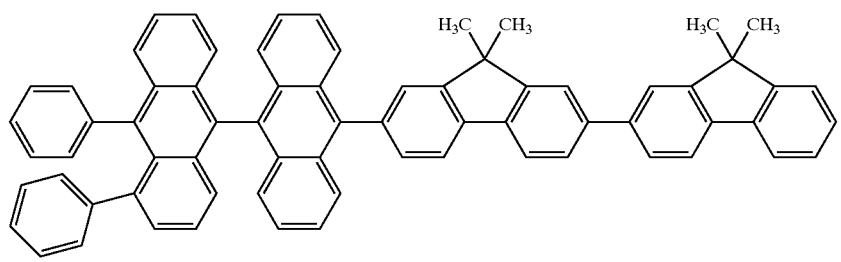
K-40
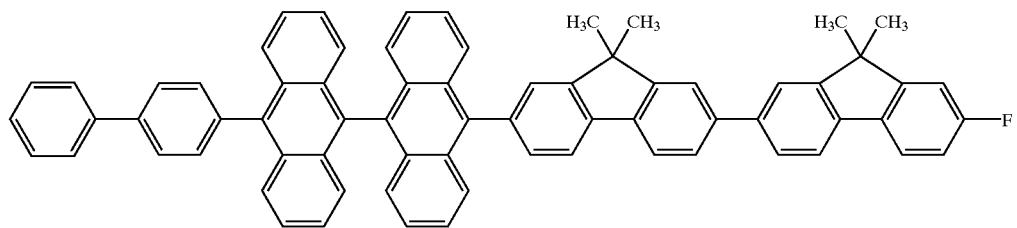
L-1
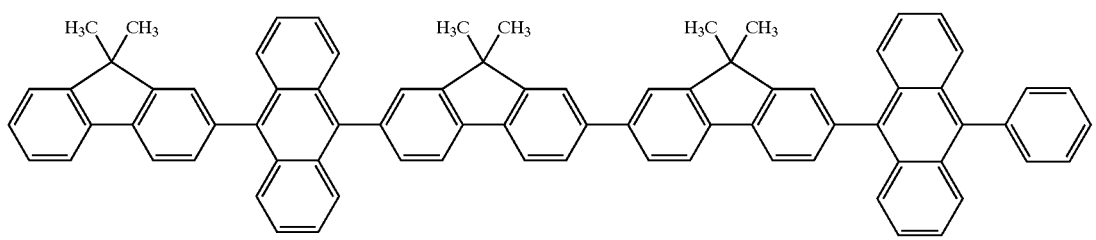
L-2
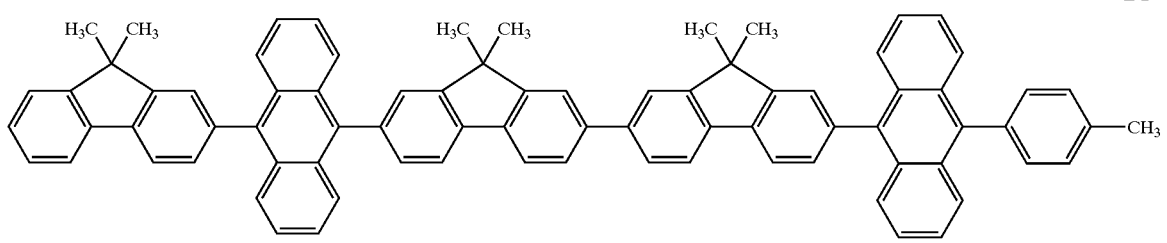
L-3
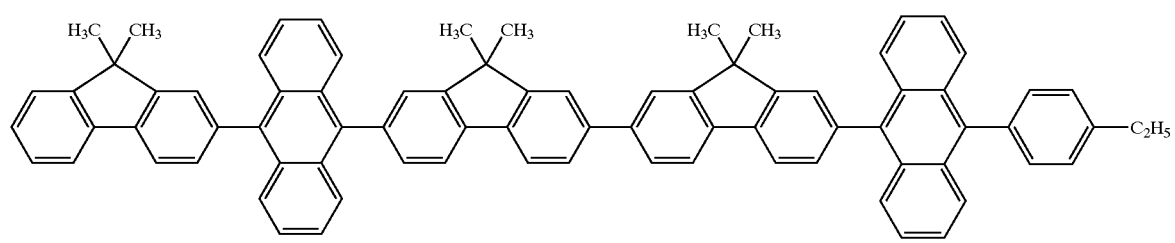
L-4
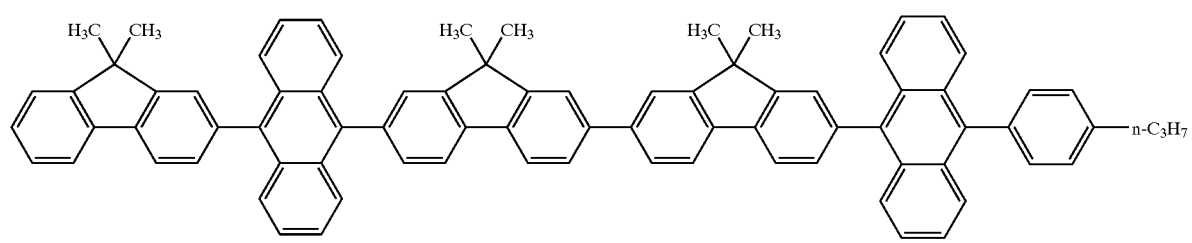

-continued
L-5
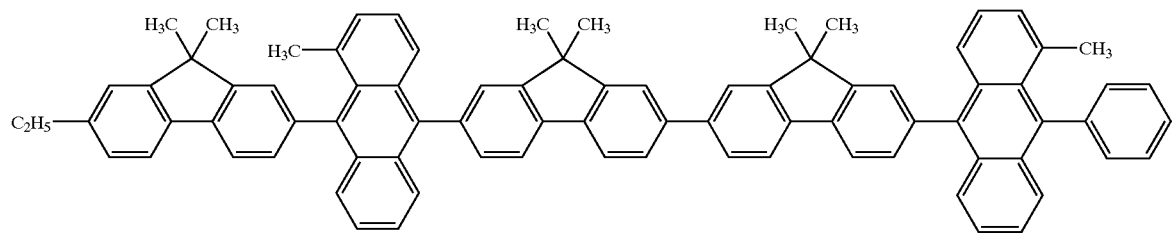
L-6
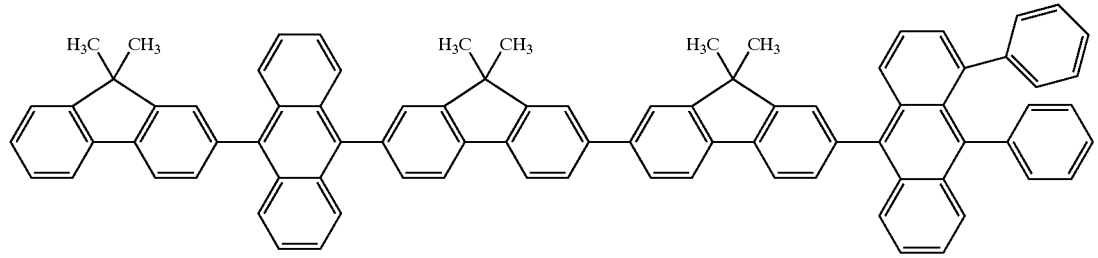
L-7
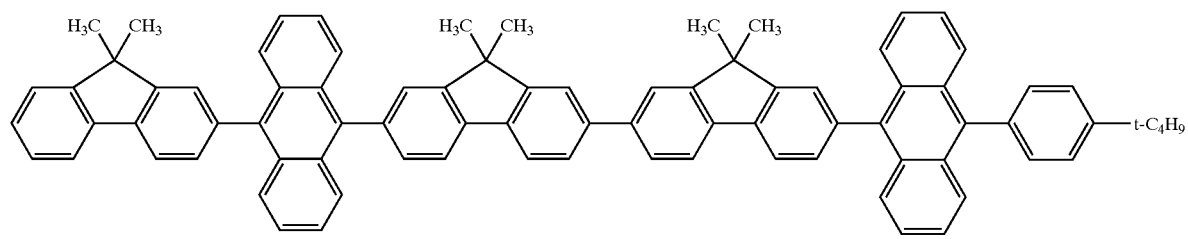
L-8
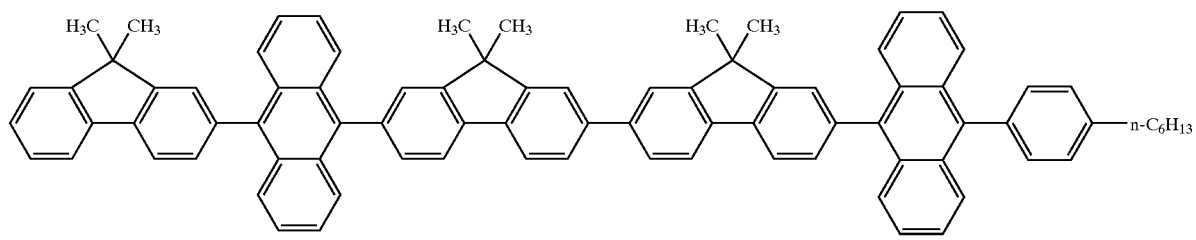
L-9
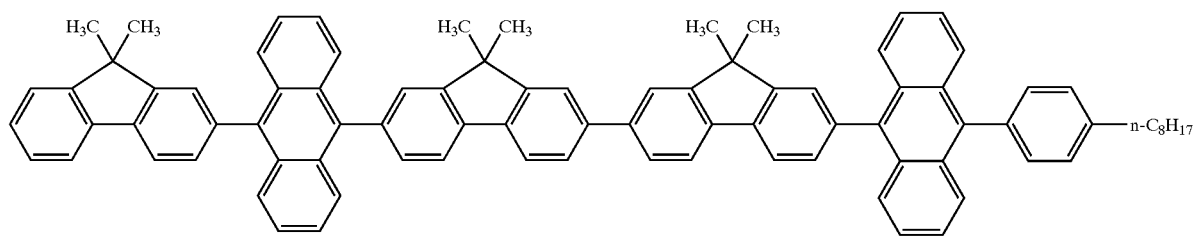
L-10
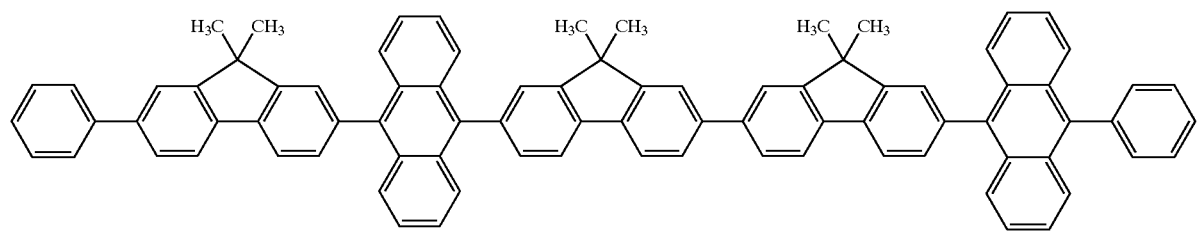

-continued
L-11
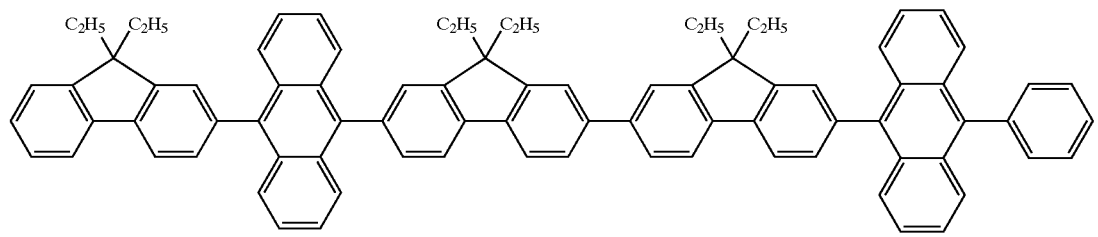
L12
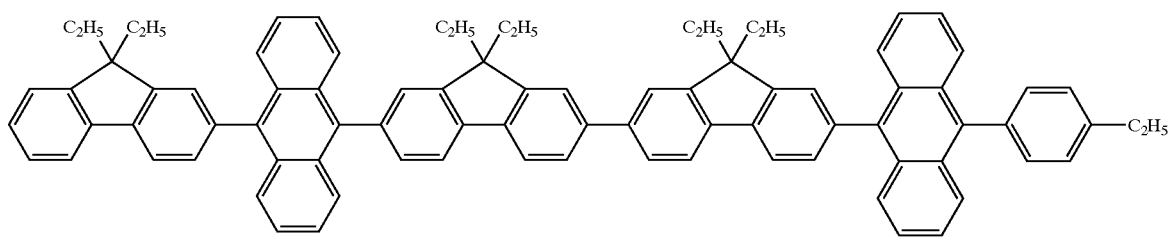
L-13
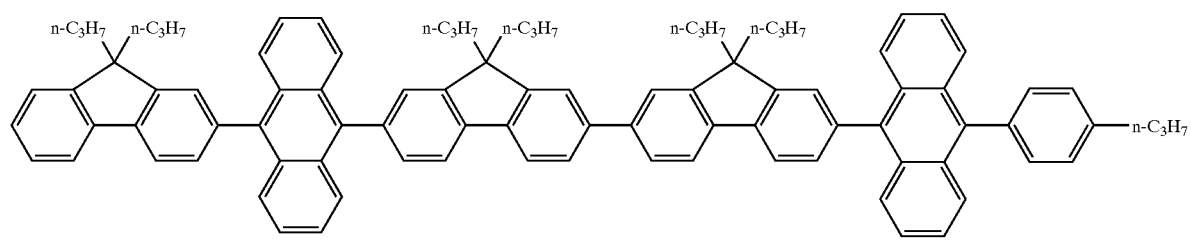
L-14
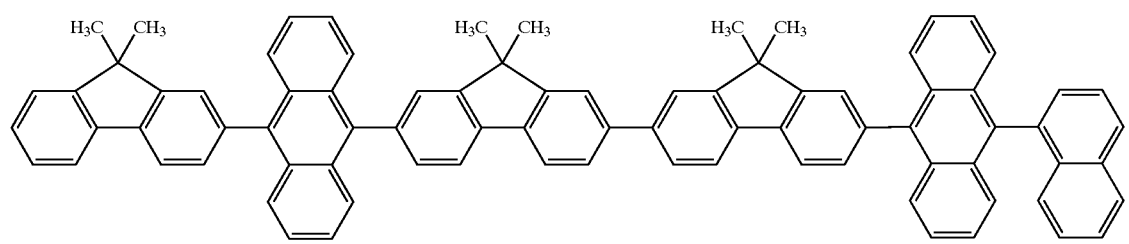
L-15
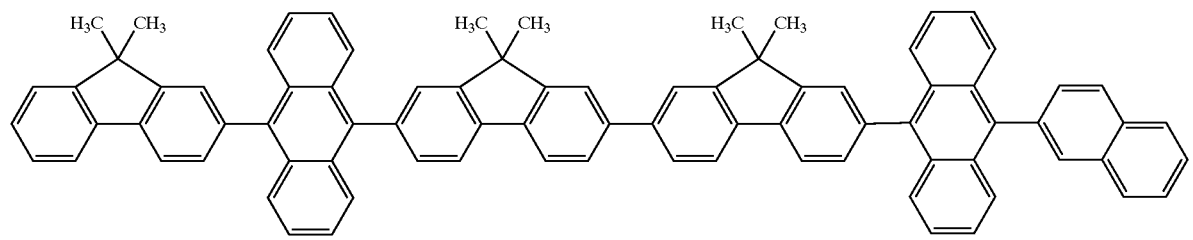
L-16
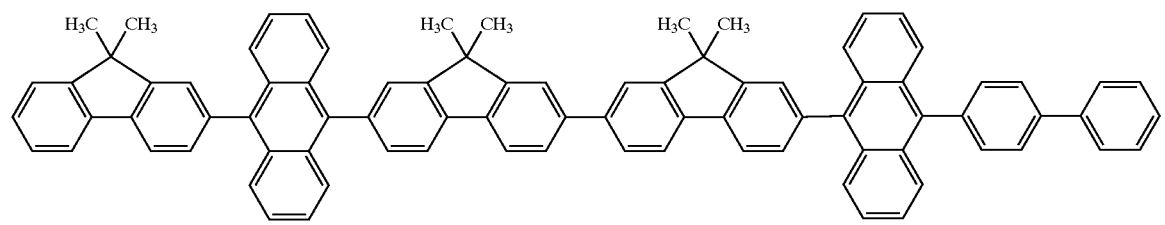

L-17
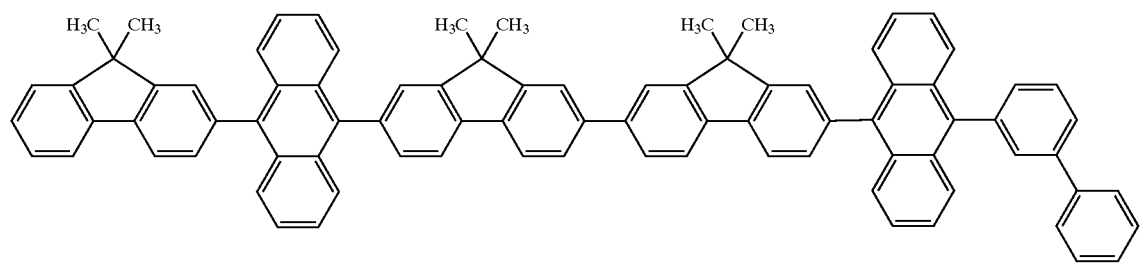
L-18
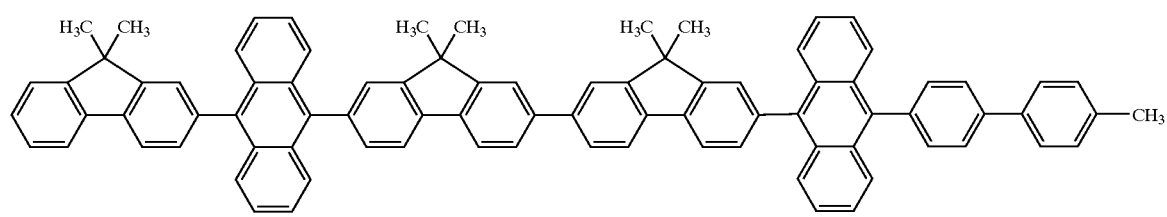
L-19
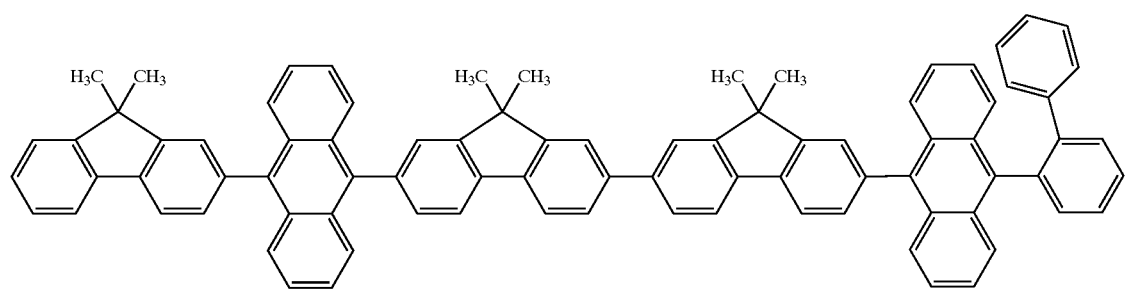
L-20
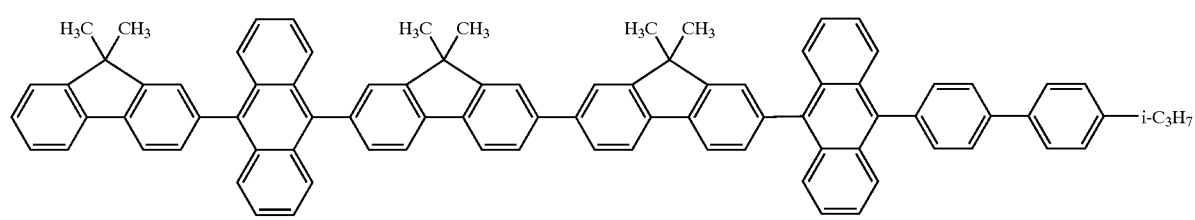
L-21
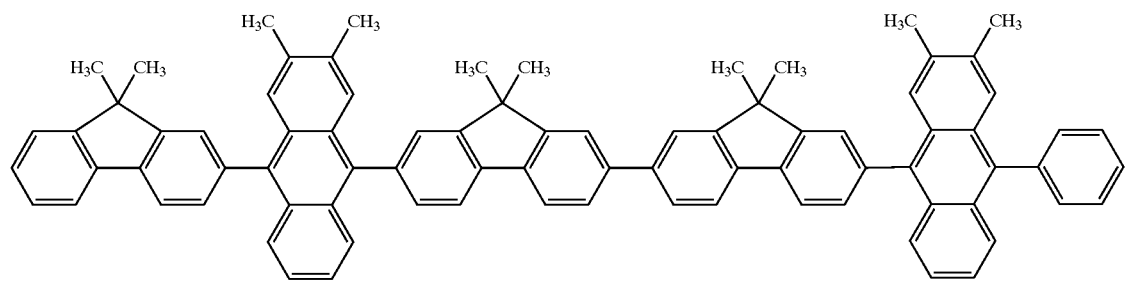
L-22
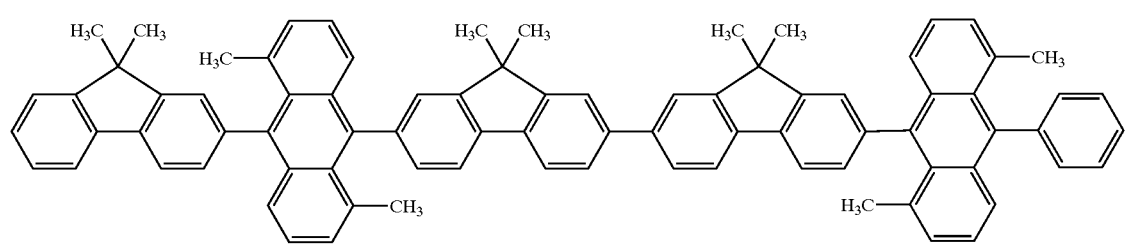

-continued
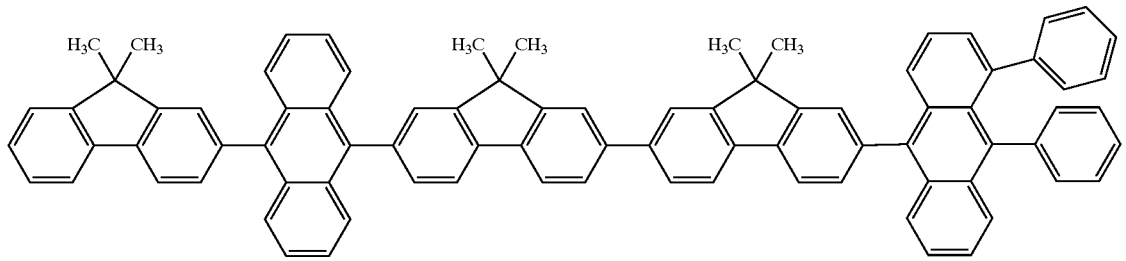
L-23
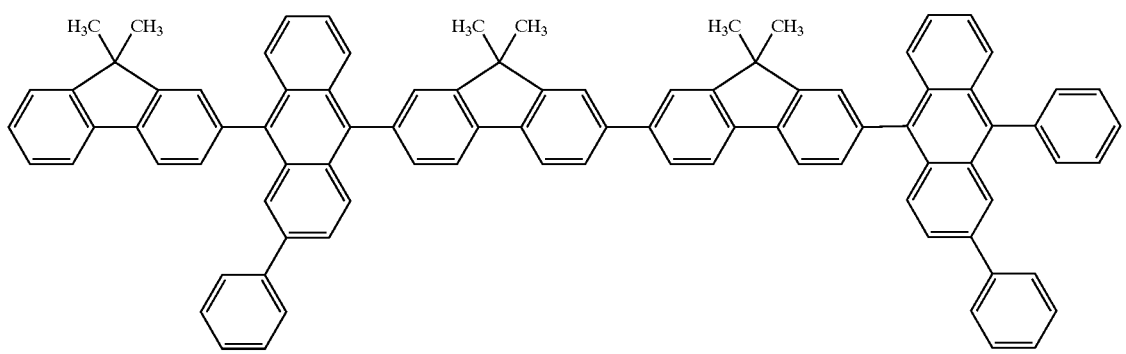
L-24
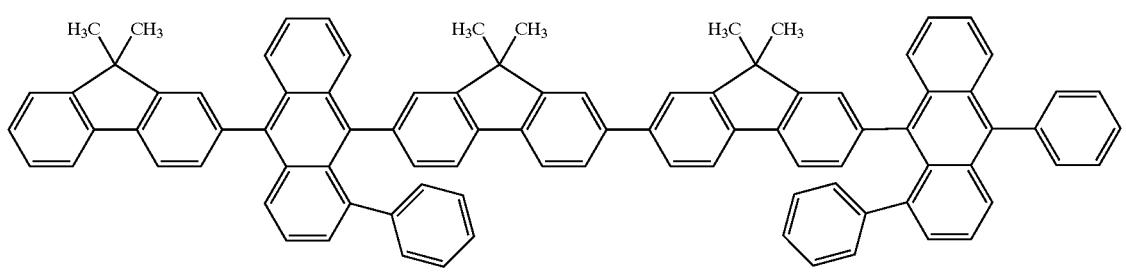
L-25
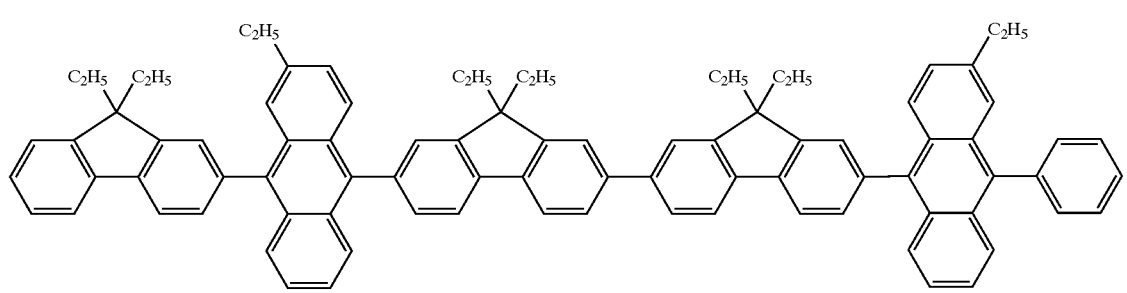
L-26
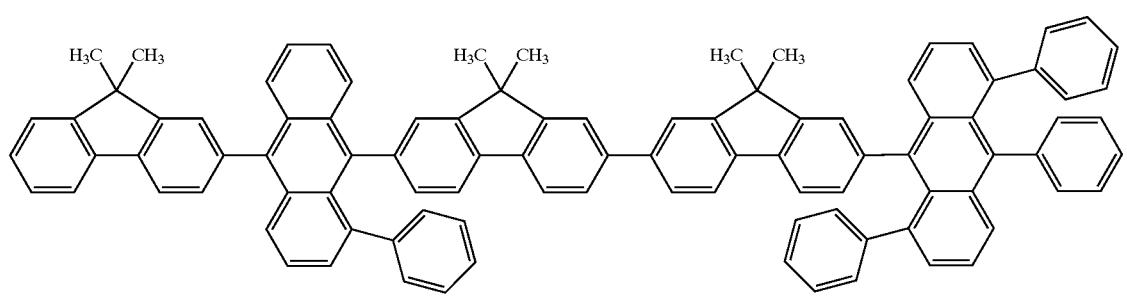
L-27

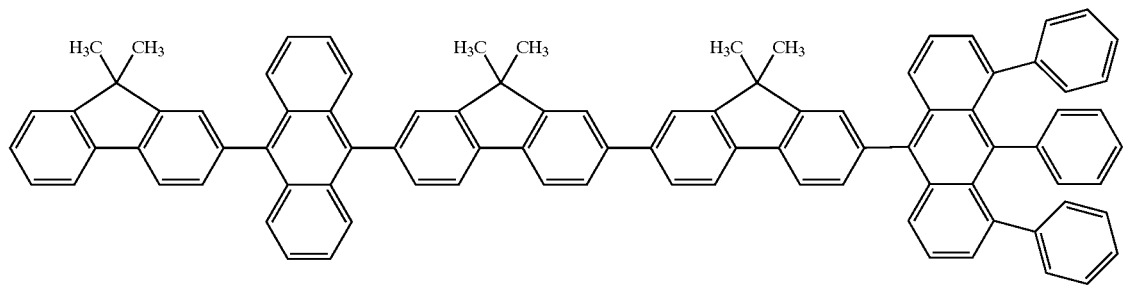
L-28
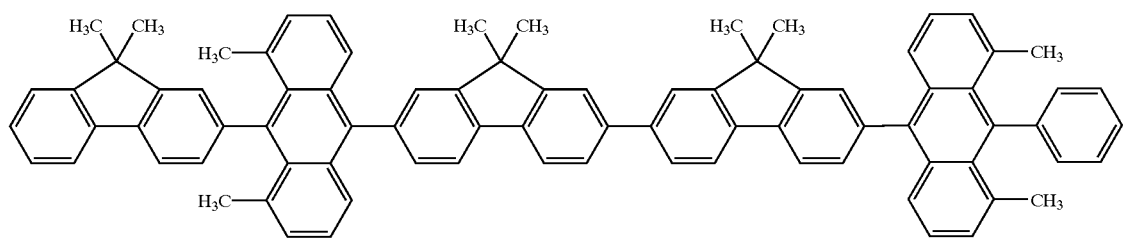
L-29
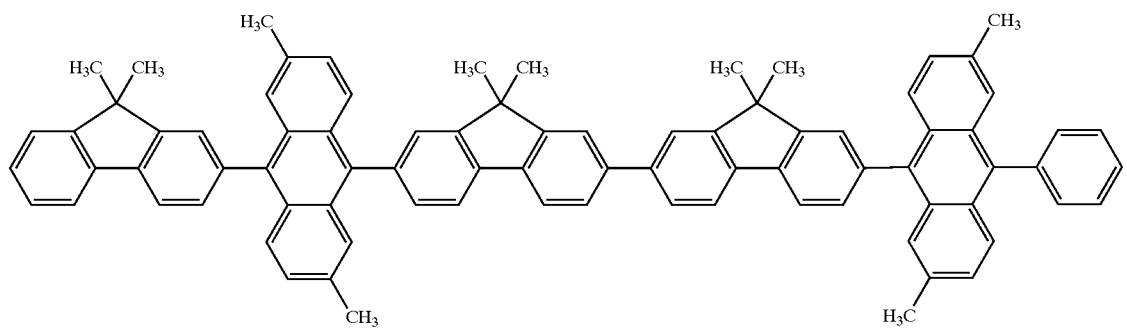
L-30
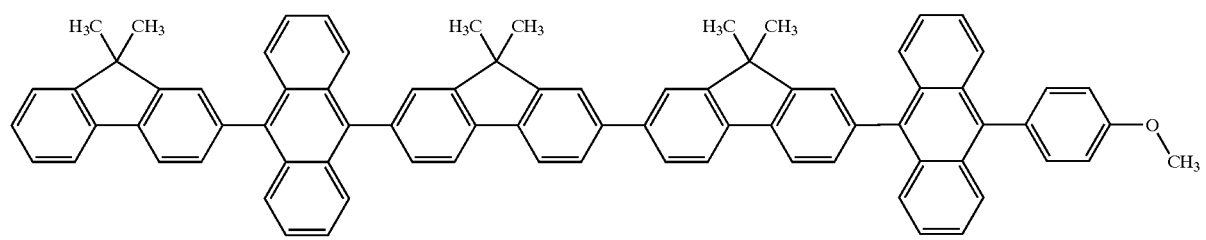
L-31
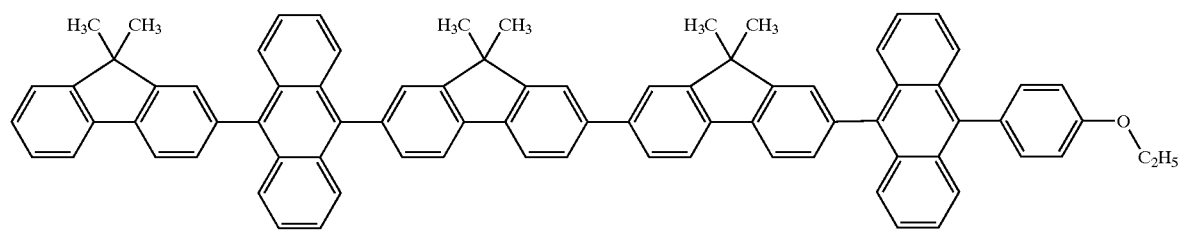
L-32

-continued
L-33
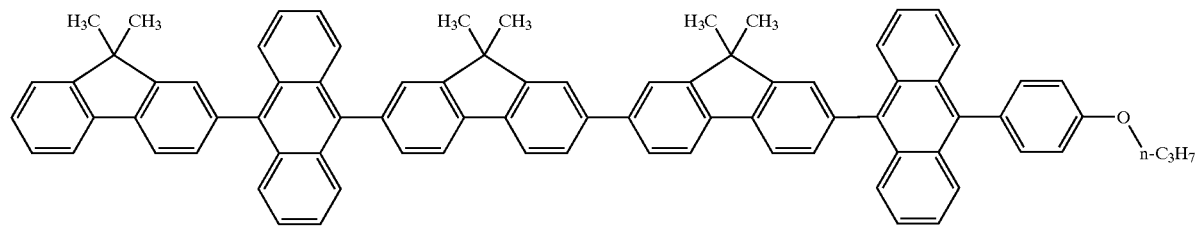
L-34
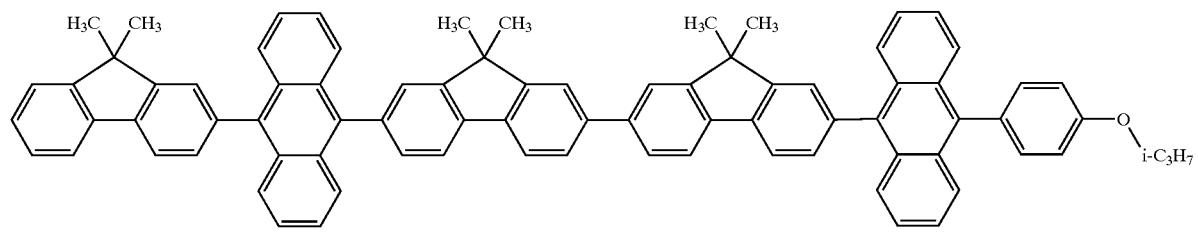
L-35
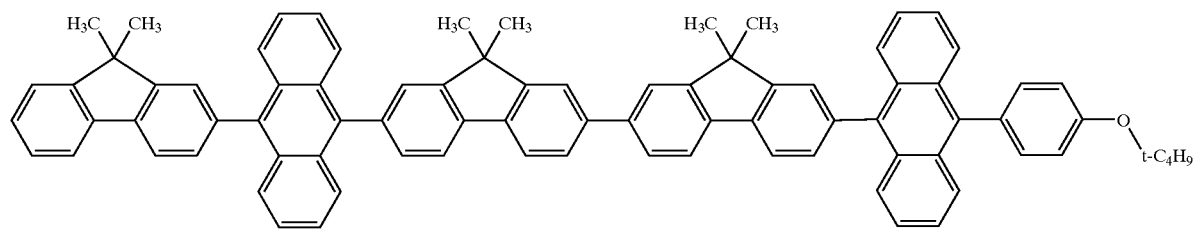
L-36
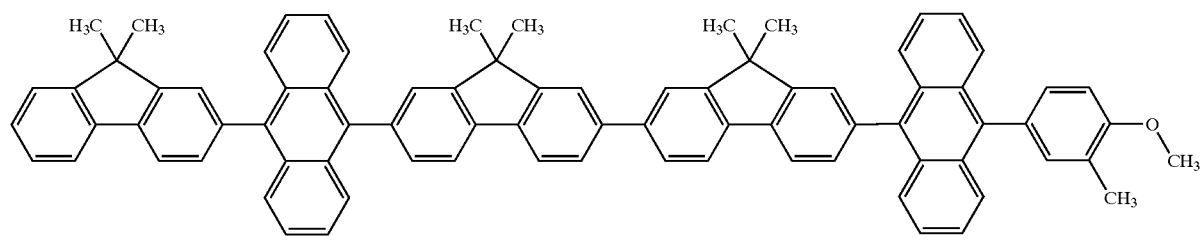
L-37
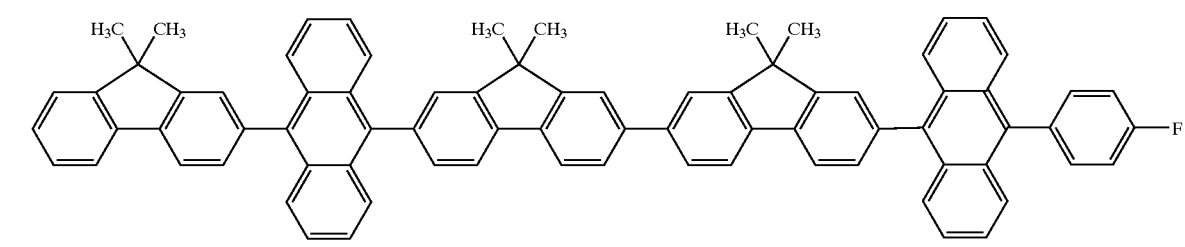
L-38
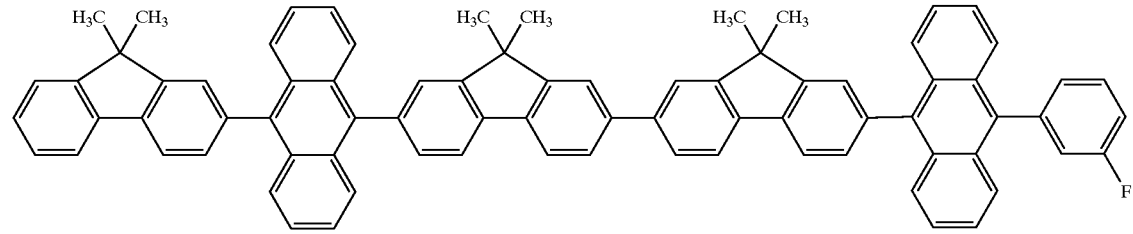

-continued
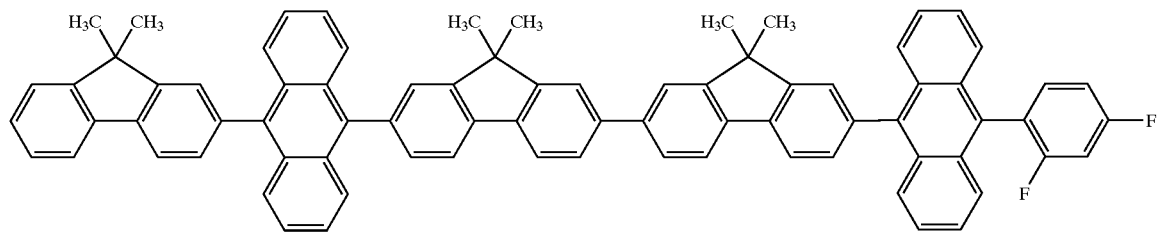
L-39
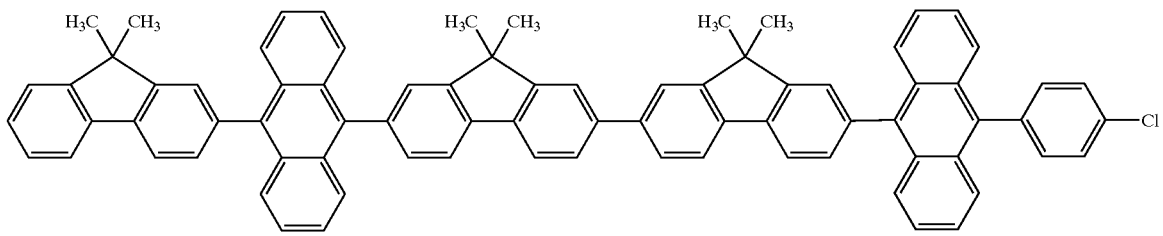
L-40
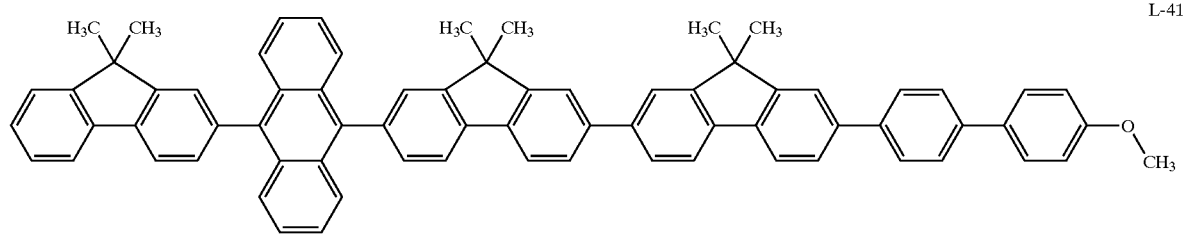
L-41
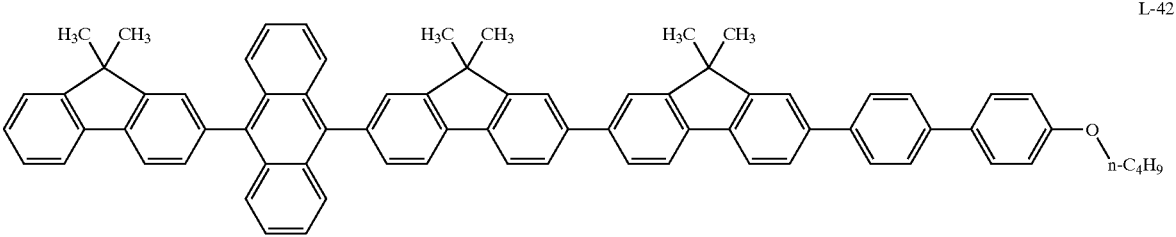
L-42
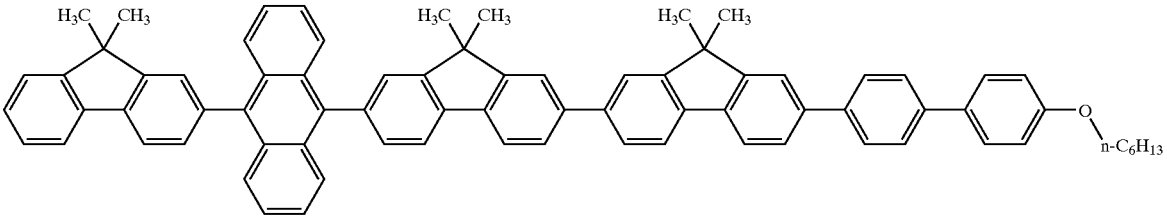
L-43
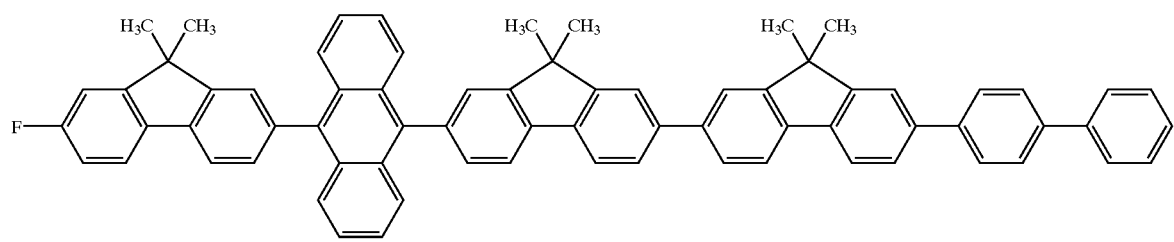
L-44

-continued
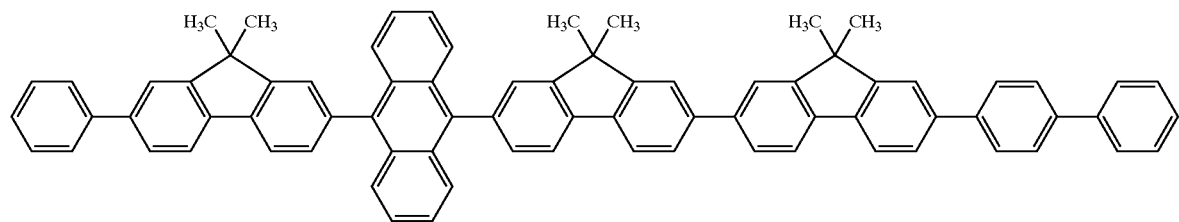
L-45
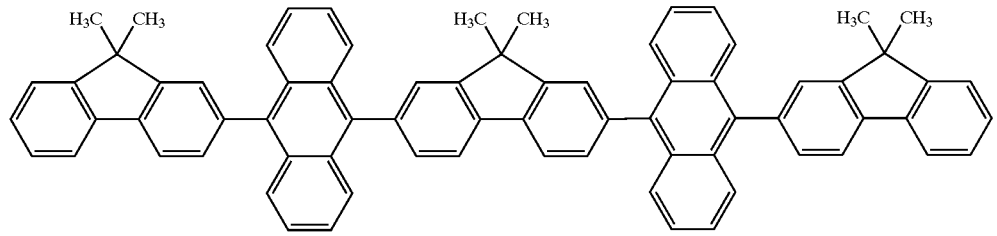
M-1
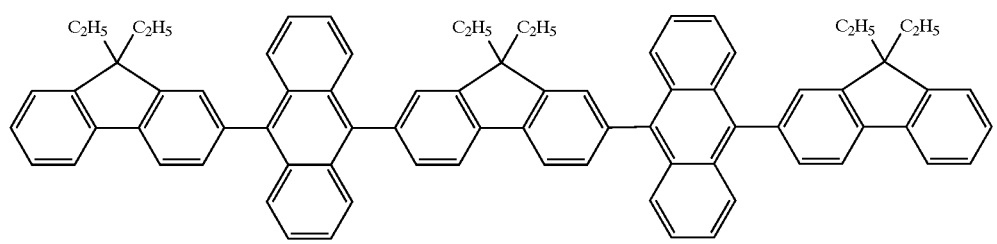
M-2
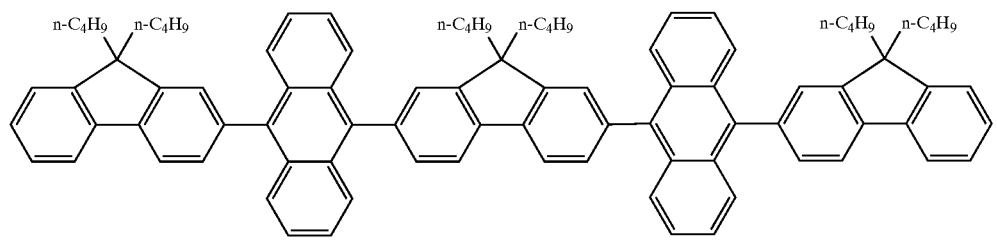
M-3
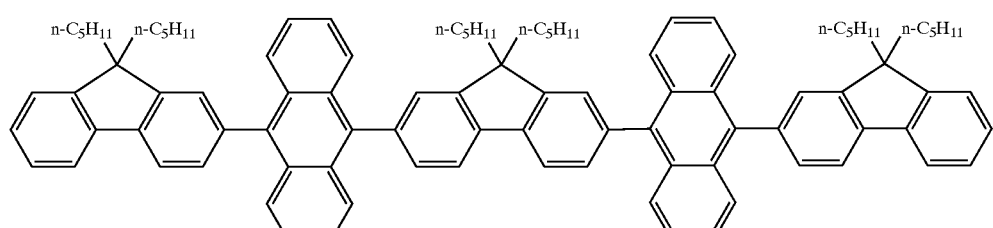
M-4
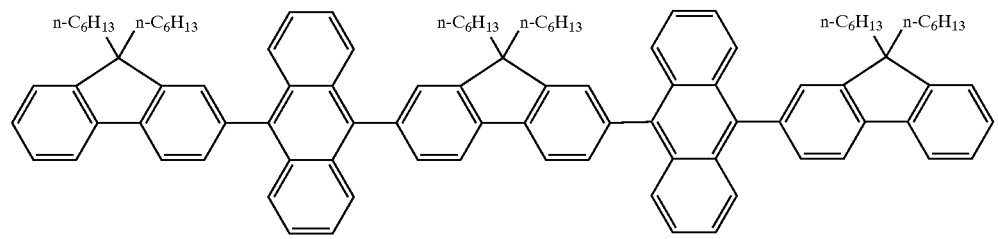
M-5

-continued
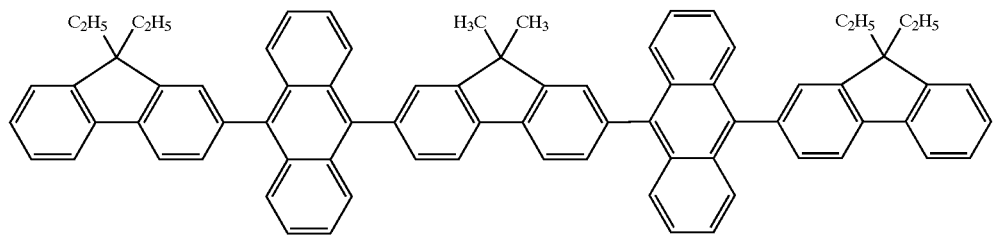
M-6
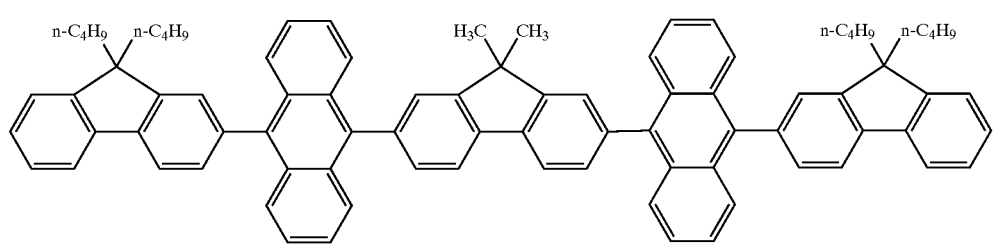
M-7
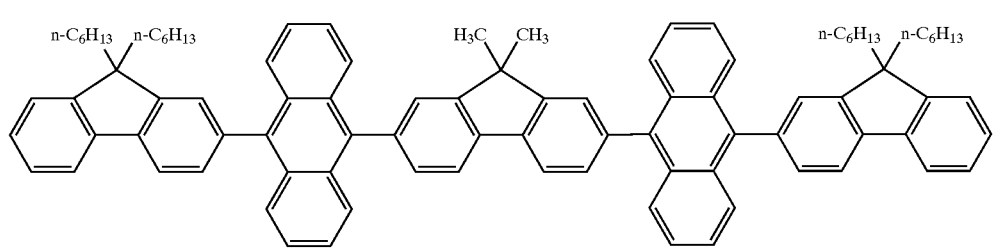
M-8
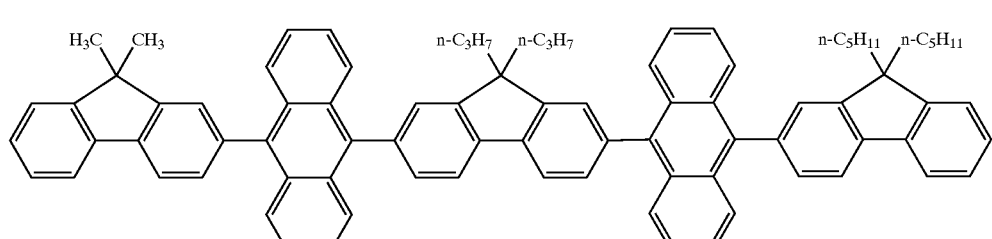
M-9
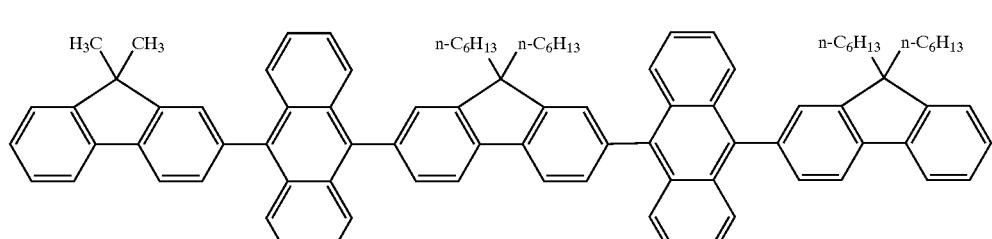
M-10
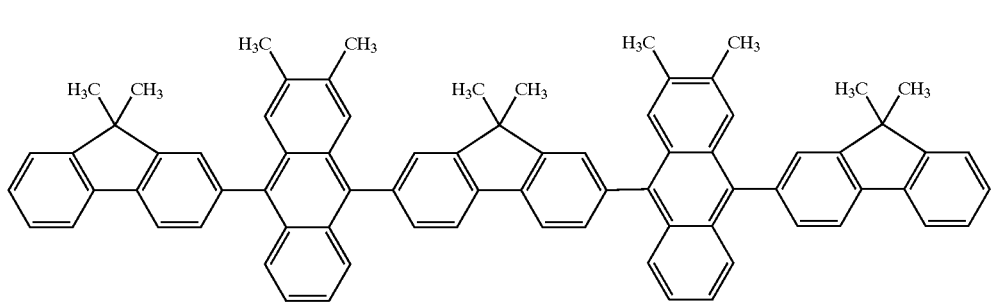
M-11

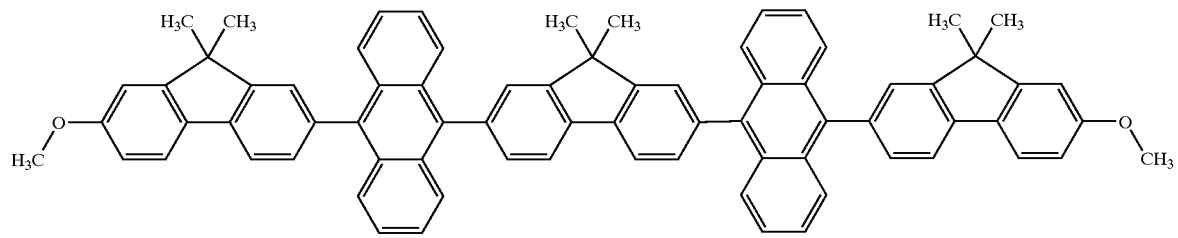
M-12
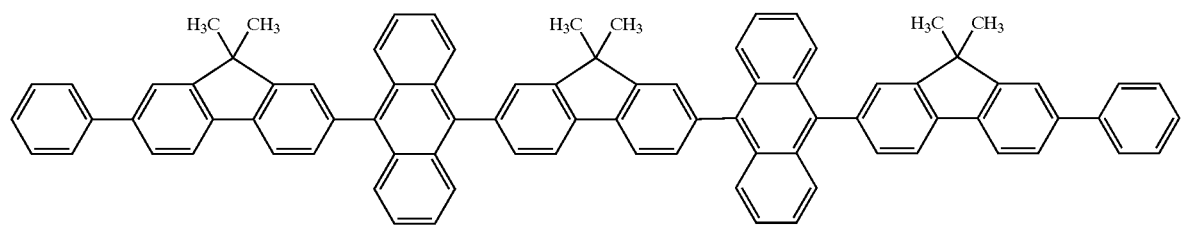
M-13
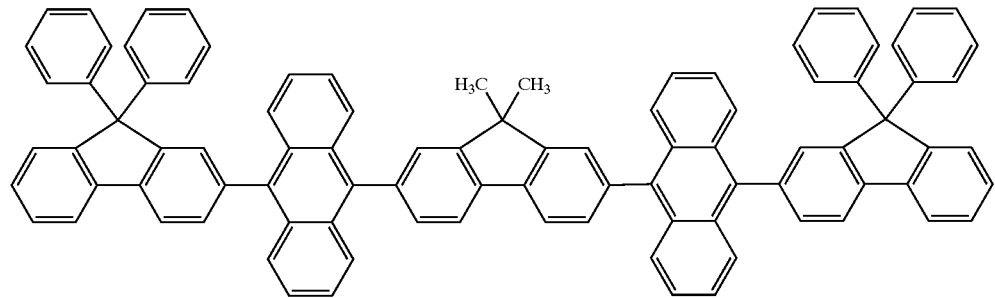
M-14
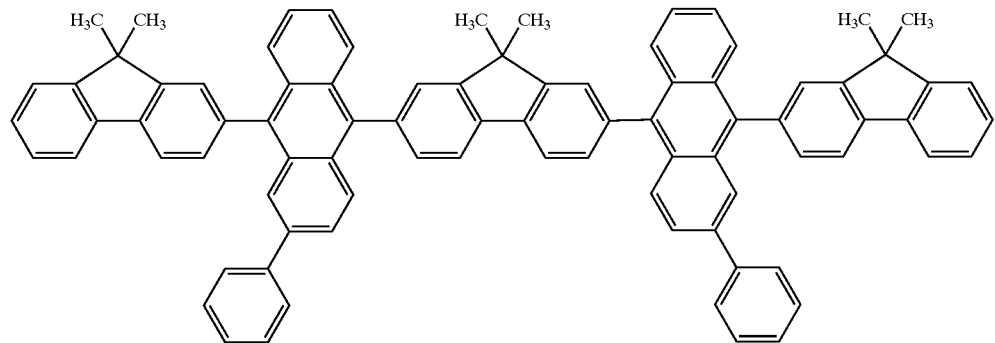
M-15
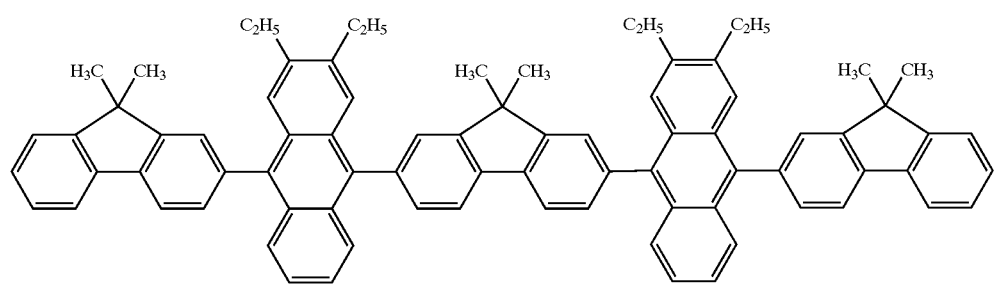
M-16

-continued
M-17
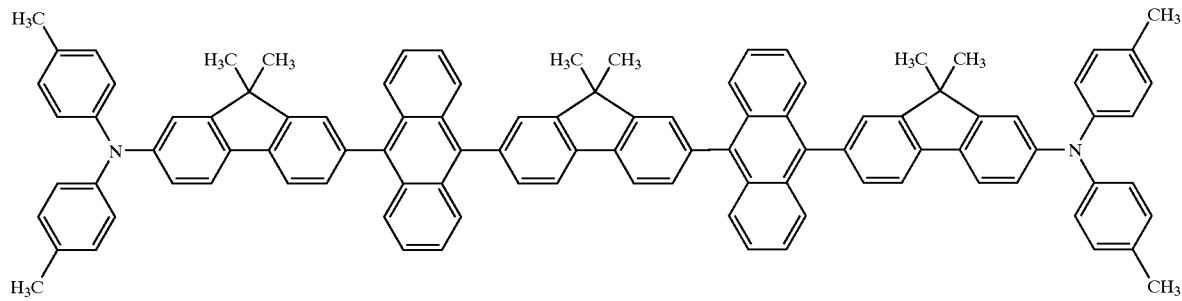
M-18
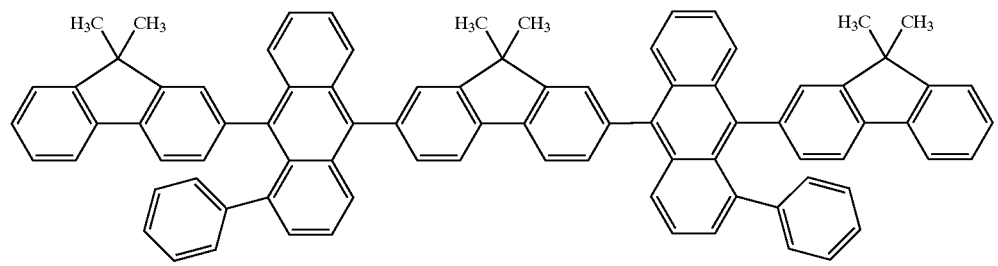
M-19
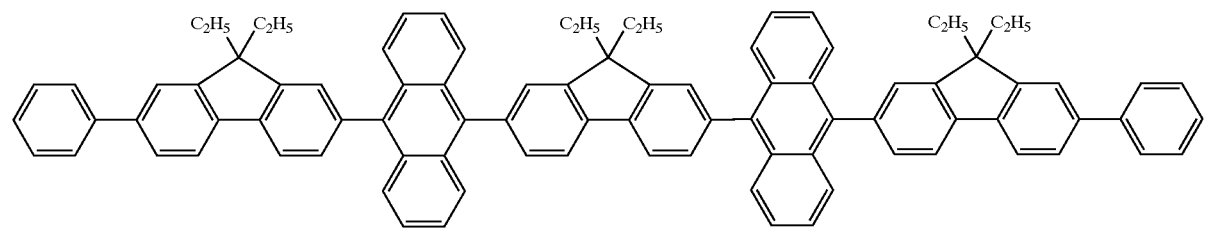
M-20
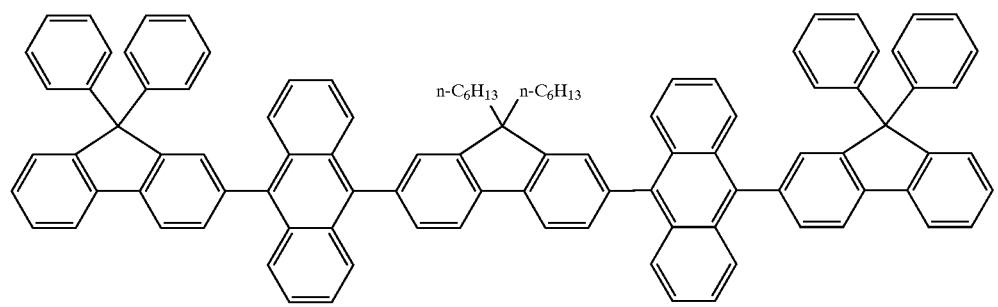
M-21
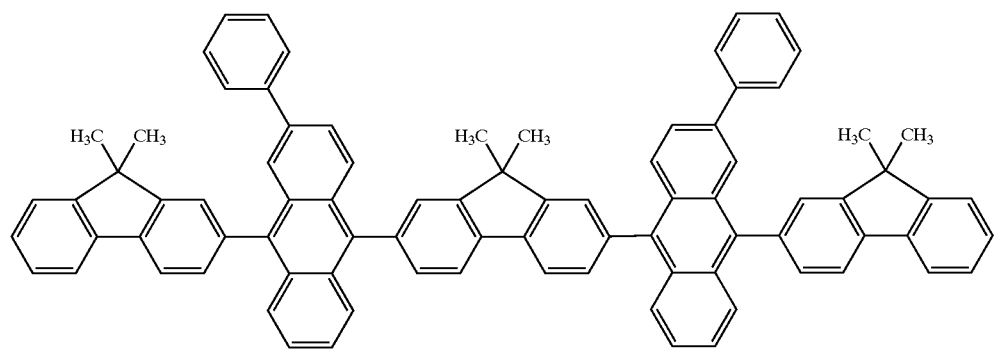

-continued
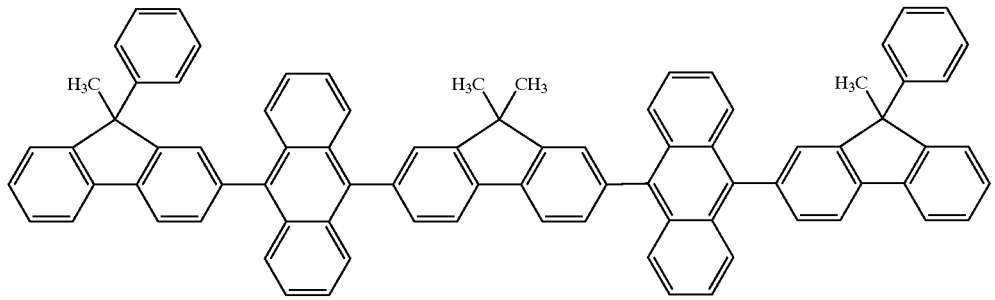
M-22
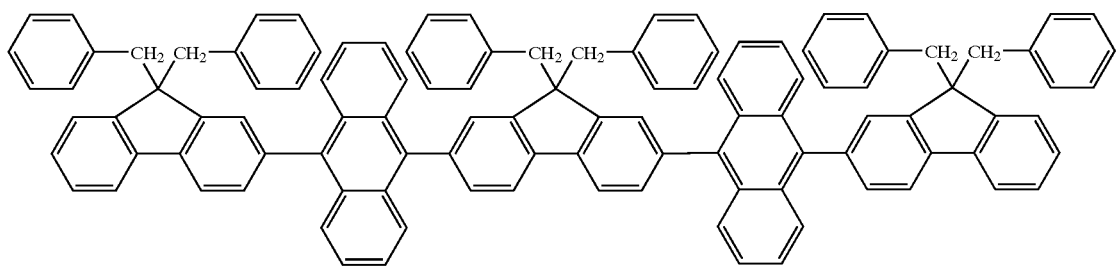
M-23
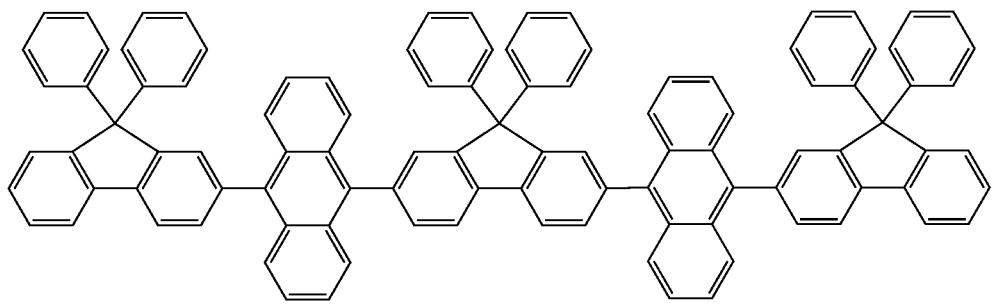
M-24
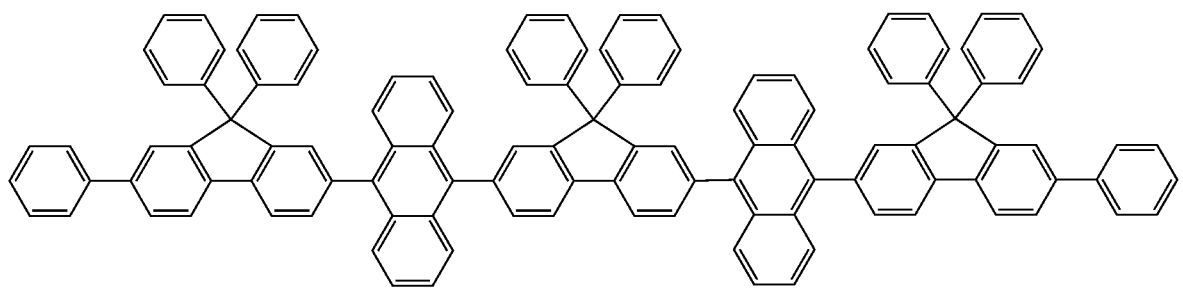
M-25
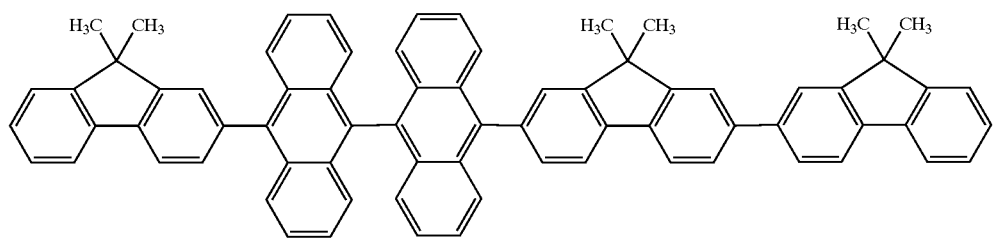
N-1

-continued
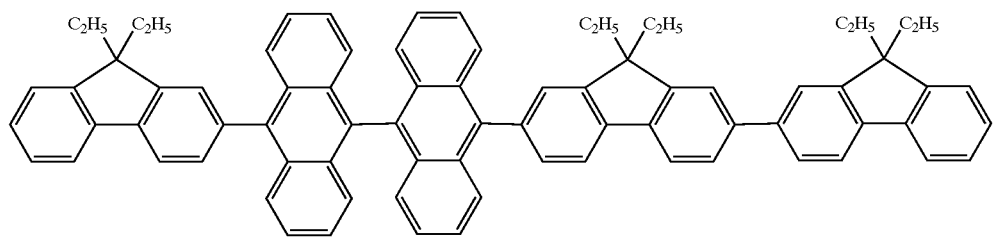 N-2
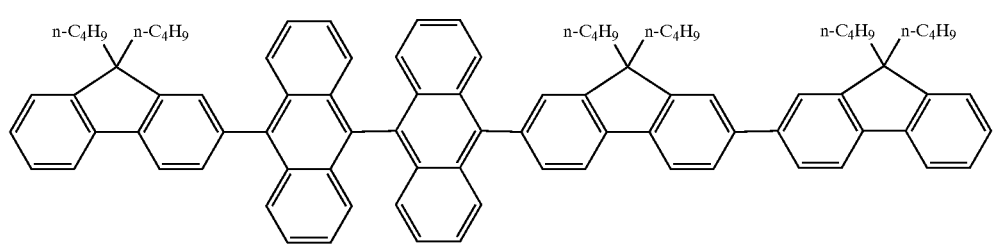 N-3
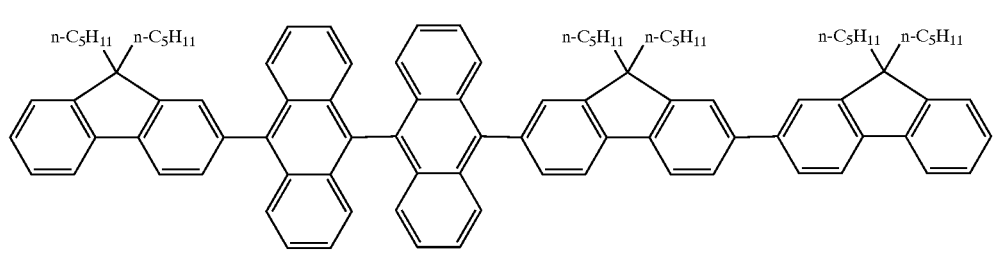 N-4
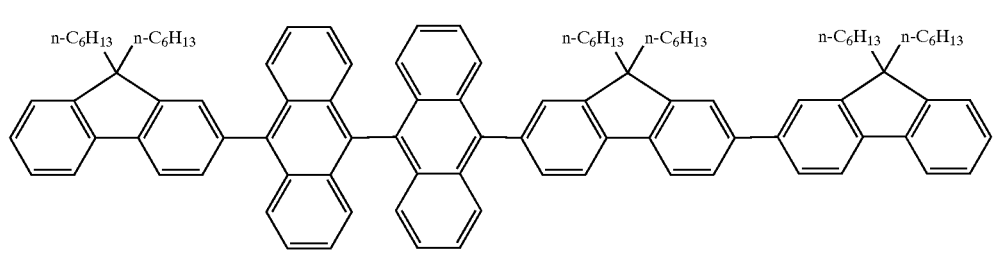 N-5
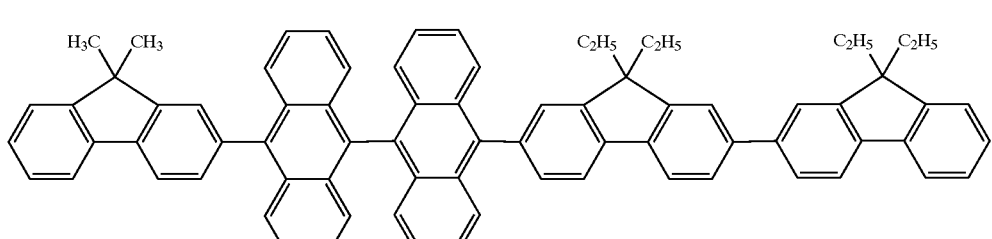 N-6
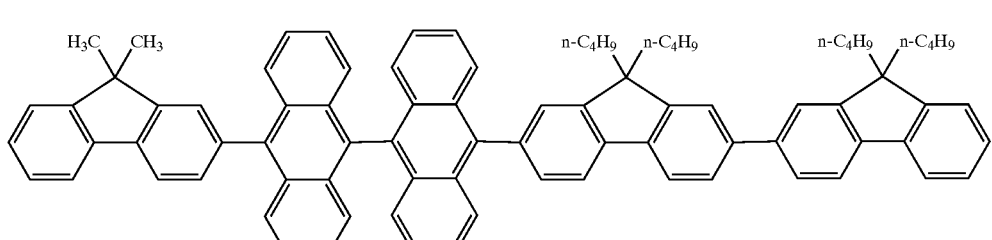 N-7

-continued
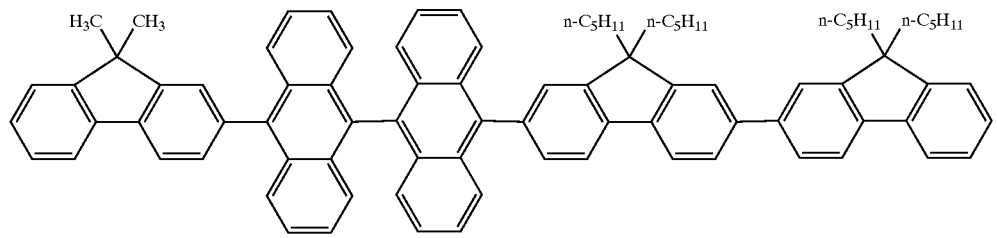
N-8
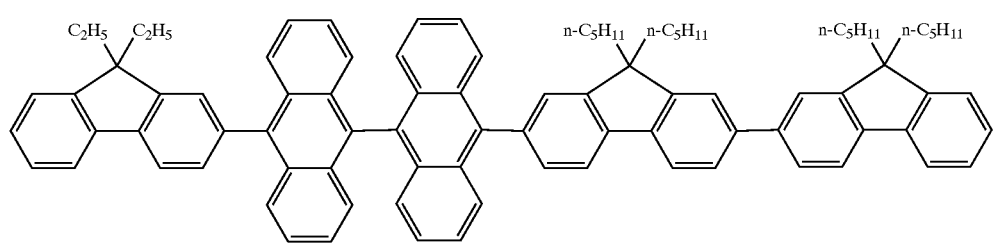
N-9
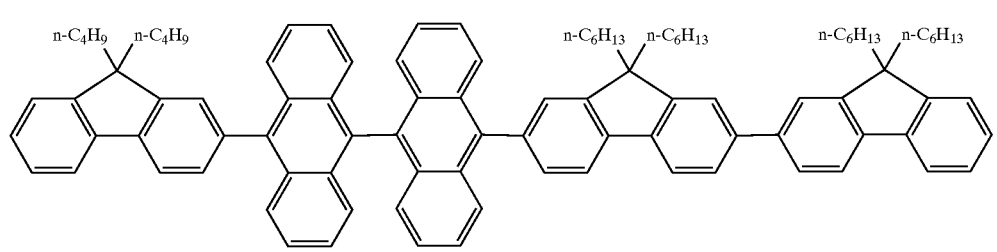
N-10
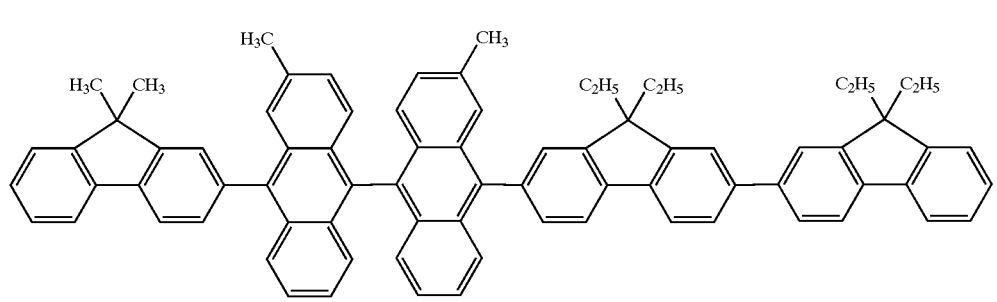
N-11
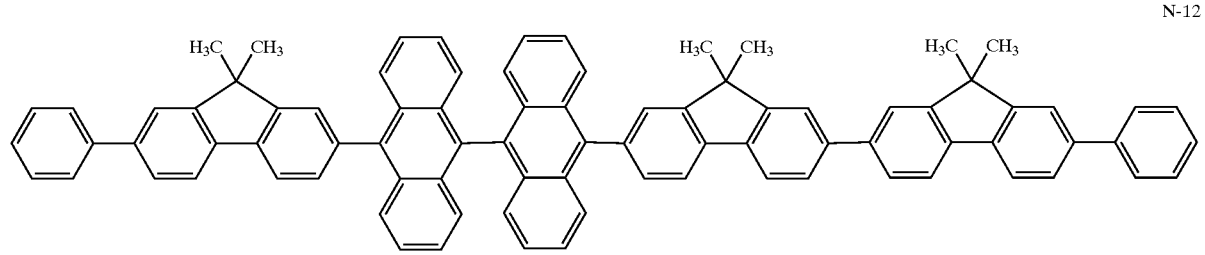
N-12
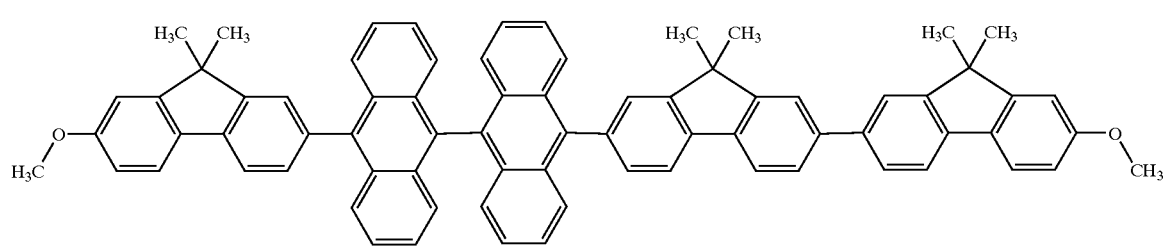
N-13

N-14
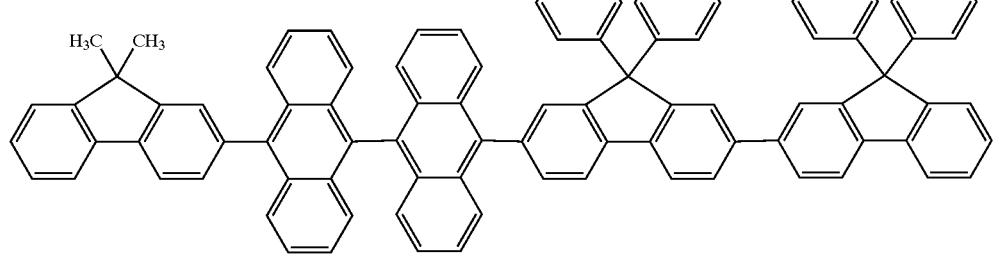
N-15
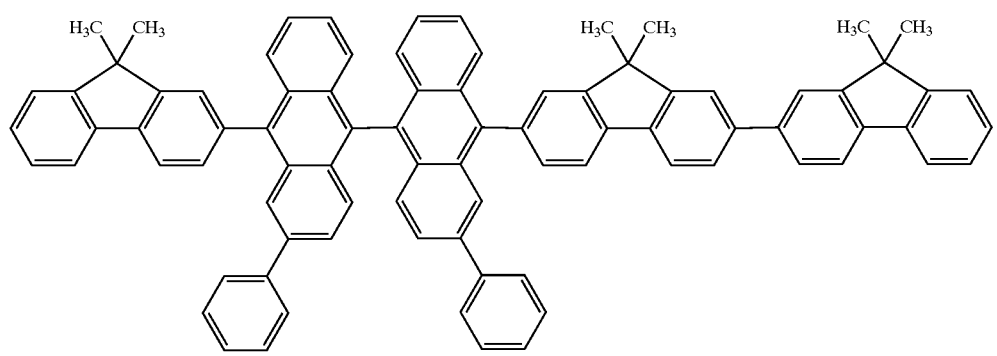
N-16
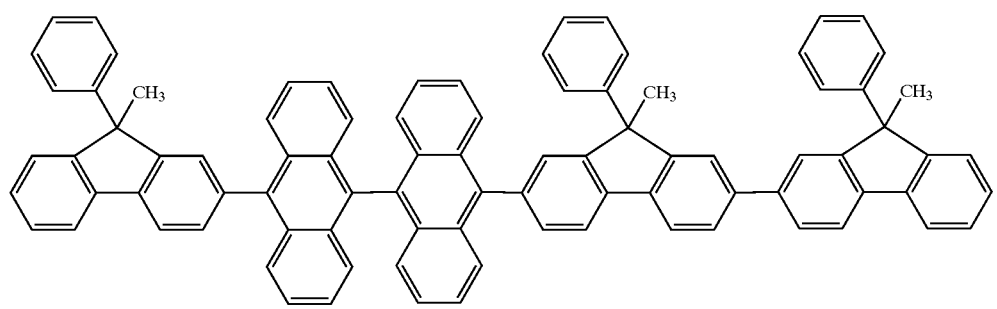
N-17
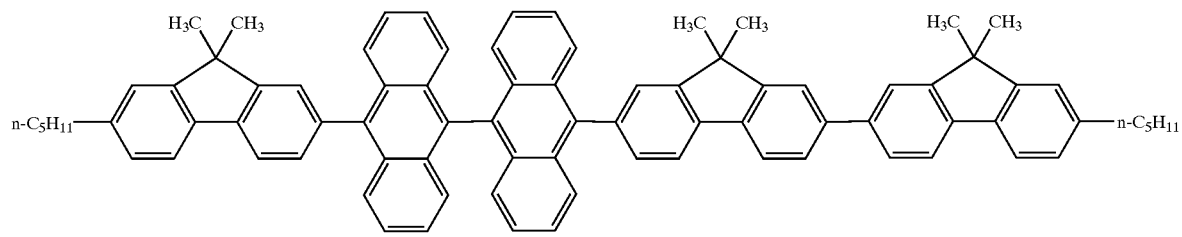
N-18
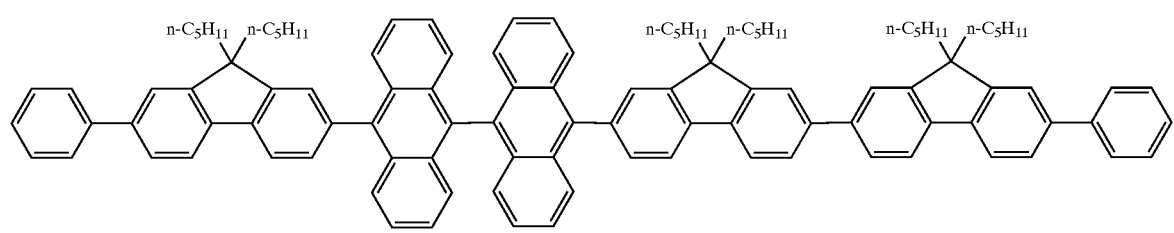

N-19
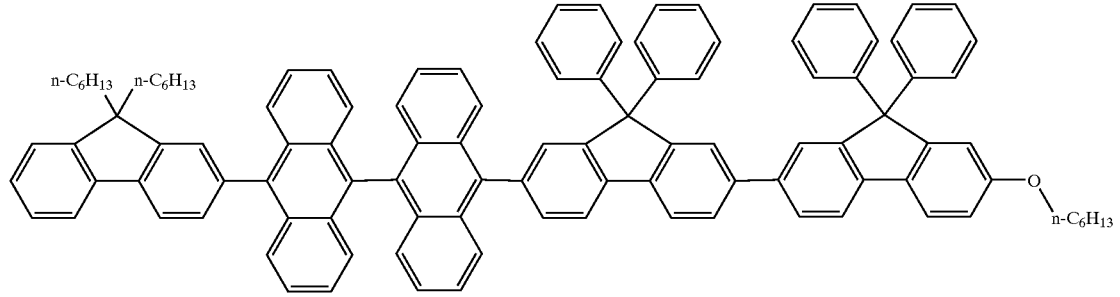
N-20
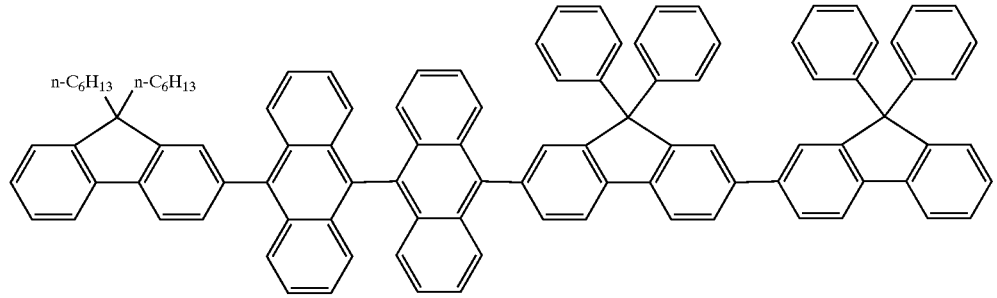
N-21
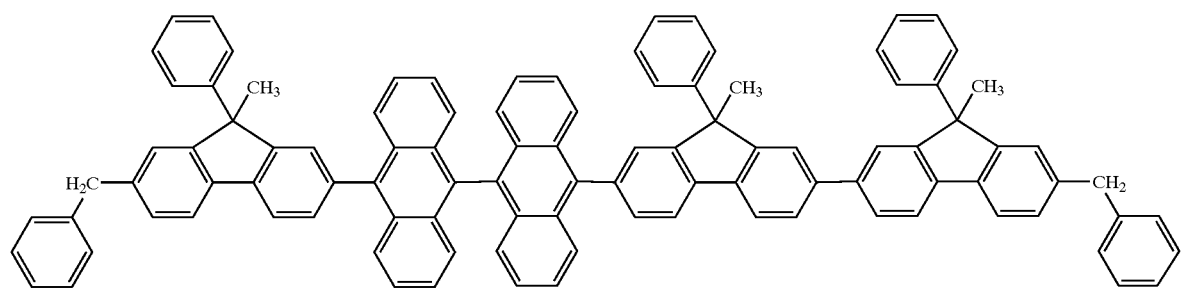
N-22
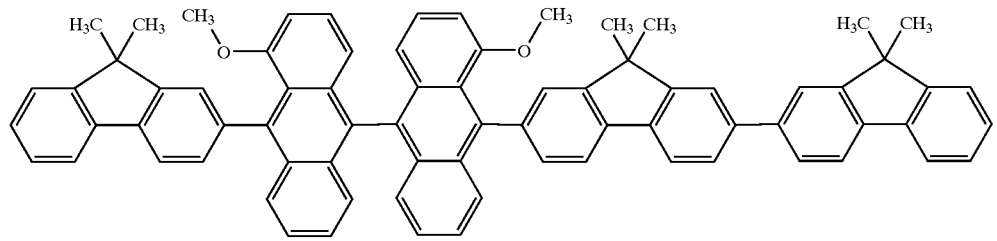
N-23
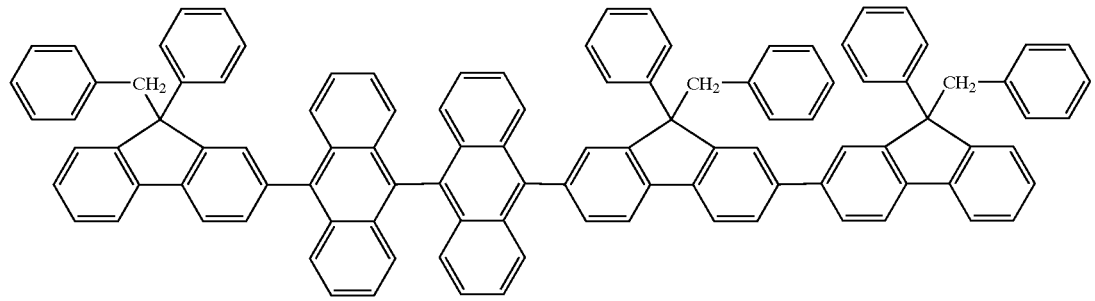

-continued
N-24
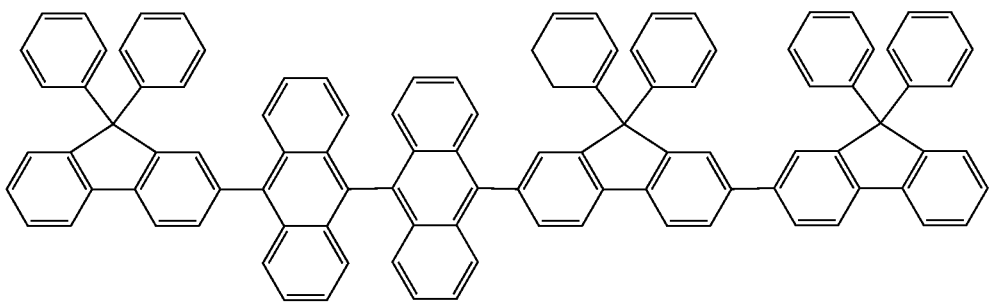
N-25
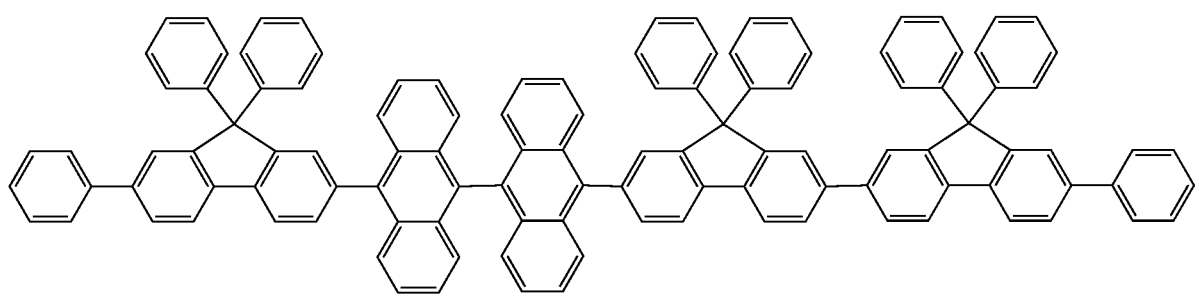
O-1
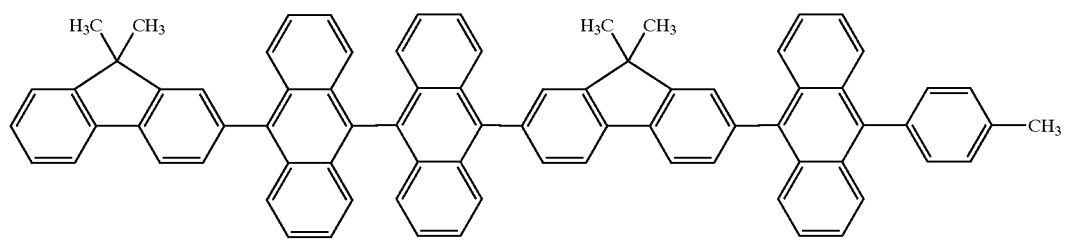
O-2
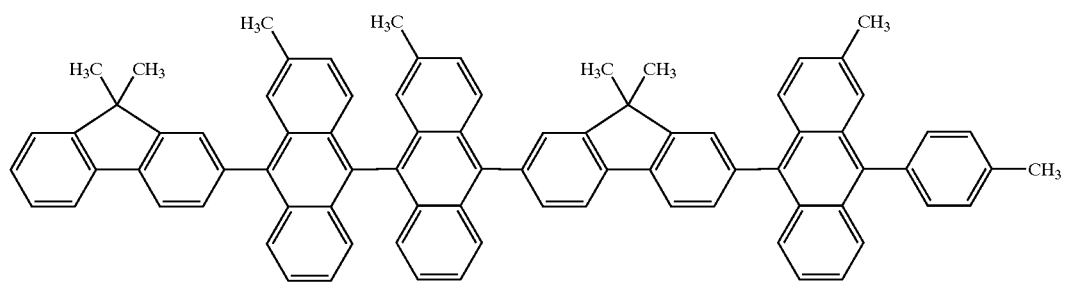
O-3
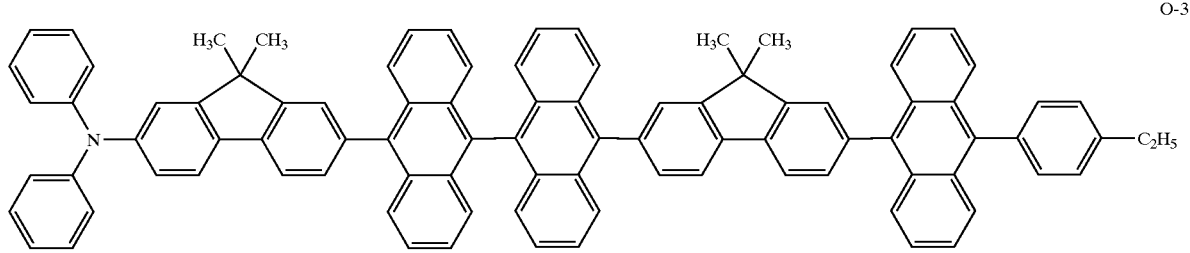

-continued
O-4
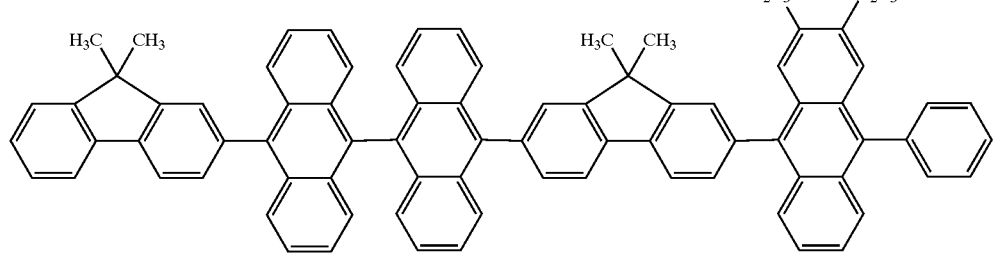
O-5
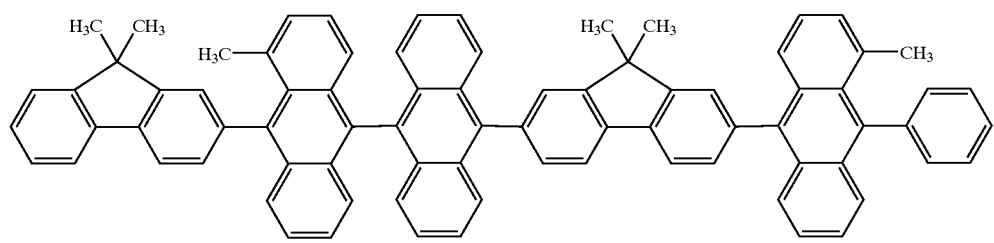
O-6
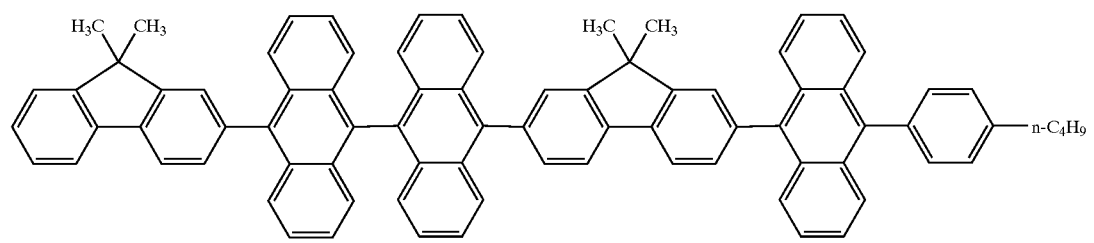
O-7
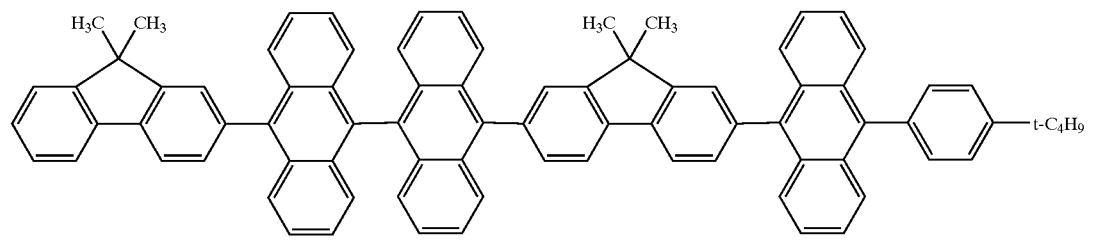
O-8
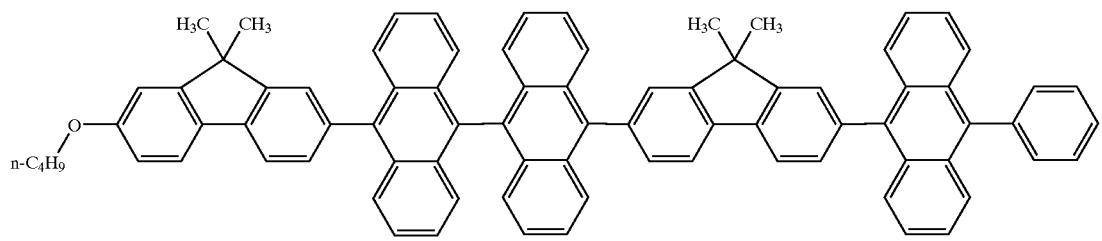
O-9
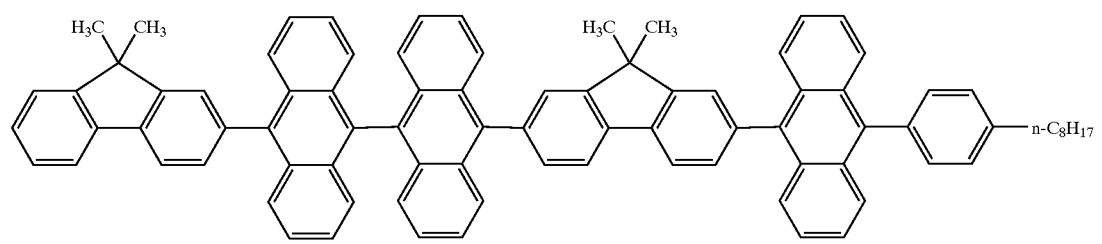

-continued
O-10
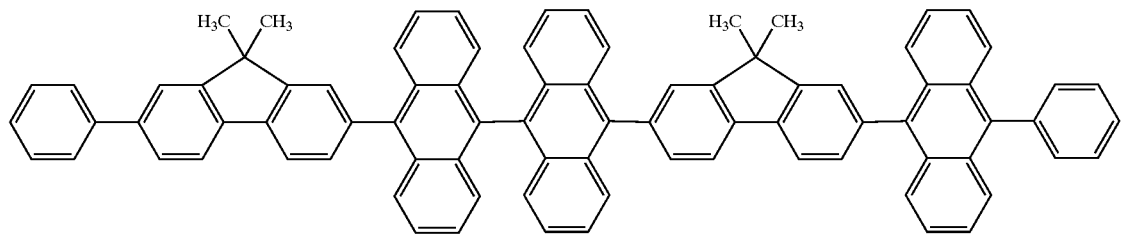
O-11
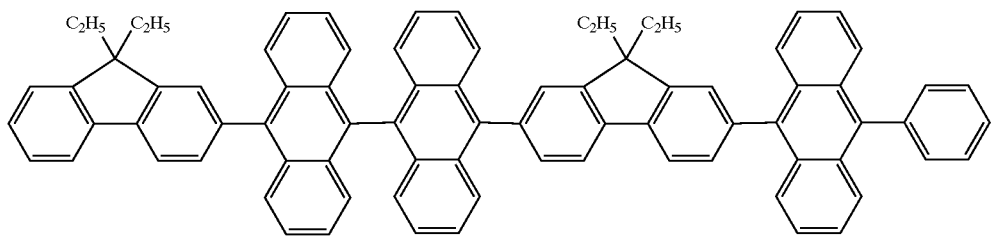
O-12
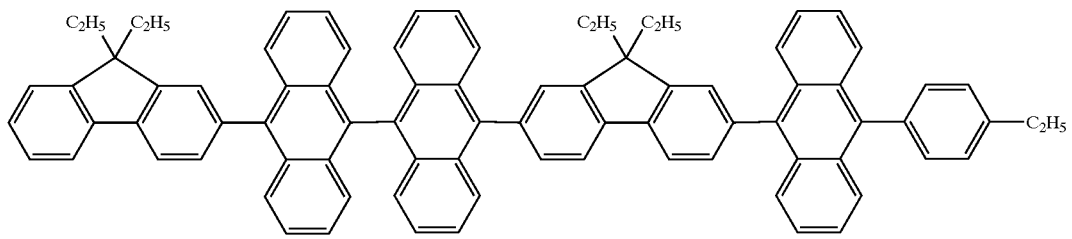
O-13
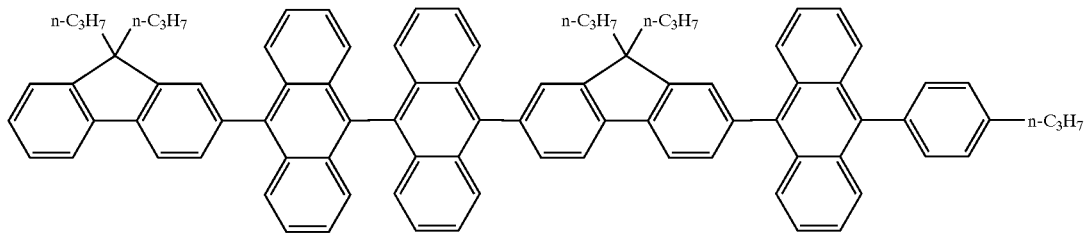
O-14
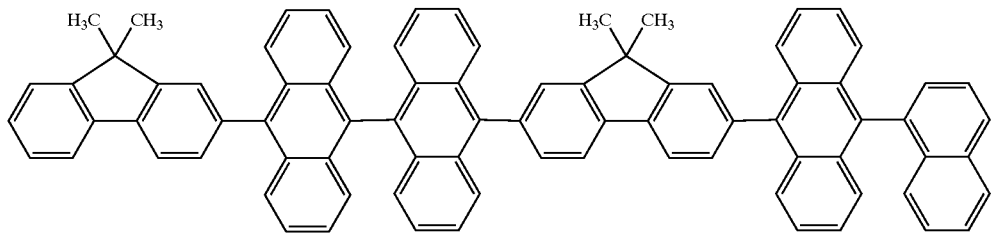
O-15
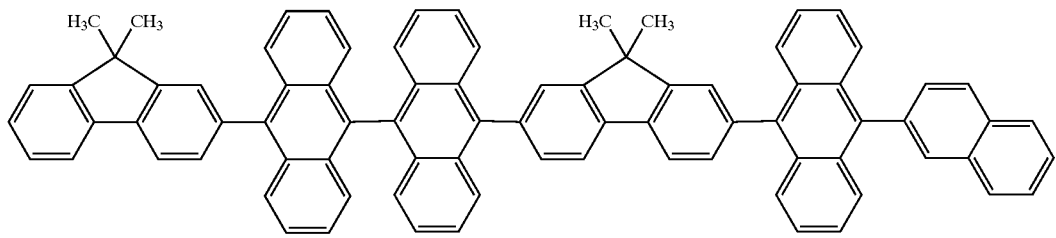

-continued
O-16
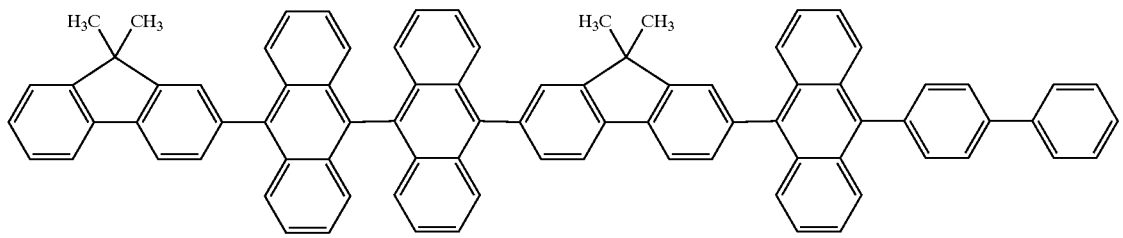
O-17
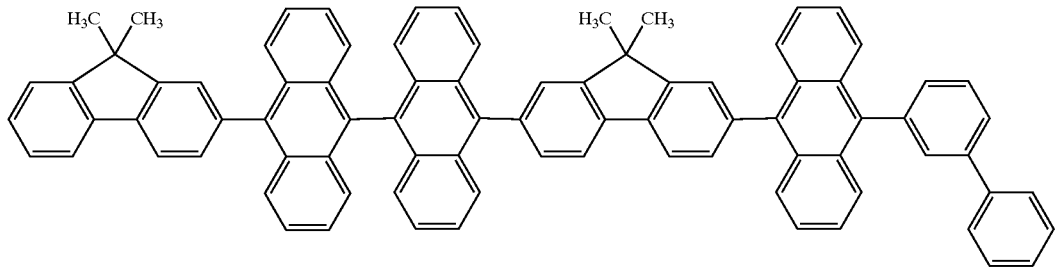
O-18
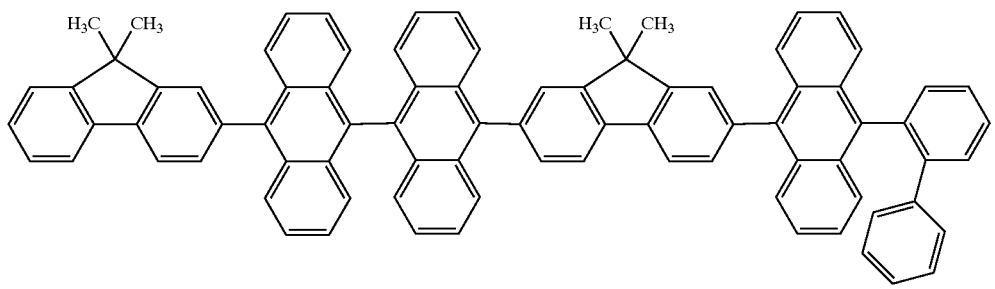
O-19
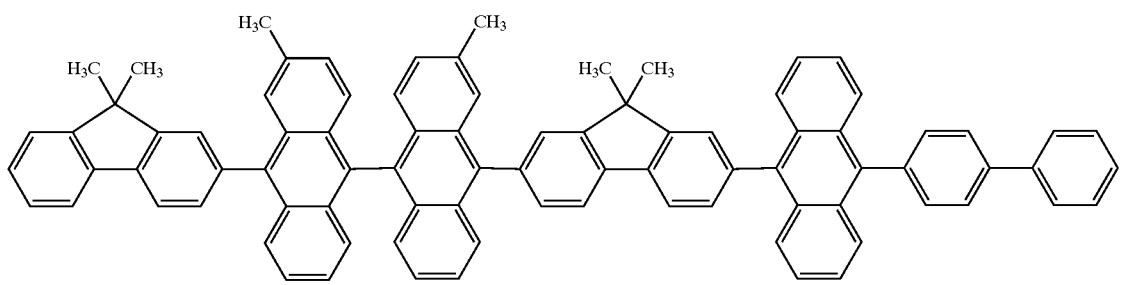
O-20
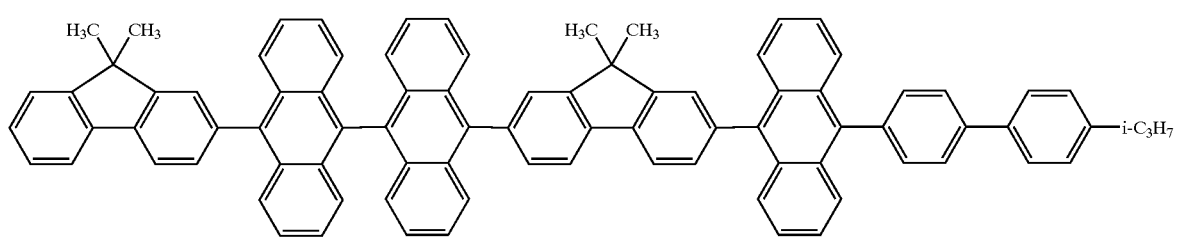
O-21
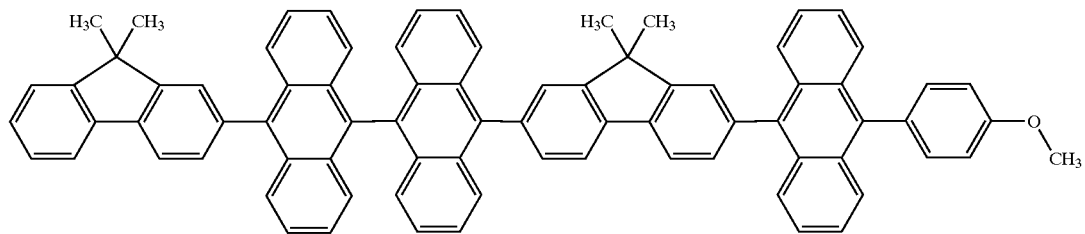

-continued
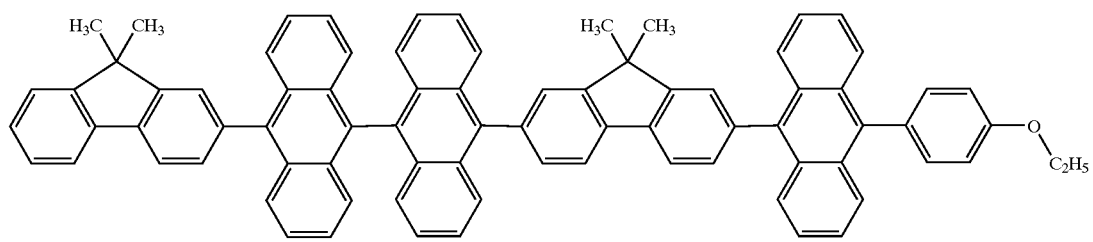
O-22
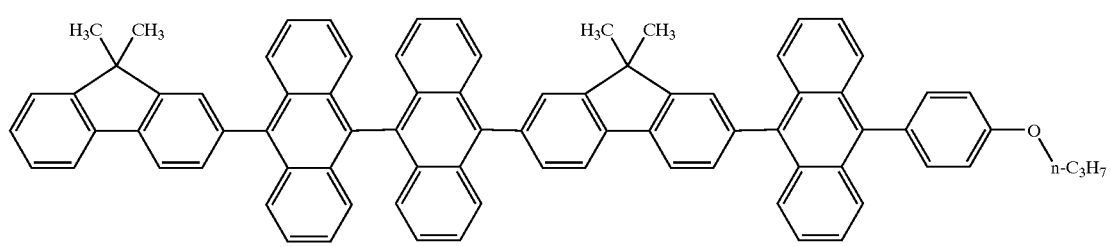
O-23
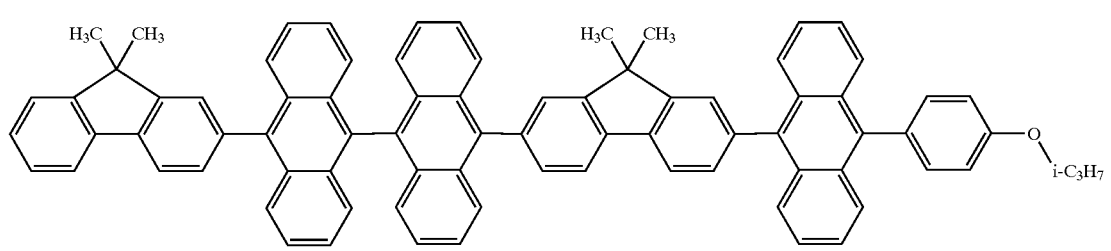
O-24
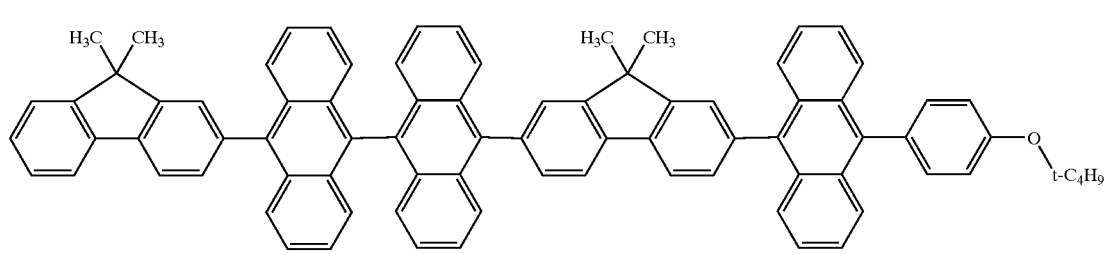
O-25
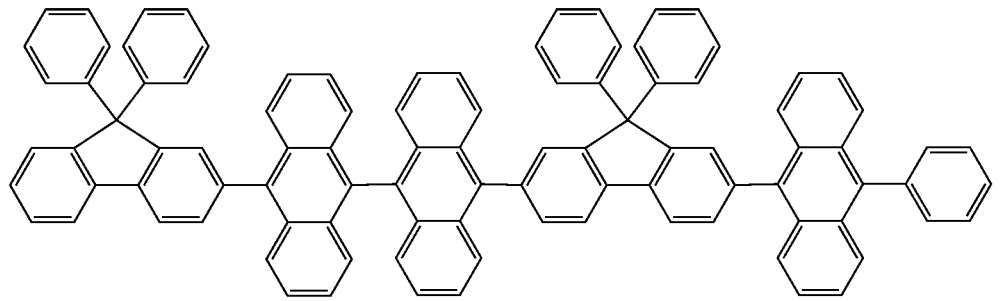
O-26
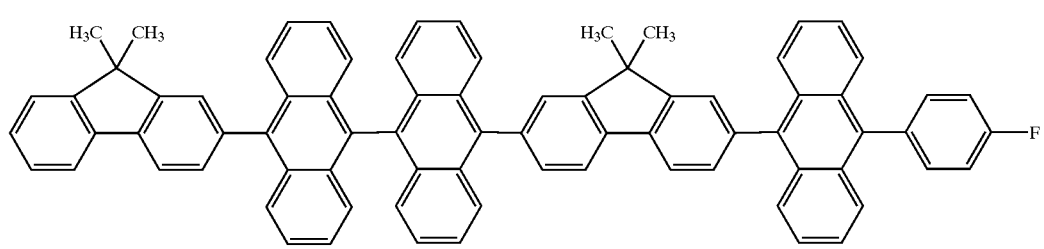
O-27

-continued
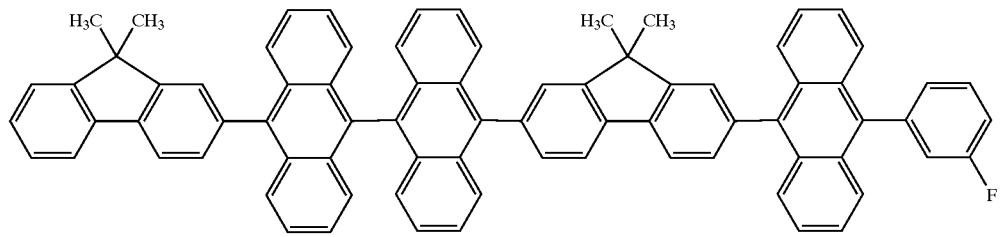
O-28
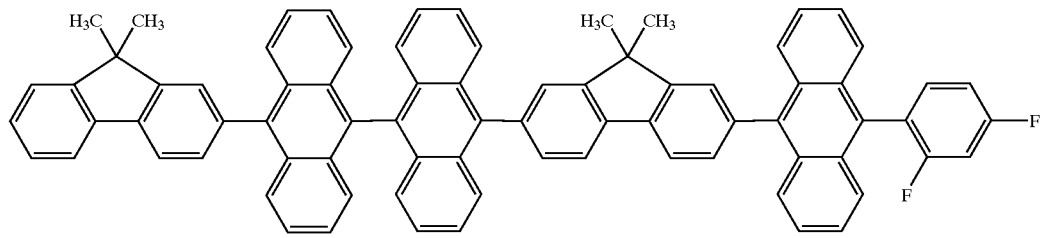
O-29
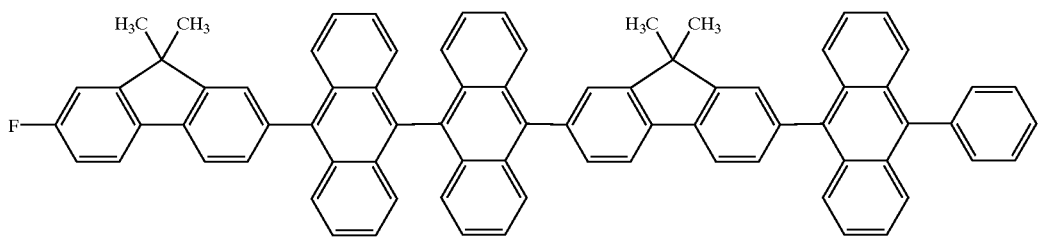
O-30
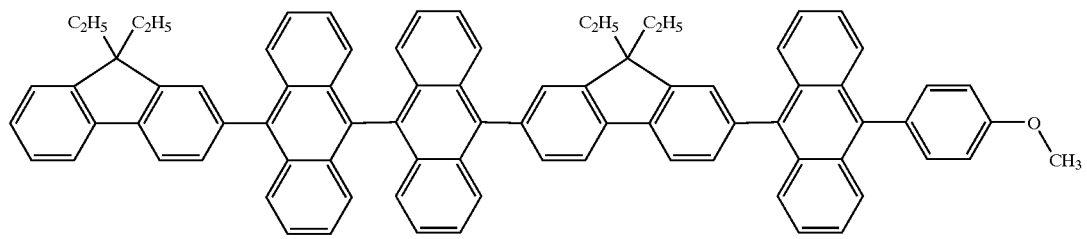
O-31
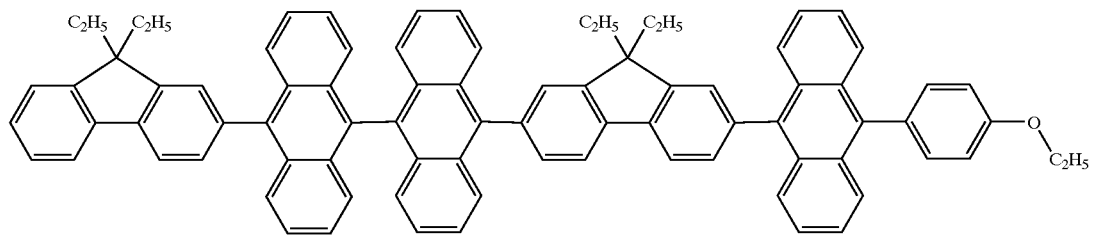
O-32
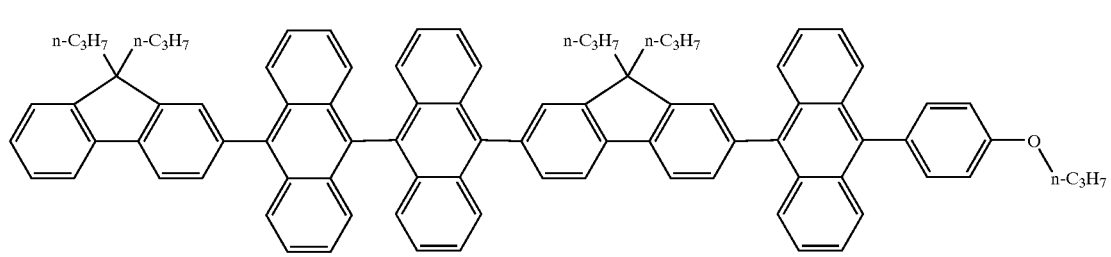
O-33

O-34
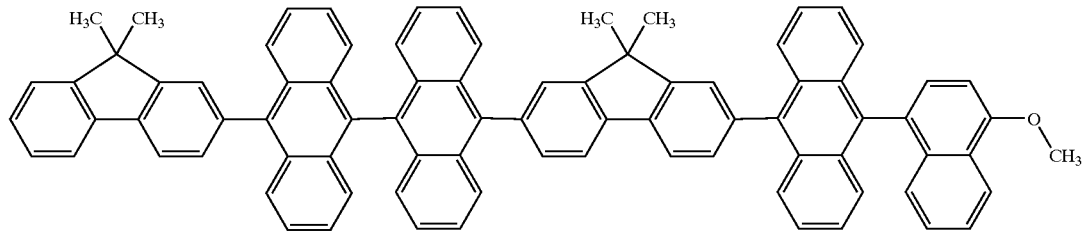
O-35
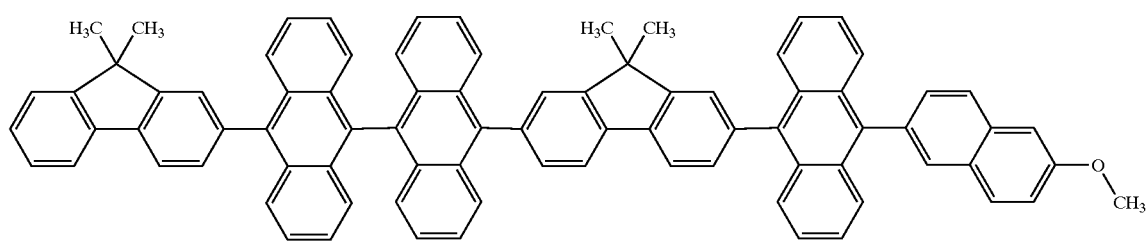
O-36
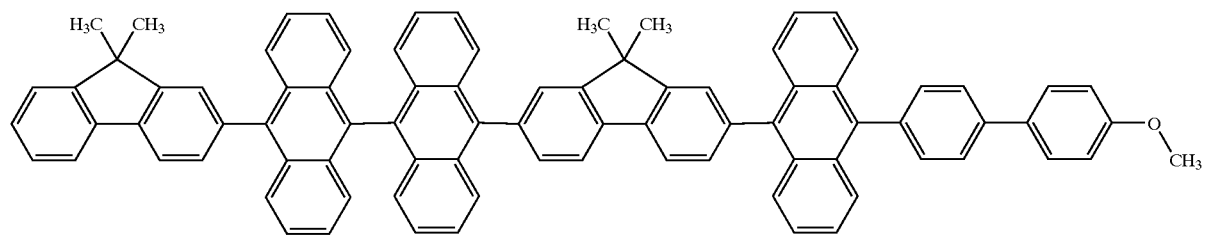
O-37
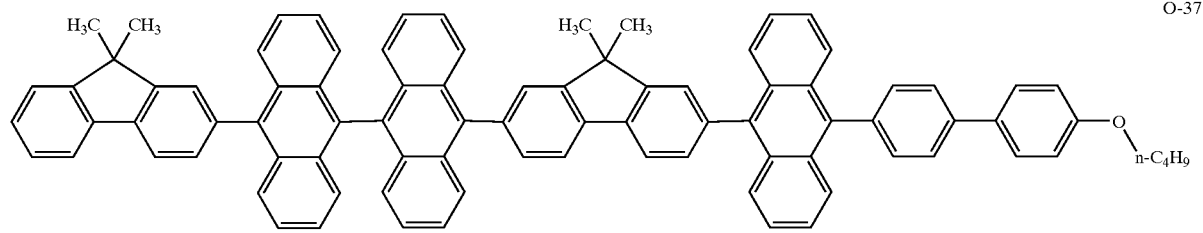
O-38
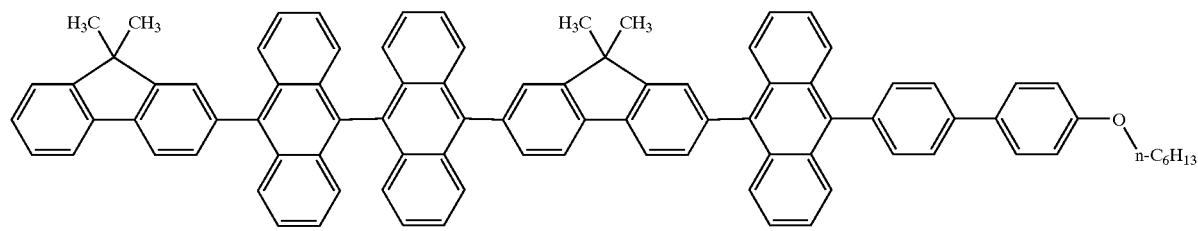
O-39
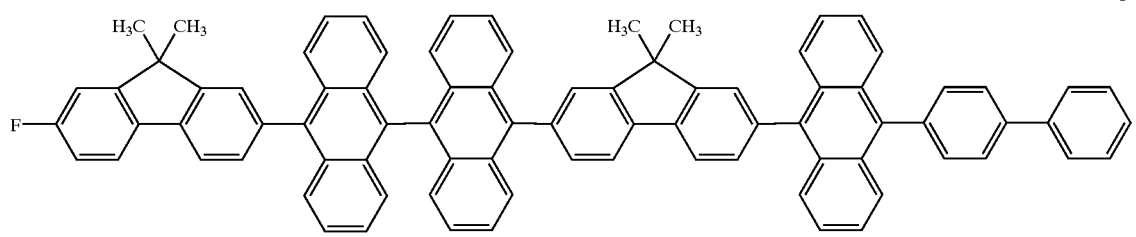

-continued
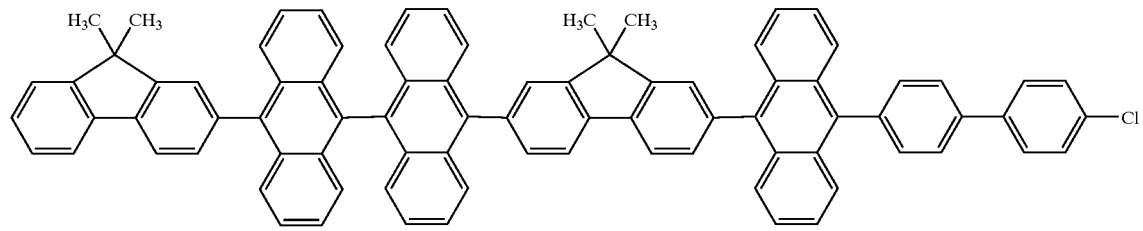
O-40
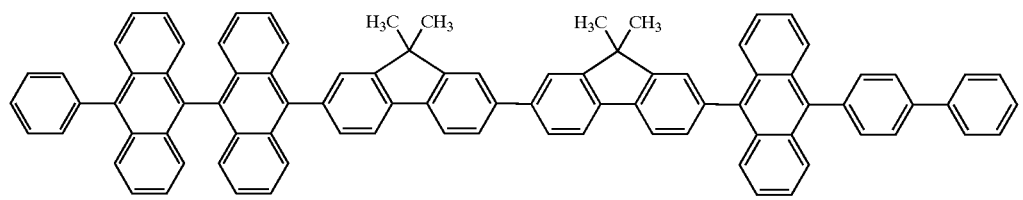
P-1
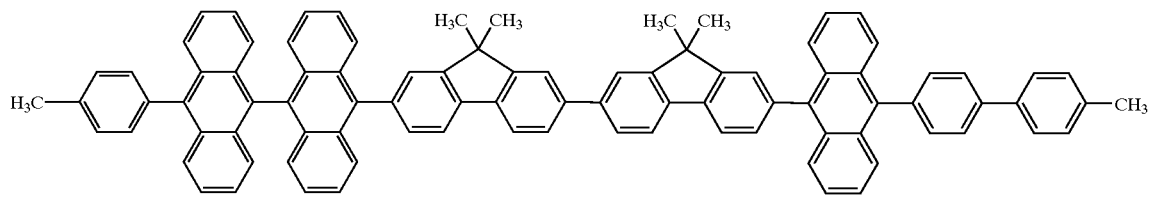
P-2
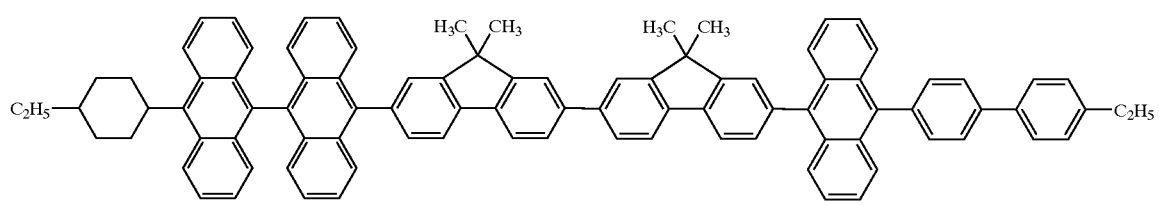
P-3
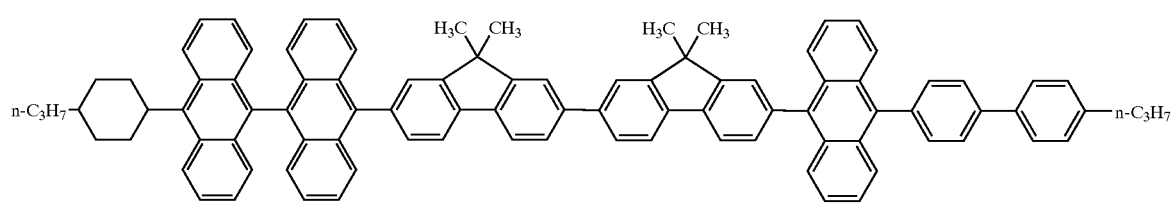
P-4
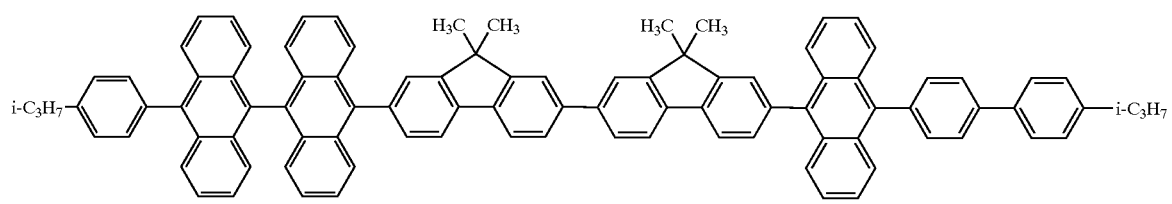
P-5
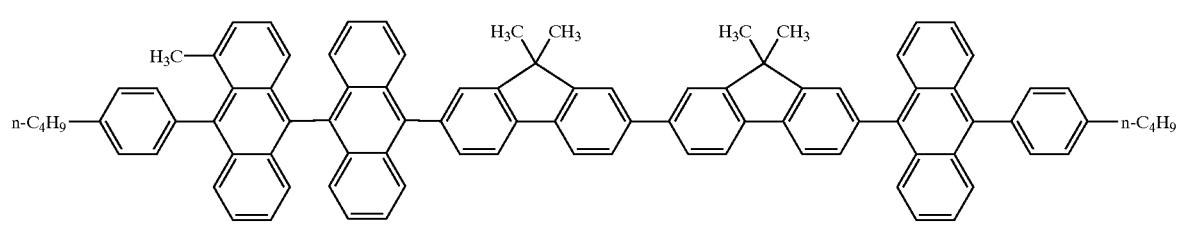
P-6

-continued
P-7
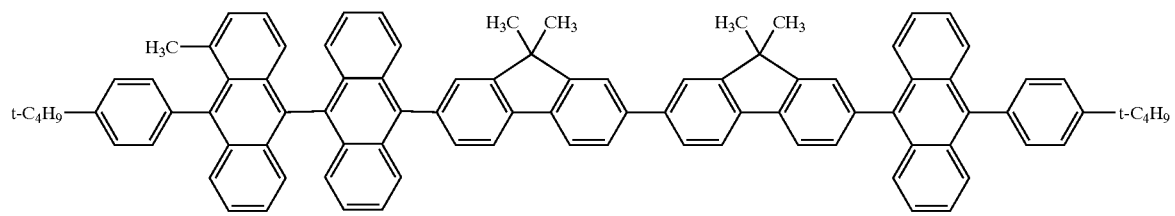
P-8
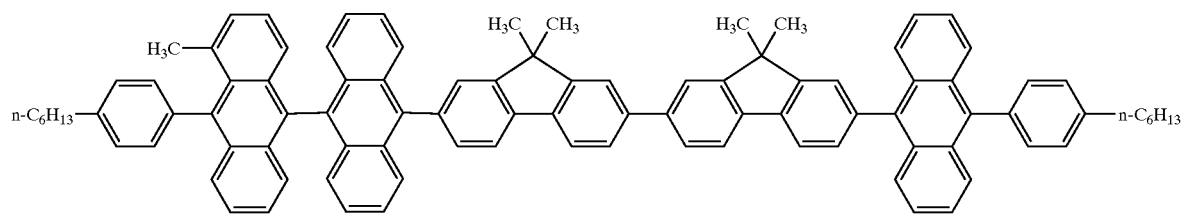
P-9
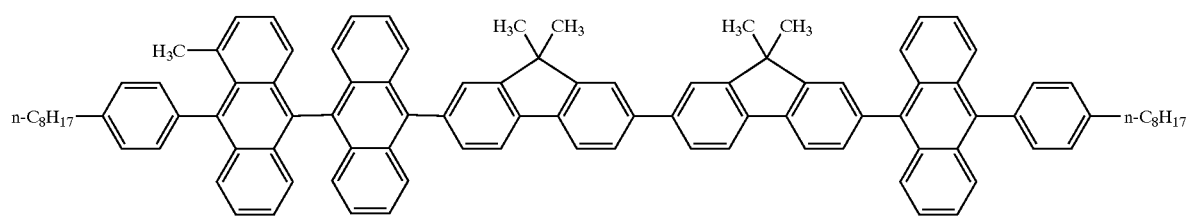
P-10
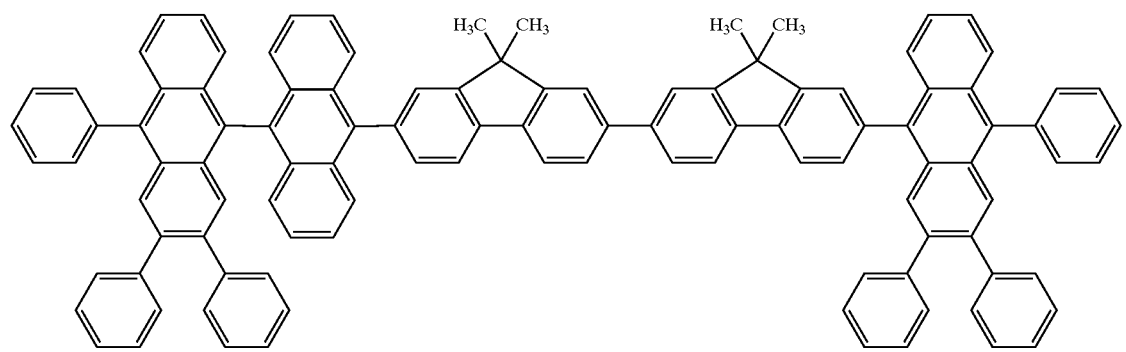
P-11
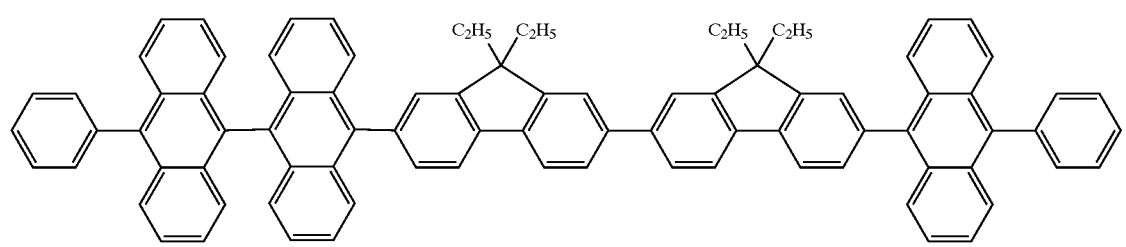
P-12
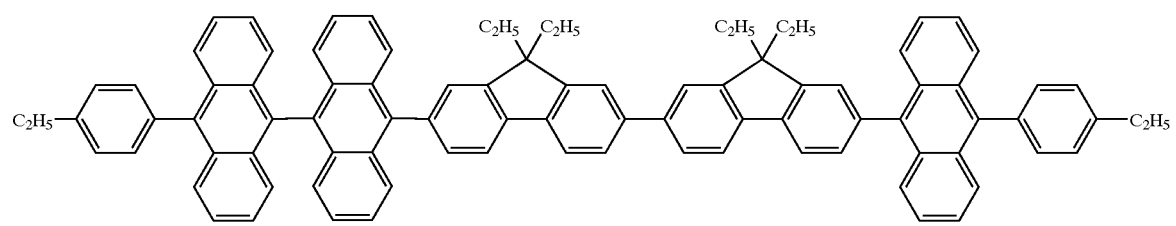

-continued
P-13
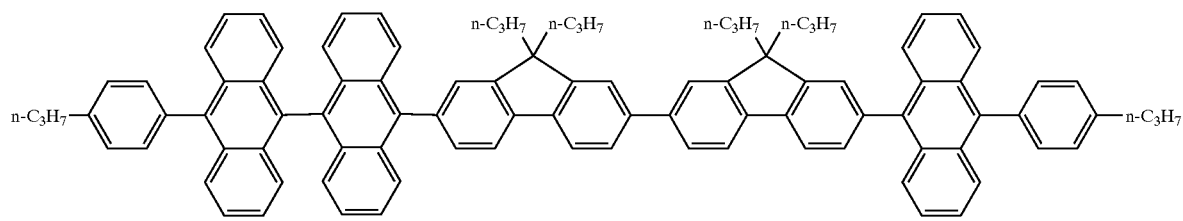
P-14
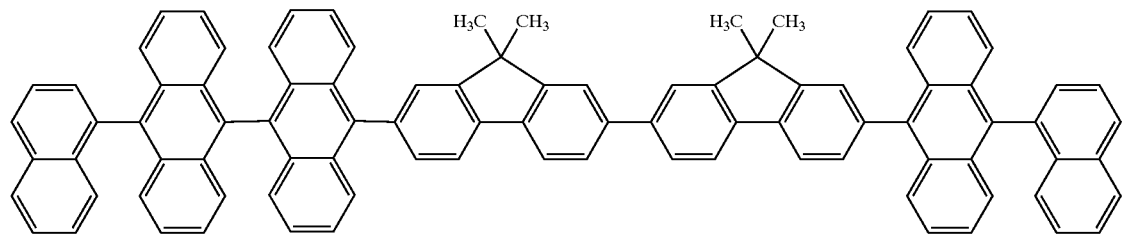
P-15
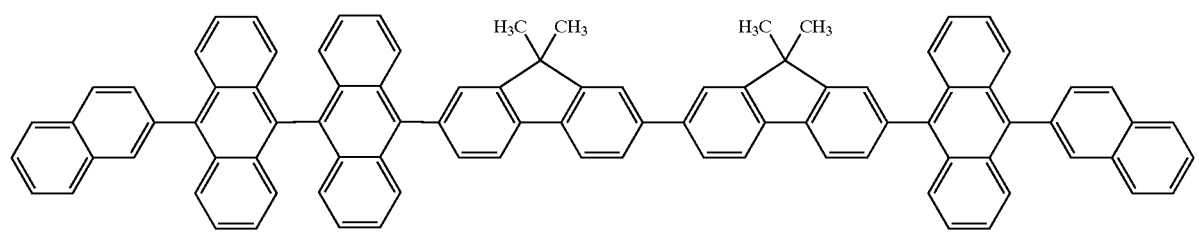
P-16
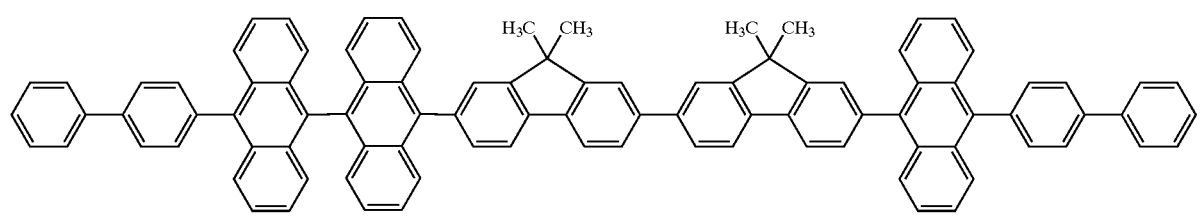
P-17
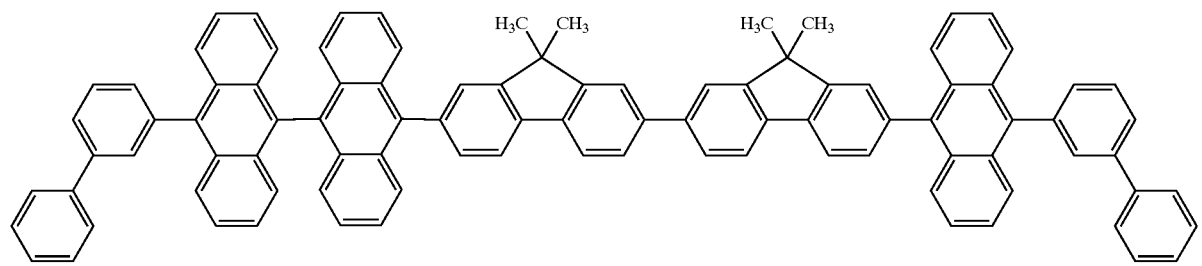
P-18
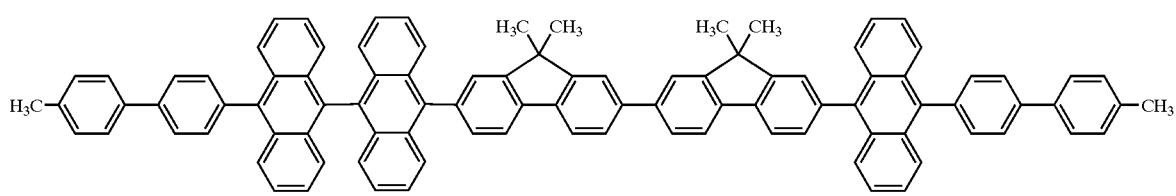

-continued
P-19
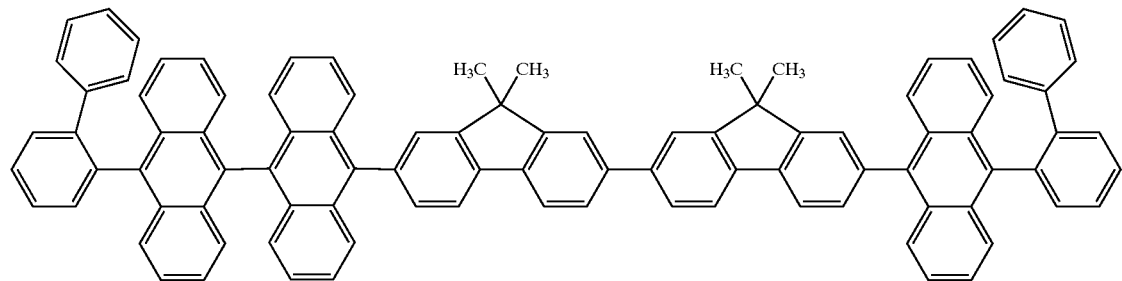
P-20
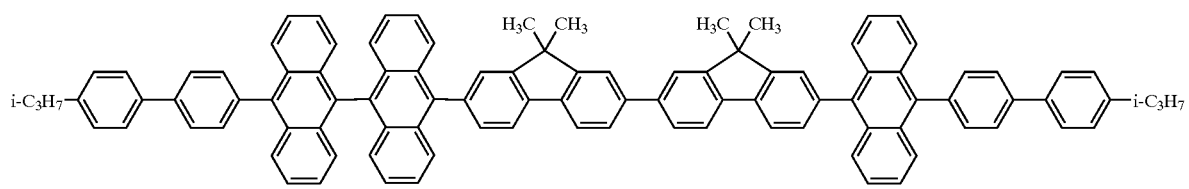
P-21
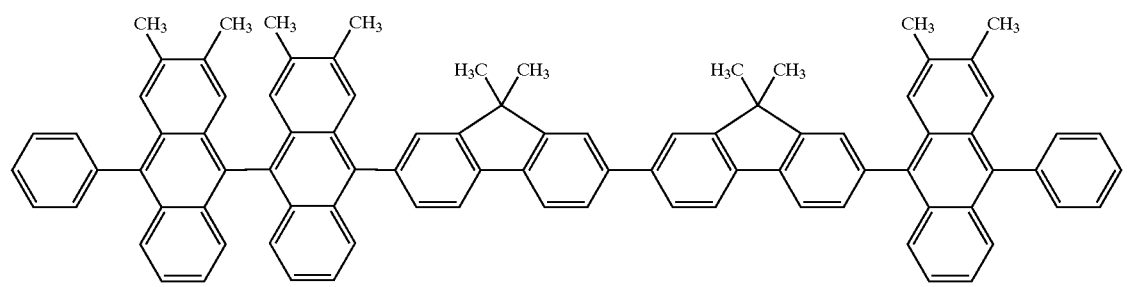
P-22
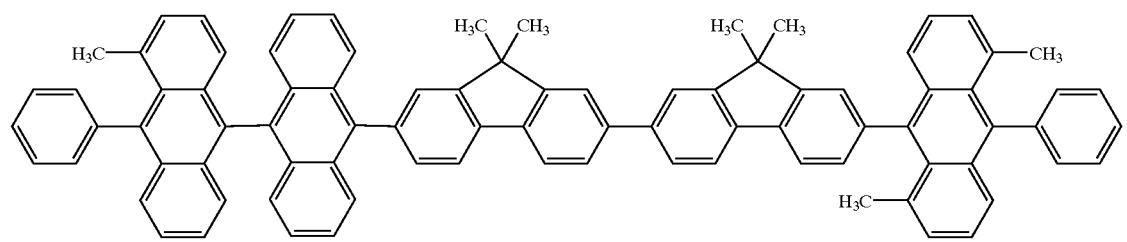
P-23
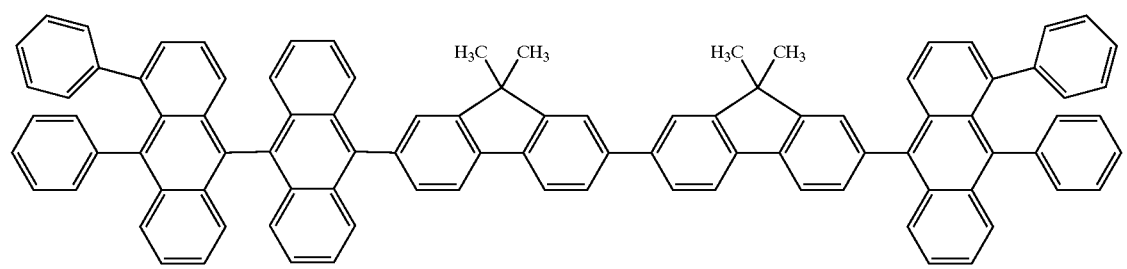

-continued
P-24
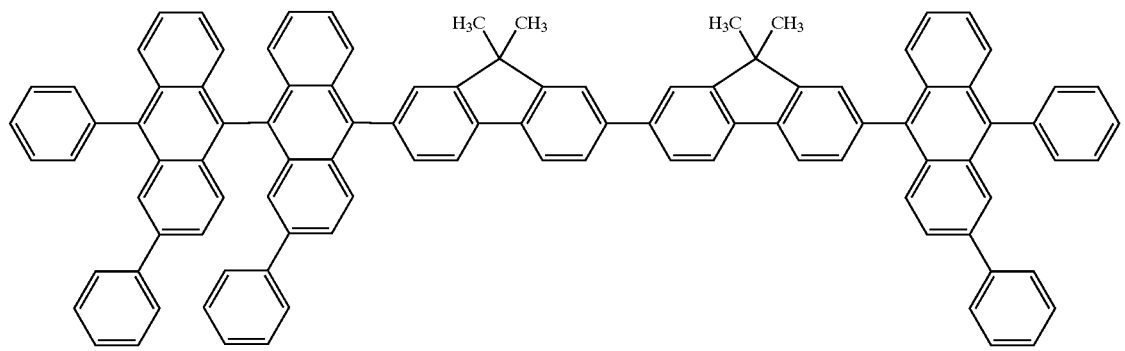
P-25
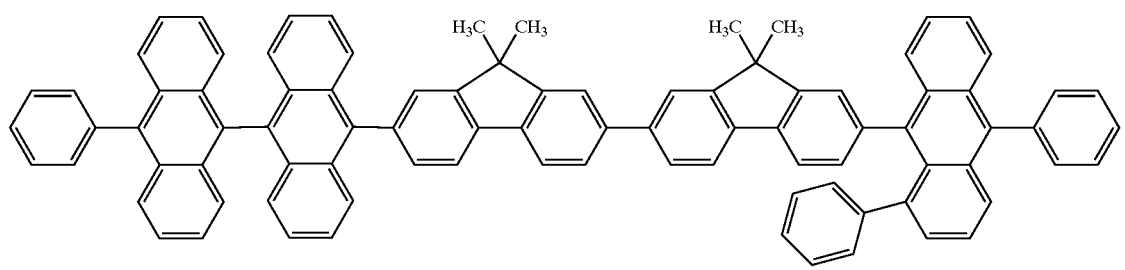
P-26
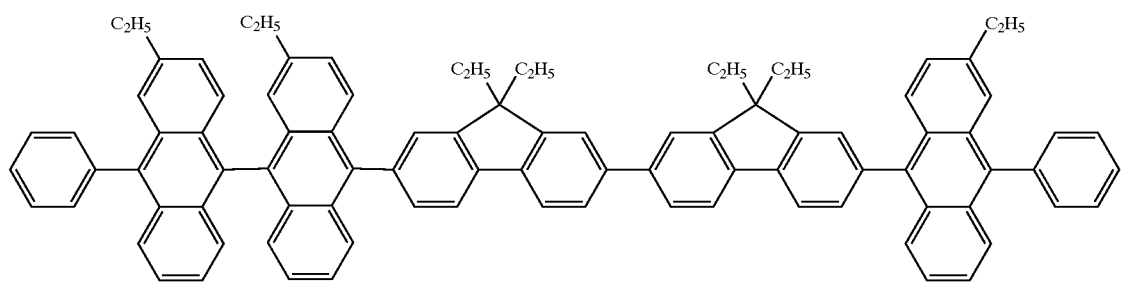
P-27
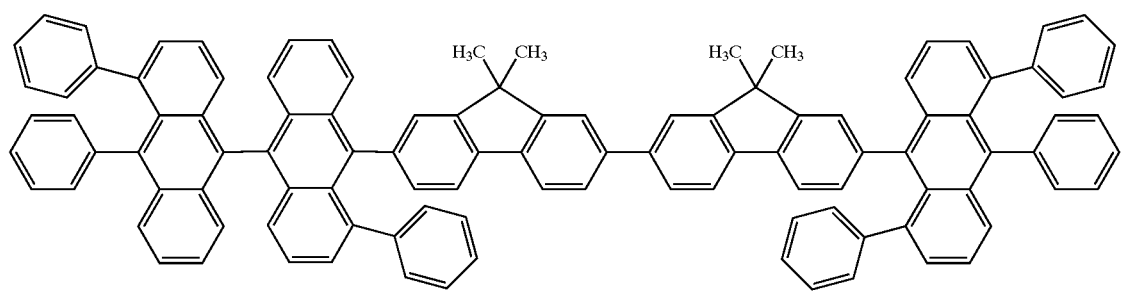
P-28
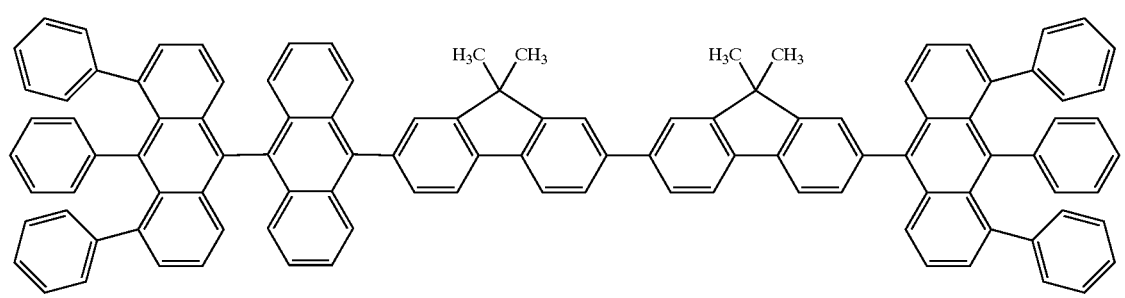

-continued
P-29
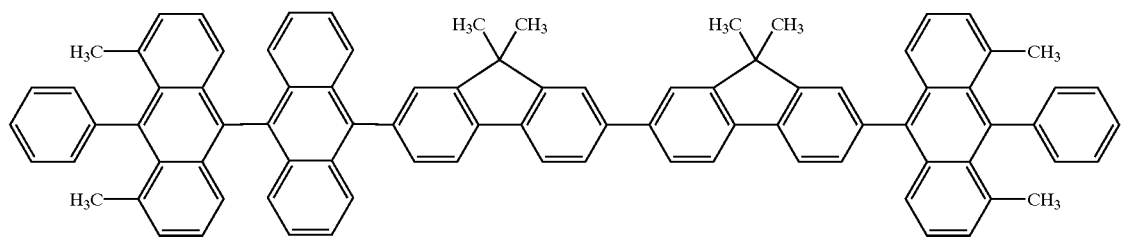
P-30
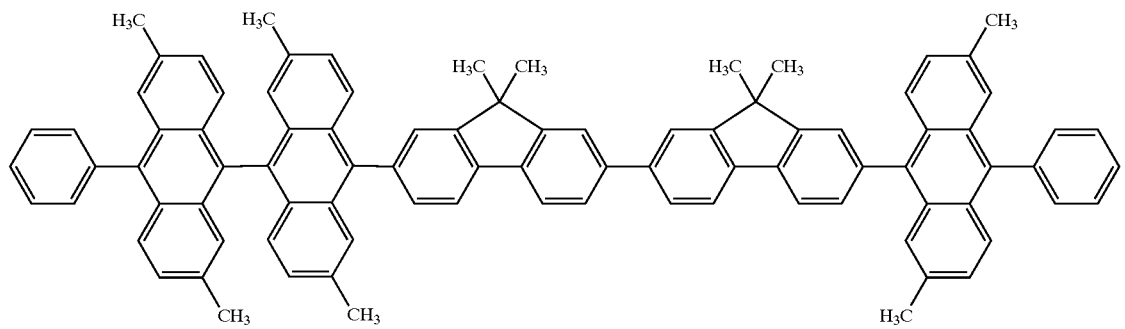
P-31
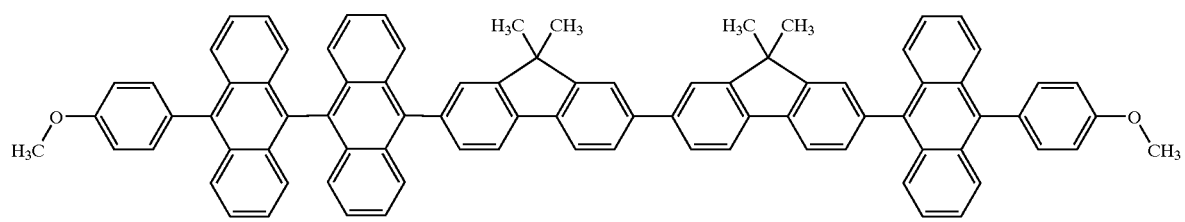
P-32
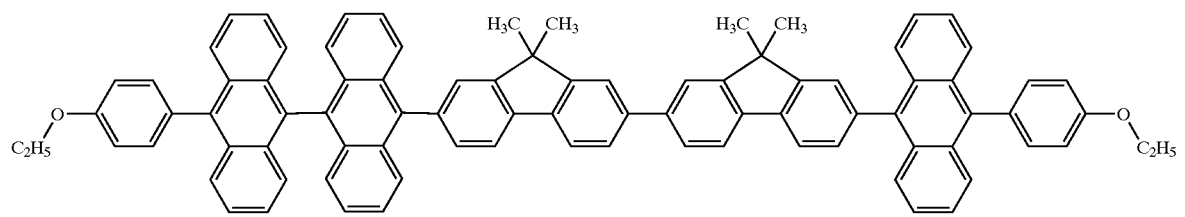
P-33
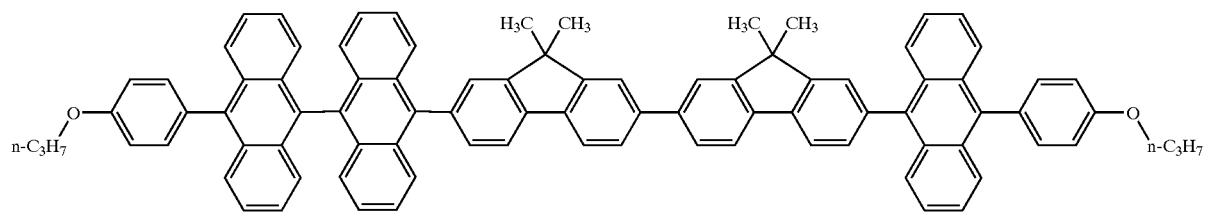
P-34
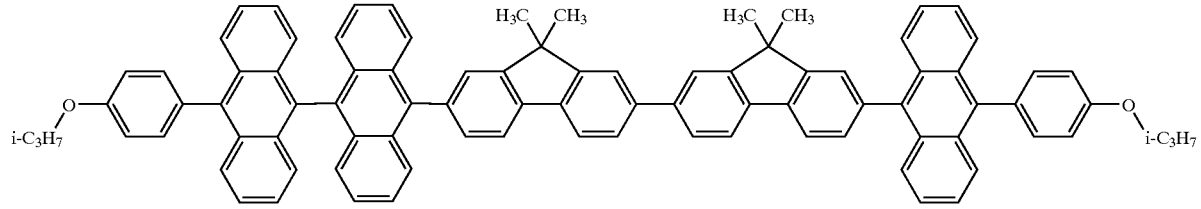

-continued
P-35
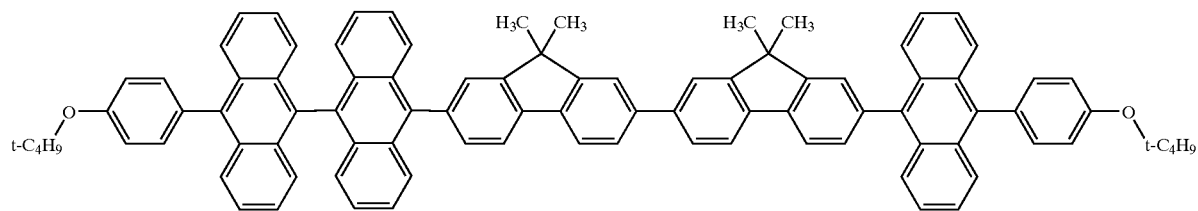
P-36
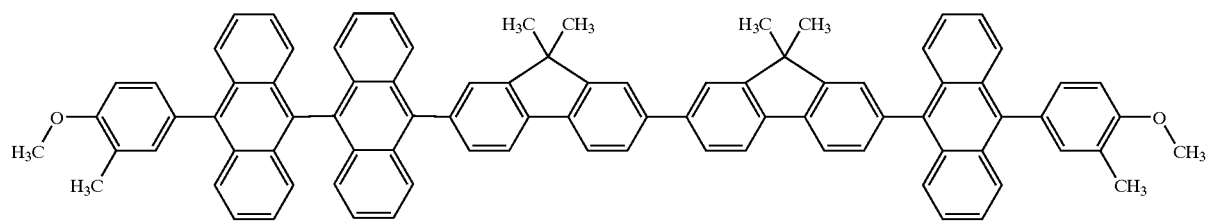
P=37
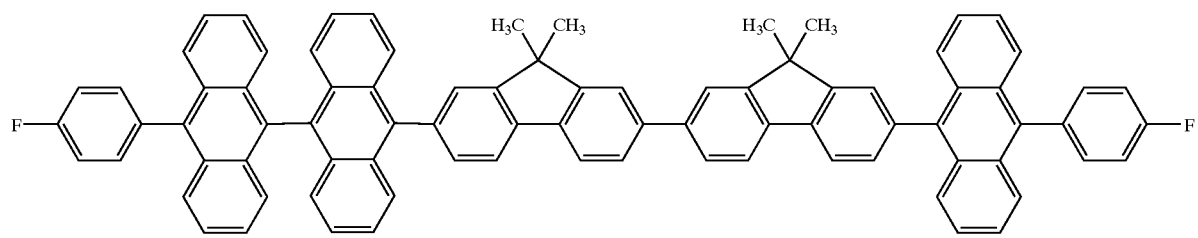
P-38
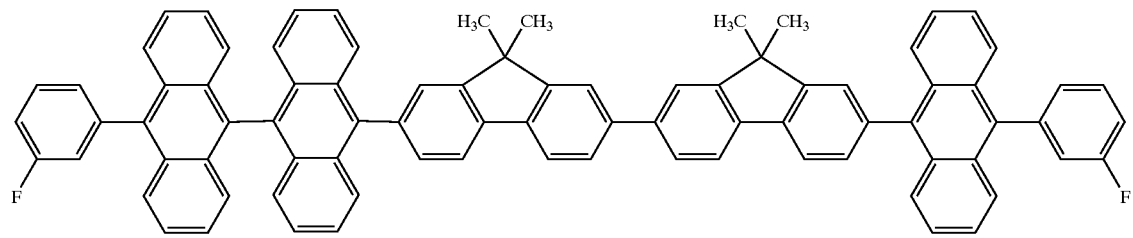
P-39
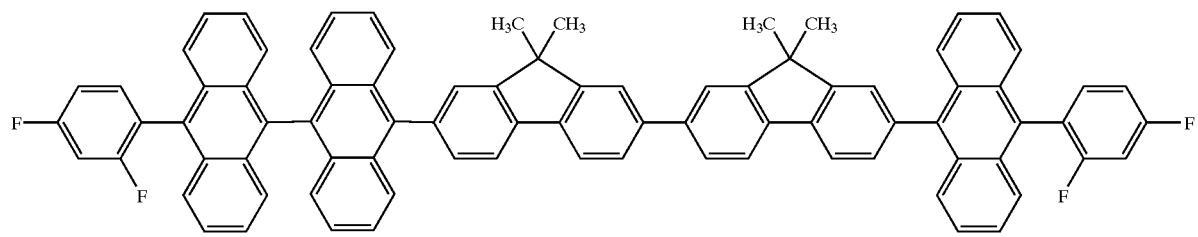
P-40
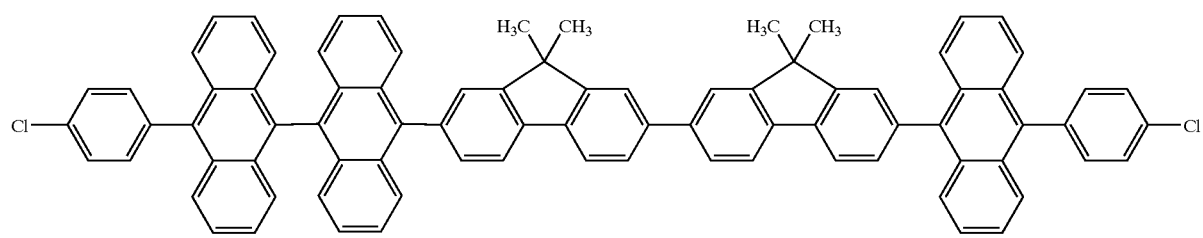

-continued
P-36
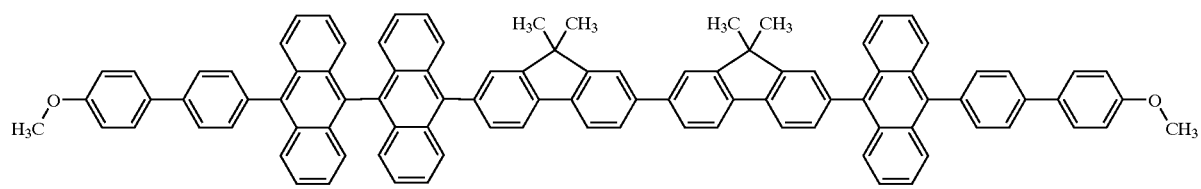
P-37
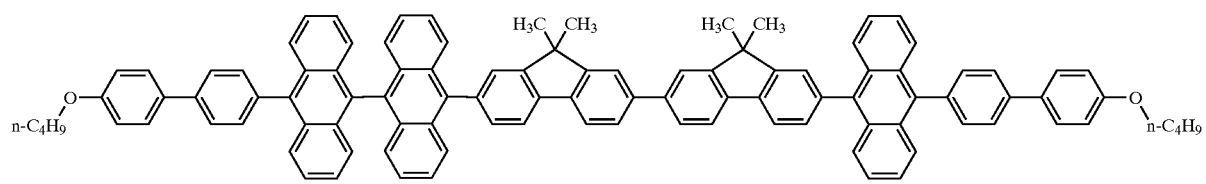
P-38
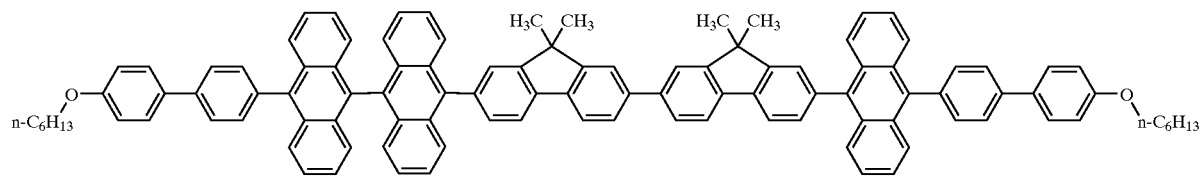
P-39
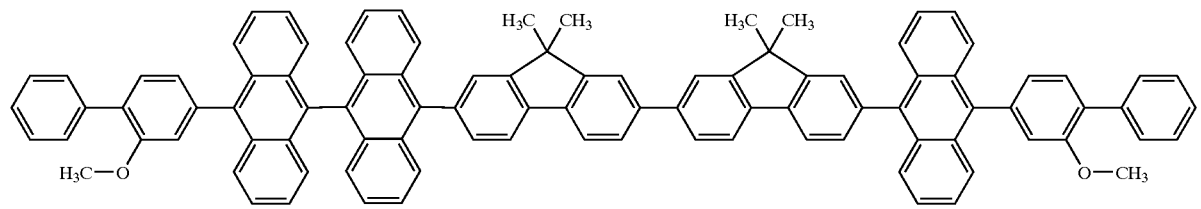
P-40
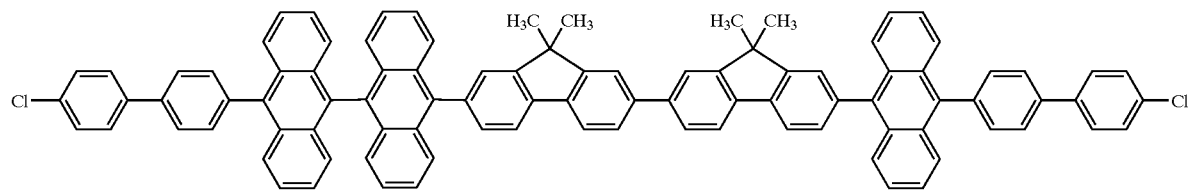
Q-1
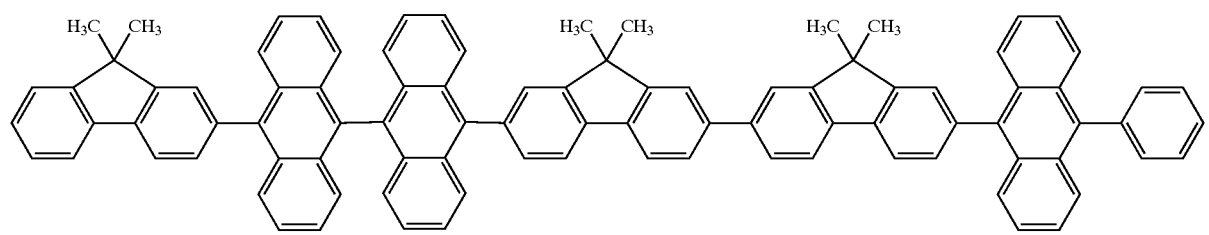
Q-2
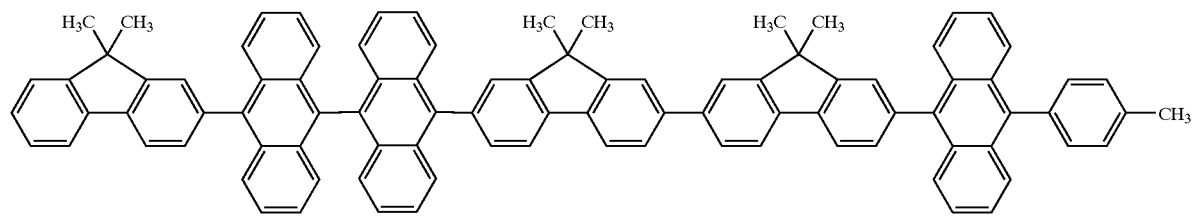

-continued
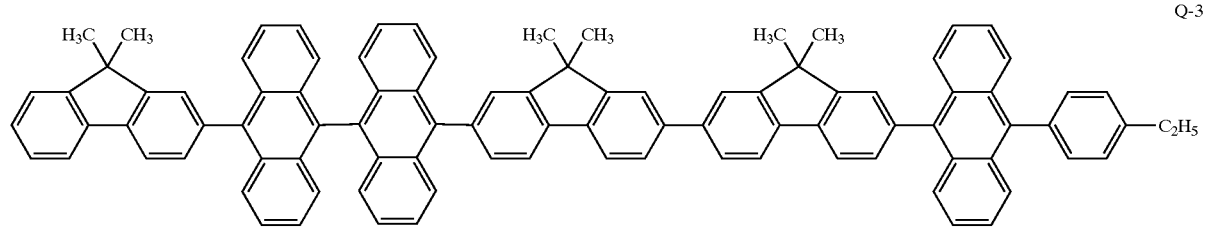
Q-3
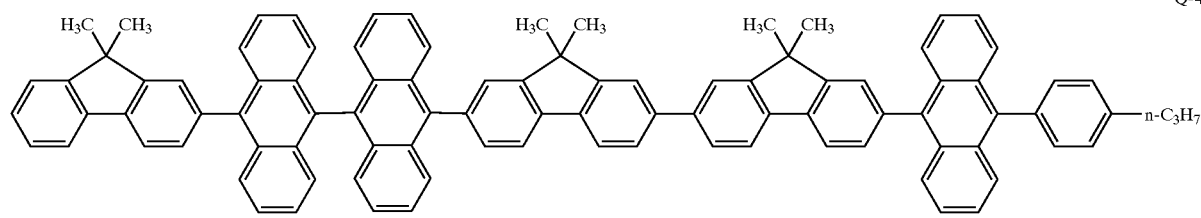
Q-4
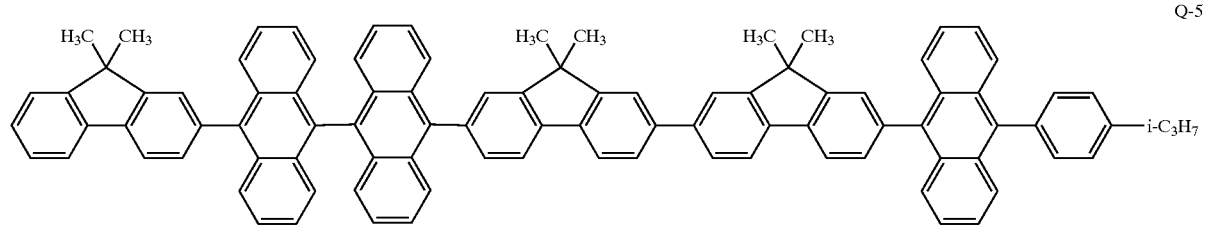
Q-5
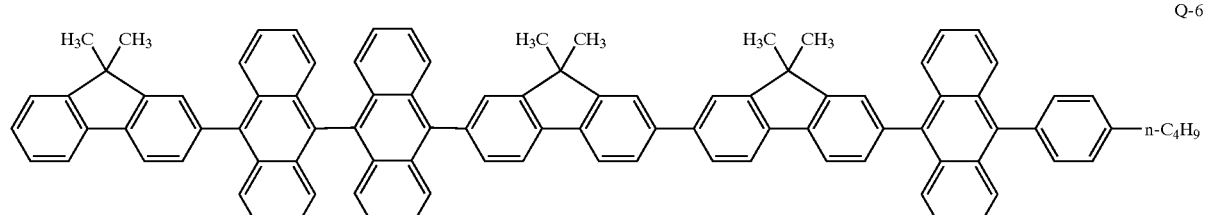
Q-6
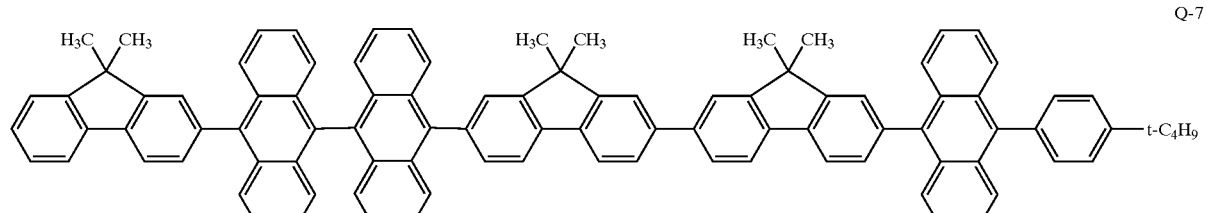
Q-7
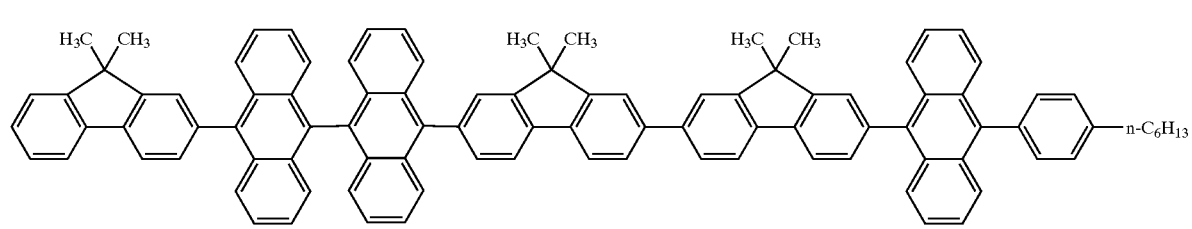
Q-8
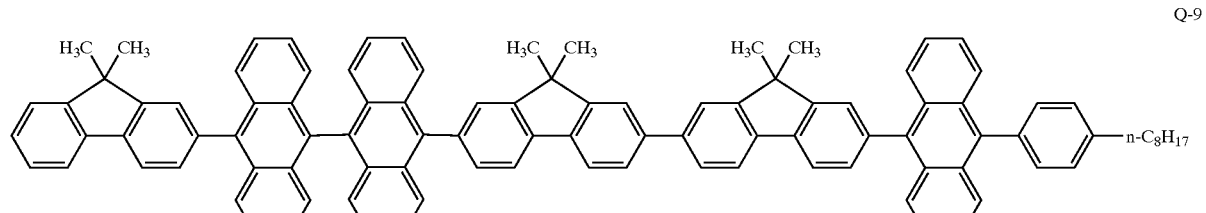
Q-9

-continued
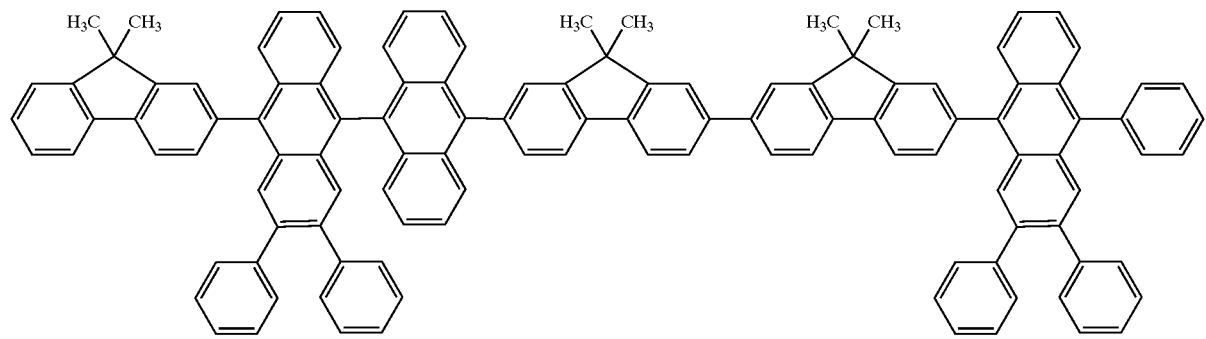
Q-10
Q-11
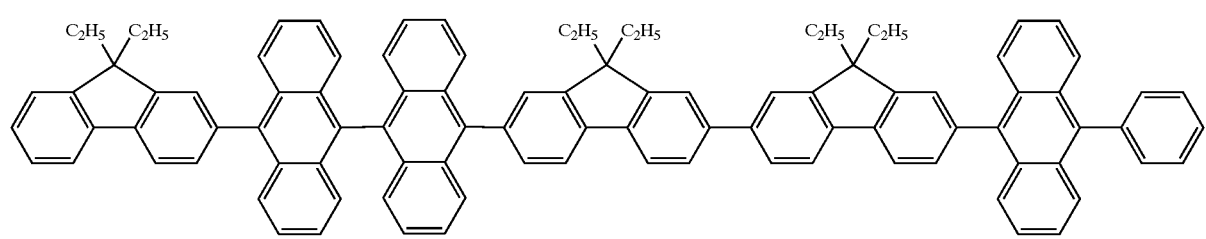
Q-12
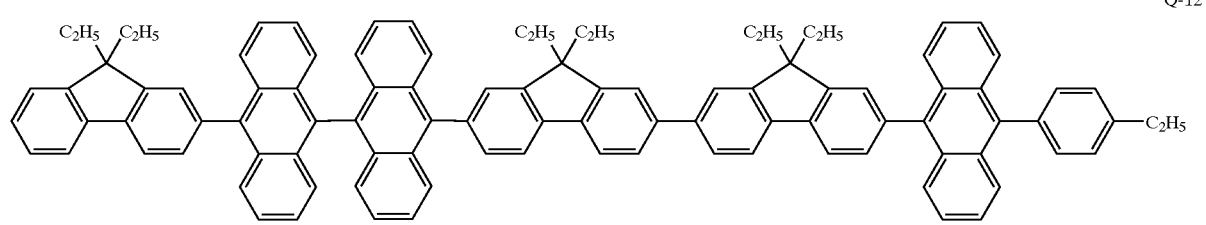
Q-13
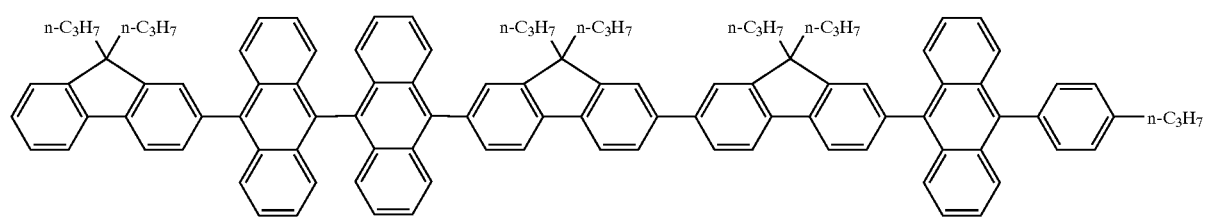
Q-14
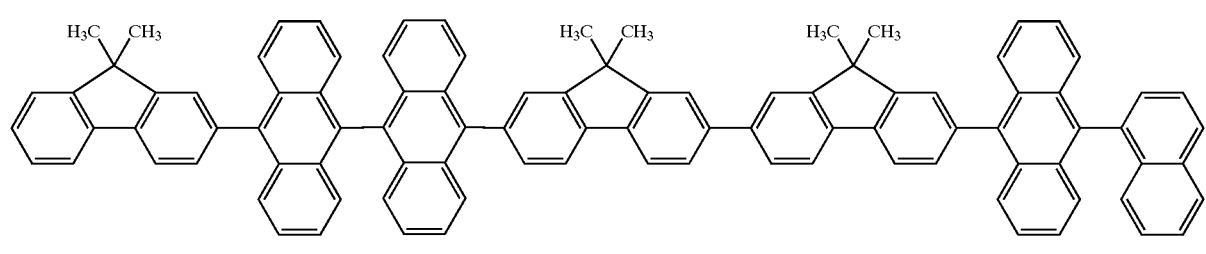
Q-15
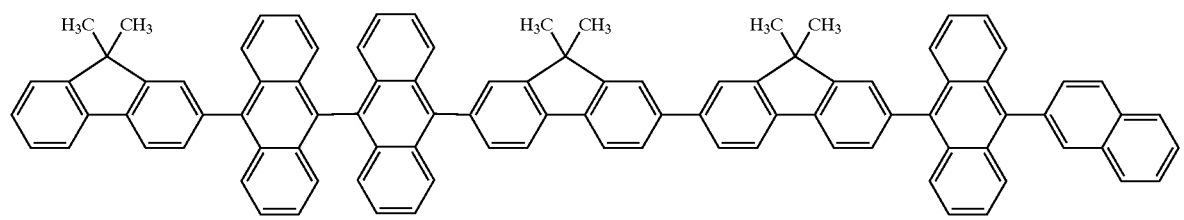

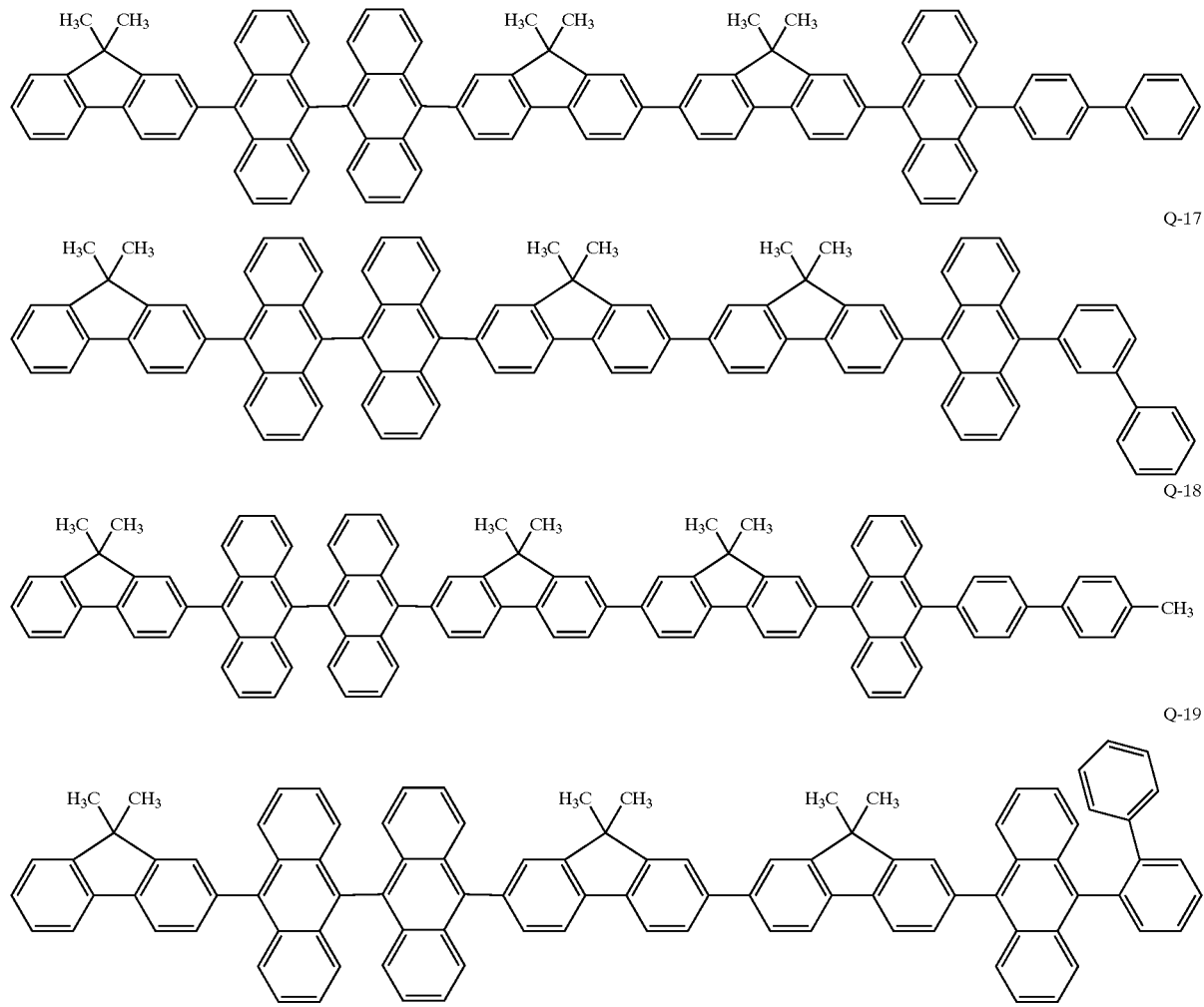

Compounds A according to the invention are preferably compounds represented by Illustrative Compound Nos. A-1 to A-60, B-1 to B-60, C-1 to C-45, F-1 to F-40, G-1 to G-25, I-1 to I-45 and M-1 to M-25, more preferably compounds represented by Illustrative Compound Nos. A-1 to A-60, B-1 to B-60, C-1 to C-45, F-1 to F-40, I-1 to I-45 and M-1 to M-25, further preferably compounds represented by Illustrative Compound Nos. A-1 to A-60, B-1 to B-60, C-1 to C-45 and M-1 to M-25.

Compounds A according to the invention can be produced by, for example, the following process. That is, compounds A can be produced by, for example, reacting halogenoanthracene derivatives with fluorenylboric acid derivatives in the presence of, for example, palladium compounds [for example, tetrakis(triphenylphosphine)palladium and bis(triphenylphosphine)palladium dichloride] and bases (for example, sodium carbonate, sodium hydrogencarbonate and triethylamine) [for example, the process described in Chem. Rev., 95, 2457 (1995) can be referred to].

Further, compounds A according to the invention can be produced by, for example, reacting anthrylboric acid derivatives with halogenofluorene derivatives in the presence of, for example, palladium compounds [for example, tetrakis(triphenylphosphine)palladium and bis(triphenylphosphine)palladium dichloride] and bases (for example, sodium carbonate, sodium hydrogencarbonate and triethylamine) [for example, the process described in Chem. Rev., 95, 2457 (1995) can be referred to].

The compounds represented by the formula (1) according to the invention can be produced by, for example, the following process.

That is, for example, compounds A can be produced by reacting boric acid compounds represented by the following the formula (7) with compounds represented by the following the formula (8) in the presence of, for example, palladium compounds [for example, tetrakis(triphenylphosphine) palladium and bis(triphenylphosphine)palladium chloride] and bases (for example, sodium carbonate, sodium hydrogencarbonate and triethylamine) [for example, the process described in Chem. Rev., 95, 2457 (1995) can be referred to].

$$X_1\text{-}(F_1)_j\text{-}(A_1)_k\text{-}B(OH)_2 \qquad (7)$$

$$Y_1\text{-}(F_2)_l\text{-}(A_2)_m\text{-}(F_3)_n\text{-}X_2 \qquad (8)$$

wherein $A_1$, $A_2$, $F_1$, $F_2$, $F_3$, $X_1$, $X_2$, j, k, l, m and n have the same meanings as in the formula (1), and $Y_1$ represents a halogen atom.

In the formula (8), $Y_1$ represents a halogen atom, preferably, a chlorine atom, a bromine atom or an iodine atom.

Further, the compounds represented by the formula (1) can be produced by, for example, reacting compounds represented by the following the formula (9) with boric acid compounds represented by the following the formula (10) in the presence of, for example, palladium compounds [for example, tetrakis(triphenylphosphine)palladium and bis(triphenylphosphine)palladium dichloride] and bases (for example, sodium carbonate, sodium hydrogencarbonate and triethylamine) [for example, the process described in Chem. Rev., 95, 2457 (1995) can be referred to].

 (9)

 (10)

wherein $A_1$, $A_2$, $F_1$, $F_2$, $F_3$, $X_1$, $X_2$, j, k, l, m and n have the same meanings as in the formula (1), and $Y_2$ represents a halogen atom.

In the formula (9), $Y_2$ represents a halogen atom, preferably, a chlorine atom, a bromine atom or an iodine atom.

Incidentally, the compounds represented by the formula (7) and the formula (10) can be produced by, for example, reacting compounds represented by the formula (9) and the formula (8) with a lithio compound or a Grignard reagent that can be formed by a reaction of n-butyl lithium and metallic magnesium and, for example, trimethoxyborane, triisopropoxyborane or the like.

Further, of the compounds represented by the formula (1), the compounds in which $A_1$ is a substituted or unsubstituted anthracen-9,10-diyl group can be produced by, for example, the following process. That is, of the compounds represented by the formula (1), the compounds in which $A_1$ is a substituted or unsubstituted anthracen-9,10-diyl group and k is 1 can be produced by dehydro-aromatizing compounds obtained by reacting compounds represented by the formula (8) and the following formula (11) with a lithio compound or a Grignard reagent that can be formed by a reaction of n-butyl lithium and metallic magnesium and substituted or unsubstituted anthraquinone in the presence of an acid (for example, hydriodic acid).

 (11)

wherein $F_1$, $X_1$ and j have the same meanings as in the formula (1), and $Y_3$ represents a halogen atom.

In the formula (11), $Y_3$ represents a halogen atom, preferably a chlorine atom, a bromine atom or an iodine atom.

Likewise, of the compounds represented by the formula (1), the compounds in which $A_1$ is a substituted or unsubstituted anthracen-9,10-diyl group and k is 2 can be produced by dehydro-aromatizing compounds obtained by reacting compounds represented by the formula (8) and the formula (11) with a lithio compound or a Grignard reagent that can be formed by a reaction of n-butyl lithium and metallic magnesium and substituted or unsubstituted bianthrone in the presence of an acid (for example, hydriodic acid).

Compounds A according to the invention are produced, as required, in the form of a solvate with a solvent (for example, an aromatic hydrocarbon solvent such as toluene or the like). Compounds A according to the invention include such solvates, and, of course, include solvent-free substances.

In the organic electroluminescent element of the invention, of course, solvent-free substances of compounds A according to the invention and also such solvates are available.

Incidentally, when compounds A according to the invention are used in the organic electroluminescent element, it is advisable to use compounds of which the purity is increased by a purification method such as a recrystallization method, a column chromatography method, a sublimation purification method or a combination of these methods.

The organic electroluminescent element is usually formed such that at least one luminescent layer containing at least one luminescent component is held between a pair of electrodes. In consideration of performance levels of hole injection, hole transport, electron injection and electron transport of compounds used in the luminescent layer, a hole injection transport layer containing a hole injection transport component and/or an electron injection transport layer containing an electron injection transport component can also be formed as required.

For example, when a hole injection performance, a hole transport performance and/or an electron injection performance and an electron transport performance of a compound used in the luminescent layer are good, it is possible to provide an element of a type that the luminescent layer serves also as a hole injection transport layer and/or an electron injection transport layer. Of course, it is also possible, as required, to provide an element of a type free from both a hole injection transport layer and an electron injection transport layer (monolayer-type element).

Further, each of the hole injection transport layer, the electron injection transport layer and the luminescent layer may be a monolayer structure or a multilayer structure. With respect to the hole injection transport layer and the electron injection transport layer, each layer can be formed such that a layer having an injection performance and a layer having a transport performance are provided separately.

In the organic electroluminescent element of the invention, compounds A according to the invention are preferably used as a hole injection transport component, a luminescent component or an electron injection transport component, more preferably as a hole injection transport component or a luminescent component, further preferably as a luminescent component.

In the organic electroluminescent element of the invention, compounds A according to the invention may be used either singly or in combination.

Figure 2:
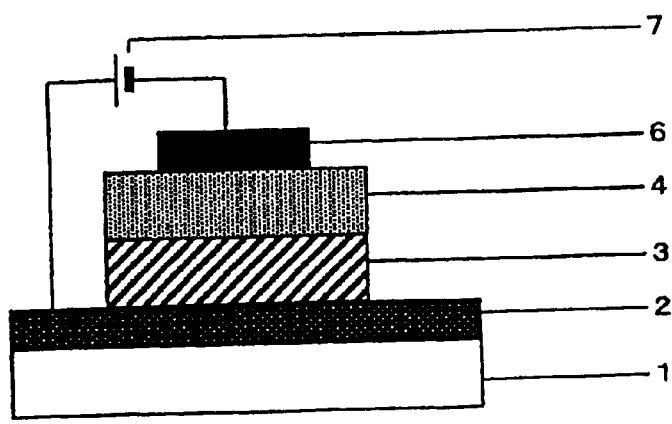
Figure 3:
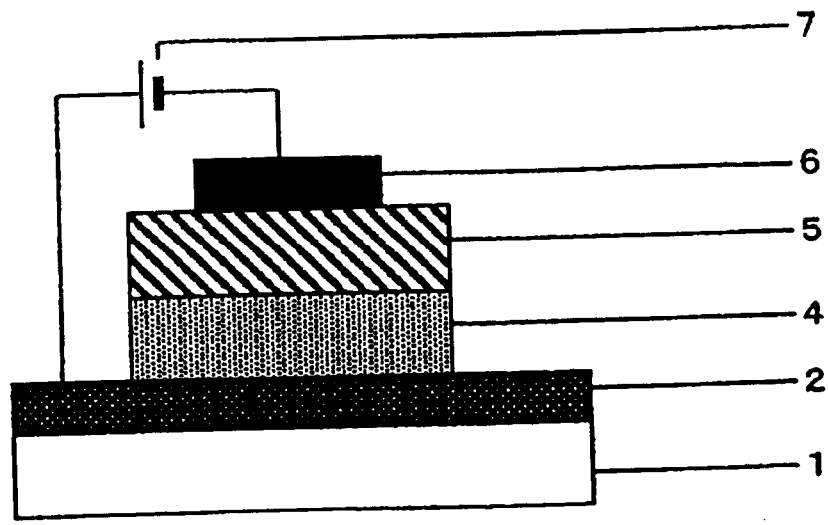
Figure 4:
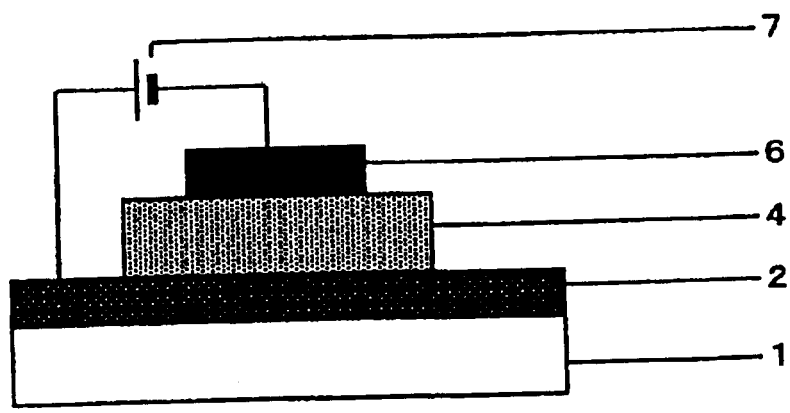
Figure 5:
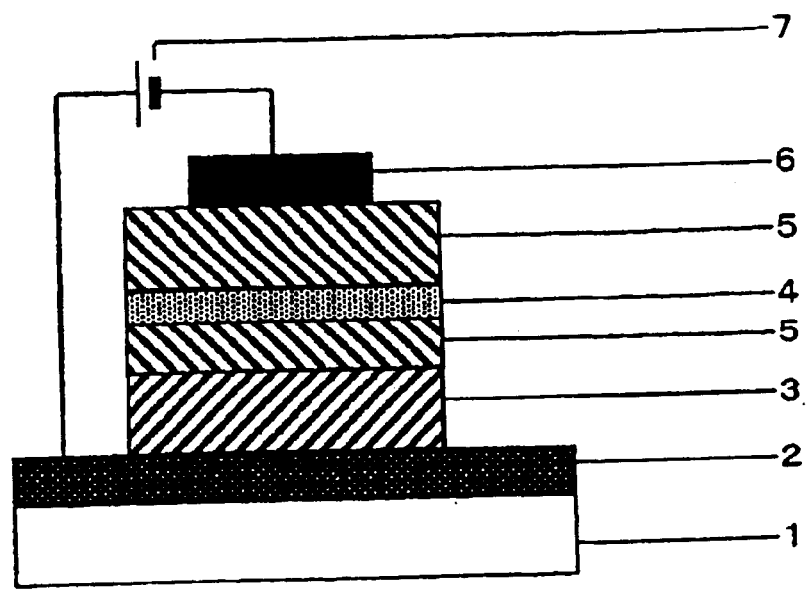
Figure 6:
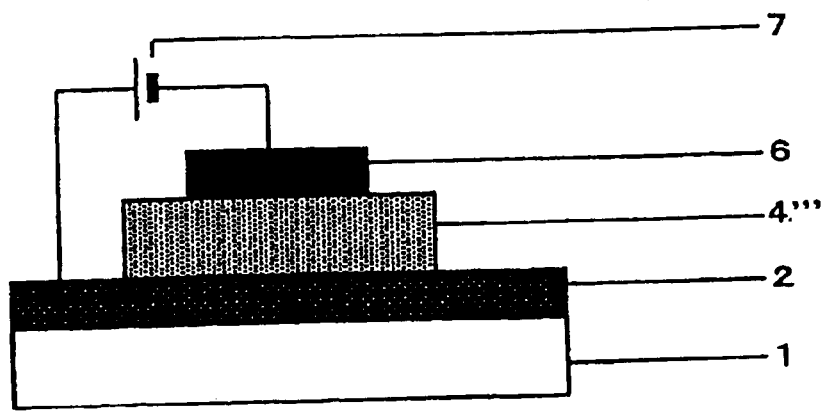
Figure 7:
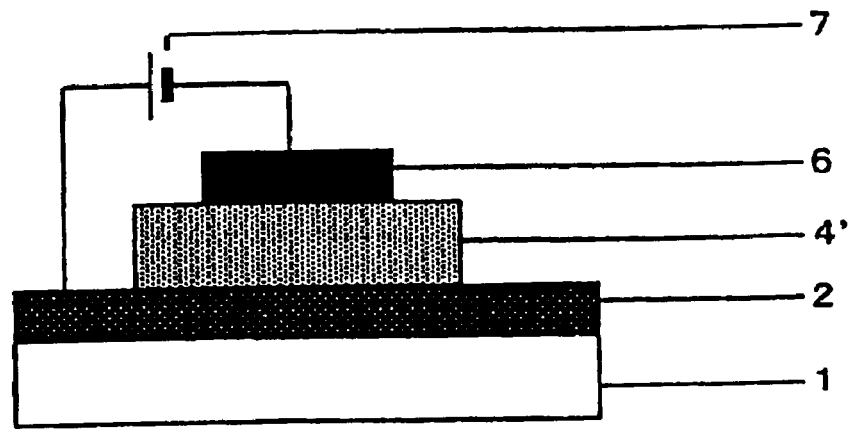
Figure 8:
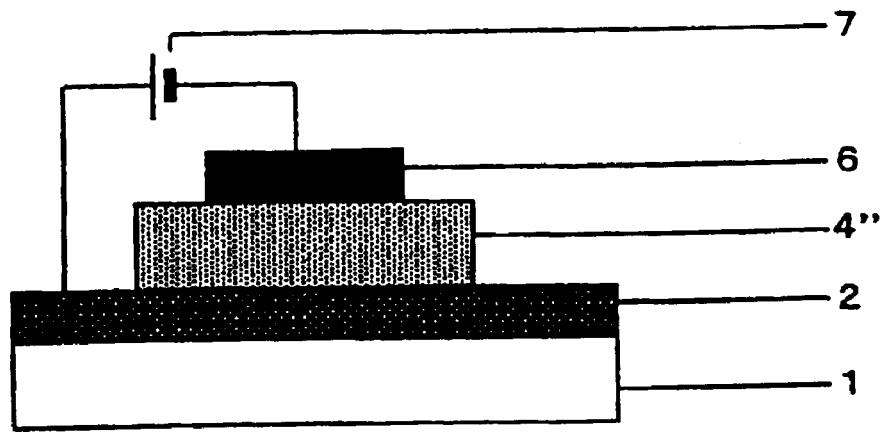

The structure of the organic electroluminescent element of the invention is not particularly limited. Examples thereof can include (A) an anode/hole injection transport layer/luminescent layer/electron injection transport layer/cathode-type element (FIG. 1), (B) an anode/hole injection transport layer/luminescent layer/cathode-type element (FIG. 2), (C) an anode/luminescent layer/electron injection transport layer/cathode-type element (FIG. 3), and (D) an anode/luminescent layer/cathode-type element (FIG. 4). Moreover, (E) an anode/hole injection transport layer/electron injection transport layer/luminescent layer/electron injection transport layer/cathode-type element (FIG. 5) which is an element of a type with a luminescent layer held between electron injection transport layers is also available. With respect to the (D)-type element structure, the element of the type with the luminescent component in the form of one layer held between a pair of electrodes is included. Further, there are, for example, (F) an element of a type in which a combination of a hole injection transport component, a luminescent component and an electron injection transport component in the form of one layer is held between a pair of electrodes (FIG. 6), (G) an element of a type in which a combination of a hole injection transport component and a luminescent component in the form of one layer is held between a pair of electrodes (FIG. 7), and (H) an element of a type in which a combination of a luminescent component and an electron injection transport component in the form of one layer is held between a pair of electrodes (FIG. 8).

In the organic electroluminescent element of the invention, these element structures are not critical. In each type of the element, a hole injection transport layer, a luminescent layer or an electron injection transport layer can be formed as plural layers. Further, in each type of the element, it is also possible that a combined layer of a hole injection transport component and a luminescent component is formed between a hole injection transport layer and a luminescent layer and/or a combined layer of a luminescent component and an electron injection transport component is formed between a luminescent layer and an electron injection transport layer.

With respect to the structure of the organic electroluminescent element, the (A)-type element, the (B)-type element, the (C)-type element, the (E)-type element, the (F)-type element, the (G)-type element or the (H)-type element is preferable. The (A)-type element, (B)-type element, the (C)-type element, the (F)-type element or the (H)-type element is more preferable.

As the organic electroluminescent element of the invention, for example, (A) the anode/hole injection transport layer/luminescent layer/electron injection transport layer/cathode-type element shown in FIG. 1 is described.

In FIG. 1, 1 is a substrate, 2 an anode, 3 a hole injection transport layer, 4 a luminescent layer, 5 a hole injection transport layer, 6 a cathode and 7 a power supply.

It is advisable that the electroluminescent element of the invention is supported by the substrate 1. The substrate is not particularly limited. It is advisable that the substrate is transparent or semitransparent. Examples thereof include substrates made of a glass plate, a transparent plastic sheet (for example, a sheet of polyester, polycarbonate, polysulfone, polymethyl methacrylate, polypropylene, polyethylene or the like), a semitransparent plastic sheet, quarts, transparent ceramics and a composite sheet of a combination of these. Further, a luminescent color can be controlled by combining the substrate with, for example, a color filter film, a color conversion film or a dielectric reflecting mirror.

In the anode 2, it is advisable to use a metal, an alloy or an electroconductive compound having a relatively large work function as an electrode material.

Examples of the electrode material used in the anode can include gold, platinum, silver, copper, cobalt, nickel, palladium, vanadium, tungsten, tin oxide, zinc oxide, ITO (indium·tin·oxide), polythiophene and polypyrrole. These electrode materials may be used either singly or in combination.

The anode can be formed on the substrate by a method such as a deposition method, a sputtering method or the like using these electrode materials. Further, the anode may be a monolayer structure or a multilayer structure.

A sheet electric resistance of the anode is set at, preferably less than several hundreds of ohms/□, preferably 5 to 50Ω/□.

A thickness of the anode varies with the electrode material used. It is set at, generally 5 to 1,000 nm, preferably 10 to 500 nm.

The hole injection transport layer 3 is a layer having a performance of facilitating injection of holes from the anode and a performance of transporting holes injected.

The hole injection transport layer can be formed using at least one of compounds A according to the invention and/or other compounds having a hole injection transport performance (for example, phthalocyanine derivatives, triarylmethane derivatives, triarylamine derivatives, oxazole derivatives, hydrazone derivatives, stilbene derivatives, pyrazoline derivatives, polysilane derivatives, polyphenylenevinylene and its derivatives, polythiophene and its derivatives, and poly-N-vinylcarbazole derivatives).

By the way, the compounds having the hole injection transport performance may be used either singly or in combination.

Preferable examples of other compounds having the hole injection transport performance which are used in the invention include triarylamine derivatives (for example, 4,4'-bis[N-phenyl-N-(4"-methylphenyl)amino]biphenyl, 4,4'-bis[N-phenyl-N-(3"-methylphenyl)amino]biphenyl, 4,4'-bis[N-phenyl-N-(3"-methoxyphenyl)amino]biphenyl, 4,4'-bis[N-phenyl-N-(1"-naphthyl)amino]biphenyl, 3,3'-dimethyl-4,4'-bis[N-phenyl-N-(3"-methylphenyl)amino]biphenyl, 1,1-bis[4'-[N,N-di(4"-methylphenyl)amino]phenyl]cyclohexane, 9,10-bis[N-(4'-methylphenyl)-N-(4"-n-butylphenyl)amino]phenanthrene, 3,8-bis(N,N-diphenylamino)-6-phenylphenanthridine, 4-methyl-N,N-bis[4",4'''-bis[N',N'-di(4-methylphenyl)amino]biphenyl-4-yl]aniline, N,N'-bis[4-(diphenylamino)phenyl]-N,N'-diphenyl-1,3-diaminobenzene, N,N'-bis[4-(diphenylamino)phenyl]-N,N'-diphenyl-1,4-diaminobenzene, 5,5"-bis[4-(bis[4-methylphenyl]amino)phenyl-2,2':5',2"-terthiophene, 1,3,5-tris(diphenylamino)benzene, 4,4',4"-tris(N-carbazolyl)triphenylamine, 4,4',4"-tris[N-(3'''-methylphenyl)-N-phenylamino]triphenylamine, 4,4',4"-tris[N,N-bis(4'''-tert-butylbiphenyl-4''''-yl)amino]triphenylamine, 1,3,5-tris(N-(4'-diphenylaminophenyl)-N-phenylamino]benzene), polythiophene and its derivatives, and poly-N-vinylcarbazole derivatives.

When compounds A according to the invention and the other compounds having the hole injection transport performance are used in combination, the ratio of compounds A according to the invention that are occupied in the hole injection transport layer is preferably adjusted to between 0.1 and 40% by weight.

The luminescent layer 4 is a layer containing a compound having a hole and electron injection performance, their transport performance and a performance of generating excitons by recombination of holes and electrons.

The luminescent layer can be formed using at least one of compounds A according to the invention and/or other compounds having a luminescent performance (for example, acridone derivatives, quinacridone derivatives, diketo pyrrolopyrrole derivatives, polycyclic aromatic compounds [for example, rubrene, anthracene, tetracene, pyrene, perylene, chrysene, decacyclene, coronene, tetraphenylcyclopentadiene, pentaphenylcyclohexadiene, 9,10-diphenylanthracene, 9,10-bis(phenylethynyl)anthracene, 1,4-bis(9'-ethynylanthracenyl)benzene, 4,4'-bis(9"-ethinylanthracenyl)biphenyl], triarylamine derivatives [for example, the foregoing compounds can be mentioned as compounds having the hole injection transport performance], organic metal complexes [for example, tris(8-quinolinolato)aluminum, bis(10-benzo[h]quinolinolato)beryllium, 2-(2'-hydroxyphenyl)benzoxazole zinc salt, 2-(2'-hydroxyphenyl)benzothiazole zinc salt, 4-hydroxyacridine zinc salt, 3-hydroxyflavone zinc salt, 5-hydroxyflavone beryllium salt, and 5-hydroxyflavone aluminum salt], stilbene derivatives [for example, 1,1,4,4-tetraphenyl-1,3-butadiene, 4,4'-bis(2,2-diphenylvinyl)biphenyl, 4,4'-bis[(1,1,2-triphenyl)ethenyl]biphenyl, coumalin derivatives [for example, coumalin 1, coumalin 6, coumalin 7, coumalin 30, coumalin 106, coumalin 138, coumalin 151, coumalin 152, coumalin 153, coumalin 307, coumalin 311, coumalin 314, coumalin 334, coumalin 338, coumalin 343 and coumalin 500], pyran derivatives [for example, DCM1 and DCM 2], oxazone derivatives [for example, Nile Red], benzothiazole derivatives, benzoxazole derivatives, benzimidazole derivatives, pyrazine derivatives, cinnamate ester derivatives, poly-N-vinylcarbazole and its derivatives, polythiophene and its derivatives, polyphenylene and its derivatives, polyfluorene and its derivatives, polyphenylenevinylene and its derivatives, polybiphenylenevinylene and its derivatives, polyterphenylenevinylene and its derivatives, polynaphthylenevinylene and its derivatives, and polythienylenevinylene and its derivatives].

In the organic electroluminescent element of the invention, it is advisable that the luminescent layer contains compounds A according to the invention.

In the organic electroluminescent element of the invention, compounds A according to the invention may be used in the luminescent layer either singly or in combination with other compounds having a luminescent performance.

When compounds A according to the invention and the other compounds having the luminescent performance are used in combination, the ratio of compounds A according to the invention which are occupied in the luminescent layer is adjusted to, preferably 0.001 to 99.999% by weight, more preferably 0.01 to 99.99% by weight, further preferably 0.1 to 99.9% by weight.

The other compounds having the luminescent performance which are used in the invention are preferably luminescent organic metal complexes. As described in, for example, J. Appl. Phys., 65, 3610 (1989) and Japanese Patent Laid-Open No. 214,332/1993, the luminescent layer can be formed of a host compound and a guest compound (dopant).

The luminescent layer can be formed using compounds A according to the invention as a host compound. Further, the luminescent layer can be formed using compounds A as a guest compound.

When the luminescent layer is formed using compounds A according to the invention as a guest compound, for example, the foregoing other compounds having the luminescent performance can be mentioned as the host compound. Preferable are the luminescent metal complexes or the foregoing triarylamine derivatives.

In this case, compounds A according to the invention are used in amounts of, preferably 0.001 to 40% by weight, more preferably 0.01 to 30% by weight, especially preferably 0.1 to 20% by weight relative to the luminescent organic metal complexes or the triarylamine derivatives.

The luminescent organic metal complexes used in combination with compounds A according to the invention are not particularly limited. Luminescent organic aluminum complexes are preferable, and luminescent organic aluminum complexes having a substituted or unsubstituted 8-quinolinolato ligand are more preferable. Preferable examples of the luminescent organic metal complexes can include luminescent organic aluminum complexes represented by the formula (a) to the formula (c).

(Q)$_3$-A$_1$ (a)

wherein Q represents a substituted or unsubstituted 8-quinolinolato ligand (Q)$_2$-A$_1$-O-L (b)

wherein Q represents a substituted 8-quinolinolato ligand, O-L represents a phenolato ligand, and L represents a hydrocarbon group having 6 to 24 carbon atoms and containing a phenyl moiety)

(Q)$_2$-A$_1$-O-A$_1$-(Q)$_2$ (c)

wherein Q represents a substituted 8-quinolinolato ligand.

Specific examples of the luminescent organic metal complexes can include tris(8-quinolinolato)aluminum, tris(4-methyl-8-quinolinolato)aluminum, tris(5-methyl-8-quinolinolato)aluminum, tris(3,4-dimethyl-8-quinolinolato) aluminum, tris(4,5-dimethyl-8-quinolinolato)aluminum, tris (4,6-dimethyl-8-quinolinolato)aluminum, bis(2-methyl-8-quinolato)(phenolato)aluminum, bis(2-methyl-8-quinolinolato)(2-methylphenolato)aluminum, bis(2-methyl-8-quinolinolato)(3-methylphenolato)aluminum, bis(2-methyl-8-quinolinolato)(4-methylphenolato)aluminum, bis (2-methyl-8-quinolinolato)(2-phenylphenolato)aluminum, bis(2-methyl-8-quinolinolato)(3-phenylphenolato) aluminum, bis(2-methyl-8-quinolinolato)(4-phenylphenolato)aluminum, bis(2-methyl-8-quinolinolato) (2,3-dimethylphenolato)aluminum, bis(2-methyl-8-quinolinolato)(2,6-dimethylphenolato)aluminum, bis(2-methyl-8-quinolinolato)(3,4-dimethylphenolato)aluminum, bis(2-methyl-8-quinolinolato)(3,5-dimethylphenolato) aluminum, bis(2-methyl-8-quinolinolato)(3,5-di-tert-butylphenolato)aluminum, bis(2-methyl-8-quinolinolato)(2,6-diphenylphenolato)aluminum, bis(2-methyl-8-quinolinolato)(2,4,6-triphenylphenolato)aluminum, bis(2-methyl-8-quinolinolato)(2,4,6-trimethylphenolato) aluminum, bis(2-methyl-8-quinolinolato)(2,4,5,6-tetramethylphenolato)aluminum, bis(2-methyl-8-quinolinolato)(1-naphtholato)aluminum, bis(2-methyl-8-quinolinolato)(2-naphtholato)aluminum, bis(2,4-dimethyl-8-quinolinolato)(2-phenylphenolato)aluminum, bis(2,4-dimethyl-8-quinolinolato)(3-phenylphenolato)aluminum, bis(2,4-dimethyl-8-quinolinolato)(4-phenylphenolato) aluminum, bis(2,4-dimethyl-8-quinolinolato)(3,5-dimethylphenylphenolato)aluminum, bis(2,4-dimethyl-8-quinolinolato)(3,5-di-tert-butylphenylphenolato)aluminum, bis(2-methyl-8-quinolinolato)aluminum-$\mu$-oxo-bis(2-methyl-8-quinolinolato)aluminum, bis(2,4-dimethyl-8-quinolinolato)aluminum-$\mu$-oxo-bis(2,4-dimethyl-8-quinolinolato)aluminum, bis(2-methyl-4-ethyl-8-quinolinolato)aluminum-$\mu$-oxo-bis(2-methyl-4-ethyl-8-quinolinolato)aluminum, bis(2-methyl-4-methoxy-8-quinolinolato)aluminum-$\mu$-oxo-bis(2-methyl-4-methoxy-8-quinolinolato)aluminum, bis(2-methyl-5-cyano-8-quinolinolato)aluminum-$\mu$-oxo-bis(2-methyl-5-cyano-8-quinolinolato)aluminum, and bis(2-methyl-5-trifluoromethyl-8-quinolinolato)aluminum-$\mu$-oxo-bis(2-methyl-5-trifluoromethyl-8-quinolinolato)aluminum. Of course, the luminescent organic metal complexes may be used either singly or in combination.

The electron injection transport layer 5 is a layer containing a compound having a performance of facilitating injection of electrons from a cathode and a performance of transporting electrons injected.

The electron injection transport layer can be formed using at least one of compounds A according to the invention and/or other compounds having an electron injection transport performance (for example, organic metal complexes [for example, tris(8-quinolinolato)aluminum, bis(10-benzo[h]quinolinolato)beryllium, 5-hydroxyflavone beryllium salt, and 5-hydroxyflavone aluminum salt], oxadiazole derivatives [for example, 1,3-bis[5'-(4"-tert-butylphenyl)-1', 3',4'-oxadiazol-2'-yl]benzene], triazole derivatives [for example, 3-(4'-tert-butylphenyl)-4-phenyl-5-(4"-phenylphenyl)-1,2,4-triazole], triazine derivatives, perylene derivatives, quinoline derivatives, quinoxaline derivatives, diphenylquinone derivatives, nitro-substituted fluorenone derivatives, and thiopyran dioxide derivatives).

Incidentally, the compounds having the electron injection transport performance may be used either singly or in combination.

When compounds A according to the invention and the other compounds having the electron injection transport performance are used in combination, the ratio of compounds A according to the invention which are occupied in the electron injection transport layer is adjusted to, preferably 0.1 to 40% by weight. In the invention, it is advisable that the electron injection transport layer is formed using compounds A according to the invention and the organic metal complexes [for example, the compounds represented by the formula (a) to the formula (c)] in combination.

With respect to the cathode 6, a metal, an alloy or an electroconductive compound having a relatively small work function is used as the electrode material. Examples of the electrode material used in the cathode can include lithium, a lithium-indium alloy, sodium, a sodium-potassium alloy, calcium, magnesium, a magnesium-silver alloy, a magnesium-indium alloy, indium, ruthenium, titanium, manganese, yttrium, aluminum, an aluminum-lithium alloy, an aluminum-calcium alloy, an aluminum-magnesium alloy, and a graphite thin film. These electrode materials may be used either singly or in combination.

The cathode can be formed on the electron injection transport layer by a method such as a deposition method, a sputtering method, an ionization deposition method, an ion plating method, a cluster ion beam method or the like.

Further, the cathode may be a monolayer structure or a multilayer structure.

Incidentally, it is advisable that a sheet electric resistance of the cathode is set at less than several hundreds of ohms/□.

A thickness of the cathode varies depending on the electrode material used. It is set at, generally 5 to 1,000 nm, more preferably 10 to 500 nm.

By the way, for taking out emitted light of the organic electroluminescent element at good efficiency, it is preferable that at least one electrode of the anode and the cathode is transparent or semitransparent. In general, it is more preferable to set the material of the anode and its thickness such that a transmission of emitted light reaches more than 70%.

Further, in the organic electroluminescent element of the invention, at least one layer thereof may contain a singlet oxygen quencher. The singlet oxygen quencher is not particularly limited. Examples thereof include rubrene, a nickel complex, and diphenylisobenzofuran. Rubrene is especially preferable.

The layer containing the singlet oxygen quencher is not particularly limited. It is preferably a luminescent layer or a hole injection transport layer, more preferably a hole injection transport layer. By the way, for example, when the hole injection transport layer contains the singlet quencher, it may uniformly be contained in the hole injection transport layer or in the vicinity of a layer adjacent the hole injection transport layer (for example, the luminescent layer or the electron injection transport layer having the luminescent performance).

The content of the singlet oxygen quencher is 0.01 to 50% by weight, preferably 0.05 to 30% by weight, more preferably 0.1 to 20% by weight of the total amount of the layer (for example, the hole injection transport layer) containing the same.

A method for forming the hole injection transport layer, the luminescent layer or the electron injection transport layer is not particularly limited. It can be provided by forming a thin film by, for example, a vacuum deposition method, an ionization deposition method or a solution coating method (for example, a spin coating method, a casting method, a dip coating method, a bar coating method, a roll coating method, a Langmuir-Blodgett method or an ink jet method).

When each layer is formed by a vacuum deposition method, the conditions for the vacuum deposition are not particularly limited. It is advisable to perform the same under vacuum of $1 \times 10^{-4}$ Pa at a boat temperature (deposition source temperature) of 50 to 600° C., a substrate temperature of −50 to 300° C. and a deposition rate of 0.005 to 50 nm/sec.

In this case, the organic electroluminescent element having better characteristics can be produced by continuously forming each of the hole injection transport layer, the luminescent layer, the electron injection transport layer and the like in vacuo.

When each of the hole injection transport layer, the luminescent layer, the electron injection transport layer and the like is formed by the vacuum deposition method using plural compounds, it is advisable to conduct co-deposition by separately controlling temperatures of boats filled with the compounds.

When each layer is formed by a solution coating method, the component constituting each layer or the component and a binder resin are dissolved or dispersed in a solvent to form a coating solution.

Examples of the binder resin that can be used in each of the hole injection transport layer, the luminescent layer and the electron injection transport layer include polymer compounds such as poly-N-vinylcarbazole, polyarylate, polystyrene, polyester, polysiloxane, polymethyl acrylate, polymethyl methacrylate, polyether, polycarbonate, polyamide, polyimide, polyamide-imide, poly-p-xylene, polyethylene, polyphenylene oxide, polyether sulfone, polyaniline and its derivatives, polythiophene and its derivatives, polyphenylenevinylene and its derivatives, polyfluorene and its derivatives, and polythienylenevinylene and its derivatives. The binder resins may be used either singly or in combination.

When each layer is formed by a solution coating method, the component constituting each layer or the component and the binder resin are dissolved or dispersed in an appropriate organic solvent (hydrocarbon solvents such as hexane, octane, decane, toluene, xylene, ethylbenzene, 1-methylnaphthalene and the like, ketone solvents such as acetone, methyl ethyl ketone, methyl isobutyl ketone, cyclohexanone and the like, halogenated hydrocarbon solvents such as dichloromethane, chloroform, tetrachloromethane, dichloroethane, trichloroethane, tetrachloroethane, chlorobenzene, dichlorobenzene, chlorotoluene and the like, ester solvents such as ethyl acetate, butyl acetate, amyl acetate and the like, alcohol solvents such as methanol, propanol, butanol, pentanol, hexanol, cyclohexanol, methyl cellosolve, ethyl cellosolve, ethylene glycol and the like, ether solvents such as dibutyl ether, tetrahydrofuran, dioxane, anisole and the like, and polar solvents such as N,N-dimethylformamide, N,N-dimethylacetamide, 1-methyl-2-pyrrolidone, 1-methyl-2-imidazolidinone, dimethyl sulfoxide and the like) and/or water to form a coating solution, and a thin film can be formed by various coating methods.

Incidentally, the dispersion method is not particularly limited. The dispersion can be conducted in the form of fine particles using a ball mill, a sand mill, a paint shaker, an attritor, a homogenizer or the like. The concentration of the coating solution is not particularly limited. It can be set at a range suited for providing a desired thickness according to a coating method to be performed. The concentration of the solution is generally 0.1 to 50% by weight, preferably 1 to 30% by weight.

By the way, in case of using the binder resin, its use amount is not particularly limited. It is set at, generally 5 to 99.9% by weight, preferably 10 to 99.9% by weight, more preferably 15 to 90% by weight based on the component constituting each layer (based on the total amount of each component when forming a monolayer-type element).

A film thickness of the hole injection transport layer, the luminescent layer or the electron injection transport layer is not particularly limited. It is generally advisable to set the film thickness at 5 nm to 5 μm.

Incidentally, for preventing contact of the formed element with oxygen or moisture, it is possible to form a protecting layer (blocking layer) or to protect the element by sealing the same in an inactive substance such as paraffin, liquid paraffin, silicon oil, fluorocarbon oil, zeolite-containing fluorocarbon oil or the like.

Examples of the material used in the protecting layer can include organic polymer materials (for example, a fluorinated resin, an epoxy resin, a silicone resin, an epoxy silicone resin, polystyrene, polyester, polycarbonate, polyamide, polyimide, polyamide-imide, poly-p-xylene, polyethylene, and polyphenylene oxide), inorganic materials (for example, a diamond thin film, an amorphous silica, an electric insulating glass, a metal oxide, a metal nitride, a metal carbide, and a metal sulfide), and thermosetting resins. The materials used in the protecting layer may be used either singly or in combination. The protecting layer may be a monolayer structure or a multilayer structure.

Further, for example, a metal oxide film (for example, aluminum oxide film) or a metal fluoride film can also be formed on the electrode as a protecting layer.

Still further, for example, an interfacial layer (intermediate layer) made of, for example, an organic phosphorus compound, polysilane, organic amine derivatives or phthalocyanine derivatives can be formed on, for example, the surface of the anode.

Furthermore, the electrode, for example, the anode or its surface can be used by being treated with, for example, an acid, ammonia/hydrogen peroxide or plasma.

The organic electroluminescent element of the invention is generally used as a DC driving-type element, and can also be used as an AC driving-type element. Further, the organic electroluminescent element of the invention may be a passive driving type such as a segment type, a single matrix driving type or the like, or an active driving type such as a TFT (thin film transistor) type, an MIM (metal-insulator-metal) type or the like. A driving voltage is generally 2 to 30 V.

The organic electroluminescent element of the invention can be used in, for example, panel-type light sources, various luminescent elements, various display devices, various marks, various sensors and the like.

EXAMPLES

The invention is illustrated more specifically below by referring to Production Examples and Examples. Of course, the invention is not limited to these Examples.

Production Example 1

Production of Compound Illustrative Compound No. A-5

3.33 g of 9-bromo-10-phenylanthracene, 2.38 g of 9,9-dimethylfluoren-2-ylboric acid, 2.12 g of sodium carbonate and 0.35 g of tetrakis(triphenylphosphine)palladium were heat-refluxed in toluene (100 ml) and water (50 ml) for 5 hours. After toluene was distilled off from the reaction mixture, a solid matter precipitated was filtered. This solid matter was treated by silica gel column chromatography (eluent: toluene). After toluene was distilled off under reduced pressure, the residue was recrystallized from a mixed solvent of toluene and acetone to obtain 2.18 g of compound Illustrative Compound A-5 as a yellow crystal.

Mass analysis: m/z=446

Elemental analysis: (as $C_{35}H_{26}$)

|  | C | H |
|---|---|---|
| Calculated (%) | 94.13 | 5.87 |
| Found (%) | 94.20 | 5.80 |

Melting point 250° C. or more

By the way, this compound was sublimated under conditions of 300° C. and $1\times10^{-4}$ Pa.

Absorption maximum (in toluene) 390 nm

Production Examples 2 to 62

Various compounds were produced according to the process described in Production Example 1 except that in Production Example 1, various halogenated compounds were used instead of using 9-bromo-10-phenylanthracene and various boric acid derivatives instead of using 9,9-dimethylfluoren-2-ylboric acid.

Halogenated compounds and boric acid derivatives used and compounds produced by Illustrative Compound Numbers were shown in Tables 1 to 5.

Further, absorption maximum (NM) in toluene was also shown.

Incidentally, the compounds produced were yellow to orangish yellow crystals, and the melting point of these compounds was 250° C. or more.

TABLE 1

| Production Example | Halogenated compounds | Boric acid derivatives | Illustrative Compound No. | Absorption maximum (nm) |
|---|---|---|---|---|
| 2 | 9-bromo-10-(4'-methylphenyl)anthracene | 9,9-dimethylfluoren-2-ylboric acid | A-6 | 390 |
| 3 | 9-bromo-10-(4'-ethylphenyl)anthracene | 9,9-dimethylfluoren-2-ylboric acid | A-8 | 390 |
| 4 | 9-bromo-10-(4'-isopropylphenyl)anthracene | 9,9-dimethylfluoren-2-ylboric acid | A-9 | 392 |
| 5 | 9-bromo-10-(4'-tert-butylphenyl)anthracene | 9,9-dimethylfluoren-2-ylboric acid | A-11 | 390 |
| 6 | 9-bromo-10-[4'-(N,N-diphenylamino)phenyl]anthracene | 7-(N,N-diphenyl-amino)-9,9-dimethylfluoren-2-ylboric acid | A-13 | 392 |
| 7 | 9-bromo-10-[4'-[N-phenyl-N-(1"-naphthyl)amino]phenyl]anthracene | 9,9-dimethylfluoren-2-ylboric acid | A-14 | 392 |
| 8 | 9-bromo-10-(4'-ethylphenyl)anthracene | 9,9-diethylfluoren-2-ylboric acid | A-17 | 390 |
| 9 | 9-bromo-10-(1'-naphthyl)anthracene | 9,9-dimethylfluoren-2-ylboric acid | A-19 | 395 |
| 10 | 9-bromo-10-(4'-phenylphenyl)anthracene | 9,9-dimethylfluoren-2-ylboric acid | A-21 | 402 |
| 11 | 9-bromo-10-(2'-phenylphenyl)anthracene | 9,9-dimethylfluoren-2-ylboric acid | A-23 | 397 |
| 12 | 9-bromo-10-[4'(4"-isopropylphenyl)phenyl]anthracene | 9,9-methylfluoren-2-ylboric acid | A-25 | 401 |
| 13 | 2,3-dimethyl-9-bromo-10-phenylanthracene | 9,9-dimethylfluoren-2-ylboric acid | A-26 | 390 |

TABLE 1-continued

| Production Example | Halogenated compounds | Boric acid derivatives | Illustrative Compound No. | Absorption maximum (nm) |
|---|---|---|---|---|
| 14 | 2,6-dimethyl-9-bromo-10-phenylanthracene | 9,9-dimethylfluoren-2-ylboric acid | A-35 | 390 |
| 15 | 9-bromo-10-phenylanthracene | 9,9-diphenylfluoren-2-ylboric acid | A-38 | 398 |
| 16 | 9-bromo-10-(4'-methoxyphenyl)anthracene | 9,9-dimethylfluoren-2-ylboric acid | A-40 | 391 |
| 17 | 9-bromo-10-(4'-n-propyloxyphenyl)anthracene | 9,9-dimethylfluoren-2-ylboric acid | A-43 | 392 |

TABLE 2

| Production Example | Halogenated compounds | Boric acid derivatives | Illustrative Compound No. | Absorption maximum (nm) |
|---|---|---|---|---|
| 18 | 9-bromo-10-(4'-tert-butyloxyphenyl)anthracene | 9,9-dimethylfluoren-2-ylboric acid | A-45 | 393 |
| 19 | 9-bromo-10-(4'-fluorophenyl)anthracene | 9,9-dimethylfluoren-2-ylboric acid | A-47 | 393 |
| 20 | 9-bromo-10-(4'-n-propyloxyphenyl)anthracene | 9,9-n-propylfluoren-2-ylboric acid | A-53 | 395 |
| 21 | 9-bromo-10-(6'-methoxy-2'-naphthyl)anthracene | 9,9-dimethylfluoren-2-ylboric acid | A-55 | 398 |
| 22 | 9-bromo-10-[4'-(4"-n-hexyloxyphenyl)phenyl]anthracene | 9,9-dimethylfluoren-2-ylboric acid | A-58 | 400 |
| 23 | 9-bromo-10-(9',9'-dimethylfluoren-2'-yl)anthracene | 9,9-di-n-pentylfluoren-2-ylboric acid | C-8 | 398 |
| 24 | 9-bromo-10-(9'-methyl-9'-phenylfluoren-2'-yl)anthracene | 9,9-dimethylfluoren-2-ylboric acid | C-12 | 404 |
| 25 | 9-bromo-10-(9',9'-diphenylfluoren-2'-yl)anthracene | 9,9-dimethylfluoren-2-ylboric acid | C-14 | 407 |
| 26 | 9-bromo-10-(9',9'-diphenylfluoren-2'-yl)anthracene | 9,9-di-n-hexylfluoren-2-ylboric acid | C-20 | 408 |
| 27 | 9-bromo-10-phenylanthracene | 7-(9',9'-dimethylfluoren-2'-yl)-9,9-dimethylfluoren-2-ylboric acid | D-1 | 405 |
| 28 | 9-bromo-10-(4'-n-hexylphenyl)anthracene | 7-(9',9'-dimethylfluoren-2'-yl)-9,9-dimethylfluoren-2-ylboric acid | D-8 | 407 |
| 29 | 9-bromo-10-(4'-phenylphenyl)anthracene | 7-(9',9'-dimethylfluoren-2'-yl)-9,9-dimethylfluoren-2-ylboric acid | D-16 | 408 |
| 30 | 9-bromo-10-(4'-methoxyphenyl)anthracene | 7-(9',9'-dimethylfluoren-2'-yl)-9,9-dimethylfluoren-2-ylboric acid | D-31 | 398 |
| 31 | 9-bromo-10-phenylanthracene | 10-(9',9'-dimethylfluoren-2'-yl)anthracen-9-ylboric acid | E-1 | 416 |
| 32 | 9-bromo-10-[4'-(N,N-diphenylamino)phenyl]anthracene | 10-(9',9'-dimethylfluoren-2'-yl)anthracen-9-ylboric acid | E-7 | 414 |

TABLE 3

| Production Example | Halogenated compounds | Boric acid derivatives | Illustrative Compound No. | Absorption maximum (nm) |
|---|---|---|---|---|
| 33 | 9-bromo-10-(4'-phenylphenyl)anthracene | 10-(9',9'-dimethylfluoren-2'-yl)anthracen-9-ylboric acid | E-16 | 418 |
| 34 | 9'-bromo-10-(2'-phenylphenyl)anthracene | 10-(9',9'-dimethylfluoren-2'-yl)anthracen-9-ylboric acid | E-18 | 414 |
| 35 | 9-bromo-10-(4'-methoxyphenyl)anthracene | 10-(9',9'-dimethylfluoren-2'-yl)anthracen-9-ylboric acid | E-21 | 410 |
| 36 | 9-bromo-10-(6'-methoxy-2'-naphthyl)anthracene | 10-(9',9'-dimethylfluoren-2'-yl)anthracen-9-ylboric acid | E-35 | 420 |
| 37 | 9-(7'-iodo-9',9'-dimethylfluoren-2'-yl)-10-(4"-ethylphenyl)anthracene | 10-(9',9'-dimethylfluoren-2'-yl)anthracen-9-ylboric acid | F-3 | 410 |
| 38 | 9-(7'-iodo-9',9'-dimethylfluoren-2'-yl)-10-(3"-phenylphenyl)anthracene | 10-(9',9'-dimethylfluoren-2'-yl)anthracen-9-ylboric acid | F-17 | 412 |
| 39 | 9-(7'-iodo-9',9'-dimethylfluoren-2'-yl)-10-[4"-(N,N-diphenylamino)phenyl]anthracene | 10-(9',9'-dimethylfluoren-2'-yl)anthracen-9-ylboric acid | F-24 | 408 |
| 40 | 2-iodo-7-(9',9'-dimethylfluoren-2'-yl)-9,9-dimethylfluorene | 10-(9',9'-dimethylfluoren-2'-yl)anthracen-9-ylboric acid | G-1 | 414 |
| 41 | 2-iodo-7-(9',9'-dimethylfluoren-2'-yl)-9,9-dimethylfluorene | 10-[7'-N,N-di(1"-naphthyl)amino-9',9'-dimethylfluoren-2'-yl]anthracen-9-ylboric acid | G-13 | 414 |
| 42 | 2-iodo-7-(9',9'-dimethylfluoren-2'-yl)-9,9-dimethylfluorene | 10-(9',9'-diphenylfluoren-2'-yl)anthracen-9-ylboric acid | G-25 | 418 |
| 43 | 9-bromo-10-(9',9'-di-n-butylfluoren-2'-yl)anthracene | 10-(9',9'-dimethylfluoren-2'-yl)anthracen-9-ylboric acid | H-7 | 420 |
| 44 | 10-bromo-10'-(4"-ethylphenyl)-9,9'-bianthryl | 7-[10'-(4"-ethylphenyl)anthracen-9'-yl]-9,9-dimethylfluoren-2-ylboric acid | J-3 | 422 |
| 45 | 10-bromo-10'-(4"-ethoxyphenyl)-9,9'-bianthryl | 7-[10'-(4"-ethoxyphenyl)anthracen-9'-yl]-9,9-dimethylfluoren-2-ylboric acid | J-22 | 422 |

TABLE 4

| Production Example | Halogenated compounds | Boric acid derivatives | Illustrative Compound No. | Absorption maximum (nm) |
|---|---|---|---|---|
| 46 | 10-bromo-10'-(4"-ethylphenyl)-9,9'-bianthryl | 7-(9',9'-dimethylfluoren-2'-yl)-9,9-dimethylfluoren-2-ylboric acid | K-3 | 416 |
| 47 | 10-bromo-10'-(1"-naphthyl)-9,9'-bianthryl | 7-(9',9'-dimethylfluoren-2'-yl)-9,9-dimethylfluoren-2-ylboric acid | K-14 | 418 |

TABLE 4-continued

| Production Example | Halogenated compounds | Boric acid derivatives | Illustrative Compound No. | Absorption maximum (nm) |
|---|---|---|---|---|
| 48 | 10-bromo-10'-(4"-phenylphenyl)-9,9'-bianthryl | 7-(9',9'-dimethylfluoren-2'-yl)-9,9-dimethylfluoren-2-ylboric acid | K-16 | 416 |
| 49 | 9-(7'-iodo-9',9'-dimethylfluoren-2'-yl)-10-(9",9"-dimethylfluoren-2"-yl)anthracene | 7-(10'-phenylanthracen-9'-yl)-9,9-dimethylfluoren-2-ylboric acid | L-1 | 415 |
| 50 | 9-(7'-iodo-9',9'-dimethylfluoren-2'-yl)-10-(9",9"-dimethylfluoren-2"-yl)anthracene | 7-[10'-(2"-phenylphenyl)anthracen-9'-yl]-9,9-dimethylfluoren-2-ylboric acid | L-19 | 413 |
| 51 | 9-(7'-iodo-9',9'-dimethylfluoren-2'-yl)-10-(9,9'-dimethylfluoren-2"-yl)anthracene | 7-[10'-(4"-ethoxyphenyl)anthracen-9'-yl]-9,9-dimethylfluoren-2-ylboric acid | L-32 | 413 |
| 52 | 10-bromo-10'-(9"9"-dimethylfluoren-2"-yl]-9,9'-bianthryl | 7-(9',9'-dimethylfluoren-2'-yl)-9,9-dimethylfluoren-2-ylboric acid | N-1 | 417 |
| 53 | 10-bromo-10'-(9",9"-di-phenylfluoren-2"-yl]-9,9'-bianthryl | 7-(9',9'-diphenylfluoren-2'-yl)-9,9-diphenylfluoren-2-ylboric acid | N-24 | 420 |
| 54 | 10-bromo-10'-(7"-N,N-diphenylamino-9"-9"-dimethylfluoren-2"-yl)-9,9'bianthryl | 7-[10'-(4"-ethylphenyl)-anthracen-9'-yl]-9,9-dimethylfluoren-2-ylboric acid | O-3 | 422 |
| 55 | 10-bromo-10'-(9",9"-dimethylfluoren-2"-yl)-9,9'-bianthryl | 7-[10'-(2"-naphthyl)anthracen-9'-yl]-9,9-dimethylfluoren-2-ylboric acid | O-15 | 424 |
| 56 | 10-bromo-10'-(9",9"-dimethyifluoren-2"-yl)-9,9'-bianthryl | 7-[10'-(4"-methoxyphenyl)anthracen-9'-yl]-9,9-dimethylfluoren-2-ylboric acid | O-21 | 412 |
| 57 | 10-phenyl-10'-(7"-iodo-9",9"-dimethylfluoren-2"-yl)-9,9'-bianthryl | 7-(10'-phenylanthracen-9'-yl)-9,9-dimethylfluoren-2-ylboric acid | P-1 | 424 |

TABLE 5

| Production Example | Halogenated compounds | Boric acid derivatives | Illustrative Compound No. | Absorption maximum (nm) |
|---|---|---|---|---|
| 58 | 10-(4'-phenylphenyl)-10'-(7"-iodo-9",9"-dimethylfluoren-2"-yl)-9,9'-bianthryl | 7-[10'-(4"-phenylphenyl)anthracen-9'-yl]-9,9-dimethylfluoren-2-ylboric acid | P-16 | 426 |
| 59 | 10-(4'-methoxyphenyl)-10'-(7"-iodo-9",9"-dimethylfluoren-2"-yl)-9,9'-bianthryl | 7-[10'-(4"-methoxyphenyl)anthracen-9'-yl]-9,9-dimethylfluoren-2-ylboric acid | P-31 | 426 |
| 60 | 10-(9',9'-dimethylfluoren-2'-yl)-10'-(7"-iodo-9",9"-dimethylfluoren-2"-yl)-9,9'-bianthryl | 7-(10'-phenylanthracen-9'-yl)-9,9-dimethylfluoren-2-ylboric acid | Q-1 | 426 |
| 61 | 10-(9',9'-dimethylfluoren-2'-yl)-10'-(7"-iodo-9",9"-dimethylfluoren-2"-yl)-9,9'-bianthryl | 7-[10'-(4"-n-butylphenyl)anthracen-9'-yl]-9,9-dimethylfluoren-2-ylboric acid | Q-6 | 426 |
| 62 | 10-(9',9'-dimethylfluoren-2'-yl)-10'-(7"-iodo-9",9"-dimethylfluoren-2"-yl)-9,9'-bianthryl | 7-[10'-(4"-methoxyphenyl)anthracen-9'-yl]-9,9-dimethylfluoren-2-ylboric acid | Q-31 | 424 |

Production Example 63

Production of Compound Illustrative Compound No. B-1

10-Phenylanthracen-9-ylboric acid (5.96 g), 4.46 g of 2,7-diiodo-9,9-dimethylfluorene, 4.24 g of sodium carbonate and 0.70 g of tetrakis(triphenylphosphine)palladium were heat-refluxed in toluene (100 ml) and water (50 ml) for 5 hours. After toluene was distilled off from the reaction mixture, a solid matter precipitated was filtered. This solid matter was treated by silica gel column chromatography (eluent: toluene). After toluene was distilled off under reduced pressure, the residue was recrystallized from a mixed solvent of toluene and acetone to obtain 4.88 g of compound Illustrative Compound No. B-1 as a yellow crystal.

Mass analysis: m/z=698

Elemental analysis: (as $C_{55}H_{38}$)

|  | C | H |
|---|---|---|
| Calculated (%) | 94.52 | 5.48 |
| Found (%) | 94.56 | 5.44 |

Melting point 250° C. or more

By the way, this compound was sublimated under conditions of 300° C. and $1\times10^{-4}$ Pa.

Absorption maximum (in toluene) 420 nm

Production Examples 64 to 99

Various compounds were produced according to the process described in Production Example 63 except that in Example 63, various boric acid derivatives were used instead of using 10-phenylanthracen-9-ylboric acid and various dihalogeno compounds instead of using 2,7-diiodo-9,9-dimethylfluorene.

Boric acid derivatives and dihalogeno compounds used and compounds produced by Illustrative Compound Numbers were shown in Tables 6 to 8.

Further, absorption maximum (NM) in toluene was also shown. By the way, the compounds produced were yellow to orangish yellow crystals, and the melting point of these compounds was 250° C. or more.

TABLE 6

| Production Example | Boric acid derivatives | Dihalogeno compounds | Illustrative Compound No. | Absorption maximum (nm) |
|---|---|---|---|---|
| 64 | 10-(4'-methylphenyl)anthracen-9-ylboric acid | 2,7-diiodo-9,9-dimethylfluorene | B-2 | 420 |
| 65 | 10-(2'-pyridyl)anthracen-9-ylboric acid | 2,7-diiodo-9,9-dimethylfluorene | B-3 | 416 |
| 66 | 10-(4'-ethylphenyl)anthracen-9-ylboric acid | 2,7-diiodo-9,9-dimethylfluorene | B-6 | 422 |
| 67 | 10-(4'-isopropyl phenyl)anthracen-9-ylboric acid | 2,7-diiodo-9,9-dimethylfluorene | B-9 | 422 |
| 68 | 10-(4'-[N,N-di(4"-methylphenyl)amino]phenyl)anthracen-9-ylboric acid | 2,7-diiodo-9,9-dimethylfluorene | B-12 | 420 |
| 69 | 10-(4'-n-decylphenyl)anthracen-9-ylboric acid | 2,7-diiodo-9,9-dimethylfluorene | B-14 | 422 |
| 70 | 10-(4'-ethylphenyl)anthracen-9-ylboric acid | 2,7-diiodo-9,9-diethylfluorene | B-17 | 420 |
| 71 | 10-(1'-naphthyl)anthracen-9-ylboric acid | 2,7-diiodo-9,9-dimethylfluorene | B-19 | 425 |
| 72 | 10-(4'-phenylphenyl)anthracen-9-ylboric acid | 27-diiodo-9,9-dimethylfluorene | B-21 | 427 |
| 73 | 10-(2'-phenylphenyl)anthracen-9-ylboric acid | 2,7-diiodo-9,9-dimethylfluorene | B-24 | 425 |
| 74 | 10-(4'-[N-phenyl-N-(4"-phenylphenyl)amino]phenyl)anthracen-9-ylboric acid | 2,7-diiodo-9,9-dimethylfluorene | B-25 | 427 |
| 75 | 10-(4'-methoxyphenyl)anthracen-9-ylboric acid | 2,7-diiodo-9,9-dimethylfluorene | B-40 | 421 |
| 76 | 10-(4'-n-propyloxyphenyl)anthracen-9-ylboric acid | 2,7-diiodo-9,9-dimethylfluorene | B-43 | 422 |
| 77 | 10-(4'-tert-butyloxyphenyl)anthracen-9-ylboric acid | 2,7-diiodo-9,9-dimethylfluorene | B-45 | 423 |
| 78 | 10-(4'-fluorophenyl)anthracen-9-ylboric acid | 2,7-diiodo-9,9-dimethylfluorene | B-47 | 423 |

TABLE 7

| Production Example | Boric acid derivatives | Dihalogeno compounds | Illustrative Compound No. | Absorption maximum (nm) |
|---|---|---|---|---|
| 79 | 10-(4'-n-propyloxyphenyl)anthracen-9-ylboric acid | 2,7-diiodo-9,9-di-n-propylfluorene | B-53 | 425 |
| 80 | 10-(6'-methoxy-2'-naphthyl)anthracen-9-ylboric acid | 2,7-diiodo-9,9-dimethylfluorene | B-55 | 428 |
| 81 | 10-[4'-(4"-n-hexyloxyphenyl)phenyl]anthracen-9-ylboric acid | 2,7-diiodo-9,9-dimethylfluorene | B-58 | 430 |
| 82 | 9,9-dimethylfluoren-2-ylboric acid | 9,10-dibromoanthracene | C-1 | 398 |
| 83 | 9,9-di-n-butylfluoren-2-ylboric acid | 9,10-dibromoanthracene | C-3 | 400 |
| 84 | 9,9-di-n-hexylfluoren-2-ylboric acid | 9,10-dibromoanthracene | C-5 | 400 |
| 85 | 7-[N,N-di(4'-methylphenyl)amino]-9,9-dimethylfluoren-2-ylboric acid | 9,10-dibromoanthracene | C-25 | 397 |
| 86 | 7-[N-phenyl-N-(1'-naphthyl)amino]-9,9-dimethylfluoren-2-ylboric acid | 1,4-dimethyl-9,10-dibromoanthracene | C-28 | 398 |
| 87 | 9,9-dimethylfluoren-2-ylboric acid | 10,10'-dibromo-9,9'-bianthryl | H-1 | 425 |
| 88 | 10-phenylanthracen-9-ylboric acid | 2-iodo-7-(7'-iodo-9',9'-dimethylfluoren-2'-yl)-9,9-dimethylfluorene | I-1 | 422 |
| 89 | 10-(4'-n-propylphenyl)anthracen-9-ylboric acid | 2-iodo-7-(7'-iodo-9',9'-dimethylfluoren-2'-yl)-9,9-dimethylfluorene | I-4 | 422 |
| 90 | 10-(4'-phenylphenyl)anthracen-9-ylboric acid | 2-iodo-7-(7'-iodo-9',9'-dimethylfluoren-2'-yl)-9,9-dimethylfluorene | I-16 | 424 |
| 91 | 10-[4'-(N,N-dimethylamino)phenyl]anthracen-9-ylboric acid | 2-iodo-7-(7'-iodo-9',9'-dimethylfluoren-2'-yl)-9,9-dimethylfluorene | I-31 | 420 |
| 92 | 10-(9',9'-dimethylfluoren-2'-yl)anthracen-9-ylboric acid | 2,7-diiodo-9,9-dimethylfluorene | M-1 | 428 |
| 93 | 10-(9',9'-di-n-butylfluoren-2'-yl)anthracen-9-ylboric acid | 2,7-diiodo-9,9-di-n-butylfluorene | M-3 | 430 |
| 94 | 10-(9',9'-di-n-hexylfluoren-2'-yl)anthracen-9-ylboric acid | 2,7-diiodo-9,9-di-n-hexylfluorene | M-5 | 430 |

TABLE 8

| Production Example | Boric acid derivatives | Dihalogeno compounds | Illustrative Compound No. | Absorption maximum (nm) |
|---|---|---|---|---|
| 95 | 10-(9',9'-diphenylfluoren-2'-yl)anthracen-9-ylboric acid | 2,7-diiodo-9,9-dimethylfluorene | M-14 | 437 |
| 96 | 10-(7'-[N,N-di(4"-methylphenyl)amino]-9',9'-dimethylfluoren-2'-yl)anthracen-9-ylboric acid | 2,7-diiodo-9,9-dimethylfluorene | M-17 | 428 |
| 97 | 10-(9',9'-diphenylfluoren-2'-yl)anthracen-9-ylboric acid | 2,7-diiodo-9,9-di-n-hexylfluorene | M-20 | 438 |
| 98 | 10-(9'-methyl-9'-phenylfluoren-2'-yl)anthracen-9-ylboric acid | 2,7-diiodo-9,9-dimethylfluorene | M-22 | 434 |
| 99 | 10-(9',9'-diphenylfluoren-2'-yl)anthracen-9-ylboric acid | 2,7-diiodo-9,9-diphenylfluorene | M-24 | 443 |

Example 1

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10⁻⁴ Pa.

First, 4,4'-bis[N-phenyl-N-(3"-methylphenyl)amino]biphenyl was deposited on the ITO transparent electrode to a thickness of 75 nm at a deposition rate of 0.2 nm/sec to form a hole injection transport layer.

Then, bis(2-methyl-8-quinolinolato)(4-phenylphenolato) aluminum and compound Illustrative Compound No. A-5 were co-deposited thereon from different deposition sources to a thickness of 50 nm at a deposition rate of 0.2 nm/sec (weight ratio 100:0.5) to form a luminescent layer.

Subsequently, tris(8-quinolinolato)aluminum was deposited to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 12 V was applied to the organic electroluminescent element produced in a dry atmosphere, a current of 54 mA/cm² was passed. Luminescence of a bluish green color having a brightness of 2,420 cd/m² was identified.

Examples 2 to 99

Organic electroluminescent elements were produced according to the process described in Example 1 except using, instead of using compound Illustrative Compound A-5 in the formation of the luminescent layer in Example 1, compound Illustrative Compound No. A-6 (Example 2), compound Illustrative Compound No. A-8 (Example 3), compound Illustrative Compound No. A-9 (Example 4), compound Illustrative Compound No. A-11 (Example 5), compound Illustrative Compound No. A-13 (Example 6), compound Illustrative Compound No. A-14 (Example 7), compound Illustrative Compound No. A-17 (Example 8), compound Illustrative Compound No. A-19 (Example 9), compound Illustrative Compound No. A-21 (Example 10), compound Illustrative Compound No. A-23 (Example 11), compound Illustrative Compound No. A-25 (Example 12), compound Illustrative Compound No. A-26 (Example 13), compound Illustrative Compound No. A-35 (Example 14), compound Illustrative Compound No. A-38 (Example 15), compound Illustrative Compound No. A-40 (Example 16), compound Illustrative Compound No. A-43 (Example 17), compound Illustrative Compound No. A-45 (Example 18), compound Illustrative Compound No. A-47 (Example 19), compound Illustrative Compound No. A-53 (Example 20), compound Illustrative Compound No. A-55 (Example 21), compound Illustrative Compound No. A-58 (Example 22), compound Illustrative Compound No. B-1 (Example 23), compound Illustrative Compound No. B-2 (Example 24), compound Illustrative Compound No. B-3 (Example 25), compound Illustrative Compound No. B-6 (Example 26), compound Illustrative Compound No. B-9 (Example 27), compound Illustrative Compound No. B-12 (Example 28), compound Illustrative Compound No. B-14 (Example 29), compound Illustrative Compound No. B-17 (Example 30), compound Illustrative Compound No. B-19 (Example 31), compound Illustrative Compound No. B-21 (Example 32), compound Illustrative Compound No. B-24 (Example 33), compound Illustrative Compound No. B-25 (Example 34), compound Illustrative Compound No. B-40 (Example 35), compound Illustrative Compound No. B-43 (Example 36), compound Illustrative Compound No. B-45 (Example 37), compound Illustrative Compound No. B-47 (Example 38), compound Illustrative Compound No. B-53 (Example 39), compound Illustrative Compound No. B-55 (Example 40), compound Illustrative Compound No. B-58 (Example 41), compound Illustrative Compound No. C-1 (Example 42), compound Illustrative Compound No. C-3 (Example 43), compound Illustrative Compound No. C-5 (Example 44), compound Illustrative Compound No. C-8 (Example 45), compound Illustrative Compound No. C-12 (Example 46), compound Illustrative Compound No. C-14 (Example 47), compound Illustrative Compound No. C-20 (Example 48), compound Illustrative Compound No. C-25 (Example 49), compound Illustrative Compound No. C-28 (Example 50), compound Illustrative Compound No. D-1 (Example 51), compound Illustrative Compound No. D-8 (Example 52), compound Illustrative Compound No. D-16 (Example 53), compound Illustrative Compound No. D-31 (Example 54), compound Illustrative Compound No. E-1 (Example 55), compound Illustrative Compound No. E-7 (Example 56), compound Illustrative Compound No. E-7 (Example 56), compound Illustrative Compound No. E-16 (Example 57), compound Illustrative Compound No. E-18 (Example 58), compound Illustrative Compound No. E-21 (Example 59), compound Illustrative Compound No. E-35 (Example 60), compound Illustrative Compound No. F-3 (Example 61), compound Illustrative Compound No. F-17 (Example 62), compound Illustrative Compound No. F-24 (Example 63), compound Illustrative Compound No. G-1 (Example 64), compound Illustrative Compound No. G-13 (Example 65), compound Illustrative Compound No. G-25 (Example 66), compound Illustrative Compound No. H-1 (Example 67), compound Illustrative Compound No. H-7 (Example 68), compound Illustrative Compound No. I-1 (Example 69), compound Illustrative Compound No. I-4 (Example 70), compound Illustrative Compound No. I-16 (Example 71), compound Illustrative Compound No. I-31 (Example 72), compound Illustrative Compound No. J-3 (Example 73), compound Illustrative Compound No. J-22 (Example 74), compound Illustrative Compound No. K-3 (Example 75), compound Illustrative Compound No. K-14 (Example 76), compound Illustrative Compound No. K-16 (Example 77), compound Illustrative Compound No. L-1 (Example 78), compound Illustrative Compound No. L-19 (Example 79), compound Illustrative Compound No. L-32 (Example 80), compound Illustrative Compound No. M-1 (Example 81), compound Illustrative Compound No. M-3 (Example 82), compound Illustrative Compound No. M-5 (Example 83), compound Illustrative Compound No. M-14 (Example 84), compound Illustrative Compound No. M-17 (Example 85), compound Illustrative Compound No. M-20 (Example 86), compound Illustrative Compound No. M-22 (Example 87), compound Illustrative Compound No. M-24 (Example 88), compound Illustrative Compound No. N-1 (Example 89), compound Illustrative Compound No. N-24 (Example 90), compound Illustrative Compound No. O-3 (Example 91), compound Illustrative Compound No. O-15 (Example 92), compound Illustrative Compound No. O-21 (Example 93), compound Illustrative Compound No. P-1 (Example 94), compound Illustrative Compound No. P-16 (Example 95), compound Illustrative Compound No. P-31 (Example 96), compound Illustrative Compound No. Q-1 (Example 97), compound Illustrative Compound No. Q-6 (Example 98) and compound Illustrative Compound No. Q-31 (Example 99). When a DC voltage of 12 V was applied to each element in a dry atmosphere, luminescence of a blue to bluish green color was identified. Further, the characteristics thereof were measured, and the results were shown in Tables 9 to 13.

Comparative Example 1

An organic electroluminescent element was produced by the process described in Example 1 except that in the formation of the luminescent layer in Example 1, only bis(2-methyl-8-quinolinolato)(4-phenylphenolato) aluminum was used without using compound Illustrative Compound No. A-5 and the deposition was conducted to a thickness of 50 nm to form a luminescent layer. When a DC voltage of 12 V was applied to this element in a dry atmosphere, luminescence of a blue color was identified. Further, the characteristics thereof were measured, and the results were shown in Table 13.

Comparative Example 2

An organic electroluminescent element was produced by the process described in Example 1 except that in the formation of the luminescent layer in Example 1, N-methyl-2-methoxyacridone was used instead of using compound Illustrative Compound No. A-5. When a DC voltage of 12 V was applied to this element in a dry atmosphere, luminescence of a blue color was identified. Further, the characteristics thereof were measured, and the results were shown in Table 13.

TABLE 9

| Organic electroluminescent element | Brightness (cd/m$^2$) | Current density (mA/cm$^2$) |
|---|---|---|
| Example 2 | 2380 | 54 |
| Example 3 | 2360 | 55 |
| Example 4 | 2320 | 54 |
| Example 5 | 2360 | 53 |
| Example 6 | 2440 | 56 |
| Example 7 | 2340 | 56 |
| Example 8 | 2330 | 55 |
| Example 9 | 2380 | 54 |
| Example 10 | 2380 | 54 |
| Example 11 | 2350 | 56 |
| Example 12 | 2440 | 54 |
| Example 13 | 2480 | 53 |
| Example 14 | 2390 | 55 |
| Example 15 | 2340 | 54 |
| Example 16 | 2510 | 55 |
| Example 17 | 2340 | 53 |
| Example 18 | 2420 | 56 |
| Example 19 | 2430 | 54 |
| Example 20 | 2420 | 54 |
| Example 21 | 2340 | 55 |
| Example 22 | 2440 | 54 |
| Example 23 | 2410 | 53 |
| Example 24 | 2350 | 55 |
| Example 25 | 2510 | 55 |

TABLE 10

| Organic electroluminescent element | Brightness (cd/m$^2$) | Current density (mA/cm$^2$) |
|---|---|---|
| Example 26 | 2370 | 54 |
| Example 27 | 2320 | 54 |
| Example 28 | 2340 | 54 |
| Example 29 | 2360 | 56 |
| Example 30 | 2330 | 55 |
| Example 31 | 2370 | 54 |
| Example 32 | 2380 | 55 |
| Example 33 | 2460 | 54 |
| Example 34 | 2340 | 54 |
| Example 35 | 2580 | 56 |
| Example 36 | 2340 | 54 |
| Example 37 | 2410 | 55 |
| Example 38 | 2380 | 55 |
| Example 39 | 2380 | 55 |
| Example 40 | 2420 | 54 |
| Example 41 | 2410 | 53 |
| Example 42 | 2350 | 56 |
| Example 43 | 2340 | 56 |
| Example 44 | 2380 | 55 |
| Example 45 | 2500 | 56 |
| Example 46 | 2360 | 55 |
| Example 47 | 2340 | 56 |
| Example 48 | 2320 | 55 |
| Example 49 | 2330 | 56 |

TABLE 11

| Organic electroluminescent element | Brightness (cd/m$^2$) | Current density (mA/cm$^2$) |
|---|---|---|
| Example 50 | 2540 | 56 |
| Example 51 | 2360 | 54 |
| Example 52 | 2340 | 55 |
| Example 53 | 2380 | 54 |
| Example 54 | 2350 | 56 |
| Example 55 | 2470 | 55 |
| Example 56 | 2330 | 56 |
| Example 57 | 2350 | 53 |
| Example 58 | 2460 | 55 |
| Example 59 | 2340 | 53 |
| Example 60 | 2420 | 55 |
| Example 61 | 2530 | 56 |
| Example 62 | 2440 | 54 |
| Example 63 | 2360 | 53 |
| Example 64 | 2340 | 55 |
| Example 65 | 2380 | 54 |
| Example 66 | 2410 | 56 |
| Example 67 | 2390 | 55 |
| Example 68 | 2340 | 56 |
| Example 69 | 2350 | 54 |
| Example 70 | 2370 | 55 |
| Example 71 | 2420 | 56 |
| Example 72 | 2480 | 55 |
| Example 73 | 2510 | 56 |

TABLE 12

| Organic electroluminescent element | Brightness (cd/m$^2$) | Current density (mA/cm$^2$) |
|---|---|---|
| Example 74 | 2380 | 53 |
| Example 75 | 2460 | 54 |
| Example 76 | 2340 | 55 |
| Example 77 | 2480 | 55 |
| Example 78 | 2350 | 54 |
| Example 79 | 2370 | 55 |
| Example 80 | 2510 | 56 |
| Example 81 | 2330 | 56 |
| Example 82 | 2340 | 55 |
| Example 83 | 2350 | 53 |
| Example 84 | 2350 | 55 |
| Example 85 | 2430 | 56 |
| Example 86 | 2340 | 56 |
| Example 87 | 2370 | 55 |
| Example 88 | 2320 | 56 |
| Example 89 | 2380 | 54 |
| Example 90 | 2350 | 56 |
| Example 91 | 2370 | 55 |
| Example 92 | 2340 | 56 |
| Example 93 | 2350 | 54 |
| Example 94 | 2370 | 55 |
| Example 95 | 2420 | 56 |
| Example 96 | 2480 | 55 |
| Example 97 | 2510 | 56 |

TABLE 13

| Organic electroluminescent element | Brightness (cd/m$^2$) | Current density (mA/cm$^2$) |
| --- | --- | --- |
| Example 98 | 2460 | 56 |
| Example 99 | 2380 | 55 |
| Comparative Example 1 | 1170 | 82 |
| Comparative Example 2 | 1550 | 74 |

Example 100

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10$^{-4}$ Pa.

First, 4,4',4''-tris[N-(3'''-methylphenyl)-N-phenylamino]triphenylamine was deposited on the ITO transparent electrode to a thickness of 50 nm at a deposition rate of 0.1 nm/sec to form a first hole injection transport layer.

Then, 4,4'-bis[N-phenyl-N-(1''-naphthyl)amino]biphenyl and compound Illustrative Compound No. A-5 were co-deposited from different deposition sources to a thickness of 20 nm at a deposition rate of 0.2 nm/sec (weight ratio 100:5.0) to form a luminescent layer serving also as a second hole injection transport layer.

Subsequently, tris(8-quinolinolato)aluminum was deposited thereon to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 15 V was applied to the organic electroluminescent element produced in a dry atmosphere, a current of 62 mA/cm$^2$ was passed. Luminescence of a bluish green color having a brightness of 2,620 cd/m$^2$ was identified.

Examples 101 to 162

Organic electroluminescent elements were produced by the process described in Example 100 except using, instead of using compound Illustrative Compound A-5 in the formation of the luminescent layer in Example 100, compound Illustrative Compound No. A-6 (Example 101), compound Illustrative Compound No. A-8 (Example 102), compound Illustrative Compound No. A-9 (Example 103), compound Illustrative Compound No. A-11 (Example 104), compound Illustrative Compound No. A-14 (Example 105), compound Illustrative Compound No. A-17 (Example 106), compound Illustrative Compound No. A-19 (Example 107), compound Illustrative Compound No. A-21 (Example 108), compound Illustrative Compound No. A-23 (Example 109), compound Illustrative Compound No. A-40 (Example 110), compound Illustrative Compound No. A-43 (Example 111), compound Illustrative Compound No. A-45 (Example 112), compound Illustrative Compound No. A-47 (Example 113), compound Illustrative Compound No. A-53 (Example 114), compound Illustrative Compound No. A-55 (Example 115), compound Illustrative Compound No. A-58 (Example 116), compound Illustrative Compound No. B-1 (Example 117), compound Illustrative Compound No. B-2 (Example 118), compound Illustrative Compound No. B-6 (Example 119), compound Illustrative Compound No. B-9 (Example 120), compound Illustrative Compound No. B-12 (Example 121), compound Illustrative Compound No. B-14 (Example 122), compound Illustrative Compound No. B-17 (Example 123), compound Illustrative Compound No. B-19 (Example 124), compound Illustrative Compound No. B-21 (Example 125), compound Illustrative Compound No. B-25 (Example 126), compound Illustrative Compound No. B-40 (Example 127), compound Illustrative Compound No. B-43 (Example 128), compound Illustrative Compound No. B-45 (Example 129), compound Illustrative Compound No. B-47 (Example 130), compound Illustrative Compound No. B-53 (Example 131), compound Illustrative Compound No. B-55 (Example 132), compound Illustrative Compound No. B-58 (Example 133), compound Illustrative Compound No. C-1 (Example 134), compound Illustrative Compound No. C-3 (Example 135), compound Illustrative Compound No. C-5 (Example 136), compound Illustrative Compound No. C-12 (Example 137), compound Illustrative Compound No. C-14 (Example 138), compound Illustrative Compound No. C-20 (Example 139), compound Illustrative Compound No. C-25 (Example 140), compound Illustrative Compound No. D-1 (Example 141), compound Illustrative Compound No. D-8 (Example 142), compound Illustrative Compound No. E-1 (Example 143), compound Illustrative Compound No. F-3 (Example 144), compound Illustrative Compound No. G-1 (Example 145), compound Illustrative Compound No. H-1 (Example 146), compound Illustrative Compound No. I-1 (Example 147), compound Illustrative Compound No. I-4 (Example 148), compound Illustrative Compound No. J-3 (Example 149), compound Illustrative Compound No. K-3 (Example 150), compound Illustrative Compound No. L-1 (Example 151), compound Illustrative Compound No. M-1 (Example 152), compound Illustrative Compound No. M-3 (Example 153), compound Illustrative Compound No. M-5 (Example 154), compound Illustrative Compound No. M-14 (Example 15-5), compound Illustrative Compound No. M-20 (Example 156), compound Illustrative Compound No. M-22 (Example 157), compound Illustrative Compound No. M-24 (Example 158), compound Illustrative Compound No. N-1 (Example 159), compound Illustrative Compound No. O-3 (Example 160), compound Illustrative Compound No. P-1 (Example 161) and compound Illustrative Compound No. Q-1 (Example 162). When a DC voltage of 15 V was applied to each element in a dry atmosphere, luminescence of a blue to bluish green color was identified. Further, the characteristics thereof were measured, and the results were shown in Tables 14 to 16.

TABLE 14

| Organic electroluminescent element | Brightness (cd/m$^2$) | Current density (mA/cm$^2$) |
| --- | --- | --- |
| Example 101 | 2450 | 56 |
| Example 102 | 2470 | 54 |
| Example 103 | 2640 | 54 |
| Example 104 | 2630 | 56 |
| Example 105 | 2580 | 57 |
| Example 106 | 2530 | 55 |
| Example 107 | 2520 | 54 |
| Example 108 | 2480 | 55 |
| Example 109 | 2520 | 57 |
| Example 110 | 2480 | 54 |
| Example 111 | 2540 | 55 |
| Example 112 | 2590 | 57 |

TABLE 14-continued

| Organic electroluminescent element | Brightness (cd/m$^2$) | Current density (mA/cm$^2$) |
|---|---|---|
| Example 113 | 2480 | 57 |
| Example 114 | 2620 | 55 |
| Example 115 | 2490 | 56 |
| Example 116 | 2550 | 54 |
| Example 117 | 2640 | 63 |
| Example 118 | 2470 | 55 |
| Example 119 | 2450 | 56 |
| Example 120 | 2620 | 54 |
| Example 121 | 2610 | 54 |
| Example 122 | 2570 | 56 |
| Example 123 | 2550 | 55 |
| Example 124 | 2580 | 56 |

TABLE 15

| Organic electroluminescent element | Brightness (cd/m$^2$) | Current density (mA/cm$^2$) |
|---|---|---|
| Example 125 | 2460 | 54 |
| Example 126 | 2520 | 57 |
| Example 127 | 2460 | 57 |
| Example 128 | 2540 | 54 |
| Example 129 | 2590 | 56 |
| Example 130 | 2580 | 57 |
| Example 131 | 2520 | 55 |
| Example 132 | 2490 | 55 |
| Example 133 | 2620 | 54 |
| Example 134 | 2510 | 55 |
| Example 135 | 2600 | 54 |
| Example 136 | 2630 | 56 |
| Example 137 | 2610 | 57 |
| Example 138 | 2550 | 56 |
| Example 139 | 2670 | 55 |
| Example 140 | 2570 | 56 |
| Example 141 | 2640 | 63 |
| Example 142 | 2470 | 55 |
| Example 143 | 2550 | 56 |
| Example 144 | 2620 | 57 |
| Example 145 | 2610 | 58 |
| Example 146 | 2570 | 56 |
| Example 147 | 2550 | 55 |
| Example 148 | 2480 | 54 |

TABLE 16

| Organic electroluminescent element | Brightness (cd/m$^2$) | Current density (mA/cm$^2$) |
|---|---|---|
| Example 149 | 2450 | 53 |
| Example 150 | 2470 | 54 |
| Example 151 | 2540 | 56 |
| Example 152 | 2510 | 55 |
| Example 153 | 2560 | 54 |
| Example 154 | 2630 | 55 |
| Example 155 | 2570 | 56 |
| Example 156 | 2620 | 55 |
| Example 157 | 2610 | 57 |
| Example 158 | 2590 | 55 |
| Example 159 | 2440 | 55 |
| Example 160 | 2590 | 57 |
| Example 161 | 2460 | 54 |

Example 163

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10$^{-4}$ Pa.

First, 4,4'-bis[N-phenyl-N-(3"-methylphenyl)amino] biphenyl was deposited on the ITO transparent electrode to a thickness of 75 nm at a deposition rate of 0.2 nm/sec to form a hole injection transport layer.

Then, bis(2-methyl-8-quinolinolato)(4-phenylphenolato) aluminum and compound Illustrative Compound No. A-6 were co-deposited thereon from different deposition sources to a thickness of 50 nm at a deposition rate of 0.2 nm/sec (weight ratio 100:1.0) to form a luminescent layer.

Subsequently, tris(8-quinolinolato)aluminum was deposited to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 12 V was applied to the organic electroluminescent element produced in a dry atmosphere, a current of 55 mA/cm$^2$ was passed. Luminescence of a bluish green color having a brightness of 2,440 cd/m$^2$ was identified.

Example 164

An organic electroluminescent element was produced by the process described in Example 163 except that in the formation of the luminescent layer in Example 163, bis(2-methyl-8-quinolinolato)aluminum-$\mu$-oxo-bis(2-methyl-8-quinolinolato)aluminum and compound Illustrative Compound No. A-21 were used instead of using bis(2-methyl-8-quinolinolato)(4-phenylphenolato)aluminum and compound Illustrative Compound A-6 and were co-deposited to a thickness of 50 nm (weight ratio 100:2.0) to form a luminescent layer.

When a DC voltage of 12 V was applied to the organic electroluminescent element produced in a dry atmosphere, a current of 55 mA/cm$^2$ was passed. Luminescence of a bluish green color having a brightness of 2,350 cd/m$^2$ was identified.

Example 165

An organic electroluminescent element was produced by the process described in Example 163 except that in the formation of the luminescent layer in Example 163, bis(2-methyl-8-quinolinolato)(4-phenylphenolato)aluminum and compound Illustrative Compound No. A-40 were used instead of using bis(2-methyl-8-quinolinolato)(4-phenylphenolato)aluminum and compound Illustrative Compound A-6 and were co-deposited to a thickness of 50 nm (weight ratio 100:1.0) to form a luminescent layer.

When a DC voltage of 12 V was applied to the organic electroluminescent element produced in a dry atmosphere, a current of 54 mA/cm$^2$ was passed. Luminescence of a bluish green color having a brightness of 2,320 cd/m$^2$ was identified.

Example 166

An organic electroluminescent element was produced by the process described in Example 163 except that in the formation of the luminescent layer in Example 163, tris(8-quinolinolato)aluminum and compound Illustrative Compound No. B-1 were used instead of using bis(2-methyl-8-quinolinolato)(4-phenylphenolato)aluminum and compound Illustrative Compound A-6 and were co-deposited to a thickness of 50 nm (weight ratio 100:3.0) to form a luminescent layer.

When a DC voltage of 12 V was applied to the organic electroluminescent element produced in a dry atmosphere, a current of 54 mA/cm$^2$ was passed. Luminescence of a bluish green color having a brightness of 2,370 cd/m$^2$ was identified.

Example 167

An organic electroluminescent element was produced by the process described in Example 163 except that in the formation of the luminescent layer in Example 163, tris(8-quinolinolato)aluminum and compound Illustrative Compound No. B-12 were used instead of using bis(2-methyl-8-quinolinolato)(4-phenylphenolato)aluminum and compound Illustrative Compound A-6 and were co-deposited to a thickness of 50 nm (weight ratio 100:6.0) to form a luminescent layer.

When a DC voltage of 12 V was applied to the organic electroluminescent element produced in a dry atmosphere, a current of 54 mA/cm$^2$ was passed. Luminescence of a bluish green color having a brightness of 2,360 cd/m$^2$ was identified.

Example 168

An organic electroluminescent element was produced by the process described in Example 163 except that in the formation of the luminescent layer in Example 163, bis(2-methyl-8-quinolinolato)aluminum-$\mu$-oxo-bis(2-methyl-8-quinolinolato)aluminum and compound Illustrative Compound No. C-1 were used instead of using bis(2-methyl-8-quinolinolato)(4-phenylphenolato)aluminum and compound Illustrative Compound A-6 and were co-deposited to a thickness of 50 nm (weight ratio 100:2.0) to form a luminescent layer.

When a DC voltage of 12 V was applied to the organic electroluminescent element produced in a dry atmosphere, a current of 55 mA/cm$^2$ was passed. Luminescence of a bluish green color having a brightness of 2,350 cd/m$^2$ was identified.

Example 169

An organic electroluminescent element was produced by the process described in Example 163 except that in the formation of the luminescent layer in Example 163, tris(8-quinolinolato)aluminum and compound Illustrative Compound No. C-12 were used instead of using bis(2-methyl-8-quinolinolato)(4-phenylphenolato)aluminum and compound Illustrative Compound A-6 and were co-deposited to a thickness of 50 nm (weight ratio 100:10.0) to form a luminescent layer.

When a DC voltage of 12 V was applied to the organic electroluminescent element produced in a dry atmosphere, a current of 55 mA/cm$^2$ was passed. Luminescence of a bluish green color having a brightness of 2,440 cd/m$^2$ was identified.

Example 170

An organic electroluminescent element was produced by the process described in Example 163 except that in the formation of the luminescent layer in Example 163, bis(2,4-dimethyl-8-quinolinolato)aluminum-$\mu$-oxo-bis(2,4-dimethyl-8-quinolinolato)aluminum and compound Illustrative Compound No. D-1 were used instead of using bis(2-methyl-8-quinolinolato)(4-phenylphenolato)aluminum and compound Illustrative Compound A-6 and were co-deposited to a thickness of 50 nm (weight ratio 100:1.0) to form a luminescent layer. When a DC voltage of 12 V was applied to the organic electroluminescent element produced in a dry atmosphere, a current of 54 mA/cm$^2$ was passed. Luminescence of a bluish green color having a brightness of 2,320 cd/m$^2$ was identified.

Example 171

An organic electroluminescent element was produced by the process described in Example 163 except that in the formation of the luminescent layer in Example 163, bis(2-methyl-8-quinolinolato)aluminum-$\mu$-oxo-bis(2-methyl-8-quinolinolato)aluminum and compound Illustrative Compound No. E-1 were used instead of using bis(2-methyl-8-quinolinolato)(4-phenylphenolato)aluminum and compound Illustrative Compound A-6 and were co-deposited to a thickness of 50 nm (weight ratio 100:2.0) to form a luminescent layer. When a DC voltage of 12 V was applied to the organic electroluminescent element produced in a dry atmosphere, a current of 54 mA/cm$^2$ was passed. Luminescence of a bluish green color having a brightness of 2,380 cd/m$^2$ was identified.

Example 172

An organic electroluminescent element was produced by the process described in Example 163 except that in the formation of the luminescent layer in Example 163, bis(2,4-dimethyl-8-quinolinolato)aluminum-$\mu$-oxo-bis(2,4-dimethyl-8-quinolinolato)aluminum and compound Illustrative Compound No. F-3 were used instead of using bis(2-methyl-8-quinolinolato)(4-phenylphenolato)aluminum and compound Illustrative Compound A-6 and were co-deposited to a thickness of 50 nm (weight ratio 100:4.0) to form a luminescent layer. When a DC voltage of 12 V was applied to the organic electroluminescent element produced in a dry atmosphere, a current of 55 mA/cm$^2$ was passed. Luminescence of a bluish green color having a brightness of 2,340 cd/m$^2$ was identified.

Example 173

An organic electroluminescent element was produced by the process described in Example 163 except that in the formation of the luminescent layer in Example 163, tris(8-quinolinolato)aluminum and compound Illustrative Compound No. M-1 were used instead of using bis(2-methyl-8-quinolinolato)(4-phenylphenolato)aluminum and compound Illustrative Compound A-6 and were co-deposited to a thickness of 50 nm (weight ratio 100:3.0) to form a luminescent layer.

When a DC voltage of 12 V was applied to the organic electroluminescent element produced in a dry atmosphere, a current of 57 mA/cm$^2$ was passed. Luminescence of a bluish green color having a brightness of 2,380 cd/m$^2$ was identified.

Example 174

An organic electroluminescent element was produced by the process described in Example 163 except that in the formation of the luminescent layer in Example 163, tris(8-quinolinolato)aluminum and compound Illustrative Compound No. M-20 were used instead of using bis(2-methyl-8-quinolinolato)(4-phenylphenolato)aluminum and compound Illustrative Compound A-6 and were co-deposited to a thickness of 50 nm (weight ratio 100:6.0) to form a luminescent layer.

When a DC voltage of 12 V was applied to the organic electroluminescent element produced in a dry atmosphere, a current of 58 mA/cm² was passed. Luminescence of a bluish green color having a brightness of 2,350 cd/m² was identified.

Example 175

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of $4\times10^{-4}$ Pa.

First, 4,4',4"-tris[N-(3'"-methylphenyl)-N-phenylamino]triphenylamine was deposited on the ITO transparent electrode to a thickness of 30 nm at a deposition rate of 0.1 nm/sec to form a first hole injection transport layer.

Next, 4,4'-bis[N-phenyl-N-(3"-methylphenyl)amino]biphenyl was deposited thereon to a thickness of 45 nm at a deposition rate of 0.2 nm/sec to form a second hole injection transport layer.

Then, bis(2-methyl-8-quinolinolato)(4-phenylphenolatoaluminum) and compound Illustrative Compound No. A-5 were co-deposited thereon from different deposition sources to a thickness of 50 nm at a deposition rate of 0.2 nm/sec (weight ratio 100:2.0) to form a luminescent layer.

Subsequently, tris(8-quinolinolato)aluminum was deposited to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 12 V was applied to the organic electroluminescent element produced in a dry atmosphere, a current of 56 mA/cm² was passed. Luminescence of a bluish green color having a brightness of 2,780 cd/m² was identified.

Example 176

An organic electroluminescent element was produced by the process described in Example 175 except that in the formation of the luminescent layer in Example 175, bis(2,4-dimethyl-8-quinolinolato)aluminum-$\mu$-oxo-bis(2,4-dimethyl-8-quinolinolato)aluminum and compound Illustrative Compound No. B-1 were used instead of using bis(2-methyl-8-quinolinolato)(4-phenylphenolato)aluminum and compound Illustrative Compound A-5 and were co-deposited to a thickness of 50 nm (weight ratio 100:1.0) to form a luminescent layer. When a DC voltage of 12 V was applied to the organic electroluminescent element produced in a dry atmosphere, a current of 55 mA/cm² was passed. Luminescence of a bluish green color having a brightness of 2,680 cd/m² was identified.

Example 177

An organic electroluminescent element was produced by the process described in Example 175 except that in the formation of the luminescent layer in Example 175, bis(2-methyl-8-quinolinolato)aluminum-$\mu$-oxo-bis(2-methyl-8-quinolinolato)aluminum and compound Illustrative Compound No. C-1 were used instead of using bis(2-methyl-8-quinolinolato)(4-phenylphenolato)aluminum and compound Illustrative Compound A-5 and were co-deposited to a thickness of 50 nm (weight ratio 100:3.0) to form a luminescent layer.

When a DC voltage of 12 V was applied to the organic electroluminescent element produced in a dry atmosphere, a current of 57 mA/cm² was passed. Luminescence of a bluish green color having a brightness of 2,650 cd/m² was identified.

Example 178

An organic electroluminescent element was produced by the process described in Example 175 except that in the formation of the luminescent layer in Example 175, tris(8-quinolinolato)aluminum and compound Illustrative Compound No. D-1 were used instead of using bis(2-methyl-8-quinolinolato)(4-phenylphenolato)aluminum and compound Illustrative Compound A-5 and were co-deposited to a thickness of 50 nm (weight ratio 100:2.0) to form a luminescent layer.

When a DC voltage of 12 V was applied to the organic electroluminescent element produced in a dry atmosphere, a current of 55 mA/cm² was passed. Luminescence of a bluish green color having a brightness of 2,420 cd/m² was identified.

Example 179

An organic electroluminescent element was produced by the process described in Example 175 except that in the formation of the luminescent layer in Example 175, bis(2-methyl-8-quinolinolato)aluminum-$\mu$-oxo-bis(2-methyl-8-quinolinolato)aluminum and compound Illustrative Compound No. F-24 were used instead of using bis(2-methyl-8-quinolinolato)(4-phenylphenolato)aluminum and compound Illustrative Compound A-5 and were co-deposited to a thickness of 50 nm (weight ratio 100:4.0) to form a luminescent layer.

When a DC voltage of 12 V was applied to the organic electroluminescent element produced in a dry atmosphere, a current of 58 mA/cm² was passed. Luminescence of a bluish green color having a brightness of 2,600 cd/m² was identified.

Example 180

An organic electroluminescent element was produced by the process described in Example 175 except that in the formation of the luminescent layer in Example 175, tris(8-quinolinolato)aluminum and compound Illustrative Compound No. G-1 were used instead of using bis(2-methyl-8-quinolinolato)(4-phenylphenolato)aluminum and compound Illustrative Compound A-5 and were co-deposited to a thickness of 50 nm (weight ratio 100:2.0) to form a luminescent layer.

When a DC voltage of 12 V was applied to the organic electroluminescent element produced in a dry atmosphere, a current of 54 mA/cm² was passed. Luminescence of a bluish green color having a brightness of 2,480 cd/m² was identified.

Example 181

An organic electroluminescent element was produced by the process described in Example 175 except that in the formation of the luminescent layer in Example 175, bis(2,4-dimethyl-8-quinolinolato)aluminum-$\mu$-oxo-bis(2,4-dimethyl-8-quinolinolato)aluminum and compound Illustrative Compound No. K-3 were used instead of using bis(2- methyl-8-quinolinolato)(4-phenylphenolato)aluminum and compound Illustrative Compound A-5 and were co-deposited to a thickness of 50 nm (weight ratio 100:2.0) to form a luminescent layer. When a DC voltage of 12 V was applied to the organic electroluminescent element produced in a dry atmosphere, a current of 53 mA/cm$^2$ was passed. Luminescence of a bluish green color having a brightness of 2,510 cd/m$^2$ was identified.

Example 182

An organic electroluminescent element was produced by the process described in Example 175 except that in the formation of the luminescent layer in Example 175, bis(2,4-dimethyl-8-quinolinolato)aluminum-$\mu$-oxo-bis(2,4-dimethyl-8-quinolinolato)aluminum and compound Illustrative Compound No. M-1 were used instead of using bis(2-methyl-8-quinolinolato)(4-phenylphenolato)aluminum and compound Illustrative Compound A-5 and were co-deposited to a thickness of 50 nm (weight ratio 100:3.0) to form a luminescent layer. When a DC voltage of 12 V was applied to the organic electroluminescent element produced in a dry atmosphere, a current of 56 mA/cm$^2$ was passed. Luminescence of a bluish green color having a brightness of 2,530 cd/m$^2$ was identified.

Example 183

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10$^{-4}$ Pa.

First, 4,4'-bis[N-phenyl-N-(3"-methylphenyl)amino]biphenyl was deposited on the ITO transparent electrode to a thickness of 75 nm at a deposition rate of 0.2 nm/sec to form a hole injection transport layer. Then, bis(2-methyl-8-quinolinolato)(4-phenylphenolato)aluminum and compound Illustrative Compound No. A-20 were co-deposited thereon from different deposition sources to a thickness of 50 nm at a deposition rate of 0.2 nm/sec (weight ratio 100:2.0) to form a luminescent layer.

Subsequently, 1,3-bis[5'-(4"-tert-butylphenyl)-1',3',4'-oxadiazol-2'-yl]benzene was deposited to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 12 V was applied to the organic electroluminescent element produced in a dry atmosphere, a current of 54 mA/cm$^2$ was passed. Luminescence of a bluish green color having a brightness of 2,320 cd/m$^2$ was identified.

Example 184

An organic electroluminescent element was produced by the process described in Example 183 except that in the formation of the luminescent layer in Example 183, tris(8-quinolinolato)aluminum and compound Illustrative Compound No. E-21 were used instead of using bis(2-methyl-8-quinolinolato)(4-phenylphenolato)aluminum and compound Illustrative Compound A-20 and were co-deposited to a thickness of 50 nm (weight ratio 100:4.0) to form a luminescent layer. When a DC voltage of 12 V was applied to the organic electroluminescent element produced in a dry atmosphere, a current of 56 mA/cm$^2$ was passed. Luminescence of a bluish green color having a brightness of 2,430 cd/m$^2$ was identified.

Example 185

An organic electroluminescent element was produced by the process described in Example 183 except that in the formation of the luminescent layer in Example 183, bis(2-methyl-8-quinolinolato)aluminum-$\mu$-oxo-bis(2-methyl-8-quinolinolato)aluminum and compound Illustrative Compound No. L-1 were used instead of using bis(2-methyl-8-quinolinolato)(4-phenylphenolato)aluminum and compound Illustrative Compound A-20 and were co-deposited to a thickness of 50 nm (weight ratio 100:3.0) to form a luminescent layer.

When a DC voltage of 12 V was applied to the organic electroluminescent element produced in a dry atmosphere, a current of 54 mA/cm$^2$ was passed. Luminescence of a bluish green color having a brightness of 2,380 cd/m$^2$ was identified.

Example 186

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10$^{-4}$ Pa.

First, 4,4'-bis[N-phenyl-N-(3"-methylphenyl)amino]biphenyl was deposited on the ITO transparent electrode to a thickness of 75 nm at a deposition rate of 0.2 nm/sec to form a hole injection transport layer.

Then, compound Illustrative Compound No. B-12 was deposited thereon to a thickness of 50 nm at a deposition rate of 0.2 nm/sec to form a luminescent layer.

Subsequently, tris(8-quinolinolato)aluminum was deposited to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 12 V was applied to the organic electroluminescent element produced in a dry atmosphere, a current of 58 mA/cm$^2$ was passed. Luminescence of a bluish green color having a brightness of 2,740 cd/m$^2$ was identified.

Example 187

An organic electroluminescent element was produced by the process described in Example 186 except that in the formation of the luminescent layer in Example 186, compound Illustrative Compound No. J-3 was used instead of using compound Illustrative Compound B-12.

When a DC voltage of 12 V was applied to the organic electroluminescent element produced in a dry atmosphere, a green color having a brightness of 2,660 cd/m$^2$ was identified.

Example 188

An organic electroluminescent element was produced by the process described in Example 186 except that in the formation of the luminescent layer in Example 186, compound Illustrative Compound No. L-1 was used instead of using compound Illustrative Compound No. B-12.

When a DC voltage of 12 V was applied to the organic electroluminescent element produced in a dry atmosphere, a current of 54 mA/cm$^2$ was passed. Luminescence of a bluish green color having a brightness of 2,430 cd/m$^2$ was identified.

Example 189

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10$^{-4}$ Pa.

First, 4,4'-bis[N-phenyl-N-(3"-methylphenyl)amino] biphenyl was deposited on the ITO transparent electrode to a thickness of 75 nm at a deposition rate of 0.2 nm/sec to form a hole injection transport layer.

Subsequently, compound Illustrative Compound No. A-5 was deposited thereon to a thickness of 50 nm at a deposition rate of 0.2 nm/sec to form a luminescent layer. Then, 1,3-bis[5'-(4"-tert-butylphenyl)-1',3',4'-oxadiazol-2'-yl] benzene was deposited thereon to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 14 V was applied to the organic electroluminescent element produced in a dry atmosphere, a current of 44 mA/cm$^2$ was passed. Luminescence of a bluish green color having a brightness of 1,820 cd/m$^2$ was identified.

Example 190

An organic electroluminescent element was produced by the process described in Example 189 except that in the formation of the luminescent layer in Example 189, compound Illustrative Compound No. A-9 was used instead of using compound Illustrative Compound A-5.

When a DC voltage of 14 V was applied to the organic electroluminescent element produced in a dry atmosphere, a current of 44 mA/cm$^2$ was passed. Luminescence of a bluish green color having a brightness of 1,820 cd/m$^2$ was identified.

Example 191

An organic electroluminescent element was produced by the process described in Example 189 except that in the formation of the luminescent layer in Example 189, compound Illustrative Compound No. B-55 was used instead of using compound Illustrative Compound A-5.

When a DC voltage of 14 V was applied to the organic electroluminescent element produced in a dry atmosphere, a current of 60 mA/cm$^2$ was passed. Luminescence of a bluish green color having a brightness of 1,480 cd/m$^2$ was identified.

Example 192

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10$^{-4}$ Pa.

First, 4,4'-bis[N-phenyl-N-(3"-methylphenyl)amino] biphenyl was deposited on the ITO transparent electrode to a thickness of 75 nm at a deposition rate of 0.2 nm/sec to form a hole injection transport layer.

Then, tris(8-quinolinolato)aluminum and compound Illustrative Compound No. A-17 were co-deposited thereon from different deposition sources to a thickness of 50 nm at a deposition rate of 0.2 nm/sec (weight ratio 100:1.0) to form a luminescent layer serving also as an electron transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 12 V was applied to the organic electroluminescent element produced in a dry atmosphere, a current of 53 mA/cm$^2$ was passed. Luminescence of a bluish green color having a brightness of 2,320 cd/m$^2$ was identified.

Example 193

An organic electroluminescent element was produced by the process described in Example 192 except that in the formation of the luminescent layer in Example 192, tris(8-quinolinolato)aluminum and compound Illustrative Compound No. B-17 were used instead of using tris(8-quinolinolato)aluminum and compound Illustrative Compound No. A-17 and were co-deposited to a thickness of 50 nm (weight ratio 100:1.0) to form a luminescent layer.

When a DC voltage of 12 V was applied to the organic electroluminescent element produced in a dry atmosphere, a current of 54 mA/cm$^2$ was passed. Luminescence of a bluish green color having a brightness of 2,340 cd/m$^2$ was identified.

Example 194

An organic electroluminescent element was produced by the process described in Example 193 except that in the formation of the luminescent layer in Example 193, bis(2-methyl-8-quinolinolato)aluminum-$\mu$-oxo-bis(2-methyl-8-quinolinolato)aluminum and compound Illustrative Compound No. F-24 were used instead of using tris(8-quinolinolato)aluminum and compound Illustrative Compound No. A-17 and were co-deposited to a thickness of 50 nm (weight ratio 100:2.0) to form a luminescent layer.

When a DC voltage of 12 V was applied to the organic electroluminescent element produced in a dry atmosphere, a current of 54 mA/cm$^2$ was passed. Luminescence of a bluish green color having a brightness of 2,330 cd/m$^2$ was identified.

Example 195

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of 4×10$^{-4}$ Pa.

First, compound Illustrative Compound No. A-55 was deposited on the ITO transparent electrode to a thickness of 55 nm at a deposition rate of 0.2 nm/sec to form a luminescent layer.

Then, 1,3-bis[5'-(4"-tert-butylphenyl)-1',3',4'-oxadiazol-2'-yl]benzene was deposited thereon to a thickness of 75 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

When a DC voltage of 14 V was applied to the organic electroluminescent element produced in a dry atmosphere, a current of 60 mA/cm$^2$ was passed. Luminescence of a bluish green color having a brightness of 1,500 cd/m$^2$ was identified.

Example 196

An organic electroluminescent element was produced by the process described in Example 195 except that in the formation of the luminescent layer in Example 195, compound Illustrative Compound No. B-55 was used instead of using compound Illustrative Compound A-55.

When a DC voltage of 14 V was applied to the organic electroluminescent element produced in a dry atmosphere, a current of 60 mA/cm$^2$ was passed. Luminescence of a bluish green color having a brightness of 1,480 cd/m$^2$ was identified.

Example 197

A glass substrate with an ITO transparent electrode (anode) having a thickness of 200 nm was ultrasonically cleaned using a neutral detergent, acetone and ethanol. This substrate was dried using a nitrogen gas, and further subjected to UV/ozone cleaning Then, a luminescent layer of 400 nm was formed on the ITO transparent electrode by a dip coating method using a 3% by weight dichloroethane solution containing poly-N-vinylcarbazole (weight average molecular weight 150,000), compound Illustrative Compound No. B-12, coumalin 6 ["3-(2'-benzothiazolyl)-7-diethylaminocoumarin" (luminescent component of a green color)] and DCM-1 ["4-(dicyanomethylene)-2-methyl-6-(4'-dimethylaminostyryl)-4H-pyran" (luminescent component of an orange color)] at a weight ratio of 100:5:3:2 respectively.

Then, the glass substrate having the luminescent layer was fixed on a substrate holder of a deposition device, and a deposition bath was set at reduced pressure of 4×10$^{-4}$ Pa. In addition, 3-(4'-tert-butylphenyl)-4-phenyl-5-(4"-phenylphenyl)-1,2,4-triazole was deposited on the luminescent layer to a thickness of 20 nm at a deposition rate of 0.2 nm/sec, and tris(8-quinolinolato)aluminum was further deposited thereon to a thickness of 30 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. When a DC voltage of 12 V was applied to the organic electroluminescent element produced in a dry atmosphere, a current of 73 mA/cm$^2$ was passed. Luminescence of a bluish green color having a brightness of 1,350 cd/m$^2$ was identified.

Examples 198 to 205

Organic electroluminescent elements were produced by the process described in Example 197 except using, instead of using compound Illustrative Compound No. B-12 in Example 197, compound Illustrative Compound No. B-43 (Example 198), compound Illustrative Compound No. C-3 (Example 199), compound Illustrative Compound No. C-5 (Example 200), compound Illustrative Compound No. E-7 (Example 201), compound Illustrative Compound No. E-18 (Example 202), compound Illustrative Compound No. F-24 (Example 203), compound Illustrative Compound No. I-4 (Example 204) and compound Illustrative Compound No. M-5 (Example 205). When a DC voltage of 12 V was applied to each element in a dry atmosphere, luminescence of a white color was observed. Further, the characteristics thereof were measured, and the results were shown in Table 17.

TABLE 17

| Organic electroluminescent element | Brightness (cd/m$^2$) | Current density (mA/cm$^2$) |
| --- | --- | --- |
| Example 198 | 1280 | 76 |
| Example 199 | 1250 | 74 |
| Example 200 | 1240 | 76 |
| Example 201 | 1260 | 75 |
| Example 202 | 1340 | 75 |
| Example 203 | 1230 | 73 |
| Example 204 | 1380 | 75 |
| Example 205 | 1260 | 74 |

Example 206

A glass substrate with an ITO transparent electrode (anode) having a thickness of 200 nm was ultrasonically cleaned using a neutral detergent, acetone and ethanol. This substrate was dried using a nitrogen gas, and further subjected to UV/ozone cleaning Then, a luminescent layer of 300 nm was formed on the ITO transparent electrode by a dip coating method using a 3% by weight dichloroethane, solution containing poly-N-vinylcarbazole (weight average molecular weight 150,000), 1,3-bis[5'-(4"-tert-butylphenyl)-1',3',4'-oxadiazolyl-2'-yl] benzene and compound Illustrative Compound No. C-3 at a weight ratio of 100:30:3 respectively. Subsequently, the glass substrate having the luminescent layer was fixed on a substrate holder of a deposition device, and a deposition bath was set at reduced pressure of 4×10$^{-4}$ Pa.

Further, magnesium and silver were co-deposited thereon to a thickness of 200 nm at a deposition rate of 0.2 nm/sec (weight ratio 10:1) to form a cathode, and an organic electroluminescent element was produced.

When a DC voltage of 15 V was applied to the organic electroluminescent element produced in a dry atmosphere, a current of 66 mA/cm$^2$ was passed. Luminescence of a bluish green color having a brightness of 1,520 cd/m$^2$ was identified.

Example 207

An organic electroluminescent element was produced by the process described in Example 206 except that in the formation of the luminescent layer in Example 206, compound Illustrative Compound No. M-3 was used instead of using compound Illustrative Compound No. C-3.

When a DC voltage of 15 V was applied to the organic electroluminescent element produced in a dry atmosphere, a current of 65 mA/cm$^2$ was passed. Luminescence of a blue color having a brightness of 1,540 cd/m$^2$ was identified.

Comparative Example 3

An organic electroluminescent element was produced by the process described in Example 206 except that in the formation of the luminescent layer in Example 206, 1,1,4,4-tetraphenyl-1,3-butadiene was used instead of using compound Illustrative Compound No. C-3.

When a DC voltage of 15 V was applied to the organic electroluminescent element produced in a dry atmosphere, a current of 86 mA/cm$^2$ was passed. Luminescence of a blue color having a brightness of 760 cd/m$^2$ was identified.

Example 208

A glass substrate with an ITO transparent electrode (anode) having a thickness of 200 nm was ultrasonically cleaned using a neutral detergent, acetone and ethanol. This substrate was dried using a nitrogen gas, and further subjected to UV/ozone cleaning.

Subsequently, a luminescent layer of 300 nm was formed on the ITO transparent electrode by a dip coating method using a 3% by weight dichloroethane solution containing polycarbonate (weight average molecular weight 50,000), 4,4'-bis[N-phenyl-N-(3''-methylphenyl)amino]biphenyl, bis(2-methyl-8-quinolinolato)aluminum-$\mu$-oxo-bis(2-methyl-8-quinolinolato)aluminum and compound Illustrative Compound No. A-53 at a weight ratio of 100:40:60:1 respectively. Then, the glass substrate having the luminescent layer was fixed on a substrate holder of a deposition device, and a deposition bath was set at reduced pressure of $4 \times 10^{-4}$ Pa.

Further, magnesium and silver were co-deposited on the luminescent layer to a thickness of 200 nm at a deposition rate of 0.2 nm/sec (weight ratio 10:1) to form a cathode, and an organic electroluminescent element was produced. When a DC voltage of 15 V was applied to the organic electroluminescent element produced in a dry atmosphere, a current of 61 mA/cm$^2$ was passed. Luminescence of a bluish green color having a brightness of 960 cd/m$^2$ was identified.

Example 209

An organic electroluminescent element was produced by the process described in Example 208 except that in the formation of the luminescent layer in Example 208, compound Illustrative Compound No. B-53 was used instead of using compound Illustrative Compound No. A-53.

When a DC voltage of 15 V was applied to the organic electroluminescent element produced in a dry atmosphere, a current of 62 mA/cm$^2$ was passed. Luminescence of a blue color having a brightness of 970 cd/m$^2$ was identified.

Example 210

A glass substrate with an ITO transparent electrode (anode) having a thickness of 200 nm was ultrasonically cleaned using a neutral detergent, acetone and ethanol. This substrate was dried using a nitrogen gas, further subjected to UV/ozone cleaning, and then fixed on a substrate holder of a deposition device. Thereafter, a deposition bath was set at reduced pressure of $4 \times 10^{-4}$ Pa.

First, 4,4'-bis[N-phenyl-N-(1'-naphthyl)amino]biphenyl was deposited on the ITO transparent electrode to a thickness of 75 nm at a deposition rate of 0.2 nm to form a hole injection transport layer.

Then, tris(8-quinolinolato)aluminum and compound Illustrative Compound No. A-5 were co-deposited thereon from different deposition sources at a deposition rate of 0.2 nm/sec (weight ratio 100:3.0) to form a luminescent layer.

Next, tris(8-quinolinolato)aluminum was deposited to a thickness of 50 nm at a deposition rate of 0.2 nm/sec to form an electron injection transport layer.

Further, magnesium and silver were co-deposited thereon to a thickness of 200 nm at a deposition rate of 0.2 nm/sec (weight ratio 10:1) to form a cathode, and an organic electroluminescent element was produced. By the way, the deposition was conducted while maintaining the state of reduced pressure of the deposition bath.

The organic electroluminescent element produced was continuously driven in a dry atmosphere at a constant current density of 10 mA/cm$^2$. Luminescence of a bluish green color with 6.7 V and a brightness of 520 cd/m$^2$ was identified at the initial stage. A half-life of the brightness was 2,400 hours.

Examples 211 to 218

Organic electroluminescent elements were produced by the process described in Example 210 except using, instead of using compound Illustrative Compound No. A-5 in Example 210, compound Illustrative Compound No. A-6 (Example 211), compound Illustrative Compound No. A-23 (Example 212), compound Illustrative Compound No. B-1 (Example 213), compound Illustrative Compound No. B-3 (Example 214), compound Illustrative Compound No. B-24 (Example 215), compound Illustrative Compound No. C-1 (Example 216), compound Illustrative Compound No. C-28 (Example 217) and compound Illustrative Compound No. M-1 (Example 218).

Each element was continuously driven in a dry atmosphere at a constant current density of 10 mA/cm$^2$. Luminescence of a blue to bluish green color was identified from each element. Further, the characteristics thereof were measured, and the results were shown in Table 18.

Comparative Example 4

An organic electroluminescent element was produced by the process described in Example 210 except that in the formation of the luminescent layer in Example 210, 9,10-diphenylanthracene was used instead of using compound Illustrative Compound No. A-5.

The organic electroluminescent element produced was continuously driven in a dry atmosphere at a constant current density of 10 mA/cm$^2$. Luminescence of a blue color was identified from the element. Further, the characteristics thereof were measured, and the results were shown in Table 18.

TABLE 18

| Organic electroluminescent element | Initial characteristics (cd/m$^2$) | Brightness Voltage (V) | Half-life (hr) |
| --- | --- | --- | --- |
| Example 211 | 530 | 6.5 | 2400 |
| Example 212 | 550 | 6.4 | 2300 |
| Example 213 | 540 | 6.6 | 2400 |
| Example 214 | 560 | 6.5 | 2500 |
| Example 215 | 540 | 6.6 | 2300 |
| Example 216 | 540 | 6.5 | 2500 |

TABLE 18-continued

| Organic electroluminescent element | Initial characteristics (cd/m$^2$) | Brightness Voltage (V) | Half-life (hr) |
|---|---|---|---|
| Example 217 | 530 | 6.5 | 2400 |
| Example 218 | 560 | 6.4 | 2200 |
| Comparative Example 4 | 430 | 7.2 | 900 |

INDUSTRIAL APPLICABILITY

The invention has made it possible to provide an organic electroluminescent element having an excellent luminescent brightness and a long luminescent life, and further to provide hydrocarbon compounds suited for the luminescent element.

What is claimed is:

1. Hydrocarbon compounds represented by the formula (1)

$$X_1\text{-}(F_1)_j\text{-}(A_1)_k\text{-}(F_2)_l\text{-}(A_2)_m\text{-}(F_3)_n\text{-}X_2 \tag{1}$$

wherein $A_1$ and $A_2$, independently from each other, represent a substituted or unsubstituted anthracen-diyl group, $F_1$, $F_2$ and $F_3$, independently from each other, represent a substituted or unsubstituted fluoren-diyl group, wherein the substituted fluoren-diyl group has as a substituent a halogen atom, a linear, branched or cyclic alkyl group, a linear, branched or cyclic alkoxy group, a substituted or unsubstituted amino group, a furfuryl group, a thienyl group, a pyridyl group, or a substituted or unsubstituted aralkyl group, $X_1$ and $X_2$, independently from each other, represent a hydrogen atom, a halogen atom, a linear, branched or cyclic alkyl group, a linear, branched or cyclic alkoxy group, a substituted or unsubstituted amino group, a substituted or unsubstituted aryl group, or a substituted or unsubstituted aralkyl group, j, m and n represent 0 or 1, k and l represent 1 or 2, when k is 2 $A_1$'s may be the same or different, and when l is 2 $F_2$'s may be the same or different, with the proviso that when j and n are 0 and k, l, and m are 1, then $X_1$ and $X_2$ are not a substituted or unsubstituted amino group.

2. The hydrocarbon compounds according to claim 1, wherein k is 1.

3. The hydrocarbon compounds according to claim 1, wherein $A_1$ and $A_2$ are an anthracen-9,10-diyl group, and $F_1$, $F_2$ and $F_3$ are a fluoren-2,7-diyl group.

4. The hydrocarbon compounds according to claim 1, wherein j and n are 0, l is 1, and k+m is 2.

5. The hydrocarbon compounds according to claim 4, wherein $A_1$ and $A_2$ are an anthracen-9,10-diyl group, and $F_2$ is a fluoren-2,7-diyl group.

6. Materials for an organic electroluminescent element according to claim 1.

7. An organic electroluminescent element in which at least one layer containing at least one of the materials for the organic electroluminescent element according to claim 6 is held between a pair of electrodes.

8. The organic electroluminescent element according to claim 7, wherein the layer containing the material for the organic electroluminescent element is a luminescent layer.

9. The organic electroluminescent element according to claim 7, wherein the layer containing the material for the organic electroluminescent element further contains a luminescent organic metal complex.

10. The organic electroluminescent element according to claim 7, wherein the layer containing the material for the organic electroluminescent element further contains triarylamine derivatives.

11. The organic electroluminescent element according to claim 7, wherein a hole injection transport layer is further provided between a pair of electrodes.

12. The organic electroluminescent element according to claim 7, wherein an electron injection transport layer is further provided between a pair of electrodes.

13. Hydrocarbon compounds represented by the formula (2)

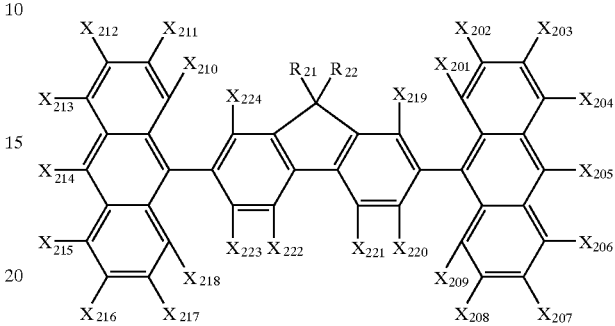

(2)

wherein $R_{21}$ and $R_{22}$, independently from each other, represent a hydrogen atom, a linear, branched or cyclic alkyl group, a substituted or unsubstituted furfuryl group, thienyl group or pyridyl group, or a substituted or unsubstituted aralkyl group, and $X_{201}$ to $X_{214}$, independently from each other, represent a hydrogen atom, a halogen atom, a linear, branched or cyclic alkyl group, a linear, branched or cyclic alkoxy group, a substituted or unsubstituted amino group, or a substituted or unsubstituted aryl group, provided $R_{21}$, $R_{22}$ and $X_{201}$ to $X_{224}$ are not an anthryl group or a fluorenyl group and $X_{205}$ and $X_{214}$ are not a substituted or unsubstituted amino group.

14. The hydrocarbon compounds according to claim 13, wherein $X_{205}$ and $X_{214}$ are a halogen atom, a linear, branched or cyclic alkyl group, a linear, branched or cyclic alkoxy group, or a substituted or unsubstituted aryl group.

15. The hydrocarbon compounds according to claim 13, wherein $X_{201}$, $X_{204}$, $X_{206}$, $X_{209}$, $X_{210}$, $X_{213}$, $X_{215}$ and $X_{218}$ are a hydrogen atom, a halogen atom, a linear, branched or cyclic alkyl group, or a linear, branched or cyclic alkoxy group.

16. Hydrocarbon compounds represented by the formula (3)

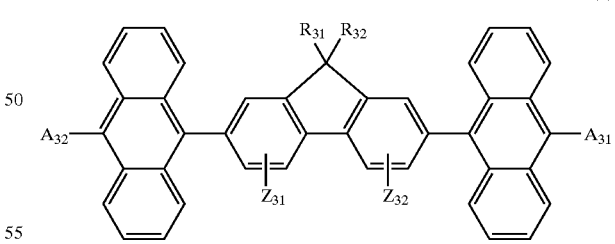

(3)

wherein $R_{31}$ and $R_{32}$, independently from each other, represent a hydrogen atom, a linear, branched or cyclic alkyl group, a substituted or unsubstituted furfuryl group, thienyl group or pyridyl group, or a substituted or unsubstituted aralkyl group, $A_{31}$ and $A_{32}$, independently from each other, represent a substituted or unsubstituted aryl group, and $Z_{31}$ and $Z_{32}$, independently from each other, represent a hydrogen. atom, a halogen atom, a linear, branched or cyclic alkyl group, a linear, branched or cyclic alkoxy group, or a substituted or unsubstituted aryl group.

* * * * *